United States Patent [19]
Winn et al.

[11] Patent Number: 5,622,971
[45] Date of Patent: Apr. 22, 1997

[54] ENDOTHELIN ANTAGONISTS

[75] Inventors: Martin Winn, Deerfield; Steven A. Boyd, Mundelein; Charles W. Hutchins, Gurnee; Hwan-Soo Jae, Glencoe; Andrew S. Tasker, Gurnee; Thomas W. von Geldern, Richmond; Jeffrey A. Kester, Deerfield; Bryan K. Sorensen, Waukegan, all of Ill.

[73] Assignee: Abbott Laboratories, Abbott Park, Ill.

[21] Appl. No.: 457,935

[22] Filed: Jun. 1, 1995

Related U.S. Application Data

[60] Division of Ser. No. 442,575, May 30, 1995, abandoned, which is a continuation-in-part of Ser. No. 334,717, Nov. 4, 1994, abandoned, which is a continuation-in-part of Ser. No. 293,349, Aug. 19, 1994, abandoned.

[51] Int. Cl.$^6$ ............ A61K 31/44; C07D 211/08
[52] U.S. Cl. ............ 514/315; 514/89; 514/91; 514/316; 514/317; 514/319; 514/320; 514/321; 514/322; 546/192; 546/195; 546/196; 546/197; 546/198; 546/199; 546/208; 546/209; 546/210; 546/215; 546/225; 546/227; 546/229; 546/236; 546/237; 546/242; 546/243; 546/244; 546/245; 546/246; 546/247; 546/248; 548/112; 548/129; 548/132; 548/263.2; 548/243
[58] Field of Search ............ 546/192, 195, 546/196, 197, 198, 199, 208, 209, 210, 215, 225, 227, 229, 236, 237, 242, 243, 244, 245, 246, 247, 248; 548/21, 22, 24; 514/89, 91, 315, 316, 317, 319, 320, 321, 322

[56] References Cited

U.S. PATENT DOCUMENTS

| | | | |
|---|---|---|---|
| 3,342,833 | 9/1967 | Fremery | 514/315 |
| 4,340,715 | 7/1982 | Gounder et al. | 514/315 |

FOREIGN PATENT DOCUMENTS

| | | |
|---|---|---|
| 2275926 | of 1994 | United Kingdom . |
| 9308799 | 5/1993 | WIPO . |
| 9402474 | 2/1994 | WIPO . |
| 9414434 | 7/1994 | WIPO . |
| 9505372 | 2/1995 | WIPO . |
| 9505376 | 2/1995 | WIPO . |
| 9504534 | 2/1995 | WIPO . |

OTHER PUBLICATIONS

Tsuge, et al., *Chemistry Letters*, 801–804 (1984).
Tsuge, et al., *Bull. Chem. Soc. Jpn.*, 59:2537 (1986).
CA 90:121571 [2] Benzopyrano (4, 3–c) pyridine derivatives. Santroch et al., 1979.
CA 94:174887a Antidepressant . . . –3–phenylpiperidines. Ehrgott et al., pp. 709, 1981.
CA 94:103132g Synthesis . . . agents. Rahman et al., p. 721, 1981.
CA 105:22628s Synthesis . . . glycolates. Banglun, p. 763, 1986.

*Primary Examiner*—Joseph K. McKane
*Attorney, Agent, or Firm*—Steven R. Crowley; Michael J. Ward

[57] ABSTRACT

A compound of the formula (I):

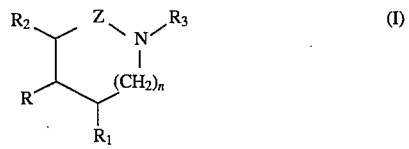

or a pharmaceutically acceptable salt thereof is disclosed, as well as processes for and intermediates in the preparation thereof, and a method of antagonizing endothelin.

22 Claims, No Drawings

ENDOTHELIN ANTAGONISTS

This is a division of U.S. patent application Ser. No. 08/442,575, filed May 30, 1995, now abandoned, which is a continuation-in-part of U.S. patent application Ser. No. 08/334,717, filed Nov. 4, 1994, now abandoned, which is a continuation-in-part of U.S. patent application Ser. No. 08/293,349, filed Aug. 19, 1994, now abandoned.

TECHNICAL FIELD

The present invention relates to compounds which are endothelin antagonists, processes for making such compounds, synthetic intermediates employed in these processes and methods and compositions for antagonizing endothelin.

BACKGROUND OF THE INVENTION

Endothelin (ET) is a 21 amino acid peptide that is produced by endothelial cells. ET is produced by enzymatic cleavage of a Trp-Val bond in the precursor peptide big endothelin (Big ET). This cleavage is caused by an endothelin convening enzyme (ECE). Endothelin has been shown to constrict arteries and veins, increase mean arterial blood pressure, decrease cardiac output, increase cardiac contractility in vitro, stimulate mitogenesis in vascular smooth muscle cells in vitro, contract non-vascular smooth muscle including guinea pig trachea, human urinary bladder strips and rat uterus in vitro, increase airway resistance in vivo, induce formation of gastric ulcers, stimulate release of atrial natriuretic factor in vitro and in vivo, increase plasma levels of vasopressin, aldosterone and catecholamines, inhibit release of renin in vitro and stimulate release of gonadotropins in vitro.

It has been shown that vasoconstriction is caused by binding of endothelin to its receptors on vascular smooth muscle (Nature 332 411 (1988), FEBS Letters 231 440 (1988) and Biochem. Biophys. Res. Commun. 154 868 (1988)). An agent which suppresses endothelin production or an agent which binds to endothelin or which inhibits the binding of endothelin to an endothelin receptor will produce beneficial effects in a variety of therapeutic areas. In fact, an anti-endothelin antibody has been shown, upon intrarenal infusion, to ameliorate the adverse effects of renal ischemia on renal vascular resistance and glomerular filtration rate (Kon, et al., J. Clin. Invest. 83 1762 (1989)). In addition, an anti-endothelin antibody attenuated the nephrotoxic effects of intravenously administered cyclosporin (Kon, et al., Kidney Int. 37 1487 (1990)) and attenuated infarct size in a coronary artery ligation-induced myocardial infarction model (Watanabe, et al., Nature 344 114 (1990)).

Clozel et al. (Nature 365:759–761 (1993)) report that Ro 46-2005, a nonpeptide ET-A/B antagonist, prevents post-ischaemic renal vasoconstriction in rats, prevents the decrease in cerebral blood flow due to subarachnoid hemorrhage (SAH) in rats, and decreases MAP in sodium-depleted squirrel monkeys when dosed orally. A similar effect of a linear tripeptide-like ET-A antagonist, BQ-485, on arterial caliber after SAH has also been recently reported (S. Itoh, T. Sasaki, K. Ide, K. Ishikawa, M. Nishikibe, and M. Yano, Biochem. Biophys. Res. Comm., 195:969–75 (1993). These results indicate that agents which antagonize ET/ET receptor binding will provide therapeutic benefit in the indicated disease states.

DISCLOSURE OF THE INVENTION

In accordance with the present invention there are compounds of the formula (I):

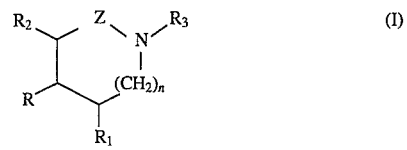

wherein

Z is —C($R_{18}$)($R_{19}$)— or —C(O)— wherein $R_{18}$ and $R_{19}$ are independently selected from hydrogen and loweralkyl;

n is 0 or 1;

R is —(CH$_2$)$_m$—W wherein m is an integer from 0 to 6 and W is (a) —C(O)$_2$—G wherein G is hydrogen or a carboxy protecting group, (b) —PO$_3$H$_2$, (c) —P(O)(OH)E wherein E is hydrogen, loweralkyl or arylalkyl, (d) —CN, (e) —C(O)NHR$_{17}$ wherein R$_{17}$ is loweralkyl, (f) alkylaminocarbonyl, (g) dialkylaminocarbonyl, (h) tetrazolyl, (i) hydroxy, (j) alkoxy, (k) sulfonamido, (l) —C(O)NHS(O)$_2$R$_{16}$ wherein R$_{16}$ is loweralkyl, haloalkyl, phenyl or dialkylamino, (m) —S(O)$_2$NHC(O)R$_{16}$,

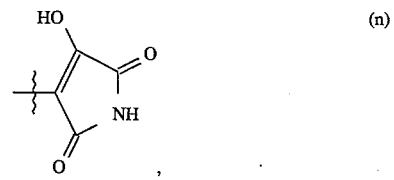
(n)

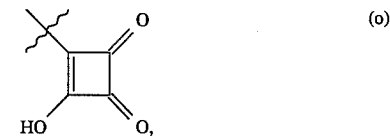
(o)

(p)

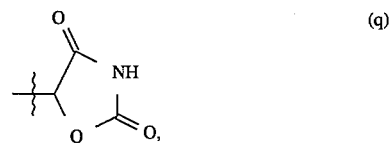
(q)

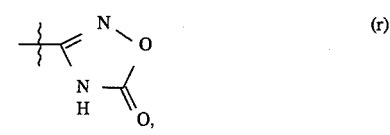
(r)

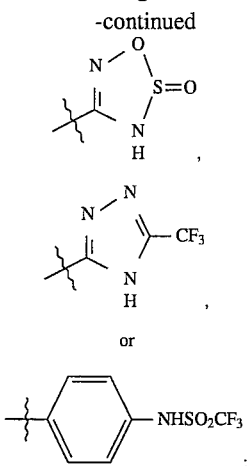

(s)

(t)

(u)

$R_1$ and $R_2$ are independently selected from hydrogen, loweralkyl, alkoxyalkyl, alkoxycarbonylalkyl, hydroxyalkyl, alkoxyalkoxyalkyl, thioalkoxyalkoxyalkyl, cycloalkyl, aryl, arylalkoxyalkyl and heterocyclic, with the proviso that one of $R_1$ and $R_2$ is other than hydrogen;

$R_3$ is (a) $R_4$—C(O)—$R_5$—, $R_6$—S(O)$_2$—$R_7$— or $R_{26}$—S(O)—$R_{27}$— wherein $R_5$ is (i) a covalent bond, (ii) alkylene, (iii) alkenylene, (iv) —N($R_{20}$)—$R_8$— or —$R_{8a}$—N($R_{20}$)—$R_8$— wherein $R_8$ and $R_{8a}$ are independently selected from alkylene and $R_{20}$ is hydrogen, loweralkyl, alkenyl, cylcoalkyl or cycloalkylalkyl or (v) —O—$R_9$— or —$R_{9a}$—O—$R_9$ wherein $R_9$ and $R_{9a}$ are independently selected from alkylene;

$R_7$ is (i) a covalent bond, (ii) alkylene, (iii) alkenylene or (iv) —N($R_{21}$)—$R_{10}$— wherein $R_{10}$ is alkylene and $R_{21}$ is hydrogen or loweralkyl;

$R_4$ and $R_6$ are independently selected from the group consisting of (i) ($R_{11}$)($R_{12}$)N— wherein $R_{11}$ and $R_{12}$ are independently selected from
(1) hydrogen,
(2) loweralkyl,
(3) alkoxyalkyl,
(4) alkenyl,
(5) alkynyl,
(6) cycloalkyl,
(7) cycloalkylalkyl,
(8) aryl,
(9) heterocyclic,
(10) arylalkyl, and
(11) (heterocyclic)alkyl,
(ii) loweralkyl,
(iii) alkenyl,
(iv) alkynyl,
(v) cycloalkyl,
(vi) cycloalkylalkyl,
(vii) aryl,
(viii) arylalkyl,
(ix) heterocyclic,
(x) (heterocyclic)alkyl and
(xi) alkoxyalkyl;

$R_{26}$ is (i)loweralkyl, (ii) haloalkyl, (iii) alkenyl, (iv) alkynyl, (v) cycloalkyl, (vi) cycloalkylalkyl, (vii) aryl, (viii) arylalkyl, (ix) heterocyclic, (x) (heterocyclic)alkyl, (xi) alkoxyalkyl or (xii) alkoxy-substituted haloalkyl; and $R_{27}$ is alkylene or alkenylene;

(b) $R_{22}$—O—C(O)—$R_{23}$— wherein $R_{22}$ is a carboxy protecting group or heterocyclic and $R_{23}$ is (i) a covalent bond, (ii) alkylene, (iii) alkenylene or (iv) —N($R_{24}$)—$R_{25}$— wherein $R_{25}$ is alkylene and $R_{24}$ is hydrogen or loweralkyl,
(c) loweralkyl,
(d) alkenyl,
(e) alkynyl,
(f) cycloalkyl,
(g) cycloalkylalkyl,
(h) aryl,
(i) arylalkyl,
(j) aryloxyalkyl,
(k) heterocyclic,
(l) (heterocyclic)alkyl,
(m) alkoxyalkyl,
(n) alkoxyalkoxyalkyl, or
(o) $R_{13}$—C(O)—CH($R_{14}$)— wherein $R_{13}$ is amino, alkylamino or dialkylamino and $R_{14}$ is aryl or $R_{15}$—C(O)— wherein $R_{15}$ is amino, alkylamino or dialkylamino;

or a pharmaceutically acceptable salt thereof.

A preferred embodiment of the invention is a compound of formula (II)

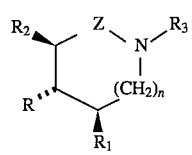

(II)

wherein the substituents —$R_2$, —R and —$R_1$ exist in a trans,trans relationship and Z, n, R, $R_1$, $R_2$, and $R_3$ are as defined above.

Another preferred embodiment of the invention is a compound of formula (I) or (II) wherein n is 0 and Z is —CH$_2$—.

Another preferred embodiment of the invention is a compound of formula (I) or (II) wherein n is 1 and Z is —CH$_2$—.

Another preferred embodiment of the invention is a compound of formula (I) or (II) wherein n is 0, Z is —CH$_2$—, and $R_3$ is $R_4$—C(O)—$R_5$—, $R_6$—S(O)$_2$—$R_7$— or $R_{26}$—S(O)—$R_{27}$— as defined above.

Another preferred embodiment of the invention is a compound of formula (I) or (II) wherein n is 0, Z is —CH$_2$—, and $R_3$ is alkoxyalkyl or alkoxyalkoxyalkyl.

A more preferred embodiment of the invention is a compound of formula (I) or (II) wherein n is 0, Z is —CH$_2$—, and $R_3$ is $R_4$—C(O)—$R_5$— wherein $R_4$ is ($R_{11}$)($R_{12}$)N— as defined above and $R_5$ is alkylene or $R_3$ is $R_6$—S(O)$_2$—$R_7$— or $R_{26}$—S(O)—$R_{27}$— wherein $R_7$ is alkylene, $R_{27}$ is alkylene and $R_6$ and $R_{26}$ are defined as above.

Another more preferred embodiment of the invention is a compound of formula (I) or (II) wherein n is 0, Z is —CH$_2$— and $R_3$ is $R_4$—C(O)—N($R_{20}$)—$R_8$— or $R_6$—S(O)$_2$—N($R_{21}$)—$R_{10}$— wherein $R_8$ and $R_{10}$ are alkylene and $R_4$, $R_6$, $R_{20}$ and $R_{21}$ are defined as above.

An even more preferred embodiment of the invention is a compound of formula (I) or (II) wherein n is 0, R is tetrazolyl or —C(O)$_2$—G wherein G is hydrogen or a carboxy protecting group or R is —C(O)—NHS(O)$_2$R$_{16}$ wherein $R_{16}$ is loweralkyl or aryl, Z is —CH$_2$—, $R_1$ and $R_2$ are independently selected from (i) loweralkyl, (ii) cylcoalkyl, (iii) substituted aryl wherein aryl is phenyl substituted with one or two substituents independently selected from loweralkyl, alkoxy, halo, alkoxyalkoxy and carboxyalkoxy and (iv) substituted or unsubstituted heterocyclic, and $R_3$ is $R_4$—C(O)—$R_5$— wherein $R_4$ is $(R_{11})(R_{12})N$— wherein $R_{11}$ and $R_{12}$ are independently selected from loweralkyl, aryl and arylalkyl and $R_5$ is alkylene; or $R_3$ is $R_4$—C(O)—N($R_{20}$)—$R_8$— or $R_6$—S(O)$_2$—N($R_{21}$)—$R_{10}$— wherein $R_4$ is loweralkyl, aryl, alkoxy, alkylamino, aryloxy or arylalkoxy and $R_6$ is loweralkyl, haloalkyl, alkoxyalkyl, aryl or arylalkyl, $R_8$ and $R_{10}$ are alkylene and $R_{20}$ and $R_{21}$ are loweralkyl; or $R_3$ is $R_6$—S(O)$_2$—$R_7$— or $R_{26}$—S(O)—$R_{27}$— wherein $R_6$ is loweralkyl, $R_7$ is alkylene, $R_{26}$ is loweralkyl and $R_{27}$ is alkylene.

A yet more preferred embodiment of the invention is a compound of formula (I) or (II) wherein n is 0, R is —C(O)$_2$—G wherein G is hydrogen or a carboxy protecting group, Z is —CH$_2$—, $R_1$ is (i) loweralkyl, (ii) cycloalkyl, (iii) phenyl, (iv) pyridyl, (v) furanyl or (vi) substituted or unsubstituted 4-methoxyphenyl, 4-fluorophenyl, 3-fluorophenyl, 2-fluorophenyl, 4-methoxymethoxyphenyl, 4-hydroxyphenyl, 4-t-butylphenyl, 1,3-benzodioxolyl, 1,4-benzodioxanyl or dihydrobenzofuranyl wherein the substituent is selected from alkoxy, alkoxyalkoxy and carboxyalkoxy, $R_2$ is 1,3-benzodioxolyl, 1,4-benzodioxanyl, dihydrobenzofuranyl, 4-methoxyphenyl, dimethoxyphenyl, fluorophenyl or difluorophenyl and $R_3$ is $R_4$—C(O)—N($R_{20}$)—$R_8$— or $R_6$—S(O)$_2$—N($R_{21}$)—$R_{10}$— wherein $R_8$ and $R_{10}$ are alkylene, $R_{20}$ and $R_{21}$ are loweralkyl, $R_4$ is loweralkyl, aryl, alkoxy, alkylamino, aryloxy or arylalkoxy and $R_6$ is loweralkyl, haloalkyl, alkoxyalkyl, aryl or arylalkyl.

Another yet more preferred embodiment of the invention is a compound of formula (I) or (II) wherein n is 0, R is —C(O)$_2$—G wherein G is hydrogen or a carboxy protecting group, Z is —CH$_2$—, $R_1$ is (i) loweralkyl, (ii) cycloalkyl, (iii) phenyl, (iv) pyridyl, (v) furanyl or (vi) substituted or unsubstituted 4-methoxyphenyl, 4-fluorophenyl, 3-fluorophenyl, 2-fluorophenyl, 4-methoxymethoxyphenyl, 4-hydroxyphenyl, 4-t-butylphenyl, 1,3-benzodioxolyl, 1,4-benzodioxanyl or dihydrobenzofuranyl wherein the substituent is selected from alkoxy, alkoxyalkoxy and carboxyalkoxy, $R_2$ is 1,3-benzodioxolyl, 1,4-benzodioxanyl, dihydrobenzofuranyl, 4-methoxyphenyl, dimethoxyphenyl, fluorophenyl or difluorophenyl and $R_3$ is $R_4$—C(O)—$R_5$— wherein $R_5$ is alkylene and $R_4$ is $(R_{11})(R_{12})N$— wherein $R_{11}$ and $R_{12}$ are independently selected from loweralkyl, aryl and arylalkyl.

The present invention also relates to processes for preparing the compounds of formula (I) and (II) and to the synthetic intermediates employed in these processes.

The present invention also relates to a method of antagonizing endothelin in a mammal (preferably, a human) in need of such treatment, comprising administering to the mammal a therapeutically effective amount of a compound of formula (I) or (II).

The invention further relates to endothelin antagonizing compositions comprising a pharmaceutical carrier and a therapeutically effective amount of a compound of formula (I) or (II).

The compounds of the invention comprise two or more asymmetrically substituted carbon atoms. As a result, racemic mixtures, mixtures of diastereomers, as well as single diastereomers of the compounds of the invention are included in the present invention. The terms "S" and "R" configuration are as defined by the IUPAC 1974 Recommendations for Section E, Fundamental Stereochemistry, Pure Appl. Chem. (1976) 45, 13–30.

The term "carboxy protecting group" as used herein refers to a carboxylic acid protecting ester group employed to block or protect the carboxylic acid functionality while the reactions involving other functional sites of the compound are carried out. Carboxy protecting groups are disclosed in Greene, "Protective Groups in Organic Synthesis" pp. 152–186 (1981), which is hereby incorporated herein by reference. In addition, a carboxy protecting group can be used as a prodrug whereby the carboxy protecting group can be readily cleaved in vivo, for example by enzymatic hydrolysis, to release the biologically active parent. T. Higuchi and V. Stella provide a thorough discussion of the prodrug concept in "Pro-drugs as Novel Delivery Systems", Vol 14 of the A.C.S. Symposium Series, American Chemical Society (1975), which is hereby incorporated herein by reference. Such carboxy protecting groups are well known to those skilled in the art, having been extensively used in the protection of carboxyl groups in the penicillin and cephalosporin fields, as described in U.S. Pat. Nos. 3,840,556 and 3,719,667, the disclosures of which are hereby incorporated herein by reference. Examples of esters useful as prodrugs for compounds containing carboxyl groups can be found on pages 14–21 of "Bioreversible Carriers in Drug Design: Theory and Application", edited by E. B. Roche, Pergamon Press, New York (1987), which is hereby incorporated herein by reference. Representative carboxy protecting groups are $C_1$ to $C_8$ loweralkyl (e.g., methyl, ethyl or tertiary butyl and the like); haloalkyl; alkenyl; cycloalkyl and substituted derivatives thereof such as cyclohexyl, cylcopentyl and the like; cycloalkylalkyl and substituted derivatives thereof such as cyclohexylmethyl, cylcopentylmethyl and the like; arylalkyl, for example, phenethyl or benzyl and substituted derivatives thereof such as alkoxybenzyl or nitrobenzyl groups and the like; arylalkenyl, for example, phenylethenyl and the like; aryl and substituted derivatives thereof, for example, 5-indanyl and the like; dialkylaminoalkyl (e.g., dimethylaminoethyl and the like); alkanoyloxyalkyl groups such as acetoxymethyl, butyryloxymethyl, valeryloxymethyl, isobutyryloxymethyl, isovaleryloxymethyl, 1-(propionyloxy)-1-ethyl, 1-(pivaloyloxyl)-1-ethyl, 1-methyl-1-(propionyloxy)-1-ethyl, pivaloyloxymethyl, propionyloxymethyl and the like; cycloalkanoyloxyalkyl groups such as cyclopropylcarbonyloxymethyl, cyclobutylcarbonyloxymethyl, cyclopentylcarbonyloxymethyl, cyclohexylcarbonyloxymethyl and the like; aroyloxyalkyl, such as benzoyloxymethyl, benzoyloxyethyl and the like; arylalkylcarbonyloxyalkyl, such as benzylcarbonyloxymethyl, 2-benzylcarbonyloxyethyl and the like; alkoxycarbonylalkyl, such as methoxycarbonylmethyl, cyclohexyloxycarbonylmethyl, 1-methoxycarbonyl-1-ethyl, and the like; alkoxycarbonyloxyalkyl, such as methoxycarbonyloxymethyl, t-butyloxycarbonyloxymethyl, 1-ethoxycarbonyloxy-1-ethyl, 1-cyclohexyloxycarbonyloxy-1-ethyl and the like; alkoxycarbonylaminoalkyl, such as t-butyloxycarbonylaminomethyl and the like; alkylaminocarbonylaminoalkyl, such as methylaminocarbonylaminomethyl and the like; alkanoylaminoalkyl, such as acetylaminomethyl and the like; heterocycliccarbonyloxyalkyl, such as 4-methylpiperazinylcarbonyloxymethyl and the like; dialkylaminocarbonylalkyl, such as dimethylaminocarbonylmethyl, diethylaminocarbonylmethyl and the like; (5-(loweralkyl)-2-oxo-1,3-dioxolen-4-yl)alkyl, such as (5-t-butyl-2-oxo-1,3-dioxolen-4-yl)methyl and the like; and (5-phenyl-2-oxo-1,3-dioxolen-4-yl)alkyl, such as (5-phenyl-2-oxo-1,3-dioxolen-4-yl)methyl and the like.

The term "N-protecting group" or "N-protected" as used herein refers to those groups intended to protect the N-terminus of an amino acid or peptide or to protect an amino group against undersirable reactions during synthetic procedures. Commonly used N-protecting groups are disclosed in Greene, "Protective Groups In Organic Synthesis," (John Wiley & Sons, New York (1981)), which is hereby incorporated by reference. N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Preferred N-protecting groups are formyl, acetyl, benzoyl, pivaloyl, t-butylacetyl, phenylsulfonyl, benzyl, t-butyloxycarbonyl (Boc) and benzyloxycarbonyl (Cbz).

The terms "loweralkyl" or "alkyl" as used herein refer to straight or branched chain alkyl radicals containing from 1 to 10 carbon atoms including, but not limited to, methyl, ethyl, n-propyl, iso-propyl, n-butyl, iso-butyl, sec-butyl, t-butyl, n-pentyl, 1-methylbutyl, 2,2-dimethylbutyl, 2-methylpentyl, 2,2-dimethylpropyl, n-hexyl and the like.

The term "alkylamino" as used herein refers to $R_{51}NH$— wherein $R_{51}$ is a loweralkyl group, for example, ethylamino, butylamino, and the like.

The term "alkylaminocarbonyl" as used herein refers to an alkylamino group, as previously defined, appended to the parent molecular moiety through a carbonyl (—C(O)—) linkage. Examples of alkylaminocarbonyl include methylaminocarbonyl, ethylaminocarbonyl, isopropylaminocarbonyl and the like.

The term "alkylaminocarbonylaminoalkyl" as used herein refers to $R_{40}$—C(O)—NH—$R_{41}$— wherein $R_{40}$ is an alkylamino group and $R_{41}$ is an alkylene group.

The term "dialkylamino" as used herein refers to $R_{56}R_{57}N$— wherein $R_{56}$ and $R_{57}$ are independently selected from loweralkyl, for example diethylamino, methyl propylamino, and the like.

The term "dialkylaminocarbonyl" as used herein refers to a dialkylamino group, as previously defined, appended to the parent molecular moiety through a carbonyl (—C(O)—) linkage. Examples of dialkylaminocarbonyl include dimethylaminocarbonyl, diethylaminocarbonyl and the like.

The term "dialkylaminocarbonylalkyl" as used herein refers to $R_{50}$—C(O)—$R_{51}$— wherein $R_{50}$ is a dialkylamino group and $R_{51}$ is an alkylene group.

The term "alkylsulfonylamino" as used herein refers to an alkyl group as previously defined appended to the parent molecular moiety through a sulfonylamino (—S(O)$_2$—NH—) group. Examples of alkylsulfonylamino include methylsulfonylamino, ethylsulfonylamino, isopropylsulfonylamino and the like.

The term "alkanoyl" as used herein refers to an alkyl group as previously defined appended to the parent molecular moiety through a carbonyl (—C(O)—) group. Examples of alkanoyl include acetyl, propionyl and the like.

The term "alkanoylamino" as used herein refers to an alkanoyl group as previously defined appended to an amino group. Examples alkanoylamino include acetamido, propionylamido and the like.

The term "alkanoylaminoalkyl" as used herein refers to $R_{43}$—NH—$R_{44}$— wherein $R_{43}$ is an alkanoyl group and $R_{44}$ is an alkylene group.

The term "alkanoyloxyalkyl" as used herein refers to $R_{30}$—O—$R_{31}$— wherein $R_{30}$ is an alkanoyl group and $R_{31}$ is an alkylene group. Examples of alkanoyloxyalkyl include acetoxymethyl, acetoxyethyl and the like.

The term "alkenyl" as used herein refers to a straight or branched chain hydrocarbon radical containing from 2 to 10 carbon atoms and also containing at least one carbon-carbon double bond. Alkenyl groups include, for example, vinyl (ethenyl), allyl (propenyl), butenyl, 1-methyl-2-buten-1-yl and the like.

The term "alkenyloxy" as used herein refers to an alkenyl group, as previously defined, connected to the parent molecular moiety through an oxygen (—O—)linkage. Examples of alkenyloxy include allyloxy, butenyloxy and the like.

The term "alkylene" denotes a divalent group derived from a straight or branched chain saturated hydrocarbon having from 1 to 10 carbon atoms by the removal of two hydrogen atoms, for example —CH$_2$—, —CH$_2$CH$_2$—, —CH(CH$_3$)—, —CH$_2$CH$_2$CH$_2$—, —CH$_2$C(CH$_3$)$_2$CH$_2$— and the like.

The term "alkenylene" denotes a divalent group derived from a straight or branched chain hydrocarbon containing from 2 to 10 carbon atoms and also containing at least one carbon-carbon double bond. Examples of alkenylene include —CH=CH—, —CH$_2$CH=CH—, —C(CH$_3$)=CH—, —CH$_2$CH=CHCH$_2$—, and the like.

The term "alkoxy" as used herein refers to $R_{41}$O— wherein $R_{41}$ is a loweralkyl group, as defined above. Examples of alkoxy include, but are not limited to, ethoxy, tert-butoxy, and the like.

The term "alkoxyalkyl" as used herein refers to an alkoxy group as previously defined appended to an alkyl radical as previously defined. Examples of alkoxyalkyl include, but are not limited to, methoxymethyl, methoxyethyl, isopropoxymethyl and the like.

The term "alkoxyalkoxy" as used herein refers to $R_{80}$O—$R_{81}$O— wherein $R_{80}$ is loweralkyl as defined above and $R_{81}$ is alkylene. Representative examples of alkoxyalkoxy groups include methoxymethoxy, ethoxymethoxy, t-butoxymethoxy and the like.

The term "alkoxyalkoxyalkyl" as used herein refers to an alkoxyalkoxy group as previously defined appended to an alkyl radical. Representative examples of alkoxyalkoxyalkyl groups include methoxyethoxyethyl, methoxymethoxymethyl, and the like.

The term "alkoxycarbonyl" as used herein refers to an alkoxyl group as previously defined appended to the parent molecular moiety through a carbonyl group. Examples of alkoxycarbonyl include methoxycarbonyl, ethoxycarbonyl, isopropoxycarbonyl and the like.

The term "alkoxycarbonylaminoalkyl" as used herein refers to $R_{38}$—C(O)—NH—$R_{39}$— wherein $R_{38}$ is an alkoxy group and $R_{39}$ is an alkylene group.

The term "alkoxycarbonylalkenyl" as used herein refers to an alkoxycarbonyl group as previously defined appended to an alkenyl radical. Examples of alkoxycarbonylalkenyl include methoxycarbonylethenyl, ethoxycarbonylethenyl and the like.

The term "alkoxycarbonylalkyl" as used herein refers to $R_{34}$—C(O)—$R_{35}$— wherein $R_{34}$ is an alkoxy group and $R_{35}$ is an alkylene group. Examples of alkoxycarbonylalkyl include methoxycarbonylmethyl, methoxcarbonylethyl, ethoxycarbonylmethyl and the like.

The term "alkoxycarbonyloxyalkyl" as used herein refers to $R_{36}$—C(O)—O—$R_{37}$— wherein $R_{36}$ is an alkoxy group and $R_{37}$ is an alkylene group.

The term "(alkoxycarbonyl)thioalkoxy" as used herein refers to an alkoxycarbonyl group as previously defined appended to a thioalkoxy radical. Examples of (alkoxycarbonyl)thioalkoxy include methoxycarbonylthiomethoxy, ethoxycarbonylthiomethoxy and the like.

The term "alkynyl" as used herein refers to a straight or branched chain hydrocarbon radical containing from 2 to 10 carbon atoms and also containing at least one carbon-carbon triple bond. Examples of alkynyl include —C≡C—H, H—C≡C—CH$_2$—, H—C≡C—CH(CH$_3$)— and the like.

The term "alkynylene" refers to a divalent group derived by the removal of two hydrogen atoms from a straight or branched chain acyclic hydrocarbon group containing from 2 to 10 carbon atoms and also containing a carbon-carbon triple bond. Examples of alkynylene include —C≡C—, —C≡C—CH$_2$—,—C≡C—CH(CH$_3$)— and the like.

The term "aminocarbonyl" as used herein refers to H$_2$N—C(O)—.

The term "aminocarbonylalkoxy" as used herein refers to H$_2$N—C(O)— appended to an alkoxy group as previously defined. Examples of aminocarbonylalkoxy include aminocarbonylmethoxy, aminocarbonylethoxy and the like.

The term "aryl" as used herein refers to a mono- or bicyclic carbocyclic ring system having one or two aromatic rings including, but not limited to, phenyl, naphthyl, tetrahydronaphthyl, indanyl, indenyl and the like. Aryl groups can be unsubstituted or substituted with one, two or three substituents independently selected from loweralkyl, halo, haloalkyl, haloalkoxy, alkenyloxy, alkoxy, alkoxyalkoxy, alkoxycarbonyl, alkoxycarbonylalkenyl, (alkoxycarbonyl)thioalkoxy, thioalkoxy, amino, alkylamino, dialkylamino, aminocarbonyl, aminocarbonylalkoxy, alkanoylamino, arylalkoxy, aryloxy, mercapto, nitro, carboxaldehyde, carboxy, carboxyalkenyl, carboxyalkoxy, alkylsulfonylamino, cyanoalkoxy, (heterocyclic)alkoxy, hydroxy, hydroxalkoxy, and tetrazolylalkoxy. In addition, substituted aryl groups include tetrafluorophenyl and pentafluorophenyl.

The term "arylalkoxy" as used herein refers to $R_{42}$O— wherein $R_{42}$ is an arylalkyl group, for example, benzyloxy, and the like.

The term "arylalkyl" as used herein refers to an aryl group as previously defined, appended to a loweralkyl radical, for example, benzyl and the like.

The term "aryloxy" as used herein refers to $R_{45}$O— wherein $R_{45}$ is an aryl group, for example, phenoxy, and the like.

The term "aryloxyalkyl" refers to an aryloxy group as previously defined appended to an alkyl radical. Examples of aryloxyalkyl include phenoxymethyl, 2-phenoxyethyl and the like.

The term "arylalkoxyalkyl" as used herein refers to a loweralkyl radical to which is appended an arylalkoxy group, for example, benzyloxymethyl and the like.

The term "aroyloxyalkyl" as used herein refers to $R_{32}$—C(O)—O—$R_{33}$— wherein $R_{32}$ is an aryl group and $R_{33}$ is an alkylene group. Examples of aroyloxyalkyl include benzoyloxymethyl, benzoyloxyethyl and the like.

The term "carboxaldehyde" as used herein refers to a formaldehyde radical, —C(O)H.

The term "carboxy" as used herein refers to a carboxylic acid radical, —C(O)OH.

The term "carboxyalkoxy" as used herein refers to a carboxy group as previously defined appended to an alkoxy radical as previously defined. Examples of carboxyalkoxy include carboxymethoxy, carboxyethoxy and the like.

The term "carboxyalkenyl" as used herein refers to a carboxy group as previously defined appended to an alkenyl radical as previously defined. Examples of carboxyalkenyl include 2-carboxyethenyl, 3-carboxy-1-ethenyl and the like.

The term "cyanoalkoxy" as used herein refers to an alkoxy radical as previously defined to which is appended a cyano (—CN) group. Examples of cyanoalkoxy include 3-cyanopropoxy, 4-cyanobutoxy and the like.

The term "cycloalkyl" as used herein refers to an aliphatic ring system having 3 to 10 carbon atoms and 1 to 3 rings including, but not limited to, cyclopropyl, cyclopentyl, cyclohexyl, norbornyl, adamantyl, and the like. Cycloalkyl groups can be unsubstituted or substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy, alkoxycarbonyl and carboxamide.

The term "cycloalkylalkyl" as used herein refers to a cycloalkyl group appended to a loweralkyl radical, including but not limited to cyclohexylmethyl.

The term "halogen" or "halo" as used herein refers to I, Br, Cl or F.

The term "haloalkyl" as used herein refers to a lower alkyl radical, as defined above, bearing at least one halogen substituent, for example, chloromethyl, fluoroethyl or trifluoromethyl and the like.

The term "haloalkoxy" as used herein refers to a lower alkoxy radical as defined above, bearing at least one halogen substituent, for example, 2-fluoroethoxy, 2,2,2-trifluoroethoxy and the like.

The term "heterocyclic ring" or "heterocyclic" or "heterocycle" as used herein refers to any 3- or 4-membered ring containing a heteroatom selected from oxygen, nitrogen and sulfur; or a 5-, 6- or 7-membered ring containing one, two or three nitrogen atoms; one oxygen atom; one sulfur atom; one nitrogen and one sulfur atom; one nitrogen and one oxygen atom; two oxygen atoms in non-adjacent positions; one oxygen and one sulfur atom in non-adjacent positions; or two sulfur atoms in non-adjacent positions. The 5-membered ring has 0–2 double bonds and the 6- and 7-membered rings have 0–3 double bonds. The nitrogen heteroatoms can be optionally quaternized. The term "heterocyclic" also includes bicyclic groups in which any of the above heterocyclic rings is fused to a benzene ring or a cyclohexane ring or another heterocyclic ring (for example, indolyl, dihydroindolyl, quinolyl, isoquinolyl, tetrahydroquinolyl, tetrahydroisoquinolyl, decahydroquinolyl, benzofuryl, dihydrobenzofuryl or benzothienyl and the like). Heterocyclics include: aziridinyl, azetidinyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, oxetanyl, furyl, tetrahydrofuranyl, thienyl, thiazolidinyl, isothiazolyl, triazolyl, tetrazolyl, isoxazolyl, oxadiazolyl, thiadiazolyl, pyrrolyl, pyrimidyl and benzothienyl. Heterocyclics also include compounds of the formula

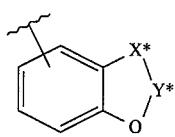

where X* is —CH₂— or —O— and Y* is —C(O)— or [—C(R")₂—]ᵥ, where R" is hydrogen or $C_1$–$C_4$-alkyl and v is 1, 2 or 3 such as 1,3-benzodioxolyl, 1,4-benzodioxanyl and the like. Heterocyclics also include bicyclic rings such as quinuclidinyl and the like.

Heterocyclics can be unsubstituted or monosubstituted or disubstituted with substituents independently selected from hydroxy, halo, oxo (=O), alkylimino (R*N= wherein R* is a loweralkyl group), amino, alkylamino, dialkylamino, alkoxy, alkoxyalkoxy, haloalkyl, cycloalkyl, aryl, arylalkyl, —COOH, —SO₃H and loweralkyl. In addition, nitrogen containing heterocycles can be N-protected.

The term "(heterocyclic)alkyl" as used herein refers to a heterocyclic group as defined above appended to a loweralkyl radical as defined above.

The term "(heterocyclic)alkoxy" as used herein refers to a heterocyclic group as defined above appended to an alkoxy radical as defined above. Examples of (heterocyclic)alkoxy include 4-pyridylmethoxy, 2-pyridylmethoxy and the like.

The term "heterocycliccarbonyloxyalkyl" as used herein refers to $R_{46}$—C(O)—O—$R_{47}$— wherein $R_{46}$ is a heterocyclic group and $R_{47}$ is an alkylene group.

The term "hydroxy" as used herein refers to —OH.

The term "hydroxyalkoxy" as used herein refers to an alkoxy radical as previously defined to which is appended a hydroxy (—OH) group. Examples of hydroxyalkoxy include 3-hydroxypropoxy, 4-hydroxybutoxy and the like.

The term "mercapto" as used herein refers to —SH.

The terms "methylenedioxy" and "ethylenedioxy" refer to one or two carbon chains attached to the parent molecular moiety through two oxygen atoms. In the case of methylenedioxy, a fused 5 membered ring is formed. In the case of ethylenedioxy, a fused 6 membered ring is formed. Methylenedioxy substituted on a phenyl ring results in the formation of a benzodioxolyl radical.

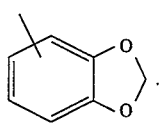

Ethylenedioxy substituted on a phenyl ring results in the formation of a benzodioxanyl radical.

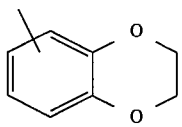

The term "tetrazolyl" as used herein refers to a radical of the formula

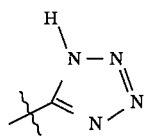

or a tautomer thereof.

The term "tetrazolylalkoxy" as used herein refers to a tetrazolyl radical as defined above appended to an alkoxy group as defined above. Examples of tetrazolylalkoxy include tetrazolylmethoxy, tetrazolylethoxy and the like.

The term "thioalkoxy" as used herein refers to $R_{70}$S— wherein $R_{70}$ is loweralkyl. Examples of thioalkoxy include, but are not limited to, methylthio, ethylthio and the like.

The term "trans,trans" as used herein refers to the orientation of substituents ($R_1$ and $R_2$) relative to the central substituent R as shown

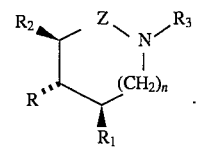

The term "trans,cis" as used herein refers to the orientation of substituents ($R_1$ and $R_2$) relative to the central substituent R as shown

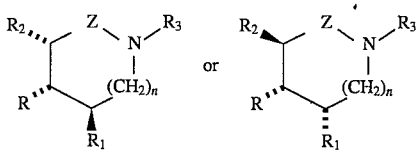

This definition encompasses both the case where R and $R_2$ are cis and R and $R_1$ are trans and the case where $R_2$ and R are trans and R and $R_1$ are cis.

The term "cis,cis" as used herein refers to the orientation of substituents ($R_1$ and $R_2$) relative to the central substituent R as shown

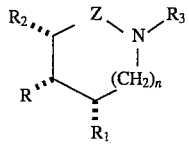

Representative compounds of the invention include:
trans,trans-2-(4-Methoxyphenyl)-4-(1,3-benzodioxol-5-yl)-1-(propylaminocarbonylmethyl)-pyrrolidine-3-carboxylic acid;
trans,trans-2-(4-Methoxyphenyl)-4-(1,3-benzodioxol-5-yl)-1-(aminocarbonylmethyl)-pyrrolidine-3-carboxylic acid;
trans,trans-2-(4-Methoxyphenyl)-4-(1,3-benzodioxol-5-yl)-1-(4-fluorobenzyl)-pyrrolidine-3-carboxylic acid;
trans,trans-2-(4-Methoxyphenyl)-4-(1,3-benzodioxol-5-yl)-1-(2-ethoxyethyl)-pyrrolidine-3-carboxylic acid;
trans,trans-2-(4-Methoxyphenyl)-4-(1,3-benzodioxol-5-yl)-1-(2-propoxyethyl)-pyrrolidine-3-carboxylic acid;
trans,trans-2-(4-Methoxyphenyl)-4-(1,3-benzodioxol-5-yl)-1-[2-(2-methoxyethoxy)ethyl]-pyrrolidine-3-carboxylic acid;
trans,trans-2-(4-Methoxyphenyl)-4-(1,3-benzodioxol-5-yl)-1-[2-(2-pyridyl)ethyl]-pyrrolidine-3-carboxylic acid;
trans,trans-2-(4-Methoxyphenyl)-4-(1,3-benzodioxol-5-yl)-1-(4-morpholinylcarbonyl)-pyrrolidine-3-carboxylic acid;
trans,trans-2-(4-Methoxyphenyl)-4-(1,3-benzodioxole-5-yl)-1-(butylaminocarbonyl)-pyrrolidine-3-carboxylic acid;
trans,trans-2-(4-Methoxyphenyl)-4-(1,3-benzodioxol-5-yl)-1-(4-methoxyphenylaminocarbonyl)-3-pyrrolidine-3-carboxylic acid;
trans,trans-2-(4-Methoxyphenyl)-4-(1,3-benzodioxol-5-yl)-1-acetylpyrrolidine-3-carboxylic acid;
trans,trans-2-(4-Methoxyphenyl)-4-(1,3-benzodioxol-5-yl)-1-(2-furoyl)-pyrrolidine-3-carboxylic acid;

trans,trans-2-(4-Methoxyphenyl)-4-(1,3-benzodioxol-5-yl)-1-(phenylaminocarbonyl)-pyrrolidine-3-carboxylic acid;

trans,trans-2-(4-Methoxyphenyl)-4-(1,3-benzodioxol-5-yl)-1-(allylaminocarbonylmethyl)-pyrrolidine-3-carboxylic acid;

trans,trans-2-(4-Methoxyphenyl)-4-(1,3-benzodioxol-5-yl)-1-(n-butylaminocarbonylmethyl)-pyrrolidine-3-carboxylic acid;

trans,trans-2-(4-Methoxyphenyl)-4-(1,3-benzodioxol-5-yl)-1-(N-n-butyl-N-methylaminocarbonylmethyl)-pyrrolidine-3-carboxylic acid;

trans,trans-2-(4-Methoxyphenyl)-4-(1,3-benzodioxol-5-yl)-1-(pyrrolidin-1-ylcarbonylmethyl)-pyrrolidine-3-carboxylic acid;

trans,trans-2-(4-Methoxyphenyl)-4-(1,3-benzodioxol-5-yl)-1-(isobutylaminocarbonylmethyl)-pyrrolidine-3-carboxylic acid;

trans,trans-2-(4-Methoxyphenyl)-4-(1,3-benzodioxol-5-yl)-1-(cyclopentylaminocarbonylmethyl)-pyrrolidine-3-carboxylic acid;

trans,trans-2-(4-Methoxyphenyl)-4-(1,3-benzodioxol-5-yl)-1-(morpholin-4-ylaminocarbonylmethyl)-pyrrolidine-3-carboxylic acid;

trans,trans-2-(4-Methoxyphenyl)-4-(1,3-benzodioxol-5-yl)-1-(2-phenoxyethyl)-pyrrolidine-3-carboxylic acid;

trans,trans-2-(4-Methoxyphenyl)-4-(1,3-benzodioxol-5-yl)-1-(2-methoxyethylaminocarbonylmethyl)-pyrrolidine-3-carboxylic acid;

trans,trans-2-(4-Methoxyphenyl)-4-(1,3-benzodioxol-5-yl)-1-(2-butoxyethyl)-pyrrolidine-3-carboxylic acid;

trans,trans-2-(1,3-Benzodioxol-5-yl)-4-(4-methoxyphenyl)-1-(propylaminocarbonylmethyl)-pyrrolidine-3-carboxylic acid;

trans,trans-2-(1,3-Benzodioxol-5-yl)-4-(4-methoxyphenyl)-1-(2-propoxyethyl)-pyrrolidine-3-carboxylic acid;

trans,trans-2-(1,3-Benzodioxol-5-yl)-4-(4-methoxyphenyl)-1-[2-(2-methoxyethoxy)ethyl)]-pyrrolidine-3-carboxylic acid;

trans,trans-2-(1,3-Benzodioxol-5-yl)-4-(4-methoxyphenyl)-1-(2-butoxyethyl)-pyrrolidine-3-carboxylic acid;

trans,trans-2-(4-Methoxyphenyl)-4-(1,4-benzodioxan-6-yl)-1-(propylaminocarbonylmethyl)-pyrrolidine-3-carboxylic acid;

trans,trans-2-(4-Methoxyphenyl)-4-(1,4-benzodioxan-6-yl)-1-(N-methyl-N-propylaminocarbonylmethyl)-pyrrolidine-3-carboxylic acid;

trans,trans-2-(4-Methoxyphenyl)-4-(1,3-benzodioxol-5-yl)-1-(N-methyl-N-butylaminocarbonylmethyl)-pyrrolidine-3-carboxylic acid;

trans,trans-2-(4-Methoxy-2-methoxymethoxyphenyl)-4-(1,3-benzodioxol-5-yl)-1-(N-methyl-N-butylaminocarbonylmethyl)-pyrrolidine-3-carboxylic acid;

trans,trans-2-(4-Methoxyphenyl)-4-(1,3-benzodioxol-5-yl)-1-(3-ethoxypropyl)-pyrrolidin-5-one-3-carboxylic acid;

trans,trans-2-(4-Methoxyphenyl)-4-(1,3-benzodioxol-5-yl)-1-(3-methoxybenzyl)-pyrrolidin-5-one-3-carboxylic acid;

trans,trans-2-(4-Methoxyphenyl)-4-(1,3-benzodioxol-5-yl)-1-(N,N-diisoamylaminocarbonylmethyl)-pyrrolidine-3-carboxylic acid;

trans,trans-2-(4-Methoxyphenyl)-4-(1,3-benzodioxol-5- yl)-1-(N,N-dipentylaminocarbonylmethyl)-pyrrolidine-3-carboxylic acid;

trans,trans-2-(4-Methoxyphenyl)-4-(1,3-benzodioxol-5-yl)-1-(N,N-di(2-methoxyethyl)aminocarbonylmethyl)-pyrrolidine-3-carboxylic acid;

trans,trans-2-(4-Methoxyphenyl)-4-(1,3-benzodioxol-5-yl)-1-(2-hexynyl)-pyrrolidine-3-carboxylic acid;

trans,trans-2-(4-Methoxyphenyl)-4-(1,3-benzodioxol-5-yl)-1-(N-cyclopropylmethyl-N-propylaminocarbonylmethyl)-pyrrolidine-3-carboxylic acid;

trans,trans-2-(4-Methoxyphenyl)-4-(1,3-benzodioxol-5-yl)-1-(N-methyl-N-pentylaminocarbonylmethyl)-pyrrolidine-3-carboxylic acid;

trans,trans-2-(4-Methoxyphenyl)-4-(1,3-benzodioxol-5-yl)-1-(N,N-diisobutylaminocarbonylmethyl)-pyrrolidine-3-carboxylic acid;

trans,trans-2-(4-Methoxyphenyl)-4-(1,3-benzodioxol-5-yl)-1-(N-methyl-N-(2-propynyl)aminocarbonylmethyl)-pyrrolidine-3-carboxylic acid;

trans,trans-2-(4-Methoxyphenyl)-4-(1,3-benzodioxol-5-yl)-1-(N-methyl-N-(n-hexyl)aminocarbonylmethyl)-pyrrolidine-3-carboxylic acid;

trans,trans-2-(4-Methoxyphenyl)-4-(1,3-benzodioxol-5-yl)-1-(N,N-di(n-butyl)aminocarbonylmethyl)-pyrrolidine-3-carboxylic acid;

trans,trans-2-(4-Methoxyphenyl)-4-(1,3-benzodioxol-5-yl)-1-(N,N-diethylaminocarbonylmethyl)-pyrrolidine-3-carboxylic acid;

trans,trans-2-(4-Methoxyphenyl)-4-(1,3-benzodioxol-5-yl)-1-(N-methyl-N-phenylaminocarbonylmethyl)-pyrrolidine-3-carboxylic acid;

trans,trans-2-(4-Methoxyphenyl)-4-(1,3-benzodioxol-5-yl)-1-(N-methyl-N-cyclohexylaminocarbonylmethyl)-pyrrolidine-3-carboxylic acid;

trans,trans-2-(4-Methoxyphenyl)-4-(1,3-benzodioxol-5-yl)-1-(N,N-di(n-propyl)aminocarbonylmethyl)-pyrrolidine-3-carboxylic acid;

trans,trans-2-(4-Methoxyphenyl)-4-(1,3-benzodioxol-5-yl)-1-(N-methyl-N-isobutylaminocarbonylmethyl)-pyrrolidine-3-carboxylic acid;

trans,trans-2-(4-Methoxyphenyl)-4-(1,3-benzodioxol-5-yl)-1-(t-butyloxycarbonylmethyl)-pyrrolidine-3-carboxylic acid;

trans,trans-2-(4-Methoxyphenyl)-4-(1-naphthyl)-1-(N-methyl-N-propyl)aminocarbonylmethyl)-pyrrolidine-3-carboxylic acid;

trans,trans-2-(4-Methoxyphenyl)-4-(2,3-dihydrobenzofuran-5-yl)-1-(N-methyl-N-propyl)aminocarbonylmethyl)-pyrrolidine-3-carboxylic acid;

trans,trans-2,4-Bis(4-methoxyphenyl)-1-(N-methyl-N-propyl)aminocarbonylmethyl)-pyrrolidine-3-carboxylic acid;

trans,trans-2-(4-Methoxyphenyl)-4-(3,4-dimethoxyphenyl)-1-(N-methyl-N-propyl)aminocarbonylmethyl)-pyrrolidine-3-carboxylic acid;

trans,trans-2-(4-Methoxyphenyl)-4-(3-methoxyphenyl)-1-(N-methyl-N-propyl)aminocarbonylmethyl)-pyrrolidine-3-carboxylic acid;

trans,trans-2-(4-Methoxyphenyl)-4-(2-naphthyl)-1-(N-methyl-N-propyl)aminocarbonylmethyl)-pyrrolidine-3-carboxylic acid;

trans,trans-2-(4-Methoxyphenyl)-4-(1,3-benzodioxol-5-yl)-1-(2-(ethylsulfinyl)ethyl)-pyrrolidine-3-carboxylic acid;

trans,trans-2-(4-Methoxyphenyl)-4-(1,3-benzodioxol-5-yl)-1-(2-(isopropylsulfonylamino)ethyl)-pyrrolidine-3-carboxylic acid;

trans,trans-2-(4-Methoxyphenyl)-4-(1,3-benzodioxol-5-yl)-1-(2-(isobutoxy)ethyl)-pyrrolidine-3-carboxylic acid;

trans,trans-2-(4-Methoxyphenyl)-4-(1,3-benzodioxol-5-yl)-1-(butylsulfonyl)-pyrrolidine-3-carboxylic acid;

trans,trans-2-(4-Methoxyphenyl)-4-(1,3-benzodioxol-5-yl)-1-(2-(N-methyl-N-isobutyrylamino)ethyl)-pyrrolidine-3-carboxylic acid;

trans,trans-2-(4-Methoxyphenyl)-4-(1,3-benzodioxol-5-yl)-1-(2-(N-methyl-N-propionylamino)ethyl)-pyrrolidine-3-carboxylic acid;

trans,trans-2-(4-Methoxyphenyl)-4-(1,3-benzodioxol-5-yl)-1-(N-methyl-N-benzylaminocarbonylmethyl)-pyrrolidine-3-carboxylic acid;

trans,trans-2-(4-Methoxyphenyl)-4-(1,3-benzodioxol-5-yl)-1-(N-ethyl-N-butylaminocarbonylmethyl)-pyrrolidine-3-carboxylic acid;

trans,trans-2-(4-Methoxyphenyl)-4-(1,3-benzodioxol-5-yl)-1-(N-methyl-N-(2,2-dimethylpropyl)aminocarbonylmethyl)-pyrrolidine-3-carboxylic acid;

trans,trans-2-(4-Methoxyphenyl)-4-(1,3-benzodioxol-5-yl)-1-(2-(N-methyl-N-butylsulfonylamino)ethyl)-pyrrolidine-3-carboxylic acid;

trans,trans-2-(4-Methoxyphenyl)-4-(1,3-benzodioxol-5-yl)-1-(2-(N-methyl-N-propylsulfonylamino)ethyl)-pyrrolidine-3-carboxylic acid;

trans,trans-2-(4-Methoxyphenyl)-4-(1,3-benzodioxol-5-yl)-1-(2-(propylsulfonyl)ethyl)-pyrrolidine-3-carboxylic acid;

trans,trans-2-(4-Methoxyphenyl)-4-(1,3-benzodioxol-5-yl)-1-N-(trans-5-methylhex-2-enyl)-pyrrolidine-3-carboxylic acid;

trans,trans-2-(4-Methoxyphenyl)-4-(1,3-benzodioxol-5-yl)-1-N-(trans-3,5-dimethylhex-2-enyl)-pyrrolidine-3-carboxylic acid;

trans,trans-2-(4-methoxyphenyl)-4-(1,3-benzodioxol-5-yl)-1-(4-heptylcarbonylmethyl)-pyrrolidine-3-carboxylic acid;

trans,trans-2-(4-Methoxyphenyl)-4-(1,3-benzodioxol-5-yl)-1-(valerylmethyl)-pyrrolidine-3-carboxylic acid;

trans,trans-2-(4-Methoxyphenyl)-4-(1,3-benzodioxol-5-yl)-1-(N-(3,4-dimethoxybenzyl)-N-methylaminocarbonylmethyl)pyrrolidine-3-carboxylic acid;

trans,trans-2-(4-Methoxyphenyl)-4-(1,3-benzodioxol-5-yl)-1-(N-(3,4-dimethoxybenzyl)aminocarbonylmethyl)pyrrolidine-3-carboxylic acid;

(2R,3R,4S)-2-(4-Methoxyphenyl)-4-(1,3-benzodioxol-5-yl)-1-((1R)-1-(N,N-dipropylaminocarbonyl)-1-butyl)pyrrolidine-3-carboxylic acid;

(2S,3S,4R)-2-(4-Methoxyphenyl)-4-(1,3-benzodioxol-5-yl)-1-((1R)-1-(N,N-dipropylaminocarbonyl)-1-butyl)pyrrolidine-3-carboxylic acid;

(2S,3S,4R)-2-(4-Methoxyphenyl)-4-(1,3-benzodioxol-5-yl)-1-((1S)-1-(N,N-dipropylaminocarbonyl)-1-butyl)pyrrolidine-3-carboxylic acid;

(2R,3R,4S)-2-(4-Methoxyphenyl)-4-(1,3-benzodioxol-5-yl)-1-((1S)-1-(N,N-dipropylaminocarbonyl)-1-butyl)pyrrolidine-3-carboxylic acid;

trans,trans-2-(4-Methoxyphenyl)-4-(1,3-benzodioxol-5-yl)-1-(N,N-di(n-butyl)aminocarbonylmethyl)-3-(5-tetrazolyl)pyrrolidine;

trans,trans-2-(4-Fluorophenyl)-4-(1,3-benzodioxol-5-yl)-1-(N,N-di(n-butyl)aminocarbonylmethyl)pyrrolidine-3-carboxylic acid;

trans,trans-2-(4-Methoxyphenyl)-4-(1,3-benzodioxol-5-yl)-1-(N,N-di(n-butyl)aminomethylcarbonyl)pyrrolidine-3-carboxylic acid;

trans,trans-2-(4-Methoxyphenyl)-4-(1,3-benzodioxol-5-yl)-1-(N-n-butyl)-N-(n-propyl)aminocarbonylmethyl)pyrrolidine-3-carboxylic acid;

trans,trans-2-(4-Methoxyphenyl)-4-(1,3-benzodioxol-5-yl)-1-[2-(N,N-di(n-propyl)aminocarbonyl)ethyl]pyrrolidine-3-carboxylic acid;

trans,trans-2-(4-Methoxyphenyl)-4-(1,3-benzodioxol-5-yl)-1-(N,N-di(n-butyl)aminocarbonyl)pyrrolidine-3-carboxylic acid;

trans,trans-2-(4-Methoxyphenyl)-4-(1,3-benzodioxol-5-yl)-1-(N,N-di(n-butyl)aminocarbonylmethyl)pyrrolidine-3-carboxylic acid sodium salt;

trans,trans-2-(4-Methoxyphenyl)-4-(1,3-benzodioxol-5-yl)-1-[2-(N,N-di(n-butyl)aminocarbonyl)ethyl]pyrrolidine-3-carboxylic acid;

trans,trans-2-(4-Methoxyphenyl)-4-(1,3-benzodioxol-5-yl)-1-{2-[N-(N,N-di(n-butyl)aminocarbonyl)-N-methylamino]ethyl}pyrrolidine-3-carboxylic acid;

trans,trans-2-(4-Methoxyphenyl)-4-(1,3-benzodioxol-5-yl)-1-(N,N-di(n-butyl)aminocarbonyl)methyl)pyrrolidine-3-(N-methanesulfonyl)carboxamide;

trans,trans-2-(4-Methoxyphenyl)-4-(1,3-benzodioxol-5-yl)-1-(N,N-di(n-butyl)aminocarbonylmethyl)pyrrolidine-3-(N-benzenesulfonyl)carboxamide;

trans,trans-2-(4-Methoxyphenyl)-4-(1,3-benzodioxol-5-yl)-1-[N,N-di(n-butyl)aminosulfonylmethyl]pyrrolidine-3-carboxylic acid;

trans,trans-2-(4-Methoxyphenyl)-4-(1,3-benzodioxol-5-yl)-1-[(N,N-dibutylamino)carbonyl-1-(RS)-ethyl]pyrrolidine-3-carboxylic acid;

trans,trans-2-(Pentyl)-4-(1,3-benzodioxol-5-yl)-1-[(N,N-dibutylamino)carbonylmethyl]pyrrolidine-3-carboxylic acid;

trans,trans-2-(Pentyl)-4-(1,3-benzodioxol-5-yl)-1-[2-(N-propyl-N-propylsulfonylamino)ethyl]pyrrolidine-3-carboxylic acid;

trans,trans-2-(Propyl)-4-(1,3-benzodioxol-5-yl)-1-[(N,N-dibutylamino)carbonylmethyl]pyrrolidine-3-carboxylic acid;

trans,trans-2-(4-Methoxyphenyl)-4-(1,3-benzodioxol-5-yl)-1-(tert-butyloxycarbonyl-aminocarbonylmethyl)-pyrrolidine-3-carboxylic acid;

trans,trans-2-(4-Methoxyphenyl)-4-(1,3-benzodioxol-5-yl)-1-[2-(N-propyl-N-butyrylamino)ethyl]pyrrolidine-3-carboxylic acid;

trans,trans-2-(4-Methoxyphenyl)-4-(1,3-benzodioxol-5-yl)-1-[2-(N-propyl-N-(ethylaminocarbonyl)amino)ethyl]pyrrolidine-3-carboxylic acid;

trans,trans-2-(4-Methoxyphenyl)-4-(1,3-benzodioxol-5-yl)-1-[2-(N-butyl-N-butyrylamino)ethyl]pyrrolidine-3-carboxylic acid;

trans,trans-2-(4-Methoxyphenyl)-4-(1,3-benzodioxol-5-yl)-1-[2-(N-propyl-N-ethoxycarbonylamino)ethyl]pyrrolidine-3-carboxylic acid;

trans,trans-2-(4-Methoxyphenyl)-4-(1,3-benzodioxol-5-yl)-1-[2-(N-methyl-N-(2-ethylbutyryl)amino)ethyl]pyrrolidine-3-carboxylic acid;

trans,trans-2-(4-Methoxyphenyl)-4-(1,3-benzodioxol-5-yl)-1-[2-(N-methyl-N-(2-propylvaleryl)amino)ethyl]pyrrolidine-3-carboxylic acid;

trans,trans-2-(4-Methoxyphenyl)-4-(1,3-benzodioxol-5-yl)-1-[2-(N-propyl-N-(tert-butyloxycarbonylmethyl)amino)ethyl]pyrrolidine-3-carboxylic acid;

trans,trans-2-(4-Methoxyphenyl)-4-(1,3-benzodioxol-5-yl)-1-[2-(N-propyl-N-(n-propylaminocarbonylmethyl)amino)ethyl]pyrrolidine-3-carboxylic acid;

trans,trans-2-(4-Methoxyphenyl)-4-(1,3-benzodioxol-5-yl)-1-[2-(N-propyl-N-(4-methoxyphenoxycarbonyl)amino)ethyl]pyrrolidine-3-carboxylic acid;

trans,trans-2-(4-Methoxyphenyl)-4-(1,3-benzodioxol-5-yl)-1-[2-(N-propyl-N-(4-methoxybenzoyl)amino)ethyl]pyrrolidine-3-carboxylic acid;

trans,trans-2-(4-Methoxyphenyl)-4-(1,3-benzodioxol-5-yl)-1-[2-(N-propyl-N-benzoylamino)ethyl]pyrrolidine-3-carboxylic acid;

trans,trans-2-(4-Methoxyphenyl)-4-(1,3-benzodioxol-5-yl)-1-[2-(N-propyl-N-benzyloxycarbonylamino)ethyl]pyrrolidine-3-carboxylic acid;

trans,trans-2-(4-Methoxyphenyl)-4-(1,3-benzodioxol-5-yl)-1-[2-(N-propyl-N-(4-methoxybenzyloxycarbonyl)amino)ethyl]pyrrolidine-3-carboxylic acid;

trans,trans-2-(4-Methoxyphenyl)-4-(1,3-benzodioxol-5-yl)-1-[2-(N-butyl-N-ethoxycarbonylamino)ethyl]pyrrolidine-3-carboxylic acid;

trans,trans-2-(4-Methoxyphenyl)-4-(1,3-benzodioxol-5-yl)-1-[2-(N-butyl-N-propoxycarbonylamino)ethyl]pyrrolidine-3-carboxylic acid;)

trans,trans-2-(4-Methoxyphenyl)-4-(1,3-benzodioxol-5-yl)-1-[2-(N-propyl-N-propoxycarbonylamino)ethyl]pyrrolidine-3-carboxylic acid;

trans,trans-1-(N,N-Di(n-butyl)aminocarbonyl)methyl-2,4-di(1,3-benzodioxol-5-yl)pyrrolidine-3-carboxylic acid;

trans,trans-1-(2-(N-(n-Butyl)-N-propylsulfonylamino)ethyl)-2-(4-methoxyphenyl)-4-(1,4-benzodioxan-6-yl)pyrrolidine-3-carboxylic acid;

trans,trans-1-(N,N-Di(n-butyl)aminocarbonylmethyl)-2-(4-methoxyphenyl)-4-(1,3-benzodioxol-5-yl)pyrrolidine-3-carboxylic acid;

trans,trans-1-(2-(N-Propyl-N-propylsulfonylamino)ethyl)-2-(4-methoxyphenyl)-4-(1,3-benzodioxol-5-yl)pyrrolidine-3-carboxylic acid;

trans,trans-1-(2-(N-Butyl-N-butylsulfonylamino)ethyl)-2-(4-methoxyphenyl)-4-(1,3-benzodioxol-5-yl)pyrrolidine-3-carboxylic acid;

trans,trans-1-(2-(N,N-Dibutylaminocarbonylmethyl)-2-(4-methoxymethoxyphenyl)-4-(1,3-benzodioxol-5-yl)pyrrolidine-3-carboxylic acid;

trans,trans-1-(2-(N,N-Dibutylaminocarbonylmethyl)-2-(4-hydroxyphenyl)-4-(1,3-benzodioxol-5-yl)pyrrolidine-3-carboxylic acid hydrochloride salt;

trans,trans-1-(2-(N-Isobutyl-N-propylsulfonylamino)ethyl)-2-(4-methoxyphenyl)-4-(1,3-benzodioxol-5-yl)pyrrolidine-3-carboxylic acid:

trans,trans-1-(2-(N-Benzenesulfonyl-N-propylamino)ethyl)-2-(4-methoxyphenyl)-4-(1,3-benzodioxol-5-yl)pyrrolidine-3-carboxylic acid:

trans,trans-1-(2-(N-(4-Methoxybenzenesulfonyl)-N-propylamino)ethyl)-2-(4-methoxyphenyl)-4-(1,3-benzodioxol-5-yl)pyrrolidine-3-carboxylic acid;

trans,trans-1-(N,N-Di(n-butyl)aminocarbonylmethyl)-2-(2-methoxyethoxy-4-methoxyphenyl)-4-(1,3-benzodioxol-5-yl)pyrrolidine-3-carboxylic acid;

trans,trans-1-(2-(N-Propyl-N-(2,4-dimethylbenzenesulfonyl) amino)ethyl)-2-(4-methoxyphenyl)-4-(1,3-benzodioxol-5-yl)pyrrolidine-3-carboxylic acid;

trans,trans-1-(2-(N-Propyl-N-(3-chloropropylsulfonyl)amino)ethyl)-2-(4-methoxyphenyl)-4-(1,3-benzodioxol-5-yl)pyrrolidine-3-carboxylic acid;

trans,trans-1-(2-(N-Propyl-N-(2-methoxyethylsulfonyl)amino)ethyl)-2-(4-methoxyphenyl)-4-(1,3-benzodioxol-5-yl)pyrrolidine-3-carboxylic acid:

trans,trans-1-(2-(N-Propyl-N-(2-ethoxyethylsulfonyl)amino)ethyl)-2-(4-methoxyphenyl)-4-(1,3-benzodioxol-5-yl)pyrrolidine-3-carboxylic acid:

trans,trans-1-(2-(N-Propyl-N-(5-dimethylamino-1-naphthylsulfonyl)amino)ethyl)-2-(4-methoxyphenyl)-4-(1,3-benzodioxol-5-yl)pyrrolidine-3-carboxylic acid;

trans,trans-1-(2-(N-Propyl-N-(ethylsulfonyl)amino)ethyl)-2-(4-methoxyphenyl)-4-(1,3-benzodioxol-5-yl)pyrrolidine-3-carboxylic acid;

trans,trans-1-(2-(N-Propyl-N-(4-methylbenzenesulfonyl)amino)ethyl)-2-(4-methoxyphenyl)-4-(1,3-benzodioxol-5-yl)pyrrolidine-3-carboxylic acid;

trans,trans-1-(N,N-Di(n-butyl)aminocarbonylmethyl)-2-(3-pyridyl)-4-(1,3-benzodioxol-5-yl)pyrrolidine-3-carboxylic acid;

trans,trans-1-(2-(N-Propyl-N-(n-butylsulfonyl)amino)ethyl)-2-(4-methoxyphenyl)-4-(1,3-benzodioxol-5-yl)pyrrolidine-3-carboxylic acid;

trans,trans-1-(2-(N-Propyl-N-(4-chlorobenzenesulfonyl)amino)ethyl)-2-(4-methoxyphenyl)-4-(1,3-benzodioxol-5-yl)pyrrolidine-3-carboxylic acid;

trans,trans-1-(2-(N-Propyl-N-(benzylsulfonyl)amino)ethyl)-2-(4-methoxyphenyl)-4-(1,3-benzodioxol-5-yl)pyrrolidine-3-carboxylic acid:

trans,trans-1-(2-(N-Propyl-N-(4-fluorobenzenesulfonyl)amino)ethyl)-2-(4-methoxyphenyl)-4-(1,3-benzodioxol-5-yl)pyrrolidine-3-carboxylic acid;

trans,trans-1-(N-Methyl-N-propylaminocarbonylmethyl)-2-(4-methoxyphenyl)-4-(4-benzofuranyl)pyrrolidine-3-carboxylic acid;

trans,trans-1-(N-Methyl-N-propylaminocarbonylmethyl)-2-(4-methoxyphenyl)-4-(6-benzofuranyl)pyrrolidine-3-carboxylic acid;

trans,trans-1-(N-Methyl-N-propylaminocarbonylmethyl)-2-(4-methoxyphenyl)-4-(6-benzo-2,3-dihydrofuranyl)pyrrolidine-3-carboxylic acid;

trans,trans-1-(N,N-Dibutylaminocarbonylmethyl)-2-(4-methoxyphenyl)-4-(4-benzofuranyl)pyrrolidine-3-carboxylic acid;

trans,trans-1-(N,N-Dibutylaminocarbonylmethyl)-2-(4-methoxyphenyl)-4-(4-benzofuranyl)pyrrolidine-3-carboxylic acid;

trans,trans-1-(N,N-Dibutylaminocarbonylmethyl)-2-(4-methoxyphenyl)-4-(6-benzofuranyl)pyrrolidine-3-carboxylic acid;

trans,trans-1-(N,N-Dibutylaminocarbonylmethyl)-2-(4-methoxyphenyl)-4-(6-benzo-2,3-dihydrofuranyl)pyrrolidine-3-carboxylic acid;

trans,trans-1-(N-Methyl-N-propylaminocarbonylmethyl)-2-(4-methoxyphenyl)-4-(5-indanyl)pyrrolidine-3-carboxylic acid;

trans,trans-1-(N-Methyl-N-propylaminocarbonylmethyl)-2-(4-methoxyphenyl)-4-(6-indolyl)pyrrolidine-3-carboxylic acid;

trans,trans-1-(N-Methyl-N-propylaminocarbonylmethyl)-2-(4-methoxyphenyl)-4-(3,4-difluorophenyl)pyrrolidine-3-carboxylic acid;

trans,trans-1-(N-Methyl-N-propylaminocarbonylmethyl)-2-(4-methoxyphenyl)-4-(phenyl)pyrrolidine-3-carboxylic acid;

trans,trans-1-(N-Methyl-N-propylaminocarbonylmethyl)-2-(4-methoxyphenyl)-4-(4-hydroxyphenyl)pyrrolidine-3-carboxylic acid;

trans,trans-1-(N-Methyl-N-propylaminocarbonylmethyl)-2-(4-methoxyphenyl)-4-(2,4-dimethoxyphenyl)pyrrolidine-3-carboxylic acid;

trans,trans-1-(N,N-Dibutylaminocarbonylmethyl-2-(4-methoxyphenyl)-4-(5-benzo-2,3-dihydrofuranyl)pyrrolidine-3-carboxylic acid;

trans,trans-1-(N,N-Dibutylaminocarbonylmethyl)-2-(4-methoxyphenyl)-4-(4-methoxyphenyl)pyrrolidine-3-carboxylic acid;

trans,trans-1-(N,N-Dibutylaminocarbonylmethyl)-2-(4-methoxyphenyl)-4-(3,4-difluorophenyl)pyrrolidine-3-carboxylic acid;

trans,trans-1-(N,N-Dibutylaminocarbonylmethyl)-2-(4-methoxyphenyl)-4-(2,4-dimethoxyphenyl)pyrrolidine-3-carboxylic acid;

trans,trans-1-(N,N-Dibutylaminocarbonylmethyl)-2-phenyl-4-(1,3-benzodioxol-5-yl)pyrrolidine-3-carboxylic acid;

trans,trans-1-(N,N-Dibutylaminocarbonylmethyl)-2-phenyl-4-(5-benzo-2,3-dihydrofuranyl)pyrrolidine-3-carboxylic acid;

trans,trans-1-(N,N-Dibutylaminocarbonylmethyl)-2-(4-t-butylphenyl)-4-(5-benzo-2,3-dihydrofuranyl)pyrrolidine-3-carboxylic acid;

trans,trans-2-(N,N-Dibutylaminocarbonylmethyl)-2-(4-methoxyphenyl)-4-(4-fluorophenyl)pyrrolidine-3-carboxylic acid;

trans,trans-1-(N,N-Dibutylaminocarbonylmethyl)-2-(3-furyl)-4-(1,3-benzodioxol-5-yl)pyrrolidine-3-carboxylic acid;

trans,trans-1-(N,N-Dibutylaminocarbonylmethyl)-2-(isopropyl)-4-(1,3-benzodioxol-5-yl)pyrrolidine-3-carboxylic acid;

trans,trans-1-(N,N-Dibutylaminocarbonylmethyl)-2-(4-t-butylphenyl)-4-(1,3-benzodioxol-5-yl)pyrrolidine-3-carboxylic acid;

trans,trans-1-(N,N-Dibutylaminocarbonylmethyl)-2-(4-t-butylphenyl)-4-(5-benzo-2,3-dihydrofuranyl)pyrrolidine-3-carboxylic acid;

trans,trans-1-(N,N-Dibutylaminocarbonylmethyl)-2-(anti-4-methoxycyclohexyl)-4-(1,3-benzodioxol-5-yl)pyrrolidine-3-carboxylic acid;

trans,trans-1-(N,N-Dibutylaminocarbonylmethyl)-2-(syn-4-methoxycyclohexyl)-4-(1,3-benzodioxol-5-yl)pyrrolidine-3-carboxylic acid;

trans,trans-1-(N,N-Dibutylaminocarbonylmethyl)-2,4-di(5-benzo-2,3-dihydrofuranyl)pyrrolidine-3-carboxylic acid;

trans,trans-1-(N,N-Dibutylaminocarbonylmethyl)-2-(3-furyl)-4-(5-benzo-2,3-dihydrofuranyl)pyrrolidine-3-carboxylic acid;

trans,trans-1-(N,N-Dibutylaminocarbonylmethyl)-2-(4-methoxyphenyl)-4-(3-fluorophenyl)pyrrolidine-3-carboxylic acid;

trans,trans-1-(N,N-Dibutylaminocarbonylmethyl)-2-(4-methoxyphenyl)-4-(3-pyridyl)pyrrolidine-3-carboxylic acid;

trans,trans-1-(N,N-Dibutylaminocarbonylmethyl)-2-(2-fluorophenyl)-4-(1,3-benzodioxol-5-yl)pyrrolidine-3-carboxylic acid;

trans,trans-1-(N,N-Dibutylaminocarbonylmethyl)-2-(3-fluorophenyl)-4-(1,3-benzodioxol-5-yl)pyrrolidine-3-carboxylic acid;

trans,trans-1-(4-N,N-Dibutylaminophenyl)-2-(4-methoxyphenyl)-4-(1,3-benzodioxol-5-yl)pyrrolidine-3-carboxylic acid;

trans,trans-1-(2-N,N-Dibutylaminopyrimidin-4-yl)-2-(4-methoxyphenyl)-4-(1,3-benzodioxol-5-yl)pyrrolidine-3-carboxylic acid;

trans,trans-3-(4-Methoxyphenyl)-5-(1,3-benzodioxol-5-yl)-1-(propylaminocarbonylmethyl)-piperidine-4-carboxylic acid;

trans,trans-3-(4-Methoxyphenyl)-5-(1,3-benzodioxol-5-yl)-1-(aminocarbonylmethyl)-piperidine-4-carboxylic acid;

trans,trans-3-(4-Methoxyphenyl)-5-(1,3-benzodioxol-5-yl)-1-(4-fluorobenzyl)-piperidine-4-carboxylic acid;

trans,trans-3-(4-Methoxyphenyl)-5-(1,3-benzodioxol-5-yl)-1-(2-ethoxyethyl)-piperidine-4-carboxylic acid;

trans,trans-3-(4-Methoxyphenyl)-5-(1,3-benzodioxol-5-yl)-1-(2-propoxyethyl)-piperidine-4-carboxylic acid;

trans,trans-3-(4-Methoxyphenyl)-5-(1,3-benzodioxol-5-yl)-1-[2-(2-methoxyethoxy)ethyl]-piperidine-4-carboxylic acid;

trans,trans-3-(4-Methoxyphenyl)-5-(1,3-benzodioxol-5-yl)-1-[2-(2-pyridyl)ethyl]-piperidine-4-carboxylic acid;

trans,trans-3-(4-Methoxyphenyl)-5-(1,3-benzodioxol-5-yl)-1-(morpholin-4-ylcarbonyl)-piperidine-4-carboxylic acid;

trans,trans-3-(4-Methoxyphenyl)-5-(1,3-benzodioxole-5-yl)-1-(butylaminocarbonyl)-piperidine-4-carboxylic acid;

trans,trans-3-(4-Methoxyphenyl)-5-(1,3-benzodioxol-5-yl)-1-(4-methoxyphenylaminocarbonyl)-3-piperidine-4-carboxylic acid;

trans,trans-3-(4-Methoxyphenyl)-5-(1,3-benzodioxol-5-yl)-1-acetylpiperidine-3-carboxylic acid;

trans,trans-3-(4-Methoxyphenyl)-5-(1,3-benzodioxol-5-yl)-1-(2-furoyl)-piperidine-3-carboxylic acid;

trans,trans-3-(4-Methoxyphenyl)-5-(1,3-benzodioxol-5-yl)-1-(phenylaminocarbonyl)-piperidine-4-carboxylic acid;

trans,trans-3-(4-Methoxyphenyl)-5-(1,3-benzodioxol-5-yl)-1-(allylaminocarbonylmethyl)-piperidine-4-carboxylic acid;

trans,trans-3-(4-Methoxyphenyl)-5-(1,3-benzodioxol-5-yl)-1-(n-butylaminocarbonylmethyl)-piperidine-4-carboxylic acid;

trans,trans-3-(4-Methoxyphenyl)-5-(1,3-benzodioxol-5-yl)-1-(N-n-butyl-N-methylaminocarbonylmethyl)-piperidine-4-carboxylic acid;

trans,trans-3-(4-Methoxyphenyl)-5-(1,3-benzodioxol-5-yl)-1-(pyrrolidin-1-ylcarbonylmethyl)-piperidine-4-carboxylic acid;

trans,trans-3-(4-Methoxyphenyl)-5-(1,3-benzodioxol-5-yl)-1-(isobutylaminocarbonylmethyl)-piperidine-4-carboxylic acid;

trans,trans-3-(4-Methoxyphenyl)-5-(1,3-benzodioxol-5-yl)-1-(cyclopentylaminocarbonylmethyl)-piperidine-4-carboxylic acid;

trans,trans-3-(4-Methoxyphenyl)-5-(1,3-benzodioxol-5-yl)-1-(morpholin-4-ylaminocarbonylmethyl)-piperidine-4-carboxylic acid;

trans,trans-3-(4-Methoxyphenyl)-5-(1,3-benzodioxol-5-yl)-1-(2-phenoxyethyl)-piperidine-4-carboxylic acid;

trans,trans-3-(4-Methoxyphenyl)-5-(1,3-benzodioxol-5-yl)-1-(2-methoxyethylaminocarbonylmethyl)-piperidine-4-carboxylic acid;

trans,trans-2-(4-Methoxyphenyl)-4-(1,3-benzodioxol-5-yl)-1-(isopropylaminocarbonylmethyl)-pyrrolidine-3-carboxylic acid;

trans,trans-2-(4-Methoxyphenyl)-4-(1,3-benzodioxol-5-yl)-1-(ethylaminocarbonylmethyl)-pyrrolidine-3-carboxylic acid;

trans,trans-2-(4-Methoxyphenyl)-4-(1,3-benzodioxol-5-yl)-1-(1-methylpropylaminocarbonylmethyl)-pyrrolidine-3-carboxylic acid;

trans,trans-2-(4-Methoxyphenyl)-4-(1,3-benzodioxol-5-yl)-1-(phenylaminocarbonylmethyl)-pyrrolidine-3-carboxylic acid;

trans,trans-2-(4-Methoxyphenyl)-4-(1,3-benzodioxol-5-yl)-1-(piperidinylcarbonylmethyl)-pyrrolidine-3-carboxylic acid;

trans,trans-2-(4-Methoxyphenyl)-4-(1,3-benzodioxol-5-yl)-1-(1-(propylaminocarbonyl)ethyl)-pyrrolidine-3-carboxylic acid;

trans,trans-2-(4-Methoxyphenyl)-4-(1,3-benzodioxol-5-yl)-1-(α-(propylaminocarbonyl)benzyl)-pyrrolidine-3-carboxylic acid;

trans,trans-2-(4-Methoxyphenyl)-4-(1,3-benzodioxol-5-yl)-1-(bis-(propylaminocarbonyl)methyl)-pyrrolidine-3-carboxylic acid;

trans,trans-2-(4-Methoxyphenyl)-4-(1,3-benzodioxol-5-yl)-1-(2-(propylaminocarbonyl)ethyl)-pyrrolidine-3-carboxylic acid;

trans,trans-2-(4-Methoxyphenyl)-4-(1,3-benzodioxol-5-yl)-1-(propylaminosulfonylmethyl)-pyrrolidine-3-carboxylic acid;

trans,trans-2-(4-Methoxyphenyl)-4-(1,3-benzodioxol-5-yl)-1-(2-phenethyl)-pyrrolidine-3-carboxylic acid;

trans,trans-2-(4-Methoxyphenyl)-4-(1,3-benzodioxol-5-yl)-1-(pentanoylmethyl)-pyrrolidine-3-carboxylic acid;

trans,trans-2-(4-Methoxyphenyl)-4-(1,3-benzodioxol-5-yl)-1-(benzoylmethyl)-pyrrolidine-3-carboxylic acid;

trans,trans-2-(4-Methoxyphenyl)-4-(1,3-benzodioxol-5-yl)-1-(hexyl)-pyrrolidine-3-carboxylic acid;

trans,trans-2-(4-Methoxyphenyl)-4-(1,3-benzodioxol-5-yl)-1-(2-hexynyl)-pyrrolidine-3-carboxylic acid;

trans,trans-2-(4-Methoxyphenyl)-4-(1,3-benzodioxol-5-yl)-1-(propoxymethylcarbonyl-pyrrolidine-3-carboxylic acid;

trans,trans-2-(4-Methoxyphenyl)-4-(1,3-benzodioxol-5-yl)-1-(phenacyl)-pyrrolidine-3-carboxylic acid;

trans,trans-2-(4-Methoxyphenyl)-4-(1,3-benzodioxol-5-yl)-1-(anilinylcarbonyl)-pyrrolidine-3-carboxylic acid;

trans,trans-2-(4-Methoxyphenyl)-4-(1,3-benzodioxol-5-yl)-1-(2-acetylaminoethyl)-pyrrolidine-3-carboxylic acid;

trans,trans-2-(4-Methoxyphenyl)-4-(1,3-benzodioxol-5-yl)-1-(2-phenoxyethyl)-pyrrolidine-3-carboxylic acid;

trans,trans-2-(4-Methoxyphenyl)-4-(1,3-benzodioxol-5-yl)-1-(2-benzodioxanylmethyl)-pyrrolidine-3-carboxylic acid;

trans,trans-2-(4-Methoxyphenyl)-4-(1,3-benzodioxol-5-yl)-1-(2-tetrahydrofuranylmethyl)-pyrrolidine-3-carboxylic acid;

trans,trans-2-(4-Methoxyphenyl)-4-(1,3-benzodioxol-5-yl)-1-(2-(propylaminocarbonylamino)ethenyl)-pyrrolidine-3-carboxylic acid;

trans,trans-2-(4-Methoxyphenyl)-4-(1,3-benzodioxol-5-yl)-1-(2-(propylaminocarbonylamino)ethyl)-pyrrolidine-3-carboxylic acid;

trans,trans-2-(4-Methoxyphenyl)-4-(1,3-benzodioxol-5-yl)-1-(3-oxohex-1-enyl)-pyrrolidine-3-carboxylic acid;

trans,trans-2-(2,4-Dimethoxyphenyl)-4-(1,3-benzodioxol-5-yl)-1-(propylaminocarbonylmethyl)-pyrrolidine-3-carboxylic acid;

trans,trans-2-(2-Carboxy-4-methoxyphenyl)-4-(1,3-benzodioxol-5-yl)-1-(propylaminocarbonylmethyl)-pyrrolidine-3-carboxylic acid;

trans,trans-2-(2-Carboxamido-4-methoxyphenyl)-4-(1,3-benzodioxol-5-yl)-1-(propylaminocarbonylmethyl)-pyrrolidine-3-carboxylic acid;

trans,trans-2-(2-Methanesulfonamido-4-methoxyphenyl)-4-(1,3-benzodioxol-5-yl)-1-(propylaminocarbonylmethyl)-pyrrolidine-3-carboxylic acid;

trans,trans-2-(2-Carbamoylmethoxy-4-methoxyphenyl)-4-(1,3-benzodioxol-5-yl)-1-(propylaminocarbonylmethyl)-pyrrolidine-3-carboxylic acid;

trans,trans-2-(2-Methoxyethoxy-4-methoxyphenyl)-4-(1,3-benzodioxol-5-yl)-1-(propylaminocarbonylmethyl)-pyrrolidine-3-carboxylic acid;

trans,trans-2-(2-Carboxymethoxy-4-methoxyphenyl)-4-(1,3-benzodioxol-5-yl)-1-(propylaminocarbonylmethyl)-pyrrolidine-3-carboxylic acid;

trans,trans-2-(4-Methoxy-2-tetrazolylmethoxyphenyl)-4-(1,3-benzodioxol-5-yl)-1-(propylaminocarbonylmethyl)-pyrrolidine-3-carboxylic acid;

trans,trans-2-(2-Allyloxy-4-methoxyphenyl)-4-(1,3-benzodioxol-5-yl)-1-(propylaminocarbonylmethyl)-pyrrolidine-3-carboxylic acid;

trans,trans 2,4-Bis(4-methoxyphenyl)-1-(propylaminocarbonylmethyl)-pyrrolidine-3-carboxylic acid;

trans,trans 2,4-Bis(1,3-benzodioxol-5-yl)-1-(propylaminocarbonylmethyl)-pyrrolidine-3-carboxylic acid;

trans,trans-2-(4-Methoxyphenyl)-4-(1,3-benzodioxol-5-yl)-1-(N-methyl-N-propylaminocarbonylmethyl)-pyrrolidine-3-carboxylic acid;

trans,trans-2-(4-Methoxyphenyl)-4-(1,3-benzodioxole-5-yl)-1-(N-methyl-N-butylaminocarbonyl)-pyrrolidine-3-carboxylic acid;

trans,trans-2-(4-Methoxyphenyl)-4-(1,3-benzodioxol-5-yl)-1-(N-methyl-N-(4-methoxyphenyl)aminocarbonyl)-3-pyrrolidine-3-carboxylic acid;

trans,trans-2-(4-Methoxyphenyl)-4-(1,3-benzodioxol-5-yl)-1-(N-methyl-N-phenylaminocarbonyl)-pyrrolidine-3-carboxylic acid;

trans,trans-2-(4-Methoxyphenyl)-4-(1,3-benzodioxol-5-yl)-1-(N-methyl-N-allylaminocarbonylmethyl)-pyrrolidine-3-carboxylic acid;

trans,trans-2-(4-Methoxyphenyl)-4-(1,3-benzodioxol-5-yl)-1-(N-methyl-N-isobutylaminocarbonylmethyl)-pyrrolidine-3-carboxylic acid;

trans,trans-2-(4-Methoxyphenyl)-4-(1,3-benzodioxol-5-yl)-1-(N-methyl-N-cyclopentylaminocarbonylmethyl)-pyrrolidine-3-carboxylic acid;

trans,trans-2-(4-Methoxyphenyl)-4-(1,3-benzodioxol-5-yl)-1-(N-methyl-N-methoxyethylaminocarbonyl)-pyrrolidine-3-carboxylic acid;

trans,trans-2-(4-Methoxyphenyl)-4-(1,3-benzodioxol-5-yl)-1-(N-methyl-N-butoxyethylaminocarbonyl)-pyrrolidine-3-carboxylic acid;

trans,trans-2-(1,3-Benzodioxol-5-yl)-4-(4-methoxyphenyl)-1-(N-methyl-N-propylaminocarbonylmethyl)-pyrrolidine-3-carboxylic acid;

trans,trans-2-(4-Methoxyphenyl)-4-(1,4-benzodioxan-6-yl)-1-(N-methyl-N-propylaminocarbonylmethyl)-pyrrolidine-3-carboxylic acid;

trans,trans-2-(4-Methoxyphenyl)-4-(1,3-benzodioxol-5-yl)-1-(N-methyl-N-isopropylaminocarbonylmethyl)-pyrrolidine-3-carboxylic acid;

trans,trans-2-(4-Methoxyphenyl)-4-(1,3-benzodioxol-5-yl)-1-(N-methyl-N-ethylaminocarbonylmethyl)-pyrrolidine-3-carboxylic acid;

trans,trans-2-(4-Methoxyphenyl)-4-(1,3-benzodioxol-5-yl)-1-(N-methyl-N-(1-methylpropyl)aminocarbonylmethyl)-pyrrolidine-3-carboxylic acid;

trans,trans-2-(4-Methoxyphenyl)-4-(1,3-benzodioxol-5-yl)-1-(N-methyl-N-phenylaminocarbonylmethyl)-pyrrolidine-3-carboxylic acid;

trans,trans-2-(4-Methoxyphenyl)-4-(1,3-benzodioxol-5-yl)-1-(1-(N-methyl-N-propylaminocarbonyl)ethyl)-pyrrolidine-3-carboxylic acid;

trans,trans-2-(4-Methoxyphenyl)-4-(1,3-benzodioxol-5-yl)-1-(α-(N-methyl-N-propylaminocarbonyl)benzyl)-pyrrolidine-3-carboxylic acid;

trans,trans-2-(4-Methoxyphenyl)-4-(1,3-benzodioxol-5-yl)-1-(N-ethyl-N-propylaminocarbonylmethyl)-pyrrolidine-3-carboxylic acid;

trans,trans-2-(4-Methoxyphenyl)-4-(1,3-benzodioxole-5-yl)-1-(N-ethyl-N-butylaminocarbonyl)-pyrrolidine-3-carboxylic acid;

trans,trans-2-(4-Methoxyphenyl)-4-(1,3-benzodioxol-5-yl)-1-(N-ethyl-N-(4-methoxyphenyl)aminocarbonyl)-3-pyrrolidine-3-carboxylic acid;

trans,trans-2-(4-Methoxyphenyl)-4-(1,3-benzodioxol-5-yl)-1-(N-ethyl-N-phenylaminocarbonyl)-pyrrolidine-3-carboxylic acid;

trans,trans-2-(4-Methoxyphenyl)-4-(1,3-benzodioxol-5-yl)-1-(N-ethyl-N-allylaminocarbonylmethyl)-pyrrolidine-3-carboxylic acid;

trans,trans-2-(4-Methoxyphenyl)-4-(1,3-benzodioxol-5-yl)-1-(N-ethyl-N-(n-butyl)aminocarbonylmethyl)-pyrrolidine-3-carboxylic acid;

trans,trans-2-(4-Methoxyphenyl)-4-(1,3-benzodioxol-5-yl)-1-(N-ethyl-N-isobutylaminocarbonylmethyl)-pyrrolidine-3-carboxylic acid;

trans,trans-2-(4-Methoxyphenyl)-4-(1,3-benzodioxol-5-yl)-1-(N-ethyl-N-cyclopentylaminocarbonylmethyl)-pyrrolidine-3-carboxylic acid;

trans,trans-2-(4-Methoxyphenyl)-4-(1,3-benzodioxol-5-yl)-1-(N-ethyl-N-methoxyethylaminocarbonylmethyl)-pyrrolidine-3-carboxylic acid;

trans,trans-2-(4-Methoxyphenyl)-4-(1,3-benzodioxol-5-yl)-1-(N-ethyl-N-butoxyethylaminocarbonyl)-pyrrolidine-3-carboxylic acid;

trans,trans-2-(1,3-Benzodioxol-5-yl)-4-(4-methoxyphenyl)-1-(N-ethyl-N-propylaminocarbonylmethyl)-pyrrolidine-3-carboxylic acid;

trans,trans-2-(4-Methoxyphenyl)-4-(1,4-benzodioxan-6-yl)-1-(N-ethyl-N-propylaminocarbonylmethyl)-pyrrolidine-3-carboxylic acid;

trans,trans-2-(4-Methoxyphenyl)-4-(1,3-benzodioxol-5-yl)-1-(N-ethyl-N-isopropylaminocarbonylmethyl)-pyrrolidine-3-carboxylic acid;

trans,trans-2-(4-Methoxyphenyl)-4-(1,3-benzodioxol-5-yl)-1-(N,N-diethylaminocarbonylmethyl)-pyrrolidine-3-carboxylic acid;

trans,trans-2-(4-Methoxyphenyl)-4-(1,3-benzodioxol-5-yl)-1-(N-ethyl-N-(1-methylpropyl)aminocarbonylmethyl)-pyrrolidine-3-carboxylic acid;

trans,trans-2-(4-Methoxyphenyl)-4-(1,3-benzodioxol-5-yl)-1-(N-ethyl-N-phenylaminocarbonylmethyl)-pyrrolidine-3-carboxylic acid;

trans,trans-2-(4-Methoxyphenyl)-4-(1,3-benzodioxol-5-yl)-1-(1-(N-ethyl-N-propylaminocarbonyl)ethyl)-pyrrolidine-3-carboxylic acid;

trans,trans-2-(4-Methoxyphenyl)-4-(1,3-benzodioxol-5-yl)-1-(α-(N-ethyl-N-propylaminocarbonyl)benzyl)-pyrrolidine-3-carboxylic acid;

trans,trans-2-(4-Methoxyphenyl)-4-(1,3-benzodioxol-5-yl)-1-(N-methyl-N-isobutylaminocarbonylmethyl)-pyrrolidine-3-carboxylic acid;

trans,trans-2-(4-Methoxyphenyl)-4-(1,3-benzodioxol-5-yl)-1-(N-methyl-N-cyclohexylaminocarbonylmethyl)-pyrrolidine-3-carboxylic acid;

trans,trans-2-(4-Methoxyphenyl)-4-(1,3-benzodioxol-5-yl)-1-(N,N-dipropylaminocarbonylmethyl)-pyrrolidine-3-carboxylic acid;

trans,trans-2-(4-Methoxyphenyl)-4-(1,3-benzodioxol-5-yl)-1-(isobutyloxyethyl)-pyrrolidine-3-carboxylic acid;

trans,trans-2-(4-Methoxyphenyl)-4-(1,3-benzodioxol-5-yl)-1-(butylsulfonyl)-pyrrolidine-3-carboxylic acid;

trans,trans-2-(4-Methoxyphenyl)-4-(1,3-benzodioxol-5-yl)-1-(isopropylsulfonylaminoethyl)-pyrrolidine-3-carboxylic acid;

trans,trans-2-(4-Methoxyphenyl)-4-(1,3-benzodioxol-5-yl)-1-(ethoxymethylcarbonylmethyl)-pyrrolidine-3-carboxylic acid;

trans,trans-2-(4-Methoxyphenyl)-4-(1,3-benzodioxol-5-yl)-1-(2-ethylbutyrylmethyl)-pyrrolidine-3-carboxylic acid;

trans,trans-2-(4-Methoxyphenyl)-4-(1,3-benzodioxol-5-yl)-1-(N-methyl-N-(3,4-dimethoxybenzyl)aminocarbonylmethyl)-pyrrolidine-3-carboxylic acid;

trans,trans-2-(4-Methoxyphenyl)-4-(1,3-benzodioxol-5-yl)-1-[(1R)-1-(N-methyl-N-propylaminocarbonyl)butyl]-pyrrolidine-3-carboxylic acid;

trans,trans-2-(4-Methoxyphenyl)-4-(1,3-benzodioxol-5-yl)-1-[(1S)-1-(N-methyl-N-propylaminocarbonyl)butyl]-pyrrolidine-3-carboxylic acid;

trans,trans-2-(4-Methoxyphenyl)-4-(1,3-benzodioxol-5-yl)-1-(3-isopropoxypropyl)-pyrrolidine-3-carboxylic acid;

trans,trans-2-(4-Methoxyphenyl)-4-(1,3-benzodioxol-5-yl)-1-(5-methylhexyl)-pyrrolidine-3-carboxylic acid;

trans,trans-2-(4-Methoxyphenyl)-4-(1,3-benzodioxol-5-yl)-1-(5-methylhexenyl)-pyrrolidine-3-carboxylic acid;

trans,trans-2-(4-Methoxyphenyl)-4-(1,3-benzodioxol-5-yl)-1-(5-methylhexenyl)-pyrrolidine-3-carboxylic acid;

trans,trans-2-(4-Methoxyphenyl)-4-(1,3-benzodioxol-5-yl)-1-(3,5-dimethyl-2-hexenyl)-pyrrolidine-3-carboxylic acid;

trans,trans-2-(4-Methoxyphenyl)-4-(1,3-benzodioxol-5-yl)-1-(2-(N-methyl-N-isobutyrylamino)ethyl)-pyrrolidine-3-carboxylic acid;

trans,trans-2-(4-Methoxyphenyl)-4-(1,3-benzodioxol-5-yl)-1-(N-methyl-N-(2,2-dimethylpropyl)aminocarbonylmethyl)-pyrrolidine-3-carboxylic acid;

trans,trans-2-(4-Methoxyphenyl)-4-(1,3-benzodioxol-5-yl)-1-(N-methyl-N-benzylaminocarbonylmethyl)-pyrrolidine-3-carboxylic acid;

trans,trans-2-(4-Methoxyphenyl)-4-(5-indanyl)-1-(N-methyl-N-propylaminocarbonylmethyl)-pyrrolidine-3-carboxylic acid;

trans,trans-2-(4-Methoxyphenyl)-4-(2,3-dihydrobenzofuran-5-yl)-1-(N-methyl-N-propylaminocarbonylmethyl)-pyrrolidine-3-carboxylic acid;

trans,trans-2-(4-Methoxyphenyl)-4-(1-methylindol-5-yl)-1-(N-methyl-N-propylaminocarbonylmethyl)-pyrrolidine-3-carboxylic acid;

trans,trans-2-(4-Methoxyphenyl)-4-(2-naphthyl)-1-(N-methyl-N-propylaminocarbonylmethyl)-pyrrolidine-3-carboxylic acid;

trans,trans-2-(4-Methoxyphenyl)-4-(1,3-benzodioxol-5-yl)-1-(N-butyl-N-phenylaminocarbonylmethyl)-pyrrolidine-3-carboxylic acid;

trans,trans-2-(4-Methoxyphenyl)-4-(1,2-dimethoxy-4-phenyl)-1-(N-methyl-N-propylaminocarbonylmethyl)-pyrrolidine-3-carboxylic acid; and trans,trans-2-(4-Methoxyphenyl)-4-(1-methoxy-3-phenyl)-1-(N-methyl-N-propylaminocarbonylmethyl)-pyrrolidine-3-carboxylic acid;

or a pharmaceutically acceptable salt thereof.

Preferred compounds of the invention are selected from the group consisting of:

trans,trans-2-(4-Methoxyphenyl)-4-(1,3-benzodioxol-5-yl)-1-(propylaminocarbonylmethyl)-pyrrolidine-3-carboxylic acid;

trans,trans-2-(4-Methoxyphenyl)-4-(1,3-benzodioxol-5-yl)-1-(2-propoxyethyl)-pyrrolidine-3-carboxylic acid;

trans,trans-2-(4-Methoxyphenyl)-4-(1,3-benzodioxol-5-yl)-1-(N-(n-propyl)-N-methylaminocarbonylmethyl)-pyrrolidine-3-carboxylic acid;

trans,trans-2-(4-Methoxyphenyl)-4-(1,3-benzodioxol-5-yl)-1-(isobutylaminocarbonylmethyl)-pyrrolidine-3-carboxylic acid;

trans,trans-2-(4-Methoxyphenyl)-4-(1,3-benzodioxol-5-yl)-1-(cyclopentylaminocarbonylmethyl)-pyrrolidine-3-carboxylic acid;

trans,trans-2-(4-Methoxy-2-methoxymethoxyphenyl)-4-(1,3-benzodioxol-5-yl)-1-(N-methyl-N-butylaminocarbonylmethyl)-pyrrolidine-3-carboxylic acid;

trans,trans-2-(4-Methoxyphenyl)-4-(1,3-benzodioxol-5-yl)-1-(N,N-diisoamylaminocarbonylmethyl)-pyrrolidine-3-carboxylic acid;

trans,trans-2-(4-Methoxyphenyl)-4-(1,3-benzodioxol-5-yl)-1-(N,N-dipentylaminocarbonylmethyl)-pyrrolidine-3-carboxylic acid;

trans,trans-2-(4-Methoxyphenyl)-4-(1,3-benzodioxol-5-yl)-1-(N,N-di(2-methoxyethyl)aminocarbonylmethyl)-pyrrolidine-3-carboxylic acid;

trans,trans-2-(4-Methoxyphenyl)-4-(1,3-benzodioxol-5-yl)-1-(N-cyclopropylmethyl-N-propylaminocarbonylmethyl)-pyrrolidine-3-carboxylic acid;

trans,trans-2-(4-Methoxyphenyl)-4-(1,3-benzodioxol-5-yl)-1-(N,N-diisobutylaminocarbonylmethyl)-pyrrolidine-3-carboxylic acid;

trans,trans-2-(4-Methoxyphenyl)-4-(1,3-benzodioxol-5-yl)-1-(N-methyl-N-(2-propynyl)aminocarbonylmethyl)-pyrrolidine-3-carboxylic acid;

trans,trans-2-(4-Methoxyphenyl)-4-(1,3-benzodioxol-5-yl)-1-(N-methyl-N-(n-hexyl)aminocarbonylmethyl)-pyrrolidine-3-carboxylic acid;

trans,trans-2-(4-Methoxyphenyl)-4-(1,3-benzodioxol-5-yl)-1-(N,N-di(n-butyl)aminocarbonylmethyl)-pyrrolidine-3-carboxylic acid;

trans,trans-2-(4-Methoxyphenyl)-4-(1,3-benzodioxol-5-yl)-1-(N,N-diethylaminocarbonylmethyl)-pyrrolidine-3-carboxylic acid;

trans,trans-2-(4-Methoxyphenyl)-4-(1,3-benzodioxol-5-yl)-1-(N-methyl-N-cyclohexylaminocarbonylmethyl)-pyrrolidine-3-carboxylic acid;

trans,trans-2-(4-Methoxyphenyl)-4-(1,3-benzodioxol-5-yl)-1-(N,N-di(n-propyl)aminocarbonylmethyl)-pyrrolidine-3-carboxylic acid;

trans,trans-2-(4-Methoxyphenyl)-4-(1,3-benzodioxol-5-yl)-1-(N-methyl-N-isobutylaminocarbonylmethyl)-pyrrolidine-3-carboxylic acid;

trans,trans-2-(4-Methoxyphenyl)-4-(1,3-benzodioxol-5-yl)-1-(2-(ethylsulfinyl)ethyl)-pyrrolidine-3-carboxylic acid;

trans,trans-2-(4-Methoxyphenyl)-4-(1,3-benzodioxol-5-yl)-1-(2-(N-methyl-N-isopropylcarbonylamino)ethyl)-pyrrolidine-3-carboxylic acid;

trans,trans-2-(4-Methoxyphenyl)-4-(1,3-benzodioxol-5-yl)-1-(2-(N-methyl-N-propionylamino)ethyl)-pyrrolidine-3-carboxylic acid;

trans,trans-2-(4-Methoxyphenyl)-4-(1,3-benzodioxol-5-yl)-1-(N-methyl-N-benzylaminocarbonylmethyl)-pyrrolidine-3-carboxylic acid;

trans,trans-2-(4-Methoxyphenyl)-4-(1,3-benzodioxol-5-yl)-1-(N-ethyl-N-butylaminocarbonylmethyl)-pyrrolidine-3-carboxylic acid;

trans,trans-2-(4-Methoxyphenyl)-4-(1,3-benzodioxol-5-yl)-1-(2-(N-methyl-N-propylsulfonylamino)ethyl)-pyrrolidine-3-carboxylic acid;

trans,trans-2-(4-Methoxyphenyl)-4-(1,3-benzodioxol-5-yl)-1-(N-(3,4-dimethoxybenzyl)-N-methylaminocarbonylmethyl)pyrrolidine-3-carboxylic acid;

trans,trans-2-(4-Methoxyphenyl)-4-(1,3-benzodioxol-5-yl)-1-(N-(3,4-dimethoxybenzyl)aminocarbonylmethyl)pyrrolidine-3-carboxylic acid;

(2R,3R,4S)-2-(4-Methoxyphenyl)-4-(1,3-benzodioxol-5-yl)-1-((1R)-1-(N,N-dipropylaminocarbonyl)-1-butyl)pyrrolidine-3-carboxylic acid;

(2S,3S,4R)-2-(4-Methoxyphenyl)-4-(1,3-benzodioxol-5-yl)-1-((1R)-1-(N,N-dipropylaminocarbonyl)-1-butyl)pyrrolidine-3-carboxylic acid;

trans,trans-2-(4-Methoxyphenyl)-4-(1,3-benzodioxol-5-yl)-1-(N,N-di(n-butyl)aminocarbonylmethyl)-3-(5-tetrazolyl)pyrrolidine;

trans,trans-2-(4-Fluorophenyl)-4-(1,3-benzodioxol-5-yl)-1-(N,N-di(n-butyl)aminocarbonylmethyl)pyrrolidine-3-carboxylic acid;

trans,trans-2-(4-Methoxyphenyl)-4-(1,3-benzodioxol-5-yl)-1-(N-n-butyl)-N-(n-propyl)aminocarbonylmethyl)pyrrolidine-3-carboxylic acid;

trans,trans-2-(4-Methoxyphenyl)-4-(1,3-benzodioxol-5-yl)-1-[2-(N,N-di(n-propyl)aminocarbonyl)ethyl]pyrrolidine-3-carboxylic acid;

trans,trans-2-(4-Methoxyphenyl)-4-(1,3-benzodioxol-5-yl)-1-(N,N-di(n-butyl)aminocarbonyl)methyl)pyrrolidine-3-(N-methanesulfonyl)carboxamide;

trans,trans-2-(4-Methoxyphenyl)-4-(1,3-benzodioxol-5-yl)-1-(N,N-di(n-butyl)aminocarbonyl)methyl)pyrrolidine-3-(N-benzenesulfonyl)carboxamide;

trans,trans-2-(4-Methoxyphenyl)-4-(1,3-benzodioxol-5-yl)-1-[(N,N-dibutylamino)carbonyl-1-(RS)-ethyl]pyrrolidine-3-carboxylic acid;

trans,trans-2-(Pentyl)-4-(1,3-benzodioxol-5-yl)-1-[(N,N-dibutylamino)carbonylmethyl]pyrrolidine-3-carboxylic acid;

trans,trans-2-(4-Methoxyphenyl)-4-(1,3-benzodioxol-5-yl)-1-[2-(N-propyl-N-butyrylamino)ethyl]pyrrolidine-3-carboxylic acid;

trans,trans-2-(4-Methoxyphenyl)-4-(1,3-benzodioxol-5-yl)-1-[2-(N-propyl-N-(ethylaminocarbonyl)amino)ethyl]pyrrolidine-3-carboxylic acid;

trans,trans-2-(4-Methoxyphenyl)-4-(1,3-benzodioxol-5-yl)-1-[2-(N-butyl-N-butyrylamino)ethyl]pyrrolidine-3-carboxylic acid;

trans,trans-2-(4-Methoxyphenyl)-4-(1,3-benzodioxol-5-yl)-1-[2-(N-propyl-N-ethoxycarbonylamino)ethyl]pyrrolidine-3-carboxylic acid;

trans,trans-2-(4-Methoxyphenyl)-4-(1,3-benzodioxol-5-yl)-1-[2-(N-methyl-N-(2-propylvaleryl)amino)ethyl]pyrrolidine-3-carboxylic acid;

trans,trans-2-(4-Methoxyphenyl)-4-(1,3-benzodioxol-5-yl)-1-[2-(N-propyl-N-(4-methoxyphenoxycarbonyl)amino)ethyl]pyrrolidine-3-carboxylic acid;

trans,trans-2-(4-Methoxyphenyl)-4-(1,3-benzodioxol-5-yl)-1-[2-(N-propyl-N-(4-methoxybenzoyl)amino)ethyl]pyrrolidine-3-carboxylic acid;

trans,trans-2-(4-Methoxyphenyl)-4-(1,3-benzodioxol-5-yl)-1-[2-(N-propyl-N-benzoylamino)ethyl]pyrrolidine-3-carboxylic acid;

trans,trans-2-(4-Methoxyphenyl)-4-(1,3-benzodioxol-5-yl)-1-[2-(N-propyl-N-benzyloxycarbonylamino)ethyl]pyrrolidine-3-carboxylic acid;

trans,trans-2-(4-Methoxyphenyl)-4-(1,3-benzodioxol-5-yl)-1-[2-(N-butyl-N-ethoxycarbonylamino)ethyl]pyrrolidine-3-carboxylic acid;

trans,trans-2-(4-Methoxyphenyl)-4-(1,3-benzodioxol-5-yl)-1-[2-(N-butyl-N-propoxycarbonylamino)ethyl]pyrrolidine-3-carboxylic acid;

trans,trans-2-(4-Methoxyphenyl)-4-(1,3-benzodioxol-5-yl)-1-[2-(N-propyl-N-propoxycarbonylamino)ethyl]pyrrolidine-3-carboxylic acid;

trans,trans-1-(N,N-Di(n-butyl)aminocarbonyl)methyl-2,4-di(1,3-benzodioxol-5-yl)pyrrolidine-3-carboxylic acid;

trans,trans-1-(2-(N-(n-Butyl)-N-propylsulfonylamino)ethyl)-2-(4-methoxyphenyl)-4-(1,3-benzodioxol-5-yl)pyrrolidine-3-carboxylic acid;

trans,trans-1-(N,N-Di(n-butyl)aminocarbonylmethyl)-2-(4-methoxyphenyl)-4-(1,3-benzodioxol-5-yl)pyrrolidine-3-carboxylic acid;

trans,trans-1-(2-(N-Propyl-N-propylsulfonylamino)ethyl)-2-(4-methoxyphenyl)-4-(1,3-benzodioxol-5-yl)pyrrolidine-3-carboxylic acid;

trans,trans-1-(2-(N-Butyl-N-butylsulfonylamino)ethyl)-2-(4-methoxyphenyl)-4-(1,3-benzodioxol-5-yl)pyrrolidine-3-carboxylic acid;

trans,trans-1-(2-(N,N-Dibutylaminocarbonylmethyl)-2-(4-methoxymethoxyphenyl)-4-(1,3-benzodioxol-5-yl)pyrrolidine-3-carboxylic acid;

trans,trans-1-(2-(N,N-Dibutylaminocarbonylmethyl)-2-(4-hydroxyphenyl)-4-(1,3-benzodioxol-5-yl)pyrrolidine-3-carboxylic acid hydrochloride salt;

trans,trans-1-(2-(N-Isobutyl-N-propylsulfonylamino)ethyl)-2-(4-methoxyphenyl)-4-(1,3-benzodioxol-5-yl)pyrrolidine-3-carboxylic acid;

trans,trans-1-(2-(N-Benzenesulfonyl-N-propylamino)ethyl)-2-(4-methoxyphenyl)-4-(1,3-benzodioxol-5-yl)pyrrolidine-3-carboxylic acid;

trans,trans-1-(2-(N-(4-Methoxybenzenesulfonyl)-N-propylamino)ethyl)-2-(4-methoxyphenyl)-4-(1,3-benzodioxol-5-yl)pyrrolidine-3-carboxylic acid;

trans,trans-1-(N,N-Di(n-butyl)aminocarbonylmethyl)-2-(2-methoxyethoxy-4-methoxyphenyl)-4-(1,3-benzodioxol-5-yl)pyrrolidine-3-carboxylic acid;

trans,trans-1-(2-(N-Propyl-N-(2,4-dimethylbenzenesulfonyl) amino)-ethyl)-2-(4-methoxyphenyl)-4-(1,3-benzodioxol-5-yl)pyrrolidine-3-carboxylic acid;

trans,trans-1-(2-(N-Propyl-N-(3-chloropropylsulfonyl)amino)ethyl)-2-(4-methoxyphenyl)-4-(1,3-benzodioxol-5-yl)pyrrolidine-3-carboxylic acid;

trans,trans-1-(2-(N-Propyl-N-(2-methoxyethylsulfonyl) amino)ethyl)-2-(4-methoxyphenyl)-4-(1,3-benzodioxol-5-yl)pyrrolidine-3-carboxylic acid;

trans,trans-1-(2-(N-Propyl-N-(2-ethoxyethylsulfonyl)amino)ethyl)-2-(4-methoxyphenyl)-4-(1,3-benzodioxol-5-yl)pyrrolidine-3-carboxylic acid;

trans,trans-1-(2-(N-Propyl-N-(5-dimethylamino-1-naphthylsulfonyl)amino)ethyl)-2-(4-methoxyphenyl)-4-(1,3-benzodioxol-5-yl)pyrrolidine-3-carboxylic acid;

trans,trans-1-(2-(N-Propyl-N-(ethylsulfonyl)amino)ethyl)-2-(4-methoxyphenyl)-4-(1,3-benzodioxol-5-yl)pyrrolidine-3-carboxylic acid;

trans,trans-1-(2-(N-Propyl-N-(4-methylbenzenesulfonyl) amino)ethyl)-2-(4-methoxyphenyl)-4-(1,3-benzodioxol-5-yl)pyrrolidine-3-carboxylic acid;

trans,trans-1-(N,N-Di(n-butyl)aminocarbonylmethyl)-2-(3-pyridyl)-4-(1,3-benzodioxol-5-yl)pyrrolidine-3-carboxylic acid;

trans,trans-1-(2-(N-Propyl-N-(n-butylsulfonyl)amino)ethyl)-2-(4-methoxyphenyl)-4-(1,3-benzodioxol-5-yl)pyrrolidine-3-carboxylic acid;

trans,trans-1-(2-(N-Propyl-N-(4-chlorobenzenesulfonyl) amino)ethyl)-2-(4-methoxyphenyl)-4-(1,3-benzodioxol-5-yl)pyrrolidine-3-carboxylic acid;

trans,trans-1-(2-(N-Propyl-N-(benzylsulfonyl)amino)ethyl)-2-(4-methoxyphenyl)-4-(1,3-benzodioxol-5-yl)pyrrolidine-3-carboxylic acid;

trans,trans-1-(2-(N-Propyl-N-(4-fluorobenzenesulfonyl) amino)ethyl)-2-(4-methoxyphenyl)-4-(1,3-benzodioxol-5-yl)pyrrolidine-3-carboxylic acid;

trans,trans-1-(N-Methyl-N-propylaminocarbonylmethyl)-2-(4-methoxyphenyl)-4-(6-benzofuranyl)pyrrolidine-3-carboxylic acid;

trans,trans-1-(N,N-Dibutylaminocarbonylmethyl)-2-(4-methoxyphenyl)-4-(4-benzofuranyl)pyrrolidine-3-carboxylic acid;

trans,trans-1-(N,N-Dibutylaminocarbonylmethyl)-2-(4-methoxyphenyl)-4-(4-benzofuranyl)pyrrolidine-3-carboxylic acid;

trans,trans-1-(N,N-Dibutylaminocarbonylmethyl)-2-(4-methoxyphenyl)-4-(6-benzofuranyl)pyrrolidine-3-carboxylic acid;

trans,trans-1-(N,N-Dibutylaminocarbonylmethyl)-2-(4-methoxyphenyl)-4-(6-benzo-2,3-dihydrofuranyl)pyrrolidine-3-carboxylic acid;

trans,trans-1-(N,N-Dibutylaminocarbonylmethyl)-2-(4-methoxyphenyl)-4-(5-benzo-2,3-dihydrofuranyl)pyrrolidine-3-carboxylic acid;

trans,trans-1-(N,N-Dibutylaminocarbonylmethyl)-2-(4-methoxyphenyl)-4-(4-methoxyphenyl)pyrrolidine-3-carboxylic acid;

trans,trans-1-(N,N-Dibutylaminocarbonylmethyl)-2-(4-methoxyphenyl)-4-(3,4-difluorophenyl)pyrrolidine-3-carboxylic acid;

trans,trans-1-(N,N-Dibutylaminocarbonylmethyl)-2-(4-methoxyphenyl)-4-(2,4-dimethoxyphenyl)pyrrolidine-3-carboxylic acid;

trans,trans-1-(N,N-Dibutylaminocarbonylmethyl)-2-phenyl-4-(1,3-benzodioxol-5-yl)pyrrolidine-3-carboxylic acid;

trans,trans-1-(N,N-Dibutylaminocarbonylmethyl)-2-Phenyl-4-(5-benzo-2,3-dihydrofuranyl)pyrrolidine-3-carboxylic acid;

trans,trans-1-(N,N-Dibutylaminocarbonylmethyl)-2-(4-t-butylphenyl)-4-(5-benzo-2,3-dihydrofuranyl)pyrrolidine-3-carboxylic acid;

trans,trans-2-(N,N-Dibutylaminocarbonylmethyl)-2-(4-methoxyphenyl)-4-(4-fluorophenyl)pyrrolidine-3-carboxylic acid;

trans,trans-1 -(N,N-Dibutylaminocarbonylmethyl)-2-(3-furyl)-4-(1,3-benzodioxol-5-yl)pyrrolidine-3-carboxylic acid;

trans,trans-1-(N,N-Dibutylaminocarbonylmethyl)-2-(isopropyl)-4-(1,3-benzodioxol-5-yl)pyrrolidine-3-carboxylic acid;

trans,trans-1-(N,N-Dibutylaminocarbonylmethyl)-2-(4-t-butylphenyl)-4-(1,3-benzodioxol-5-yl)pyrrolidine-3-carboxylic acid;

trans,trans-1-(N,N-Dibutylaminocarbonylmethyl)-2-(4-t-butylphenyl)-4-(5-benzo-2,3-dihydrofuranyl)pyrrolidine-3-carboxylic acid;

trans,trans-1-(N,N-Dibutylaminocarbonylmethyl)-2-(anti-4-methoxycyclohexyl)-4-(1,3-benzodioxol-5-yl)pyrrolidine-3-carboxylic acid;

trans,trans-1-(N,N-Dibutylaminocarbonylmethyl)-2-(syn-4-methoxycyclohexyl)-4-(1,3-benzodioxol-5-yl)pyrrolidine-3-carboxylic acid;

trans,trans-1-(N,N-Dibutylaminocarbonylmethyl)-2,4-di(5-benzo-2,3-dihydrofuranyl)pyrrolidine-3-carboxylic acid;

trans,trans-1-(N,N-Dibutylaminocarbonylmethyl)-2-(3-furyl)-4-(5-benzo-2,3-dihydrofuranyl)pyrrolidine-3-carboxylic acid;

trans,trans-1-(N,N-Dibutylaminocarbonylmethyl)-2-(4-methoxyphenyl)-4-(3-fluorophenyl)pyrrolidine-3-carboxylic acid;

trans,trans-2-(4-Methoxyphenyl)-4-(1,3-benzodioxol-5-yl)-1-(N-butyl-N-phenylaminocarbonylmethyl)-pyrrolidine-3-carboxylic acid;

trans,trans-1-(N,N-Dibutylaminocarbonylmethyl)-2-(2-fluorophenyl)-4-(1,3-benzodioxol-5-yl)pyrrolidine-3-carboxylic acid; and trans,trans-1-(N,N-Dibutylaminocarbonylmethyl)-2-(3-fluorophenyl)-4-(1,3-benzodioxol-5-yl)pyrrolidine-3-carboxylic acid;

or a pharmaceutically acceptable salt thereof.

Particularly preferred is the compound trans,trans-2-(4-methoxyphenyl)-4-(1,3-benzodioxol-5-yl)-1-(N,N-di(n-butyl)aminocarbonylmethyl)-pyrrolidine-3-carboxylic acid; or a pharmaceutically acceptable salt thereof.

Most particularly preferred is the compound (2R,3R,4S)-(+)-2-(4-methoxyphenyl)-4-(1,3-benzodioxol-5-yl)-1-(N,N-di(n-butyl)aminocarbonylmethyl)-pyrrolidine-3-carboxylic acid; or a pharmaceutically acceptable salt thereof.

Methods for preparing the compounds of the invention are shown in Schemes I–XIV.

Scheme I illustrates the general procedure for preparing the compounds of the invention when n and m are 0, Z is —CH$_2$— and W is —CO$_2$H. A β-ketoester 1, where E is loweralkyl or a carboxy protecting group and R$_1$ is aryl or heterocyclic, is reacted with a nitro vinyl compound 2, where R$_2$ is aryl or heterocyclic, in the presence of a base (for example, 1,8-diazabicyclo[5.4.0]undec-7-ene (DBU) or sodium ethoxide or sodium hydride and the like) in an inert solvent such as toluene, benzene, tetrahydrofuran or ethanol and the like. The condensation product 3 is reduced (for example, hydrogenation using a Raney nickel or platinum catalyst). The resulting amine cyclizes to give the dihydro pyrrole 4. Reduction of 4 (for example, sodium cyanoborohydride or catalytic hydrogenation and the like) in a protic solvent such as ethanol or methanol and the like gives the pyrrolidine compound 5 as a mixture of cis-cis, trans,trans and cis,trans products. Chromatographic separation removes the cis-cis isomer leaving a mixture of the trans,trans and cis,trans isomers which is further elaborated. The cis-cis isomer can be epimerized (for example, using sodium ethoxide in ethanol) to give the trans,trans isomer and then carried on as described below. The pyrrolidine nitrogen is (1) acylated or sulfonylated with $R_3$—X ($R_3$ is $R_4$—C(O)— or $R_6$—S(O)$_2$— and X is a leaving group such as a halide (Cl is preferred) or X taken together with $R_4$—C(O)— or $R_6$—S(O)$_2$— forms an activated ester including esters or anhydrides derived from formic acid, acetic acid and the like, alkoxycarbonyl halides, N-hydroxysuccinimide, N-hydroxyphthalimide, N-hydroxybenzotriazole, N-hydroxy-5-norbornene-2,3-dicarboxamide, 2,4,5-trichlorophenol and the like) or (2) alkylated with $R_3$—X where X is a leaving group (for example, X is a halide (for example, Cl, Br or I) or X is a leaving group such as a sulfonate (for example, mesylate, tosylate, triflate and the like)) in the presence of a base such as diisopropyl ethylamine or triethylamine and the like to give the N-derivatized pyrrolidine 6 which is still a mixture of trans,trans and cis,trans isomers. Hydrolysis of the ester 6 (for example, using a base such a sodium hydroxide in EtOH/H$_2$O) selectively hydrolyzes the trans,trans ester to give a mixture of 7 and 8, which are readily separated.

Scheme II illustrates a general procedure for preparing the compounds of the invention when n is 1, m is 0, Z is —CH$_2$— and W is —CO$_2$H. A substituted benzyl chloride 9 is reacted with a lithio dithiane 10 in an inert solvent such as THF or dimethoxyethane to give the alkylated adduct 11. The anion of compound 11 is formed using a base such as n-butyllithium and then reacted with $R_1$—CH$_2$—X' wherein X' is a leaving group such as a halide or sulfonate to give compound 12. The dithiane protecting group is cleaved (for example, using a mercuric salt in water) to give the keto compound 13. Reaction of ketone 13 with benzyl amine and formaldehyde gives the keto piperidine compound 14. Treatment of compound 14 with an activated nitrile such as trimethylsilyl cyanide followed by a dehydrating agent such as phosphorous oxychloride provides the isomeric ene nitriles 15. Reduction of the double bond (for example, using sodium borohydride) affords the piperidinyl nitrile 16. Hydrolysis of the nitrile using hydrochloric acid in the presence of a carboxy protecting reagent (for example, an alkyl alcohol) affords ester 17 (where E is a carboxy protecting group). Debenzylation by catalytic hydrogenation under acidic conditions affords the free piperidine compound 18. Compound 18 is further elaborated by the procedures described in Scheme I for compound 5 to give the final product compound 19.

Scheme III illustrates a general procedure for preparing the compounds of the invention when m and n are 0, Z is —C(O)— and W is —CO$_2$H. β-Keto ester 20 (wherein E is loweralkyl or a carboxy protecting group) is reacted with an α-haloester 21 (where J is lower alkyl or a carboxy protecting group and the halogen is bromine, iodine or chlorine) in the presence of a base such as NaH or potassium tert-butoxide or lithium diisopropylamide in an inert solvent such as THF or dimethoxyethane to give diester 22. Treating compound 22 with $R_3$—NH$_2$ and heating in acetic acid gives the cyclic compound 23. The double bond is reduced (for example, by catalytic hydrogenation using a palladium on carbon catalyst or sodium cyanoborohydride reduction) to give pyrrolidone 24. Epimerization with sodium ethoxide in ethanol to give the desired trans,trans configuration, followed by sodium hydroxide hydrolysis of the ester, affords the desired trans,trans carboxylic acid 25.

Scheme IV illustrates a general procedure for preparing the compounds of the invention when n is 0, m is 1, Z is —CH$_2$— and W is —CO$_2$H. The trans,trans compound 7, prepared in Scheme I, is homologated by the Arndt-Eistert synthesis. The carboxy terminus is activated (for example, by making the acid chloride using thionyl chloride) to give compound 52, where L is a leaving group (in the case of an acid chloride, L is Cl). Compound 52 is treated with diazomethane to give the diazo ketone 53. Rearrangement of compound 53 (for example, using water or an alcohol and silver oxide or silver benzoate and triethylamine, or heating or photolysis in the presence of water or an alcohol) affords the acetic acid compound 54 or an ester which may be hydrolyzed. Compounds where m is from 2 to 6 can be obtained by repetition of the above described process.

A preferred embodiment is shown in Schemes V and VI. A benzoyl acetate 26 is reacted with a nitro vinyl benzodioxolyl compound 27 using 1,8-diazabicyclo[5.4.0]undec-7-ene (DBU) as the base in toluene to give compound 28. Catalytic hydrogenation using Raney nickel leads to reduction of the nitro group to an amine and subsequent cyclization to give the dihydropyrrole 29. The double bond is reduced with sodium cyanoborohydride to give the pyrrolidine compound 30 as a mixture of cis-cis,trans,trans and cis,trans isomers. Chromatography separates out the cis-cis isomer, leaving a mixture of the trans,trans and cis,trans isomers (31).

Scheme VI illustrates the further elaboration of the trans,trans isomer. The mixture (31) of trans,trans and cis,trans pyrrolidines described in Scheme IV is reacted with N-propyl bromoacetamide in acetonitrile in the presence of ethyldiisopropylamine to give the alkylated pyrrolidine compound 32, still as a mixture of trans,trans and cis,trans isomers. Sodium hydroxide in ethanol-water hydrolyzes the ethyl ester of the trans,trans compound but leaves the ethyl ester of the cis,trans compound untouched, thus allowing separation of the trans,trans carboxylic acid 33 from the cis,trans ester 34.

Scheme VII illustrates the preparation of a specific piperidinyl compound. Benzodioxolyl methyl chloride 35 is reacted with lithio dithiane 36 to give the alkylated compound 37. Treatment of compound 37 with 4-methoxybenzyl chloride in the presence of lithium diisopropylamide gives compound 38. Cleavage of the dithiane protecting group using a mercuric salt in aqueous solution gives ketone 39. Treatment of 39 with benzylamine and formaldehyde gives the keto piperidine 40. Treatment of compound 40 with trimethylsilyl cyanide followed by phosphorous oxychloride gives the ene nitrile as a mixture of isomers 41. Sodium borohydride reduction of the double bond gives the piperidinyl nitrile 42. Hydrochloric acid hydrolysis in the presence of ethanol gives ethyl ester 43. The N-benzyl protecting group is removed by catalytic hydrogenation to give the free piperidine compound 44. Compound 44 is further elaborated by the procedures described in Scheme V for compound 31 resulting in the formation of the N-derivatized carboxylic acid 45.

A preferred embodiment of the process shown in Scheme III is shown in Scheme VIII. 4-Methoxybenzoylacetate 46 (wherein E is loweralkyl or a carboxy protecting group) is reacted with an benzodioxolyl α-bromoacetate 47 (wherein E is lower alkyl or a carboxy protecting group) in the presence of NaH in THF to give diester 48. Treating compound 48 with ethoxypropylamine and heating in acetic acid gives the cyclic compound 49. The double bond is reduced by catalytic hydrogenation using a palladium on carbon catalyst to give pyrrolidone 50. Epimerization with sodium ethoxide in ethanol to give the desired trans,trans configuration is followed by sodium hydroxide hydrolysis of the ester to afford the desired trans,trans carboxylic acid 51.

Scheme IX illustrates the preparation of compounds where n is 0, Z is —$CH_2$—, and W is other than carboxylic acid. Compound 55, which can be prepared by the procedures described in Scheme IV, is converted (for example, using peptide coupling condition, e.g. N-methylmorpholine, EDCI and HOBt, in the presence of ammonia or other amide forming reactions) to give carboxamide 56. The carboxamide is dehydrated (for example, using phosphorus oxychloride in pyridine) to give nitrile 57. Nitrile 57 under standard tetrazole forming conditions (sodium azide and triethylamine hydrochloride or trimethylsilylazide and tin oxide) is reacted to give tetrazole 58. Alternatively nitrile 57 is reacted with hydroxylamine hydrochloride in the presence of a base (for example, potassium carbonate, sodium carbonate, sodium hydroxide, triethylamine, sodium methoxide or NaH) in a solvent such as DMF, DMSO, or dimethylacetamide to give amidoxime 59. The amidoxime 59 is allowed to react with a methyl or ethyl chloroformate in a conventional organic solvent (such as, chloroform, methylene chloride, dioxane, THF, acetonitrile or pyridine) in the presence of a base (for example, triethylamine, pyridine, potassium carbonate and sodium carbonate) to give an O-acyl compound. Heating of the O-acyl amidoxime in an inert solvent (such as benzene, toluene, xylene, dioxane, THF, dichloroethane, or chloroform and the like) results in cyclization to compound 60. Alternatively reacting the amidoxime 59 with thionyl chloride in an inert solvent (for example, chloroform, dichloromethane, dixoane and THF and the like) affords the oxathiadiazole 61.

Scheme X illustrates the preparation of compounds in which $R_3$ is an acylmethylene group. A carboxylic acid 62 (where $R_4$ is as previously defined herein) is treated with oxalyl chloride in a solution of methylene chloride containing a catalytic amount of N,N-dimethylformamide to give the acid chloride. Treatment of the acid chloride with excess ethereal diazomethane affords a diazoketone, and then treatment with anhydrous HCl in dioxane gives the α-chloroketone 63. Pyrrolidine ester 5 where E is lower alkyl or a carboxy protecting group, prepared in Scheme I, is alkylated with the α-chloroketone 63 to provide alkylated pyrrolidine 64. Carboxy deprotection (for example, hydrolysis of an alkyl ester using lithium or sodium hydroxide in ethanol-water) gives the alkylated pyrrolidine acid 65.

Scheme XI illustrates the preparation of "reverse amides and sulfonamides". The carboxy protected pyrrolidine 5, prepared in Scheme I, is reacted with a difunctionalized compound X—$R_8$—X where $R_8$ is alkylene and X is a leaving group (for example a halide where Br is preferred) to give N-alkylated compound 66. Treatment of 66 with an amine ($R_{20}NH_2$) affords secondary amine 67. This amine (67) can be reacted with an activated acyl compound (for example, $R_4$—C(O)—Cl) and then carboxy deprotected (for example, hydrolysis of an ester or hydrogenation of a benzyl moiety) to afford amide 68. Alternatively amine 67 can be reacted with an activated sulfonyl compound (for example, $R_6$—$S(O)_2$—Cl) and then carboxy deprotected (for example, hydrolysis of an ester or hydrogenation of a benzyl moiety) to afford sulfonamide 69.

Scheme XII illustrates a method for synthesizing pyrrolidines by an azomethine ylide type [3+2]-cycloaddition to an acrylate. General structures such as compound 70 are known to add to unsaturated esters such as 71 to provide pyrrolidines such as compound 72 (O. Tsuge, S. Kanemasa, K. Matsuda. Chem. Lett. 1131–4 (1983), O. Tsuge, S. Kanemasa, T. Yamada, K. Matsuda, J. Org. Chem. 52 2523–30 (1987), and S. Kanemasa, K. Skamoto, O. Tsuge, Bull. Chem. Soc. Jpn. 62 1960–68 (1989)). A specific example is also shown in Scheme XII. Silylimine 73 is reacted with acrylate 74 in the presence of trimethylsilyl triflate and tetrabutylammonium fluoride to give the desired pyrrolidine 75 as a mixture of isomers. This method can be modified to provide the N-acetamido derivatives directly by reacting 73 and 74 with the appropriate bromoacetamide (for example, dibutyl bromoacetamide) in the presence of tetrabutylammonium iodide and cesium fluoride to give compound 76.

Scheme XIII illustrates a method for producing an enantiomerically pure pyrrolidine 80, which can be further elaborated on the pyrrolidine nitrogen. Intermediate racemic pyrrolidine ester 77 (for example, prepared by the procedure described in Scheme V) is Boc-nitrogen protected (for example, by treatment with $Boc_2O$) and then the ester is hydrolyzed (for example, using sodium or lithium hydroxide in ethanol and water) to give t-butyl carbamoyl pyrrolidine carboxylic acid 78. The carboxylic acid is converted to its (+)-cinchonine salt, which can be recrystallized (for example from ethyl acetate and hexane or chloroform and hexane) to afford the diastereomerically pure salt. This diastereomerically pure salt can be neutralized (for example, with sodium carbonate or citric acid) to afford enantiomerically pure carboxylic acid 79. The pyrrolidine nitrogen can be deprotected (for example, using trifluoroacetic acid) and the ester reformed by the use of ethanolic hydrochloric acid to give salt 80. Alternatively one can use ethanol HCl to cleave the protecting group and form the ester in one step. The pyrrolidine nitrogen can be further elaborated (for example, by treatment with the dibutyl amide of bromoacetamide in acetonitrile in the presence of diisopropylethylamine) to give optically active compound 81. The use of (−)-cinchonine will give the opposite enantiomer.

Scheme XIV describes another procedure for preparation of pyrrolidines. Pyrrolidines may be synthesized by the use of an azomethine ylide cycloaddition to an acrylate derivative as described by Cottrell, I. F., et.al., J. Chem. Soc., Perkin Trans. 1, 5:1091–97 (1991). Thus, the azomethine ylide precursor 82 (where $R_{55}$ is hydrogen or methyl) is condensed with a substituted acrylate 83 (wherein $R_2$ is as described herein and $R_{56}$ is loweralkyl) under acidic conditions to afford the substituted pyrrolidine 84. The N-protecting group can be removed (for example, by hydrogenolysis of an N-benzyl group) to give 85, which can be alkylated under the conditions described above to provide the N-substituted pyrrolidine 86. Standard ester hydrolysis of 86 produces the desired pyrrolidine carboxylic acid 87.

5,622,971
Scheme I
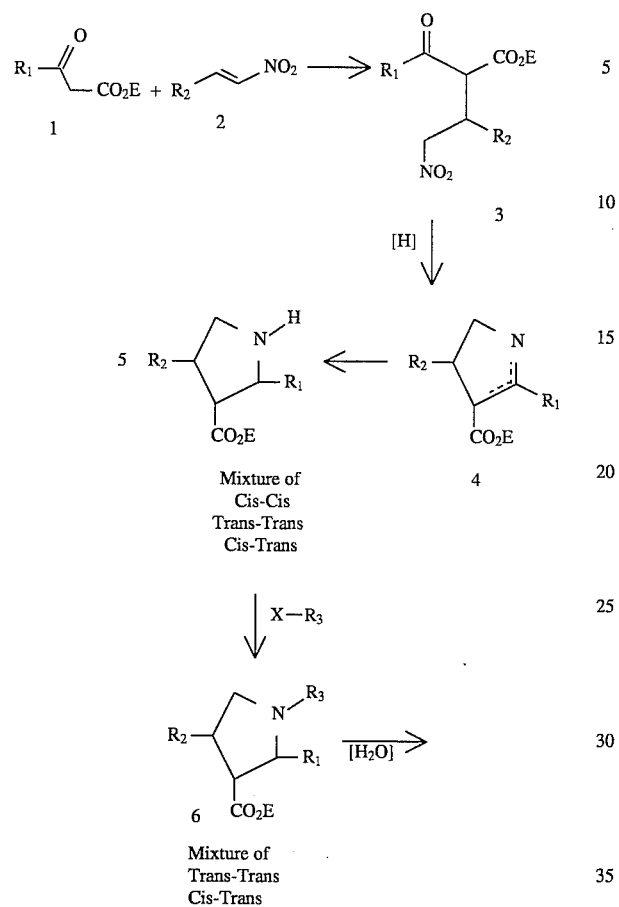
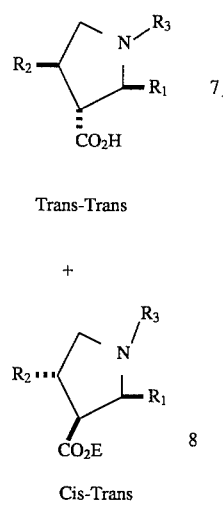
Trans-Trans
+
Cis-Trans
Scheme II
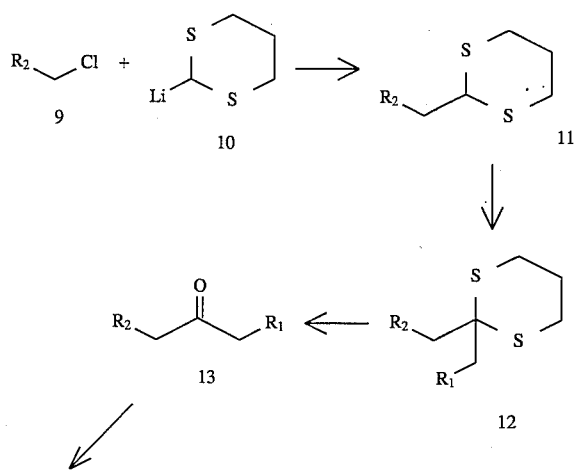

-continued
Scheme II
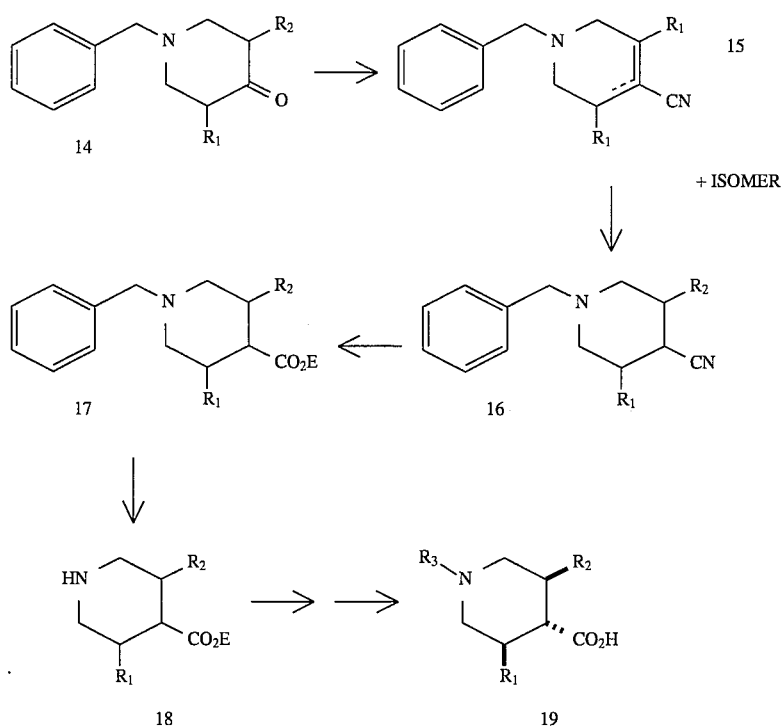
Scheme III
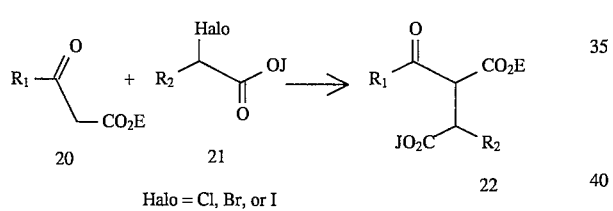
Halo = Cl, Br, or I
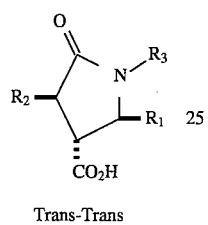
Trans-Trans
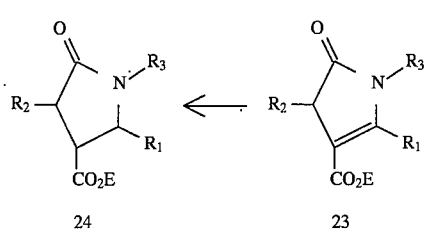
Scheme IV
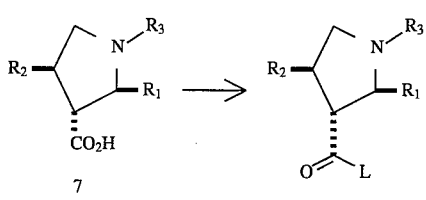
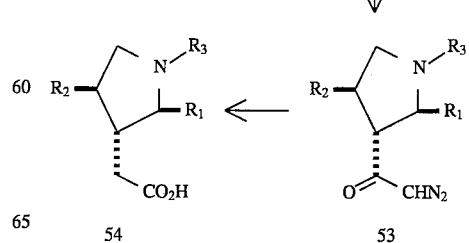

Scheme V
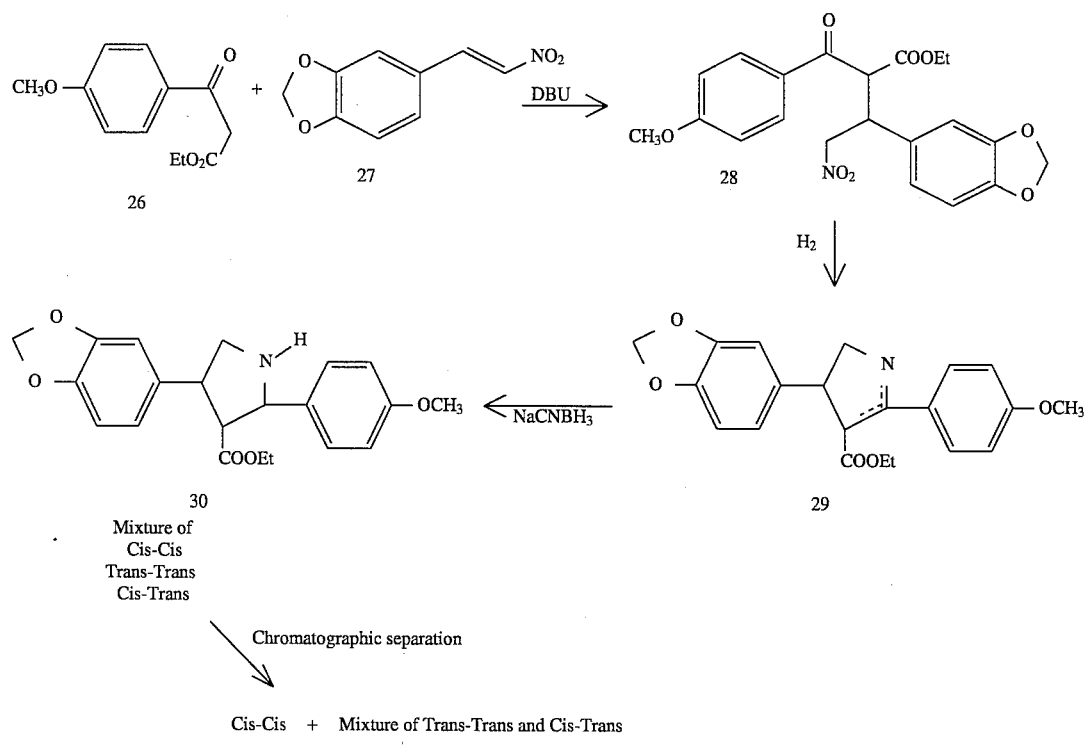
Scheme VI
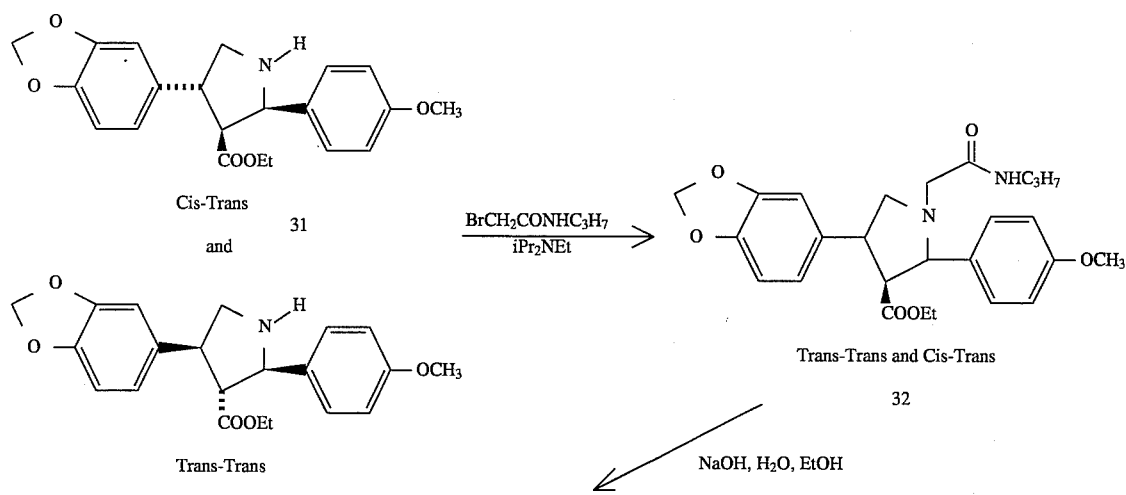

5,622,971
-continued
Scheme VI
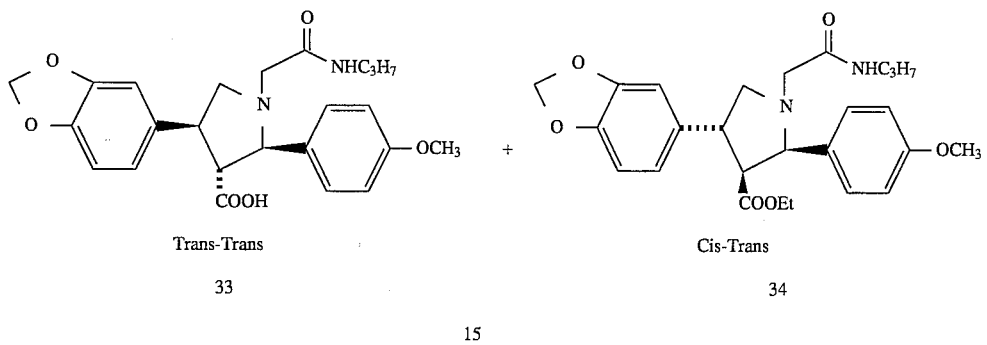
Scheme VII
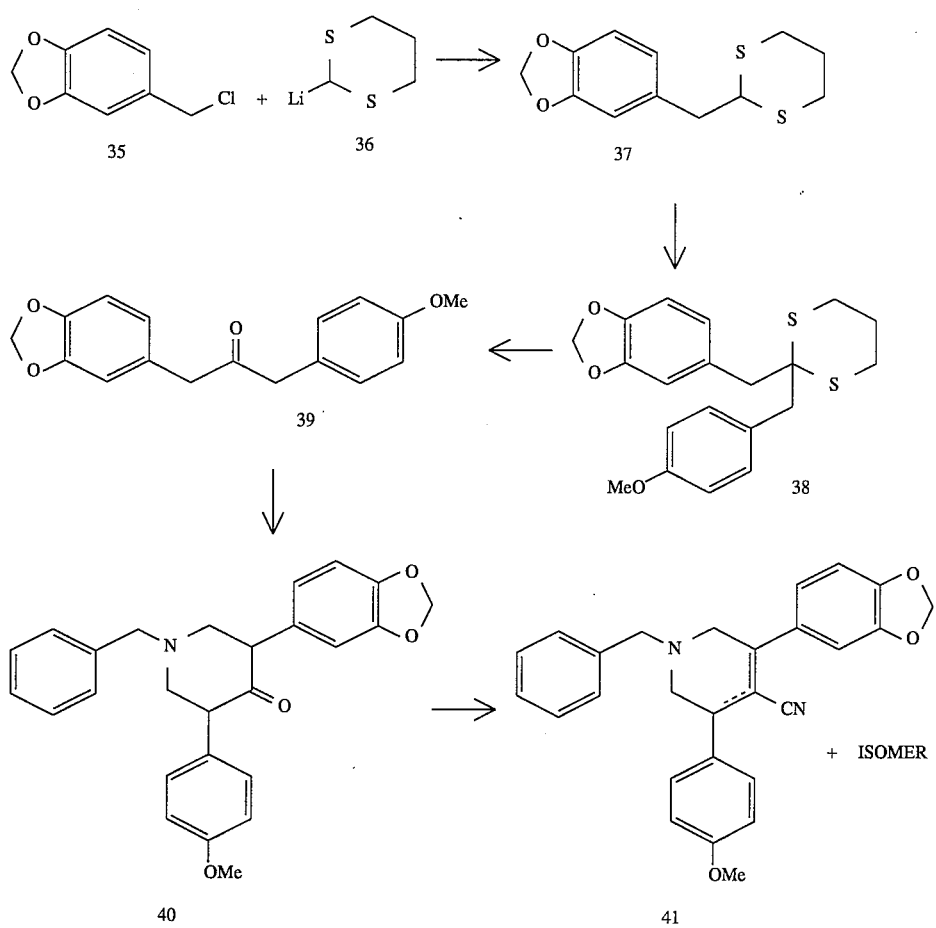

-continued
Scheme VII
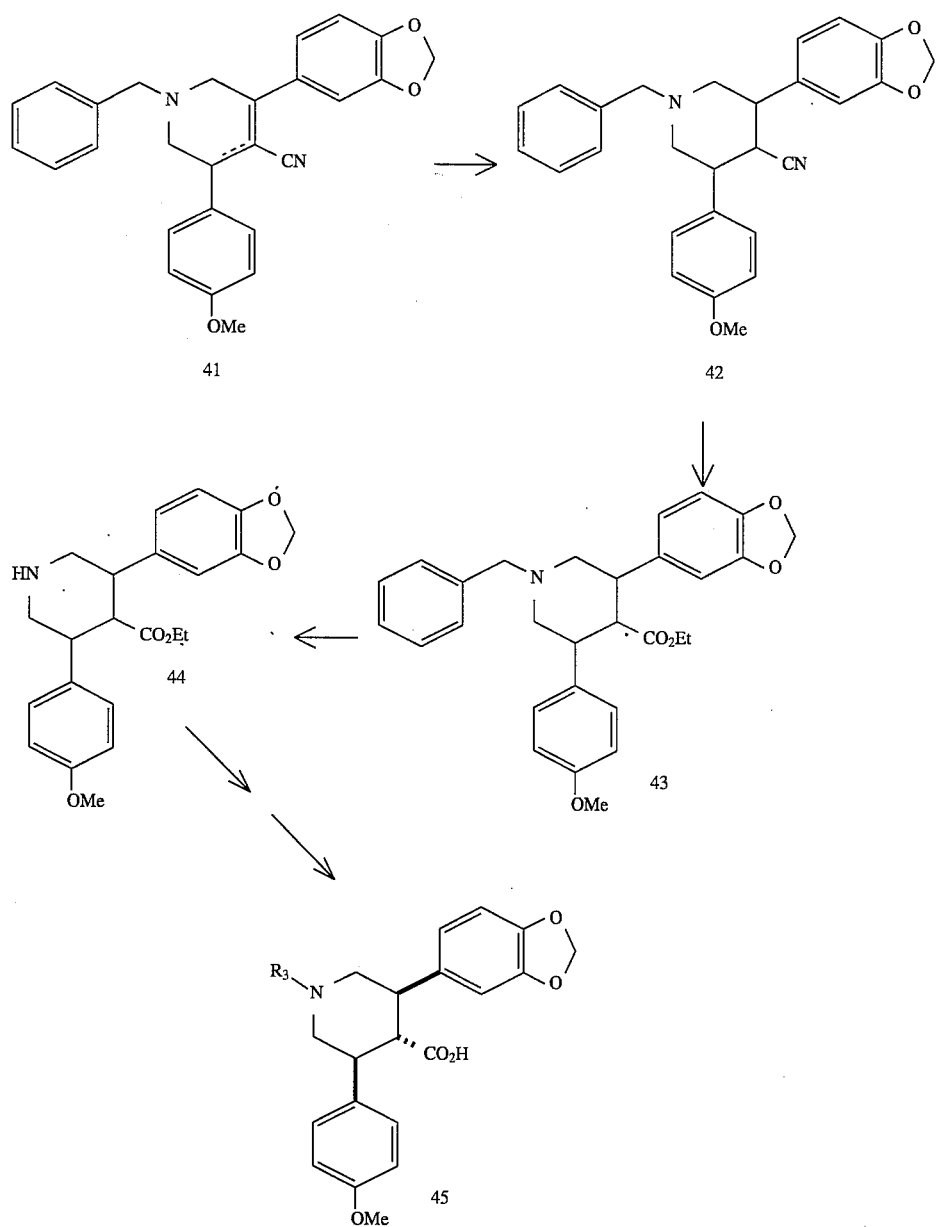
Scheme VIII
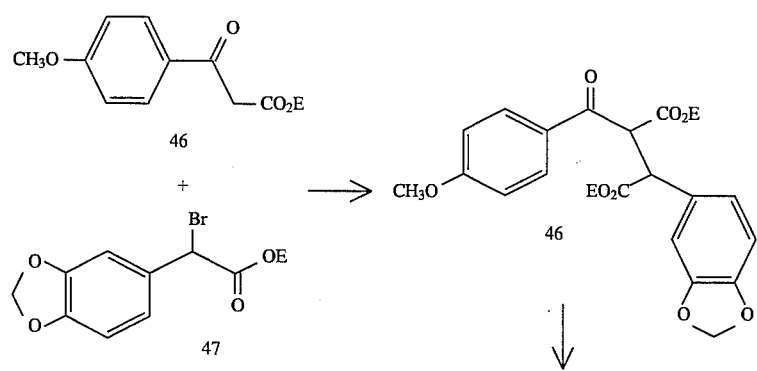

-continued
Scheme VIII
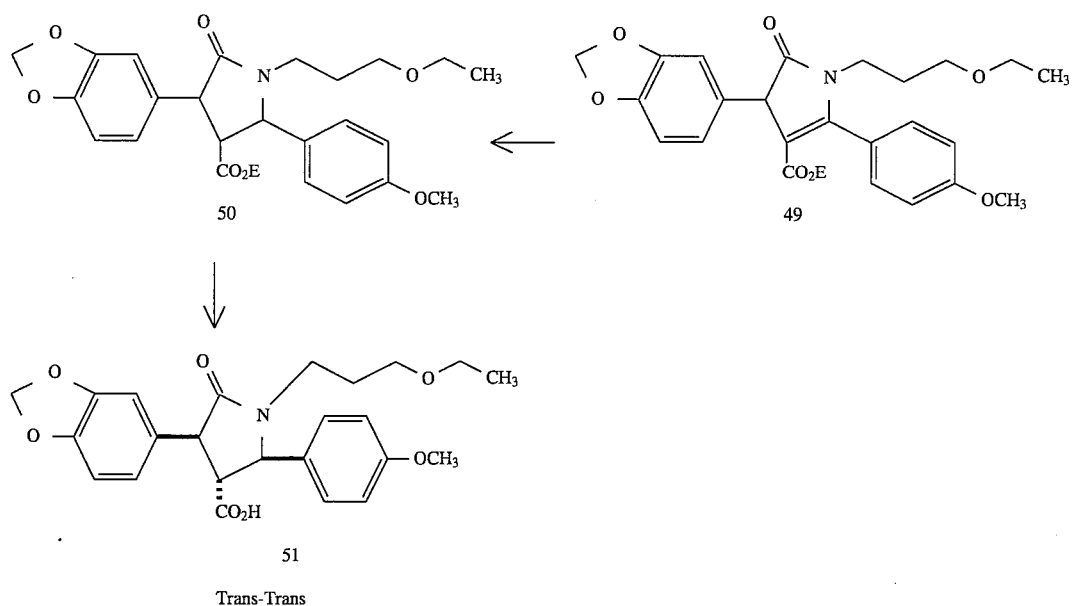
Trans-Trans
Scheme IX
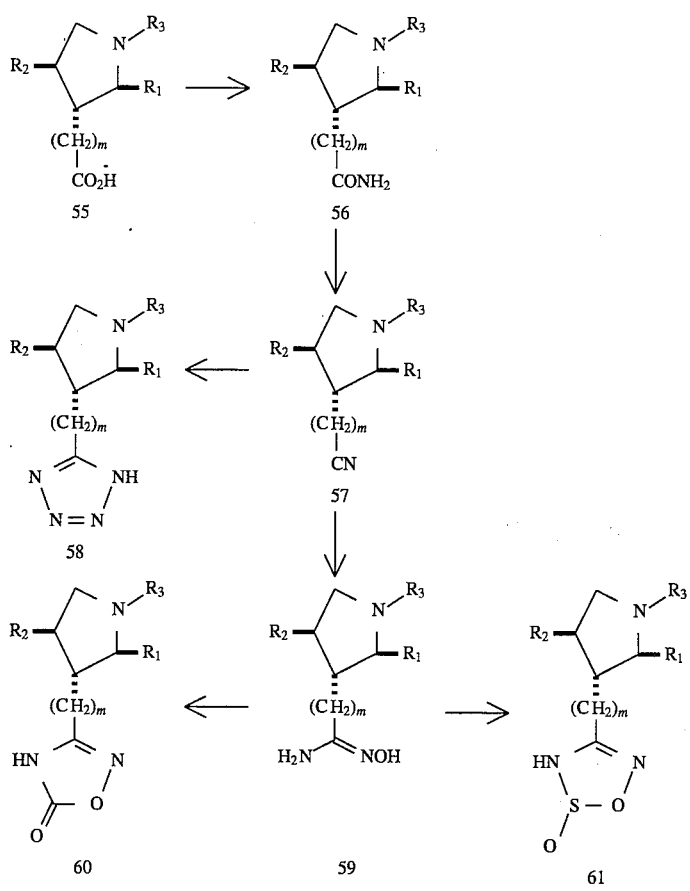

Scheme X
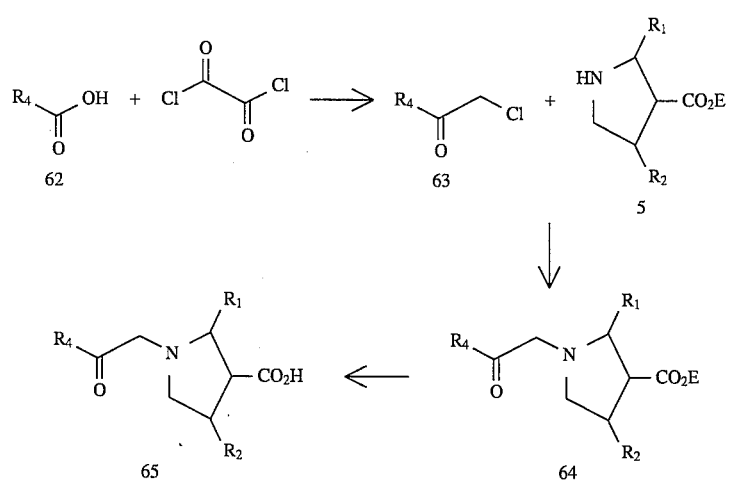
Scheme XI
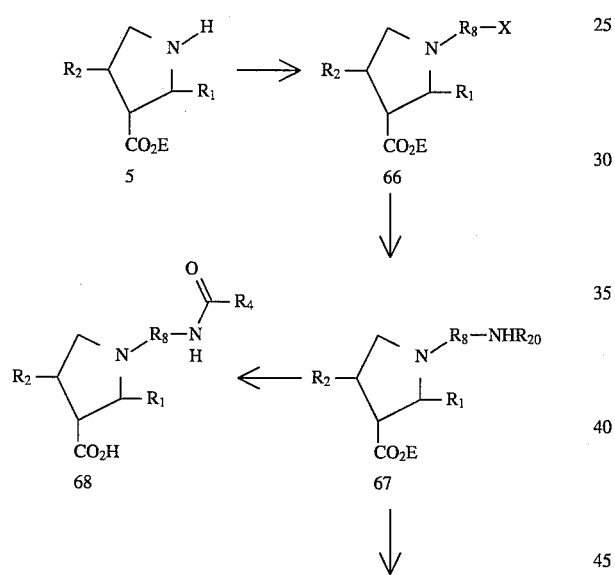
-continued
Scheme XI
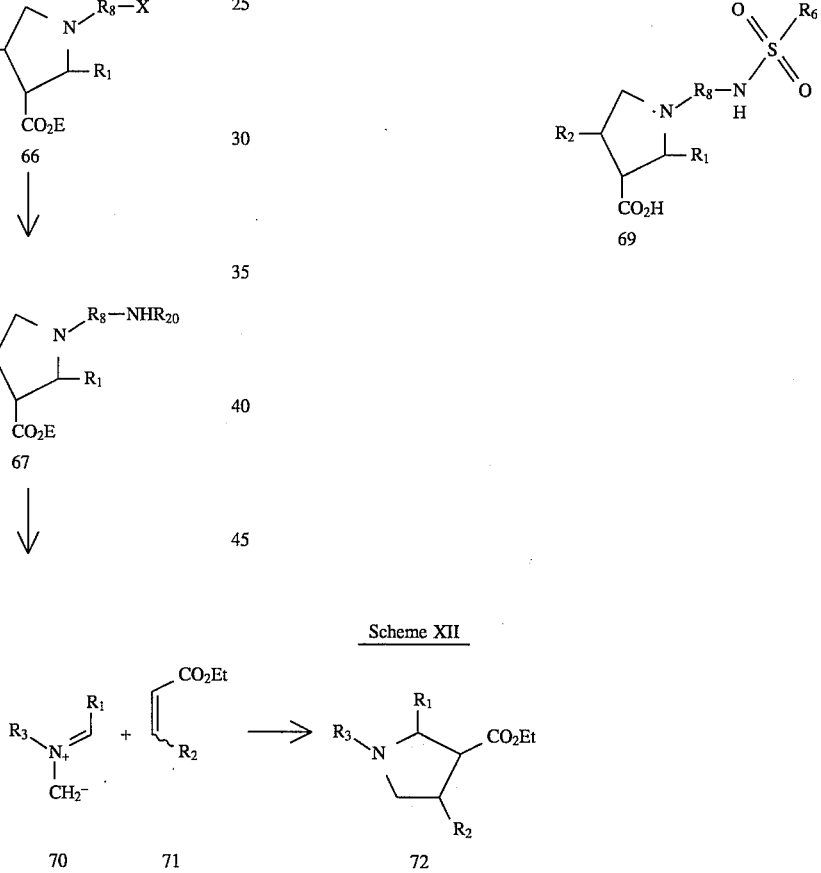
Scheme XII -continued
Scheme XII
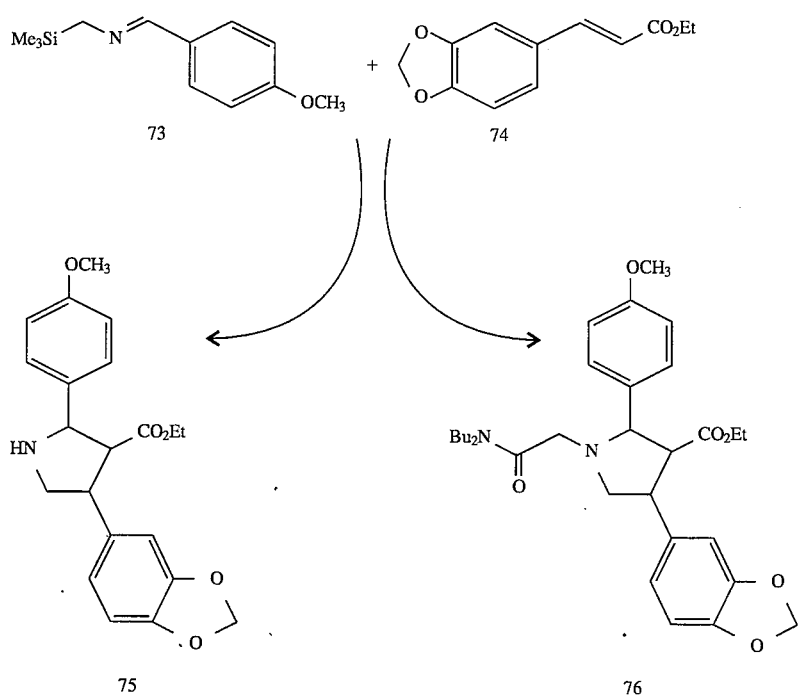
Scheme XIII
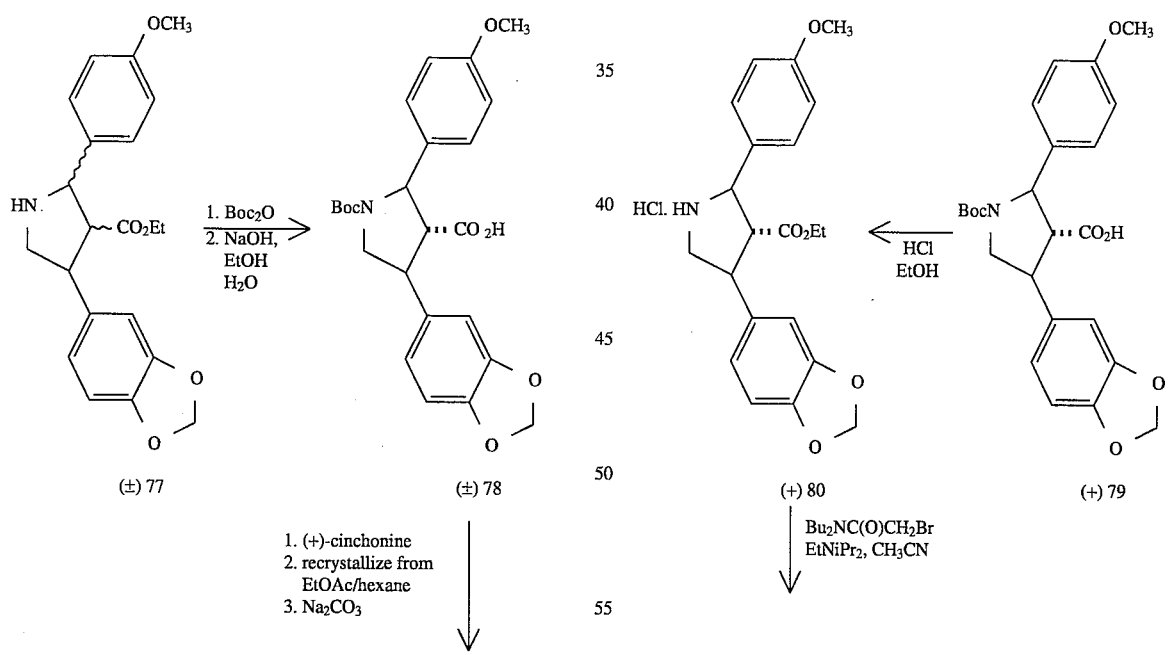

-continued
Scheme XIII

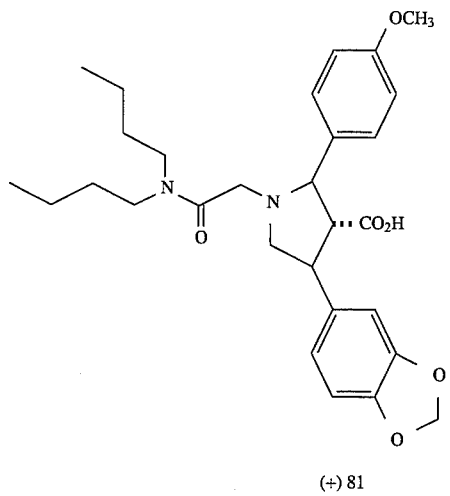

(+) 81

SCHEME XIV

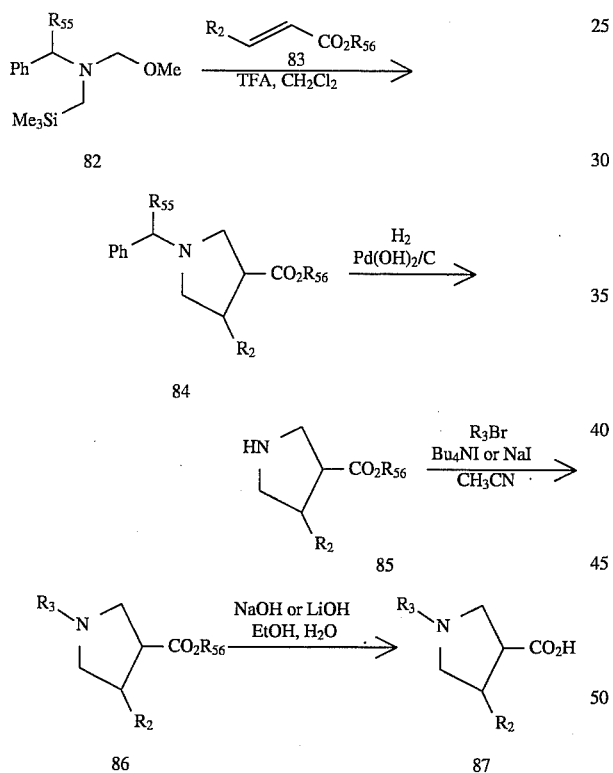

Compounds which are useful as intermediates for the preparation of compounds of the invention are:

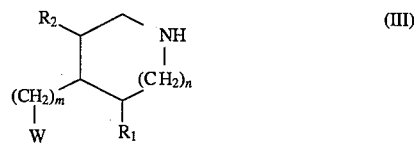

wherein n is 0 or 1;
m is 0 to 6;
W is (a) —C(O)$_2$—G where G is hydrogen or a carboxy protecting group, (b) —PO$_3$H$_2$, (c) —P(O)(OH)E where E is hydrogen, loweralkyl or arylalkyl, (d) —CN, (e) —C(O)NHR$_{17}$ where R$_{17}$ is loweralkyl, (f) alkylaminocarbonyl, (g) dialkylaminocarbonyl, (h) tetrazolyl, (i) hydroxy, (j) alkoxy, (k) sulfonamido, (l) —C(O)NHS(O)$_2$R$_{16}$ where R$_{16}$ is loweralkyl, haloalkyl, phenyl or dialkylamino, (m) —S(O)$_2$NHC(O)R$_{16}$,

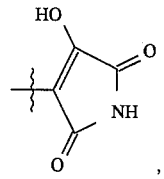 (n)

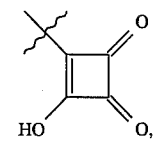 (o)

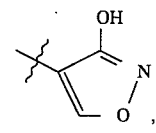 (p)

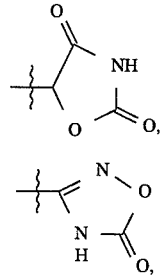 (q)

(r)

(s)

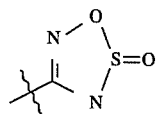 (t)

or

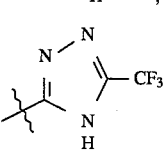

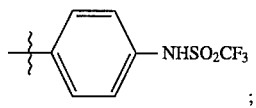 (u)

;

and

R$_1$ and R$_2$ are independently selected from hydrogen, loweralkyl, alkoxyalkyl, alkoxycarbonylalkyl, hydroxyalkyl, alkoxyalkoxyalkyl, thioalkoxyalkoxyalkyl, cycloalkyl, aryl, arylalkoxyalkyl and heterocyclic, with the proviso that one of $R_1$ and $R_2$ is other than hydrogen; or a salt thereof; and a compound of the formula:

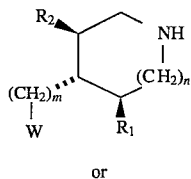
(IV)

or

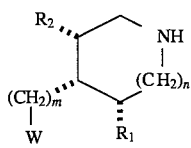
(V)

wherein n is 0 or 1;
m is 0 to 6;
W is (a) —$C(O)_2$—G where G is hydrogen or a carboxy protecting group, (b) —$PO_3H_2$, (c) —$P(O)(OH)E$ where E is hydrogen, loweralkyl or arylalkyl, (d) —CN, (e) —$C(O)NHR_{17}$ where $R_{17}$ is loweralkyl, (f) alkylaminocarbonyl, (g) dialkylaminocarbonyl, (h) tetrazolyl, (i) hydroxy, (j) alkoxy, (k) sulfonamido, (l) —$C(O)NHS(O)_2R_{16}$ where $R_{16}$ is loweralkyl, haloalkyl, phenyl or dialkylamino, (m) —$S(O)_2NHC(O)R_{16}$,

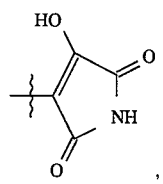
(n)

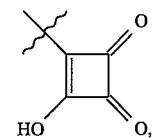
(o)

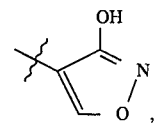
(p)

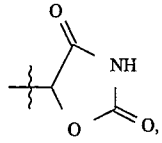
(q)

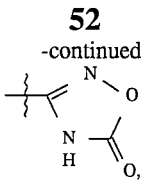
(r)

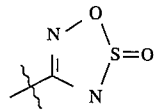
(s)

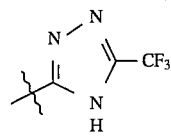
(t)

or

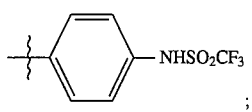
(u)

;

and $R_1$ and $R_2$ are independently selected from hydrogen, loweralkyl, alkoxyalkyl, alkoxycarbonylalkyl, hydroxyalkyl, alkoxyalkoxyalkyl, thioalkoxyalkoxyalkyl, cycloalkyl, aryl, arylalkoxyalkyl and heterocyclic, with the proviso that one of $R_1$ and $R_2$ is other than hydrogen; or a salt thereof.

Preferred intermediates include compounds of formula (IV) and (V) wherein
m is zero or 1;
W is —$CO_2$—G wherein G is hydrogen or a carboxy protecting group, and $R_1$ and $R_2$ are as defined above.

Particularly preferred intermediates are compounds of formula (IV) and (V) wherein
n and m are both 0;
W is —$CO_2$—G wherein G is hydrogen or a carboxy protecting group; and $R_1$ is (i)loweralkyl, (ii) cycloalkyl, (iii) phenyl, (iv) pyridyl, (v) furanyl or (vi) substituted or unsubstituted 4-methoxyphenyl, 4-fluorophenyl, 3-fluorophenyl, 2-fluorophenyl, 4-methoxymethoxyphenyl, 4-hydroxyphenyl, 4-t-butylphenyl, 1,3-benzodioxolyl, 1,4-benzodioxanyl or dihydrobenzofuranyl wherein the substituent is selected from alkoxy, alkoxyalkoxy and carboxyalkoxy and $R_2$ is 1,3-benzodioxolyl, 1,4-benzodioxanyl, dihydrobenzofuranyl, 4-methoxyphenyl, dimethoxyphenyl, fluorophenyl or difluorophenyl.

The foregoing may be better understood by reference to the following examples which are provided for illustration and not intended to limit the scope of the inventive concept. The following abbreviations are used: Boc for tertbutyloxycarbonyl, Cbz for benzyloxycarbonyl, DBU for 1,8-diazabicyclo[5.4.0]undec-7-ene, EDCI for 1-(3-dimethylaminopropyl-3-ethylcarbodiimide hydrochloride, EtOAc for ethyl acetate, EtOH for ethanol, HOBt for 1-hydroxybenzotriazole, $Et_3N$ for triethylamine and THF for tetrahydrofuran.

EXAMPLE 1 trans,trans-2-(4-Methoxyphenyl)-4-(1,3-benzodioxol-5-yl)-1-(propylaminocarbonylmethyl)-pyrrolidine-3-carboxylic Acid

EXAMPLE 1A

Ethyl 2-(4-methoxybenzoyl)-4-nitromethyl-3-(1,3-benzodioxole-5-yl)butyrate

To ethyl (4-methoxybenzoyl)acetate (23.0 g, 0.104 mol), prepared by the method of Krapcho et al., Org. Syn. 47, 20

(1967), and 5-(2-nitrovinyl)-1,3-benzodioxole (17.0 g, 0.088 mol) dissolved in 180 mL of toluene and heated to 80° C. was added 1,8-diazabicyclo[5,4,0]undec-7-ene (DBU, 0.65 g) with stirring. The mixture was heated until all the nitro starting material dissolved. The solution was stirred without heating for 30 minutes and then an additional 0.65 g of DBU was added. After stirring an additional 45 minutes, thin layer chromatography (5% ethyl acetate in methylene chloride) indicated the absence of nitro starting material. Toluene (200 mL) was added, and the organic phase was washed with dilute hydrochloric acid and NaCl solution. The organic phase was dried over sodium sulfate and then concentrated under reduced pressure. The residue obtained was chromatographed on silica gel eluting with 3:1 hexane-ethyl acetate to give 21.22 g of the desired product as a mixture of isomers and 9.98 g. of recovered ethyl (4-methoxybenzoyl)acetate.

EXAMPLE 1B

Ethyl 2-(4-methoxyphenyl)-4-(1,3-benzodioxol-5-yl)-4,5-dihydro-3H-pyrrole-3-carboxylate The compound resulting from Example 1A (21 g) in 500 mL of ethanol was hydrogenated under 4 atmospheres of hydrogen pressure using a Raney nickel 2800 catalyst (51 g). (The Raney nickel was washed with ethanol three times before use.) The catalyst was removed by filtration, and the solution was concentrated under reduced pressure. The residue obtained was chromatographed on silica gel eluting with 8.5% ethyl acetate in methylene chloride to give 12.34 g of the desired product.

EXAMPLE 1C

Ethyl 2-(4-methoxyphenyl-4-(1,3-benzodioxol-5-yl)-pyrrolidine-3-carboxylate) as a mixture of cis-cis; trans,trans; and cis,trans-isomers The compound resulting from Example 1B (11.89 g, 0.324 mol) was dissolved in 27 mL of tetrahydrofuran and 54 mL of ethanol. Sodium cyanoborohydride (2.35 g, 0.374 mol) and 5 mg bromocresol green were added. To this blue solution was added dropwise a solution of 1:2 concentrated HCl in ethanol at such a rate that the color was kept at light yellow-green. After the yellow color persisted without additional HCl, the solution was stirred an additional 20 minutes. The solution was concentrated in vacuo and then partitioned between chloroform and an aqueous potassium bicarbonate solution. The organic phase was separated, dried over sodium sulfate, and concentrated under reduced pressure. The residue was chromatographed on silica gel eluting with 85:15 ethyl acetate-hexane to give 5.96 g. of a mixture of 64% trans,trans-compound and 34% cis,trans-compound. Further elution with pure ethyl acetate gave 0.505 g of an unknown solid followed by 3.044 g of pure cis,cis-compound.

EXAMPLE 1D trans,trans-2-(4,Methoxyphenyl)-4-(1,3-benzodioxol-5-yl)-1-(propylaminocarbonylmethyl)-pyrrolidine-3-carboxylic acid The mixture of 64% trans,trans- and 34% cis,trans-pyrrolidines (the mixture resulting from Example 1C) (5.72 g, 15.50 mmol), ethyldiisopropylamine (4.20 g, 32.56 mmol), and N-propyl bromoacetamide (3.42 g, 19.0 mmol), prepared by the method of Weaver, W. E. and Whaley, W. M., J. Amer. Chem. Soc., 69: 515 (1947), in 30 mL of acetonitrile was heated at 50° C. for 1 hour. The solution was concentrated in vacuo. The residue was dissolved in toluene, shaken with potassium bicarbonate solution, dried over sodium sulfate and concentrated in vacuo to give 7.16 g of product as a mixture of trans,trans- and cis,trans-ethyl esters.

This mixture was dissolved in a solution of 50 mL of ethanol and 15 mL of water containing 5.00 g of sodium hydroxide and stirred for 3 hours at room temperature. The solution was concentrated in vacuo and 60 mL of water added. The mixture was extracted with ether to remove the unreacted cis,trans-ethyl ester. The aqueous phase was treated with hydrochloric acid until slightly cloudy. It was then further neutralized with acetic acid to give the crude acid product. The crude product was filtered and purified by dissolving it in tetrahydrofuran, drying over sodium sulfate, concentrating in vacuo, and crystallizing from ether to give 3.230 g of the title compound. m.p. 151°–153° C. $^1$H NMR (CD$_3$OD, 300 MHz) δ 0.87 (t, J=7 Hz, 3H), 1.49 (sextet, J=7 Hz, 2H), 2.84 (d, J=16 Hz, 1H), 2.95–3.20 (m, 4H), 3.20 (d, J=16 Hz, 1H), 3.34–3.42 (m, 1H), 3.58–3.66 (m, 1H), 3.78 (s, 3H), 3.88 (d, J=10 Hz, 1H), 5.92 (s, 2H), 6.75 (d, J=8 Hz, 1H), 6.86 (dd, J=8 Hz, J=1 Hz, 1H), 6.90 (d, J=9 Hz, 2H), 7.02 (d, J=1 Hz, 1H), 7.40 (d, J=9 Hz, 2H).

EXAMPLE 2 trans,trans-2-(4-Methoxyphenyl)-4-(1,3-benzodioxol-5-yl)-1-(aminocarbonylmethyl)-pyrrolidine-3-carboxylic Acid Using the method described in Example 1D, 300 mg of the mixture of 64% trans,trans- and 34% cis,trans-pyrrolidines (the mixture resulting from Example 1C), 220 mg of diisopropylethylamine and 184 mg iodoacetamide were reacted at 45° C. in 1 mL acetonitrile to give 291 mg of a mixture of trans,trans- and cis,trans- N-alkylated esters. A portion (270 mg.) was hydrolyzed with 200 mg NaOH in 1 mL of water and 3 mL of ethanol; a chloroform extraction was used to remove the unreacted cis,trans- ethyl ester. The isolation and purification procedures described in Example 1D were used to give 134 mg of the title compound. m.p. 246°–248° C. $^1$H NMR (DMSO-d$_6$, 300 MHz) δ 2.61 (d, J=16 Hz, 1H), 2.71 (t, J=9 Hz, 1H), 2.90 (t, J=9 Hz, 1H), 2.98 (d, J=16 Hz, 1H), 3.25–3.35 (m, 1H), 3.45–3.55 (m, 1H), 3.71 (s, 3H) 3.75 (d, J=10 Hz, 1H), 6.00 (s, 2H), 6.81 (s, 2H), 6.90 (d, J=8 Hz, 2H), 7.10 (s, 1H), 7.17 (s, 1H), 7.34 (s, 1H), 7.38 (d, J=8 Hz, 2H).

EXAMPLE 3 trans,trans-2-(4-Methoxyphenyl)-4-(1,3-benzodioxol-5-yl)-1-(4-fluorobenzyl)-pyrrolidine-3-carboxylic Acid Using the method described in Example 1D, 300 mg of the mixture of 64% trans,trans- and 34% cis,trans- pyrrolidines (the mixture resulting from Example 1C), 220 mg of diisopropylethylamine and 185 mg of 4-fluorobenzyl bromide were reacted at room temperature for 3 hours in 1 mL of acetonitrile to give 387 mg of a mixture of trans,trans- and cis,trans-N-alkylated esters. A portion (360 mg) was hydrolyzed with 250 mg NaOH in 1 mL of water and 4 mL of ethanol to give 160 mg of the title compound as an amorphous powder. $^1$H NMR (CDCl$_3$, 300 MHz) δ 2.74 (t, J=9 Hz, 1H), 2.95 (t, J=7 Hz, 1H), 2.98 (d, J=14 Hz, 1H), 3.07 (dd, J=9 Hz, 1 Hz, 1H), 3.42–3.53 (m, 1H), 3.70 (d, J=9 Hz, 1H), 3.78 (d, J=14, 1H), 3.81 (s, 3H), 5.92 (s, 2H), 6.70 (d, J=8 Hz, 1H) 6.77 (dd, J=8 Hz, 1 Hz, 1H), 6.91 (d, J=9 Hz, 2H), 6.94–7.00 (m, 3H), 7.20–7.25 (M, 1H), 7.44 (d, J=9 Hz, 2H).

EXAMPLE 4 trans,trans-2-(4-Methoxyphenyl)-4-(1,3-benzo-dioxol-5-yl)-1-(2-ethoxyethyl)-pyrrolidine-3-carboxylic Acid Using the method described in Example 1D, 300 mg. of the mixture of 64% trans,trans- and 34% cis,trans-pyrrolidines (the mixture resulting from Example 1C), 220 mg of diisopropylethylamine and 152 mg of 2-bromoethyl ethyl ether were refluxed in 1.5 mL acetonitrile for 3 hours (bath temperature at 95° C.) to give 346 mg of a mixture of trans,trans- and cis,trans-esters. Hydrolysis with 250 mg NaOH in 1 mL of water and 3 mL of ethanol afforded 140 mg of the title compound. m.p. 88°–90° C. $^1$H NMR (CDCl$_3$, 300 MHz) δ 1.25 (t, J=7 Hz, 3H), 2.21–2.32 (m, 1H), 2.70–2.80 (m, 1H), 2.85–2,94 (m, 2H), 3.38–3.55 (m, 6H), 3.67 (d, J=10 Hz, 1H), 3.79 (s, 3H), 5.94 (s, 2H), 6.72 (d, J=8 Hz, 1H), 6.84 (m, 1H), 6.84 (d, J=9 Hz, 2H), 7.08 (d, J=1 Hz, 1H), 7.33 (d, J=9 Hz, 2H).

EXAMPLE 5 trans,trans-2-(4-Methoxyphenyl)-4-(1,3-benzo-dioxol-5-yl)-1-(2-propoxyethyl)-pyrrolidine-3-carboxylic Acid Using the method described in Example 1D, 520 mg of the mixture resulting from Example 1C, 364 mg of diisopropylethylamine, 50 mg potassium iodide and 350 mg 2-chloroethyl propyl ether were reacted at 125° C. in 0.5 mL acetonitrile for 4 hours to give 517 mg of a mixture of trans,trans- and cis,trans-esters. A portion (500 mg) was hydrolyzed with 315 mg NaOH in 1 mL of water and 4 mL of ethanol to give 225 mg of the title compound as an amorphous powder. $^1$H NMR (CDCl$_3$, 300 MHz) δ 0.87 (t, J=7 Hz, 3H), 1.53 (sextet, J=7 Hz, 2H), 2.28–2.41 (m, 1H), 2.71–2.83 (m, 1H), 2.92–3.08 (m, 2H), 3.30 (t, J=7 Hz, 2H), 3.40–3.60 (m, 4H), 3.72–3.83 (m, 1H), 3.76 (s, 3H), 5.92 (s, 2H), 6.71 (d, J=8 Hz, 2H), 6.74 (dd, J=8 Hz, 1 Hz), 6.71 (d, J=9 Hz, 2H), 7.07 (d, J=9 Hz, 2H), 7.73 (d, J=9 Hz, 2H).

EXAMPLE 6 trans,trans-2-(4-Methoxyphenyl)-4-(1,3-benzo-dioxol-5-yl)-1-[2-(2-methoxyethoxy)ethyl]pyrrolidine-3-carboxylic Acid

EXAMPLE 6A

Ethyl trans,trans-2-(4-methoxyphenyl)-4-(1,3-benzo-dioxol-5-yl) pyrrolidine-3-carboxylate To the pure cis,cis-compound resulting from Example 1C (3.02 g) dissolved in 10 mL of ethanol was added 20 drops of a solution of 21% sodium ethoxide in ethanol. The reaction mixture was refluxed overnight, at which time thin layer chromatography in ethyl acetate indicated the absence of starting material. The NaOEt was neutralized with HCl in ethanol, and the solution was concentrated in vacuo. The residue was taken up in toluene and extracted with potassium bicarbonate in water. The toluene was dried over sodium sulfate and concentrated under reduced pressure to give 2.775 of the title compound which was pure by TLC (ethyl acetate).

EXAMPLE 6B trans,trans-2-(4-Methoxyphenyl)-4-(1,3-benzo-dioxol-5-yl)-1-[2-(2-methoxyethoxy)ethyl]-pyrrolidine-3-carboxylic Acid Using the method described in Example 1D, 250 mg of the compound resulting from Example 6A, 150 mg of 2-(2-methoxyethoxy)ethyl bromide and 175 mg diisopropylethylamine in 1 mL acetonitrile were heated at 100° C. for 3 hours to give 229 mg of the trans,trans-ester. A portion (200 mg) was hydrolyzed with 125 mg NaOH in 1 mL of water and 2 mL of ethanol to give 151 mg of the title compound as an amorphous powder. $^1$H NMR (CD$_3$OD, 300 MHz) δ 2.9–3.9 (m, 13H), 3.81 (s, 3H), 4.49 (d, J=10 Hz, 1H), 5.94 (s, 2H), 6.79 (d, J=8 Hz, 1H), 6.89 (dd, J=8 Hz, 1 Hz, 1H), 7.00 (d, J=9 Hz, 2H), 7.05 (d, J =1 Hz, 1H), 7.49 (d, J=9 Hz, 2H).

EXAMPLE 7 trans,trans-2-(4-Methoxyphenyl)-4-(1,3-benzo-dioxol-5-yl)-1-[2-(2-pyridyl)ethyl]-pyrrolidine-3-carboxylic Acid The compound resulting from Example 6A (250 mg), 2-vinyl pyridine (355 mg) and one drop of acetic acid were dissolved in 2-methoxyethanol, and stirred at 100° C. for 2.5 hours. Toluene was added, and the solution was washed with potassium bicarbonate solution. The solution was dried over potassium bicarbonate and concentrated in vacuo. Toluene was added and the solution re-concentrated. This was done until the odor of 2-vinylpyridine was gone. The residue was taken up in hot heptane, filtered to remove a small amount of insoluble impurity, and concentrated in vacuo to give 225 mg of intermediate ester. The ester was hydrolyzed by the method described in Example 1D to give 202 mg of the title compound as the dihydrate. m.p. 77°–80° C. $^1$H NMR (CD$_3$OD, 300 MHz) δ 2.8–3.3 (m, 6H), 3.55–3.70 (m, 2H), 3.76 (s, 3H), 3.99 (d, J=10 Hz, 1H), 5.92 (d, J=1 Hz, 2H), 6.72 (d, J=8 Hz, 1H), 6.80 (dd, J=8 Hz, 1 Hz), 6.85 (d, J=9 Hz, 2H), 6.92 (d, J=1 Hz, 1H), 7.20 (d, J=9 Hz, 2H), 7.20–7.32 (m, 2H), 7.70–7.80 (m, 2H), 8.40 (d, J=4 Hz, 1).

EXAMPLE 8 trans,trans-2-(4-Methoxyphenyl)-4-(1,3-benzo-dioxol-5-yl)-1-(morpholin-4-ylcarbonyl)-pyrrolidine-3-carboxylic Acid To the compound resulting from Example 6A (300 mg) and 164 mg triethylamine dissolved in 2 mL of methylene chloride and cooled in an ice bath was added 146 mg 1-morpholinocarbonyl chloride. The mixture was stirred 3 hours at room temperature. Toluene was added and the solution was washed with potassium bicarbonate solution, dried over sodium sulfate and concentrated in vacuo to give the intermediate ester. The ester was hydrolyzed by the method described in Example 1D to give 288 mg of the title compound. m.p. 244°–246° C. $^1$H NMR (DMSO-d$_6$, 300 MHz) δ 2.96 (dd, J=12 Hz, 13 Hz, 1H), 3.03–3.13 (m, 2H), 3.20–3.30 (m, 2H), 3.40–3.60 (m, 5H), 3.74 (s, 3H), 3.70–3.85 (m, 3H), 5.10 (d, J=10 Hz, 1H), 5.99 (d, J=1 Hz, 2H), 6.80–6.90 (m, 2H), 6.87 (d, J=9 Hz, 2H), 7.07 (s, 1H), 7.25 (d, J=9 Hz, 2H).

EXAMPLE 9 trans,trans-2-(4-Methoxyphenyl)-4-(1,3-benzodioxole-5-yl)-1-(butylaminocarbonyl)-pyrrolidine-3-carboxylic Acid To the compound resulting from Example 6A (300 mg) dissolved in 2 mL tetrahydrofuran and cooled in an ice bath was added 88 mg of butyl isocyanate. After 40 minutes at room temperature, toluene was added, and the solution was concentrated in vacuo to give the intermediate ester. The ester was hydrolyzed by the method described in Example 1D to give 232 mg of the title compound. m.p. 220°–221° C. 1H NMR (DMSO-$d_6$, 300 MHz) δ 0.78 (t, J=7 Hz, 3H), 1.10 (sextet, J=7 Hz, 2H), 1.22 (quintet, J=7 Hz, 2H), 2.78–3.05 (m, 3H), 3.40–3.56 (m, 2H), 3.74 (s, 3H), 3.95–4.05 (m, 1H), 4.93 (d, J=9 Hz, 1H), 5.80 (t, broad J=7 Hz, 1H), 5.99 (s, 2H), 6.78–6.86 (m, 2H), 6.88 (d, J=9 Hz, 2H), 7.00 (d, J=1 Hz, 1H), 7.12 (d, J=9 Hz, 2H).

EXAMPLE 10 trans,trans-2-(4-Methoxyphenyl)-4-(1,3-benzodioxol-5-yl)-1-(4-methoxyphenylaminocarbonyl)-3-pyrrolidine-3-carboxylic Acid The compound resulting from Example 6A (300 mg) was treated with 133 mg of 4-methoxyphenyl isocyanate by the procedure described in Example 9. The resulting ester was hydrolyzed with NaOH using the method described in Example 1D to give 279 mg of the title compound. m.p. 185°–187° C. $^1$H NMR (CDCl$_3$, 300 MHz) δ 3.23 (dd, J=12 Hz, 13 Hz, 1H), 3.55–3.68 (m, 2H), 3.72 (s, 3H), 3.83 (s, 3H), 4.50–4.65 (m, 1H), 5.06 (d, J=10 Hz, 1H), 5.90 (s, 1H), 5.95 (s, 1H), 6.72 (d, J=9 Hz, 2H), 6.7–6.8 (m, 3H), 6.92 (d, J=9 Hz, 2H), 6.97 (d, J=9 Hz, 2H), 7.37 (d, J=9 Hz, 2H).

EXAMPLE 11 trans,trans-2-(4-Methoxyphenyl)-4-(1,3-benzodioxol-5-yl)-1-acetylpyrrolidine-3-carboxylic Acid The compound resulting from Example 6A (250 mg) in 0.5 mL of toluene was treated with 200 mg of acetic anhydride. After stirring 2 hours at room temperature, water was added and the acetic acid neutralized with potassium bicarbonate. The mixture was extracted with toluene to give 273 mg of the intermediate ester. A portion of the ester (200 mg) was hydrolyzed using the method of Example 1D to give 211 mg of the title compound. m.p. 248°–250° C. Rotational isomers are seen in the NMR. $^1$H NMR (DMSO-$D_6$, 300 MHz) δ 1.55 and 2.00 (s, 3H), 2.94 and 3.03 (dd, J=12 Hz, 13 Hz, 1H), 3.3–3.6 (m, 2H), 3.72 and 3.76 (s, 3H), 4.12 and 4.28 (dd, J=12 Hz, 7 Hz, 1H), 4.95 and 5.04 (d, J=10 Hz, 1H), 6.00 (s, 2H), 6.75–6.87 (m, 3H), 6.95 and 7.04 (d, J=9 Hz, 2H 7.18 and 7.32 (d, J=9 Hz, 2H).

EXAMPLE 12 trans,trans-2-(4-Methoxyphenyl)-4-(1,3-benzodioxol-5-yl)-1-(2-furoyl)-pyrrolidine-3-carboxylic Acid To the compound resulting from Example 6A (300 mg) and 164 mg triethylamine dissolved in 2 mL methylene chloride and cooled in an ice bath was added 138 mg of 2-furoyl chloride. The mixture was stirred 30 minutes at room temperature and then worked up by the procedures described in Example 8 to give the intermediare ester. The ester was hydrolyzed by the procedure described in Example 1D to give 269 mg of the title compound as an amorphous powder. $^1$H NMR (DMSO-$d_6$, 300 MHz) δ 3.06 (dd, J=12 Hz, 13 Hz, 1H), 3.3–3.6 (m, 2H), 4.25 (m, 1H), 5.19 (d, J=10 Hz, 1H), 6.67.4 (m, 8H), 7.8–7.9 (m, 1H).

EXAMPLE 13 trans,trans-2-(4-Methoxyphenyl)-4-(1,3-benzodioxol-5-yl)-1-(phenylaminocarbonyl-pyrrolidine-3-carboxylic Acid Starting with the compound resulting from Example 6A, phenyl isocyanate and the procedures described in Example 9, the title compound was prepared. m.p. 209°–211° C. $^1$H NMR (DMSO-$d_6$, 300 MHz) δ 3.03 (dd, 1H), 3.55 (m, 1H), 3.70 (m, 1H), 3.72 (s, 3H), 4.15 (m, 1H), 5.13 (d, 1H), 6.00 (s, 2H), 6.88 (m, 5H), 7.07–7.20 (m, 3H), 7.30 (d, 2H), 7.38 (d, 2H), 8.20 (bs, 1H).

EXAMPLE 14 trans,trans-2-(4-Methoxyphenyl)-4-(1,3-benzodioxol-5-yl)-1-(allylaminocarbonylmethyl)-pyrrolidine-3-carboxylic Acid Using the procedures described in Example 1 the title compound was prepared. m.p. 138°–140° C. $^1$H NMR (CDCl$_3$, 300 MHz) δ 2.84 (d, 1H), 2.90–3.10 (dt, 2H), 3.28 (d, 1H), 3.35 (dd, 1H), 3.62 (m, 1H), 3.72–3.97 (m, 3H), 3.80 (s, 3H), 5.13 (bd, 2H), 5.80 (m, 1H), 5.97 (s, 2H), 6.74–6.97 (m, 5H), 7.38 (d, 2H).

EXAMPLE 15 trans,trans-2-(4-Methoxyphenyl)-4-(1,3-benzodioxol-5-yl)-1-(n-butylaminocarbonylmethyl)-pyrrolidine-3-carboxylic Acid Using the procedures described in Example 1 the title compound was prepared. m.p. 105°–107° C. $^1$H NMR (CDCl$_3$, 300 MHz) δ 0.90 (t, 3H), 1.30 (m, 2H), 1.45 (m, 2H), 2.80 (d, 1H), 2.87–3.35 (m, 6H), 3.62 (m, 1H), 3.80 (s, 3H) 5.97 (s, 2H), 6.75–6.92 (m, 5H), 7.28 (d, 2H).

EXAMPLE 16 trans,trans-2-(4-Methoxyphenyl)-4-(1,3-benzodioxol-5-yl)-1-(N-(n-propyl)-N-methylaminocarbonylmethyl)-pyrrolidine-3-carboxylic Acid Using the procedures described in Example 1 the title compound was prepared as an amorphous solid. Rotational isomers are seen in the NMR. $^1$H NMR (CDCl$_3$, 300 MHz) δ 0.73, 0.84 (2t, 3H), 1.49 (m, 2H), 2.80 (dd, 1H), 2.85 (2s, 3H), 2.95–3.20 (m, 3H), 3.20–3.40 (m, 1H), 3.40 (d, 1H), 3.60 (m, 1H), 3.79 (s, 3H), 5.93 (s, 2H), 6.73 (d, 1H), 6.86 (m, 2H), 7.03 (m, 1H), 7.32 (d, 2H).

EXAMPLE 17 trans,trans-2-(4-Methoxyphenyl)-4-(1,3-benzodioxol-5-yl)-1-(pyrrolidin-1-ylcarbonylmethyl)-pyrrolidine-3-carboxylic Acid Using the procedures described in Example 1 the title compound was prepared as an amorphous solid. $^1$H NMR (CDCl$_3$, 300 MHz) δ 1.40–1.70 (m, 6H), 2.80 (d, 1H), 3.00 (m, 2H), 3.24–3.43 (m, 5H), 3.60 (m, 2H), 3.73 (d, 1H) 3.80

(s, 3H), 5.95 (s, 2H), 6.74 (d, 1H), 6.80–6.90 (m, 3H), 7.04 (d, 1H), 7.30 (d, 2H).

EXAMPLE 11 trans,trans-2-(4-Methoxyphenyl)-4-(1,3-benzo-dioxol-5-yl)-1-(isobutylaminocarbonylmethyl)-pyrrolidine-3-carboxylic Acid Using the procedures described in Example 1 the title compound was prepared. m.p. 175°–177° C. $^1$H NMR (CD$_3$OD, 300 MHz) δ 0.87 (dd, 6H), 1.75 (septet, 1H), 2.85 (d, 1H), 2.90–3.10 (m, 4H), 3.23 (d, 1H), 3.40 (m, 1H), 3.58–3.67 (m, 1H), 3.78 (s, 3H), 3.89 (d, 1H), 5.92 (s, 2H), 6.76 (d, 1H), 6.86 (dd, 1H), 6.91 (d, 2H), 7.02 (d, 1H), 7.40 (d, 2H).

EXAMPLE 19 trans,trans-2-(4-Methoxyphenyl)-4-(1,3-benzo-dioxol-5-yl)-1-(cyclopentylaminocarbonylmethyl)-pyrrolidine-3-carboxylic Acid Using the procedures described in Example 1 the title compound was prepared. m.p. 137°–139° C. $^1$H NMR (CDCl$_3$, 300 MHz) δ 1.34 (m, 2H), 1.62 (m, 4H), 1.90 (m, 2H), 2.76 (d, 1H), 2.90 (t, 1H), 3.04 (dd, 1H), 3.22 (d, 1H), 3.28 (dd, 1H), 3.40 (m, 1H), 3.80 (s, 3H), 4.15 (m, 1H), 5.97 (d, 2H), 6.75–6.95 (m, 5H), 7.27 (m, 2H).

EXAMPLE 20 trans,trans-2-(4-Methoxyphenyl)-4-(1,3-benzo-dioxol-5-yl)-1-(morpholin-4-ylaminocarbonylmethyl)-pyrrolidine-3-carboxylic Acid Using the procedures described in Example 1 the title compound was prepared as an amorphous solid. $^1$H NMR (CDCl$_3$, 300 MHz) δ 2.82 (d, 1H), 3.00 (m, 2H), 3.24 (m, 1H), 3.30–3.52 (m, 4H), 3.52–3.75 (m, 8H), 3.80 (s, 3H), 5.95 (s, 2H), 6.75 (d, 1H), 6.84 (d, 3H), 7.00 (s, 1H), 7.28 (d, 2H).

EXAMPLE 21 trans,trans-2-(4-Methoxyphenyl)-4-(1,3-benzo-dioxol-5-yl)-1-(2-phenoxyethyl)-pyrrolidine-3-carboxylic Acid Using the procedures described in Example 4 the title compound was prepared as an amorphous solid. $^1$H NMR (CD$_3$OD, 300 MHz) δ 2.82 (m, 1H), 2.96 (dd, 1H), 3.13 (m, 1H), 3.32 (m, 1H), 3.51–3.70 (m, 2H), 3.77 (s, 3H), 4.00 (d, 1H), 4.07 (m, 2H), 5.91 (s, 2H), 6.72 (d, 1H), 6.80–6.95 (m, 6H), 7.03 (d, 1H), 7.22 (dd, 2H), 7.39 (d, 2H).

EXAMPLE 22 trans,trans-2-(4-Methoxyphenyl)-4-(1,3-benzo-dioxol-5-yl)-1-(2-methoxyethylaminocarbonylmethyl)-pyrrolidine-3-carboxylic Acid Using the procedures described in Example 1 the title compound was prepared. m.p. 107°–109° C. $^1$H NMR (CD$_3$OD, 300 MHz) δ 2.82 (d, 1H), 2.97 (q, 2H), 3.21 (d, 1H), 3.38 (m, 1H), 3.32 (s, 3H), 3.44 (m, 4H), 3.62 (m, 1H), 3.79 (s, 3H), 3.86 (d, 1H), 5.93 (s, 2H), 6.76 (d, 1H), 6.85 (dd, 1H), 6.91 (d, 2H), 7.01 (d, 1H), 7.38 (d, 2H).

EXAMPLE 23 trans,trans-2-(4-Methoxyphenyl)-4-(1,3-benzo-dioxol-5-yl)-1-(2-butoxyethyl)-pyrrolidine-3-carboxylic Acid Using the procedures described in Example 4 the title compound was prepared. m.p. 53°–55° C. $^1$H NMR (CDCl$_3$, 300 MHz) δ 0.88 (t, J=7 Hz, 3H), 1.32 (sextet, J=7 Hz, 2H), 1.50 (pentet, J=7 Hz, 2H), 2.27 (tt, J=6 Hz, 6 Hz, 1H), 2.92 (q, J=10 Hz, 2H), 3.35 (t, J=7 Hz, 2H), 3.42–3.56 (m, 4H), 3.68 (d, J=10 Hz), 1H), 3.78 (s, 3H), 5.94 (s, 2H), 6.73 (d, J=8 Hz, 1H), 6.83 (d, J=9 Hz, 2H), 6.82–6.87 (m, 1H), 7.06 (d, J=2 Hz, 1H), 7.32 (d, J=9 Hz, 2H). MS m/e 442 (M+H)$^+$.

EXAMPLE 24 trans,trans-2-(1,3-Benzodioxol-5-yl)-4-(4-methoxyphenyl)-1-(propylaminocarbonylmethyl)-pyrrolidine-3-carboxylic Acid Using the procedures described in Example 1 and substituting ethyl (1,3-benzodioxol-5-ylcarbonyl)acetate for ethyl (4-methoxybenzoyl)acetate and 4-(2-nitrovinyl)anisole for 5-(2-nitrovinyl)-1,3-benzodioxol-5yl afforded the title compound. m.p. 97°–99° C. $^1$H NMR (CDCl$_3$, 300 MHz) δ 0.78 (t, J=7 Hz, 3H), 1.39 (sextet, J=7 Hz, 2H), 2.72 (d, J=16 Hz, 1H), 2.74 (t, J=10 Hz, 1H), 2.80–3.10 (m, 4H), 3.26–3.38 (m, 1H), 3.53 (m, 1H), 3.73 (s, 3H), 3.80 (d, J=10 Hz, 2H), 7.80 (t, J=6 Hz, 1H). MS (DCl/NH$_3$) m/e 441 (M+H)$^+$.

EXAMPLE 25 trans,trans-2-(1,3-Benzodioxol-5-yl)-4-(4-methoxyphenyl)-1-(2-propoxyethyl)-pyrrolidine-3-carboxylic Acid Using the procedures described in Example 5 and substituting ethyl (1,3-benzodioxol-5-ylcarbonyl)acetate for ethyl (4-methoxybenzoyl)acetate and 4-(2-nitrovinyl)anisole for 5-(2-nitrovinyl)-1,3-benzodioxol-5-yl afforded the title compound. m.p. 67°–69° C. $^1$H NMR (CDCl$_3$, 300 MHz) δ 0.89 (t, J=7 Hz, 3H), 1.56 (sextet, J=7 Hz, 2H), 2.33 (m, 1H), 2.78–3.00 (m, 3H), 3.32 (t, J=7 Hz, 2H), 3.45–3.57 (m, 4H), 3.73 (m, 1H), 3.79 (s, 3H), 5.93 (s, 2H), 6.22 (d, J=8 Hz, 1H), 6.85 (d, J=8 Hz, 3H), 6.98 (s, 1H), 7.37 (d, J=8 Hz, 2H). MS (DCl/NH$_3$) m/e 428 (M+H)$^+$.

EXAMPLE 26 trans,trans-2-(1,3-Benzodioxol-5-yl)-4-(4-methoxyphenyl)-1-[2-(2-methoxyethoxy)ethyl)]-pyrrolidine-3-carboxylic Acid Using the procedures described in Example 4 and substituting the starting materials described in Example 25 and using 2-(2-methoxyethoxy)ethylbromide to alkylate the pyrrolidine nitrogen afforded the title compound. m.p. 85°–86° C. $^1$H NMR (CD$_3$OD, 300 MHz) δ 3.18–3.90 (m, 15H), 3.79 (s, 3H), 4.57 (d, J=10 Hz, 1H), 6.02 (s, 2H), 6.91 (d, J=8 Hz, 1H), 6.95 (d, J=9 Hz, 2H), 7.06 (dd, J=8 Hz, 1H), 7.12 (dd, J=1 Hz, 1H), 7.37 (d, J=9 Hz, 2H). MS (DCl/NH$_3$) m/e 444 (M+H)$^+$.

EXAMPLE 27 trans,trans-2-(1,3-Benzodioxol-5-yl)-4-(4-methoxyphenyl)-1-(butoxyethyl)-pyrrolidine-3-carboxylic Acid Using the procedures described in Example 4, substituting the starting materials described in Example 25 and using 2-ethoxyethylbromide to alkylate the pyrrolidine nitrogen afforded the title compound. m.p. 54°–56° C. $^1$H NMR (CDCl$_3$, 300 MHz) δ 0.89 (t, J=7 Hz, 3H), 1.44 (sextet, J=7 Hz, 2H), 1.52 (pentet, J=7 Hz, 2H), 2.40 (m, 1H), 2.74–2.98 (m, 3H), 3.46 (t, J=7 Hz, 2H), 3.42–3.56 (m, 4H), 3.68 (d, J=10 Hz, 1H), 3.80 (s, 3H), 5.93 (dd, J=6 Hz, 1 Hz, 2H), 6.72 (d, J=8 Hz, 1H), 6.74 (dd, J=9 Hz, 3H), 6.96 (s, 1H), 7.36 (d, J=9 Hz, 2H).

EXAMPLE 28 trans,trans-2-(4-Methoxyphenyl)-4-(1,4-benzodioxan-6-yl)-1-(propylaminocarbonylmethyl)-pyrrolidine-3-carboxylic Acid Using the procedures described in Example 1 and substituting 6-(2-nitrovinyl)-1,4-benzodioxane for 5-(2-nitrovinyl)-1,3-benzodioxole afforded the title compound. m.p. 80°–81° C. $^1$H NMR (CDCl$_3$, 300 MHz) δ 0.89 (t, J-7 Hz, 3H), 1.49 (sextet, J=7 Hz, 2H), 2.78 (d, J=16 Hz, 1H), 2.92 (t, J=10 Hz, 1H), 3.05–3.43 (m, 5H), 3.24 (d, J=16 Hz, 1H), 3.52–3.62 (m, 1H), 3.80 (s, 3H), 3.80 (t, J=10 Hz, 1H), 4.27 (s, 4H), 6.74–6.93 (m, 5H), 7.29 (d, J=9 Hz, 2H). MS (DCl/NH$_3$) m/e 455 (M+H)$^+$.

EXAMPLE 29 trans;trans-2-(4-Methoxyphenyl)-4-(1,4-benzodioxan-6-yl)-1-(N-methyl-N-propylaminocarbonylmethyl)-pyrrolidine-3-carboxylic Acid Using the procedures described in Example 1, substituting 6-(2-nitrovinyl)-1,4-benzodioxane for 5-(2-nitrovinyl)-1,3-benzodioxole and alkylating the pyrrolidine nitrogen with N-methyl-N-propyl bromoacetamide afforded the title compound. m.p. 74°–76° C. Rotational isomers are seen in the NMR. $^1$H NMR (CDCl$_3$, 300 MHz) δ 0.73, 0.83 (2t, J=7 Hz, 3H), 1.48 (m, 2H), 2.78 (dd, 1H), 2.85 (2s, 3H), 2.96–3.15 (m, 3H), 3.27–3.42 (m, 3H), 3.52–3.60 (m, 1H), 3.75 (d, 1H), 3.78 (s, 3H), 4.22 (s, 4H), 6.80–6.98 (m, 5H), 7.32 (d, 2H). MS (DCl/NH$_3$) m/e 469 (M+H)$^+$.

EXAMPLE 30 trans,trans-2-(4-Methoxyphenyl)-4-(1,3-benzodioxol-5-yl)-1-(N-methyl-N-butylaminocarbonylmethyl)-pyrrolidine-3-carboxylic Acid Using the procedures described in Example 1, the title compound was prepared. Rotational isomers are seen in the NMR. $^1$H NMR (CD$_3$OD, 300 MHz) δ 0.86 (2t, 3H), 1.04–1.50 (m, 4H), 2.85 (2s, 3H), 2.93–3.20 (m, 4H), 3.40 (m, 2H), 3.52 (dd, 1H), 3.60 (m, 1H), 3.80 (s, 3H), 3.85 (m, 1H), 5.91 (s, 2H), 6.74 (d, 1H), 6.83–6.95 (m, 3H), 7.03 (dd, 1H), 7.35 (dd, 2H).

EXAMPLE 31 trans,trans-2-(4-Methoxy-2-methoxymethoxyphenyl)-4-(1,3-benzodioxol-5-yl)-1-(N-methyl-N-butylaminocarbonylmethyl)-pyrrolidine-3-carboxylic Acid

EXAMPLE 31A

Ethyl 2-(4-methoxy-2-methoxymethoxyphenyl-4-(1, 3-benzodioxol-5-yl)-pyrrolidine-3-carboxylate)

Using the procedures described in Examples 1A and 1B and substituting ethyl (4-methoxy-2-methoxymethoxybenzoyl)acetate for ethyl (4-methoxybenzoyl)acetate afforded ethyl 2-(4-methoxy-2-methoxymethoxyphenyl)-4-(1,3-benzodioxol-5-yl)-4,5-dihydro-3H-pyrrole-3-carboxylate.

The above dihydro pyrrole carboxylate (3.0 g, 7.0 mmol) was dissolved in 20 mL of methanol, treated with 500 mg of 10% Pd/C and placed under hydrogen atmosphere for 32 hours. The catalyst was removed by filtration and the filtrate was concentrated under reduced pressure and chromatographed on silica gel eluting with ethyl acetate to afford the title compound (1.9 g, 63%) as the cis-cis isomer.

EXAMPLE 31B trans,trans-2-(4-Methoxy-2- methoxymethoxyphenyl)-4-(1,3-benzodioxol-5-yl)-1-(N-methyl-N-butylaminocarbonylmethyl)-pyrrolidine-3-carboxylic Acid The compound resulting from Example 31A was epimerized by the procedure described in Example 6A. The resulting trans,trans compound (100 mg, 0.23 mmol) was then reacted by the procedures described in Example 1D substituting N-methyl-N-butyl bromoacetamide for N-propyl bromoacetamide to give the title compound (75 mg, 62%). m.p. 65°–67° C. Rotational isomers are seen in the NMR. $^1$H NMR (CDCl$_3$, 300 MHz) δ 0.64, 0.68 (2t, J=7 Hz, 3H), 1.14, 1.12 (2 sextet, J=7 Hz, 2H), 1.40–1.48 (m, 2H), 2.86, 2.89 (2s, 3H), 2.95–3.42 (m, 6H), 3.50 (s, 3H), 3.43–3.65 (m, 2H), 3.78 (s, 3H), 4.30 (t, J=7 Hz, 1H), 5.09 (q, J=7 Hz, 2H), 5.92 (s, 2H), 6.55 (dd, J=3 Hz, 1H), 6.68 (s, 1H), 6.72 (s, 1H), 6.85 (2t, J=1 Hz, 1H), 7.04 (t, J=1 Hz, 1H), 7.42 (dd, J=3 Hz, 1H).

EXAMPLE 32 trans,trans-2-(4-Methoxyphenyl)-4-(1,3-benzodioxol-5-yl)-1-(3-ethoxypropyl)-pyrrolidin-5-ene-3-carboxylic Acid

EXAMPLE 32A

Ethyl 2-(4-methoxybenzoyl)-3-carbomethoxy-1,3-benzodioxole-5-propionate

To ethyl (4-methoxybenzoyl)acetate (4.44 g, 0.02 mmol) dissolved in 20 mL of anhydrous THF was added in portions 480 mg of NaH. The mixture was stirred for 30 minutes under nitrogen at ambient temperature. Methyl (1,3-benzodioxol-5-yl) bromoacetate (5.46 g, 0.02 tool) in 5 mL of THF was added. The mixture was stirred overnight at ambient temperature, diluted with 200 mL of EtOAc, and washed with water and brine. The organic phase was dried over sodium sulfate and concentrated in vacuo to afford the title compound (7.67 g, 92%) which was used without further purification.

EXAMPLE 32B

Ethyl 1-(3-ethoxypropyl)-2-(4-methoxyphenyl)-4-(1,3-benzodioxol-5-yl)-4,5-dihydro-5-oxo-1H-pyrrole-3-carboxylate A mixture of the compound resulting from Example 32A (700 mg, 1.69 mmol), 3-ethoxypropylamine (348 mg, 3.38 mmol) and 1 mL of acetic acid in a sealed tube was heated for 18 hours at 125° C. After cooling the contents of the tube to ambient temperature, 5 mL of water was added and the mixture extracted with ethyl acetate (2×100 mL). The combined organic extracts were washed with saturated sodium bicarbonate solution, water and brine, dried over sodium sulfate and concentrated under reduced pressure. The residue obtained was chromatographed on silica gel eluting with 3:2 hexane-ethyl acetate to give 330 mg (42%) of the title compound.

EXAMPLE 32C

Ethyl 1-(3-ethoxypropyl)-2-(4-methoxyphenyl)-4-(1,3-benzodioxol-5-yl)-pyrrolidin-5-one-3-carboxylate The compound resulting from Example 32B (300 mg, 0.64 mmol) in 15 mL of methanol was reduced with 100 mg of 10% Pd/C under hydrogen for 3 hours at ambient temperature. The catalyst was removed by filtration and the filtrate was concentrated under reduced pressure to give the title compound.

EXAMPLE 32D trans,trans-2-(4-Methoxyphenyl)-4-(1,3-benzodioxol-5-yl)-1-(3-ethoxypropyl)-pyrrolidin-5-one-3-carboxylic Acid To the compound resulting from Example 32C (100 mg, 0.21 mmol) dissolved in 1 mL of ethanol was added 3 drops of a solution of 21% sodium ethoxide in ethanol. The mixture was heated to 70°–80° C. for 3 hours, and then a solution of sodium hydroxide (100 mg) in 1 mL of water was added and heating was continued for 1 additional hour. The reaction mixture was cooled to ambient temperature, the ethanol was removed under reduced pressure, and water was added to the residue which was washed with ether. The aqueous layer was neutralized with 3M HCl and allowed to stand overnight. The white crystalline solid was collected by filtration to give the title compound (60 mg, 64%). m.p. 134°–140° C. $^1$H NMR (DMSO-$d_6$, 300 MHz) δ 1.04 (t, J=7 Hz, 3H), 1.55 (sextet, J=7 Hz, 2H), 2.48–2.56 (m, 1H), 2.93 (dd, J=9 Hz, 1H), 3.25 (t, J=7 Hz, 2H), 3.28–3.40 (m, 2H), 3.48–3.57 (m, 1H), 3.78 (s, 3H), 3.88 (d, J=10 Hz, 1H), 4.72 (d, J=10 Hz, 1H), 6.02 (s, 2H), 6.74 (dd, J=8 Hz, 1 Hz, 1H), 6.87 (d, J=8 Hz, 2H), 6.98 (d, J=8 Hz, 2H), 7.38 (d, J=8 Hz, 2H). MS (DCl/NH$_3$) m/e 442 (M+H)$^+$.

EXAMPLE 33 trans,trans-2-(4-Methoxyphenyl)-4-(1,3-benzodioxol-5-yl)-1-(3-methoxybenzyl)-pyrrolidin-5-one-3-carboxylic Acid Following the procedures described in Example 32 and substituting 3-methoxybenzylamine for 3-ethoxypropylamine afforded the title compound (123 mg, 65%). m.p. 150°–152° C. $^1$H NMR (CD$_3$OD, 300 MHz) δ 2.96 (dd, J=8 Hz, 10 Hz, 1H), 3.72 (s, 3H), 3.80 (s, 3H), 4.06 (d, J=10 Hz, 1H), 4.58 (d, J=8 Hz, 1H), 4.92 (q, J=16 Hz, 2H), 5.92 (s, 2H), 6.55–6.63 (m, 2H), 6.82 (d, J=8 Hz, 4H), 6.94 (d, J=8 Hz, 2H), 7.15–7.22 (m, 3H). MS (DCl/NH$_3$) m/e 475 (M+H)$^+$.

EXAMPLE 34 trans,trans-2-(4-Methoxyphenyl)-4-(1,3-benzodioxol-5-yl)-1-(N,N-diisoamylaminocarbonylmethyl)-pyrrolidine-3carboxylic Acid The title compound was prepared as an amorphous solid using the procedures described in Example 1. $^1$H NMR (CDCl$_3$, 300 MHz) δ 0.70–0.90 (m, 12H), 1.10–1.60 (m, 10H), 2.75 (d, J=13 Hz, 1H), 2.90–3.10 (m, 4H), 3.15–3.30 (m, 2H), 3.40 (d, J=10 Hz, 1H), 3.40–3.52 (m, 2H), 3.55–3.62 (m, 1H), 3.75 (d, J=12 Hz, 1H), 3.79 (s, 3H), 5.93 (dd, J=1 Hz, 3 Hz, 2H), 6.72 (d, J=8 Hz, 1H), 6.82–6.90 (m, 3H), 7.03 (d, J=2 Hz, 1H), 7.30 (d, J=9 Hz, 2H).

EXAMPLE 35 trans,trans-2-(4-Methoxyphenyl)-4-(1,3-benzodioxol-5-yl)-1-(N,N-dipentylaminocarbonylmethyl)-pyrrolidine-3-carboxylic Acid The title compound was prepared as an amorphous solid using the procedures described in Example 1. $^1$H NMR (CDCl$_3$, 300 MHz) δ 0.82 (t, J=7 Hz, 6H), 0.95–1.03 (m, 2H), 1.10–1.30 (m, 8H), 1.40–1.51 (m, 2H), 2.72 (d, J=13 Hz, 1H), 2.90–3.08 (m, 4H), 3.25–3.50 (m, 3H), 3.37 (d, J=13 Hz, 1H), 3.52–3.60 (m, 1H), 3.70 (j (?), J=10 Hz, 1H), 3.75 (s, 3H), 5.92 (dd, J=2 Hz, 5 Hz, 2H), 6.72 (d, J=8 Hz, 1H), 6.80–6.88 (m, 3H), 7.03 (d, J=2 Hz, 1H), 7.30 (d, J=9 Hz, 2H).

EXAMPLE 36 trans,trans-2-(4-Methoxyphenyl)-4-(1,3-benzodioxol-5-yl)-1-(N,N-di(2-methoxyethyl)aminocarbonylmethyl)-pyrrolidine-3-carboxylic Acid The title compound was prepared using the procedures described in Example 1. m.p. 120°–122° C. $^1$H NMR (CDCl$_3$, 300 MHz) δ 2.82 (d, J=13, 1H), 2.94–3.08 (m, 2H), 3.12 (s, 3H), 3.23 (s, 3H), 3.20–3.70 (m, 11H), 3.73 (d, J=10 Hz, 1H), 3.79 (s, 3H), 5.92 (dd, J=2 Hz, 2 Hz, 2H), 6.72 (d, J=8 Hz, 1H), 6.80–6.90 (m, 3H), 7.04 (d, J=2 Hz, 1H), 7.30 (d, J=9 Hz, 2H).

EXAMPLE 37 trans,trans-2-(4-Methoxyphenyl)-4-(1,3-benzodioxol-5-yl)-1-(2-hexynyl)-pyrrolidine-3-carboxylic Acid Using the procedures described in Example 4, 200 mg. of the pure trans,trans isomer, the compound resulting from Example 6A was reacted with 109 mg of 1-bromo-2-hexyne, prepared by the method described in Perkin I,, 2004 (1987), for 1 hour at 55° C., to give 226 mg of the intermediate ester. The ester was hydrolyzed using NaOH in ethanol-water for 3 hours at room temperature to give 175 mg of the title compound. $^1$H NMR (CDCl$_3$, 300 MHz) δ 1.00 (t, J=7 Hz, 3H), 1.54 (m, 2H), 2.14–2.22 (m, 2H), 2.96 (dd, J=7 Hz, 13 Hz, 1H), 3.07 (dd, J=18 Hz, 2 Hz, 1H), 3.15 (dd, J=9 Hz, 2 Hz, 1H), 3.26 (t, J=9 Hz, 1H), 3.36 (dd, J=18 Hz, 2 Hz, 1H), 3.47–3.55 (m, 1H), 3.79 (s, 3H), 3.88 (d, J=9 Hz, 1H), 5.95

(s, 2H), 6.72 (d, J=8 Hz, 1H), 6.80–6.88 (m, 3H), 7.03 (d, J=2 Hz, 1H), 7.22 (d, J=9 Hz, 2H).

EXAMPLE 38 trans,trans-2-(4-Methoxyphenyl)-4-(1,3-benzo-dioxol-5-yl)-1-(N-cyclopropylmethyl-N-propylaminocarbonylmethyl)-pyrrolidine-3-carboxylic Acid The title compound was prepared using the procedures described in Example 1. m.p. 167°–169° C. Rotational isomers were seen in the NMR. $^1$H NMR (CDCl$_3$, 300 MHz) δ −0.1 (m), 0.05 (m), 0.12–0.25 (m), 0.32–0.51 (m), 0.67 and 0.74 (2 triplets, 3H), 0.90–1.00 (m), 1.20–1.55 (m), 2.72 (d, J=13 Hz, 1H), 2.85–3.29 (m, 4H), 3.30–3.50 (m, 3H), 3.52–3.62 (m, 1H), 3.65–3.73 (2 doublets, J=10 Hz, 2 Hz, 1H), 3.78 (s, 3H), 5.95 (2 singlets, 2H), 6.72 (2 doublets, 2H), 6.80–6.90 (m, 3H), 7.00 and 7.05 (2 doublets, J=9 Hz, 2H).

EXAMPLE 39 trans,trans-2-(4-Methoxyphenyl)-4-(1,3-benzo-dioxol-5-yl)-1-(N-methyl-N-pentylaminocarbonylmethyl)-pyrrolidine-3-carboxylic Acid The title compound was prepared as an amorphous solid using the procedures described in Example 1. Rotational isomers were seen in the NMR. $^1$H NMR (CDCl$_3$, 300 MHz) δ 0.85 (t, J=7 Hz, 3H), 1.00–1.08 (m), 1.13–1.32 (m), 1.35–1.50 (m), 2.72–2.82 (2 doublets, J=13 Hz, 1H), 2.83 and 2.86 (2 singlets, 3H), 2.92–3.20 (m, 3H), 3.22–3.45 (m, 3H), 3.52–3.62 (m, 1H), 3.72 (2 doublets, 1H), 3.75 and 3.76 (2 singlets, 3H), 5.92 (2 singlets, 2H), 6.72 (d, J=8 Hz, 1H), 6.80–6.87 (m, 3H), 7.03 (2 doublets, J=2 Hz, 1H), 7.30 (d, J=9 Hz, 2H).

EXAMPLE 40 trans,trans-2-(4-Methoxyphenyl)-4-(1,3-benzo-dioxol-5-yl)-1-(N,N-diisobutylaminocarbonylmethyl)-pyrrolidine-3-carboxylic Acid The title compound was prepared using the procedures described in Example 1. m.p. 141°–143° C. $^1$H NMR (CDCl$_3$, 300 MHz) δ 0.54 (d, J=7 Hz, 3H), 0.70–0.90 (3 doublets, J=7 Hz, 9H), 1.60–1.75 (m, 1H), 1.90–2.02 (m, 1H), 2.67 (d, J=13 Hz, 1H), 2.70 (d, J=13 Hz, 1H), 2.84 (dd, J=6 Hz, 15 Hz, 1H), 296–3.06 (m, 2H), 3.20 (dd, J=9 Hz, 15 Hz, 1H), 3.35 (dd, J=2 Hz, 10 Hz, 1H), 3.44–3.60 (m, 4H), 3.70 (d, J=9 Hz, 1H), 3.79 (s, 3H), 5.94 (dd, J=2 Hz, 2 Hz, 2H), 6.72 (d, J=9 Hz, 1H), 6.82–6.90 (m, 3H), 7.03 (d, J=2 Hz, 1H), 7.31 (d, J=9 Hz, 2H).

EXAMPLE 41 trans,trans-2-(4-Methoxyphenyl)-4-(1,3-benzo-dioxol-5-yl)-1-(N-methyl-N-(2-propynyl)aminocarbonylmethyl)-pyrrolidine-3-carboxylic Acid The title compound was prepared as an amorphous solid using the procedures described in Example 1. Rotational isomers were seen in the NMR. $^1$H NMR (CDCl$_3$, 300 MHz) δ 2.09 and 2.32 (2 triplets, J=2 Hz, 1H), 2.80–3.10 (m, 3H), 2.90 and 2.99 (2 singlets, 3H), 3.35–3.50 (m, 2H), 3.52–3.62 (m, 1H), 3.78 (s, 3H), 4.03 (d, J=13 Hz, 1H), 4.00–4.30 (m, 3H), 5.93 (s, 2H), 6.72 (2 doublets, J=8 Hz, 1H), 6.80–6.90 (m, 3H), 7.02 and 7.11 (2 doublets, J=2 Hz, 1H), 7.30 (2 doublets, J=9 Hz, 2H).

EXAMPLE 42 trans,trans-2-(4-Methoxyphenyl)-4-(1,3-benzo-dioxol-5-yl)-1-(N-methyl-N-(n-hexyl)aminocarbonylmethyl)-pyrrolidine-3-carboxylic Acid The title compound was prepared as an amorphous solid using the procedures described in Example 1. $^1$H NMR (CDCl$_3$, 300 MHz) δ 0.85 (2 triplets, J=7 Hz, 3H), 1.00–1.50 (m, 8H), 2.72–2.82 (2 doublets, J=13 Hz, 1H), 2.81 and 2.86 (2 singlets, 3H), 2.92–3.20 (m, 3H), 3.22–3.45 (m, 3H), 3.52–3.62 (m, 1H), 3.72 (2 doublets, 1H), 3.75 and 3.76 (2 singlets 3H), 5.94 (2 singlets, 2H), 6.72 (d, J=8 Hz, 1H), 6.80–6.87 (m, 3H), 7.03 (2 doublets, J=2 Hz, 1H), 7.30 (d, J=9 Hz, 1H).

EXAMPLE 43 trans,trans-2-(4-Methoxyphenyl)-4-(1,3-benzo-dioxol-5-yl)-1-(N,N-di(n-butyl)aminocarbonylmethyl)-pyrrolidine-3-carboxylic Acid The title compound was prepared using the procedures described in Example 1. m.p. 123°–125° C. $^1$H NMR (CDCl$_3$, 300 MHz) δ 0.79 (t, J=7 Hz, 3H), 0.85 (t, J=7 Hz, 3H), 1.00–1.50 (m, 8H), 2.74 (d, J=13 Hz, 1H), 2.90–3.09 (m, 4H), 3.23–3.50 (m, 3H), 3.38 (d, J=13 Hz, 1H), 3.52–3.62 (m, 1H), 3.75 (d, J=10 Hz, 1H), 3.78 (s, 3H), 5.93 (dd, J=2 Hz, 4 Hz), 6.71 (d, J=8 Hz, 1H), 6.81–6.89 (m, 3H), 7.03 (d, J=2 Hz, 1H), 7.30 (d, J=9 Hz, 2H). MS (DCl/NH$_3$) m/e 511 (M+H)$^+$.

Anal calcd for C$_{29}$H$_{38}$N$_2$O$_6$: C, 68.21; H, 7.50; N, 5.49. Found: C, 68.07; H, 7.47; N, 5.40.

EXAMPLE 44 trans,trans-2-(4-Methoxyphenyl)-4-(1,3-benzo-dioxol-5-yl)-1-(N,N-diethylaminocarbonylmethyl)-pyrrolidine-3-carboxylic Acid The title compound was prepared using the procedures described in Example 1. m.p. 132°–134° C. $^1$H NMR (CDCl$_3$, 300 MHz) δ 0.98 (t, J=7 Hz, 3H), 1.06 (t, J=7 Hz, 3H), 2.78 (d, J=13 Hz, 1H), 2.95–3.20 (m, 4H), 3.30–350 (m, 4H), 3.55–3.65 (m, 1H), 3.76 (d, J=12 Hz, 1H), 3.79 (s, 3H), 5.93 (s, 2H), 6.72 (d, J=8 Hz, 1H), 6.80–6.90 (m, 3H), 7.02 (d, J=2 Hz, 1H), 7.32 (d, J=9 Hz, 2H).

EXAMPLE 45 trans,trans-2-(4-Methoxyphenyl)-4-(1,3-benzo-dioxol-5-yl)-1-(N-methyl-N-phenylaminocarbonylmethyl)-pyrrolidine-3-carboxylic Acid The title compound was prepared as an amorphous solid using the procedures described in Example 1. $^1$H NMR (CD$_3$OD, 300 MHz) δ 2.75–2.85 (m, 2H), 3.05–3.13 (m, 1H), 3.18 (s, 3H), 3.40–3.58 (m, 2H), 3.78 (s, 3H), 3.88 (d, J=12 Hz, 1H), 5.92 (s, 2H), 6.72 (d, J=8 Hz, 1H), 6.75–6.85 (m, 3H), 7.00–7.12 (m, 5H), 7.82–7.92 (m, 3H).

EXAMPLE 46 trans,trans-2-(4-Methoxyphenyl)-4-(1,3-benzo-dioxol-5-yl)-1-(N-methyl-N-cyclohexylaminocarbonylmethyl)-pyrrolidine-3-carboxylic Acid The title compound was prepared as an amorphous solid using the procedures described in Example 1. Rotational isomers were seen in the NMR. $^1$H NMR (CD$_3$OD, 300 MHz) δ 1.00–1.85 (m, 10H), 2.72 and 2.78 (2 singlets, 3H), 2.75–2.82 (2 doublets, J=22 Hz, 1H), 2.96–3.22 (m, 3H), 3.40–3.65 (m, 3H), 3.68 and 3.82 (2 doublets, J=10 Hz, 1H), 3.77 and 3.78 (2 singlets, 3H), 5.92 (s, 2H), 6.72 (2 doublets, J=8 Hz, 1H), 6.82–6.88 (m, 3H), 7.02 (2 doublets, J=2 Hz, 1H), 7.30–7.40 (2 doublets, J=9 Hz, 2H).

EXAMPLE 47 trans,trans-2-(4-Methoxyphenyl)-4-(1,3-benzo-dioxol-5-yl)-1-(N,N-di(n-propyl)aminocarbonylmethyl)-pyrrolidine-3-carboxylic Acid The title compound was prepared using the procedures described in Example 1. m.p. 170°–172° C. $^1$H NMR (CDCl$_3$, 300 MHz) δ 0.69 (t, J=7 Hz, 3H), 0.85 (t, J=7 Hz, 3H), 1.20–1.55 (m, 4H), 2.72 (d, J=13 Hz, 1H), 2.90–3.10 (m, 4H), 3.25–3.47 (m, 4H), 3.35–3.62 (m, 1H), 3.72 (d, J=9 Hz, 1H), 3.79 (s, 3H), 5.94 (s, 2H), 6.72 (d, d, J=8 Hz, 1H), 6.80–6.90 (m, 3H), 7.02 (d, J=2 Hz, 1H), 7.30 (d, J=9 Hz, 2H).

EXAMPLE 48 trans,trans-2-(4-Methoxyphenyl)-4-(1,3-benzo-dioxol-5-yl)-1-(N-methyl-N-isobutylaminocarbonylmethyl)-pyrrolidine-3-carboxylic Acid The title compound was prepared as an amorphous solid using the procedures described in Example 1. Rotational isomers were seen in the NMR. $^1$H NMR (CD$_3$OD, 300 MHz) δ 0.65–0.85 (4 doublets, J=7 Hz, 6H), 1.75–1.95 (m, 1H), 2.80 and 2.90 (2 singlets, 3H), 2.90–3.10 (m, 4H), 3.10–3.65 (m, 4H), 3.74 9S, 3H), 3.81 and 3.88 (2 doublets, J=10 Hz, 1 H), 5.93 (s, 2H), 6.72 (d, J=8 Hz, 1H), 6.80–6.90 (m, 3H), 7.02 (2 doublets, J=2 Hz, 1H), 7.80–7.90 (2 doublets, J=9 Hz, 2H).

EXAMPLE 49

Alternate Preparation Of Ethyl 2-(4-methoxybenzoyl)-4-nitromethyl-3-(1,3-benzodioxole-5-yl)butyrate

EXAMPLE 49A

E-2-(3,4-Methylenedioxyphenyl)-1-nitroethene

To a stirred solution of piperonal (75 g, 500 mmol) in methanol (120 mL) at 10° C. was added nitromethane (27.1 mL, 500 mmol, 1 eq) followed by the dropwise addition of sodium hydroxide (21 g, 525 mmol, 1.05 eq) in sufficient water to achieve a total volume of 50 mL while maintaining the temperature between 10°–15° C. The reaction mixture became cloudy, turning to a thick paste. The mixture was stirred for 30 minutes upon completion of the addition, and the mixture was then diluted with ice-water (~350 mL) maintaining the temperature below 5° C., until solution was achieved. The resultant solution was poured in a narrow stream (such that it just failed to break into drops) into a rapidly stirred solution of 36% hydrochloric acid (100 mL) in water (150 mL). A yellow solid precipitated (nitrostyrene), and this was collected by filtration, washed with water (1.5 L) until the filtrate was neutral. The filter cake was air dried and then recrystallized from hot ethanol (3 L) to yield E-2-(3,4-methylenedioxy)-nitrostyrene as yellow needles (53 g, 55%). $^1$H NMR (300 MHz, CDCl$_3$) δ 7.94 (1 H, d, J=13.5 Hz), 7.47 (1 H, d, J=13.5 Hz), 7.09 (1H, dd, J=7.5&2 Hz), 7.01 (1 H, d, J2 Hz), 6.87 (1H, d, J=7.5 Hz), 6.06 (2H, s). MS (DCl/NH$_3$) m/e 194 (M+H)$^+$, 211 (M+H+NH$_3$)$^+$.

EXAMPLE 49B

Ethyl 2-(4-methoxyphenyl)oxo-4-nitro-3-(3,4-methylenedioxyohenyl)butyrate

To a stirred solution of the nitrostyrene resulting from Example 49A (14.17 g, 73.34 mmol, 1.2 eq) in a mixture of propan-2-ol (75 mL) and tetrahydrofuran (175 mL) at room temperature was added successively a solution of ethyl (4-methoxybenzoyl)acetate (11.5 g, 51.7 mmol) in THF (50 mL) followed by 1,8-diazabicyclo[5,4,0]undec-7-ene (DBU) (0.45 mL, 3.0 mmol, 0.05 eq). The resultant mixture was stirred at room temperature for 1 hour, then additional DBU (0.45 mL, 3.0 mmol, 0.05 eq) was added. The mixture was stirred a further 1 hour, then the volatiles were removed in vacuo and the residue purified by flash chromatography on 500 g silica gel, eluting with 20% ethyl acetate-hexanes changing to 25% ethyl acetate-hexanes as the product eluted. The solvents were removed in vacuo to yield the nitroketoester (19.36, g, 76%) as a viscous oil. Diastereomers were seen in the NMR. $^1$H NMR (300 MHz, CDCl$_3$,) δ 8.06 (2H, d, J=9 Hz), 7.89 (2H, d, J=9 Hz), 6.96 (2H, d, J=9H), 6.91 (2H, d, J=9 Hz), 6.77 (1H, dd, J=9 Hz,3 Hz), 6.73 (1H, d, J=9 Hz), 6.65 (1H, d, J=3 Hz), 5.95 (2H, s), 5.89 (1H, d, J=4 Hz), 5.88 (1H, d, J=4 Hz), 4.90–4.60 (3H, m), 4.39 (1H, m), 4.18 (2H, q, J=7 Hz), 3.94 (2H, m), 3.80 (3H, s), 3.78 (3H, s), 1.19 (3H, t, J=7 Hz), 0.99 (3H, t, J=7 Hz), MS (DCl/NH$_3$) m/e 416 (M+H)$^+$, 433 (M+H+NH$_3$)$^+$.

EXAMPLE 50 trans,trans-2-(4-Methoxyphenyl)-4-(1,3-benzo-dioxol-5-yl)-1-(t-butyloxycarbonylmethyl)-pyrrolidine-3-carboxylic Acid To a stirred solution of the compound resulting from Example 1C (100 mg, 0.27 mmol) in acetonitrile (2 mL) was added successively diisopropylethylamine (70 μL, 0.40 mmol, 1.5 eq) and t-butyl bromoacetate (48 μL, 0.29 mmol, 1.1 eq). The mixture was stirred 2 hours, then the solvent was removed in vacuo to yield the crude diester. To a stirred solution of the diester in ethanol (1 mL) at room temperature was added 50% w/w sodium hydroxide (300 mg, 3.75 mmol) in water. The mixture was stirred 2 hours, then the volatiles were removed in vacuo. The residue was dissolved in water (5 mL), and the solution was washed with ether. The aqueous phase was acidified with acetic acid (300 μL), and then extracted with ethyl acetate (2x). The combined organic extracts were dried (Na$_2$SO$_4$), filtered, and concentrated to yield the title compound (74 mg, 60%) as a white solid. $^1$H NMR (300 MHz, CDCl$_3$) δ 7.36 (2H, d, J=8 Hz), 7.13 (1H, d, J=3 Hz), 6.90(1H, dt, J=3 Hz, 8 Hz), 6.88 (2H, d, J=8 Hz), 6.76 (1H, d, J=8 Hz), 5.96 (2H, s), 3.96 (1H, d, J=9 Hz), 3.81 (3H, s), 3.58 (1H, ddd, J=12, 10 Hz,3 Hz), 3.52 (1H, dd, J=9 Hz,3 Hz), 3.32 (1H, d, J=17 Hz), 3.08 (1H, t, J=10 Hz), 2.92 (1H, dd, J=9 Hz,7 Hz), 2.83 (1H, d, J=17 Hz). MS (DCl/NH$_3$) m/e 456 (M+H)$^+$.

Anal calc for $C_{29}H_{29}NO_7 \cdot 0.3 H_2O$: C, 65.07; H, 6.48; N, 3.04. Found: C, 65.02; H, 6.42; N, 2.93.

EXAMPLE 51 trans,trans-2-(4-Methoxyphenyl)-4-(1-naphthyl)-1-(N-methyl-N-propyl)aminocarbonylmethyl)-pyrrolidine-3-carboxylic Acid The title compound was prepared by the procedures described in Examples 1 and 49 substituting naphthalene-1-carboxaldehyde for piperonal in Example 49A. Rotational isomers are seen in the NMR. $^1$H NMR (300 MHz, CDCl$_3$) δ 8.29 (1H, bd, J=8 Hz), 7.86 (2H, d, J=8 Hz), 7.75 (1H, d, J=8 Hz), 7.49 (3H, m), 7.34 (2H, dd, J=3 Hz,9 Hz), 6.83 (2H, dd, J=9 Hz,2 Hz), 4.50 (1H, m), 3.94 (1H, dd, J=9 Hz,2 Hz), 3.78 (3H, s), 3.65 (1H, m), 3.49 (1H, d, J=14 Hz), 3.40–2.93 (5H, m), 2.91, 2.83 (3H, s), 1.48 (2H, sept, J=7 Hz), 0.83, 0.77 (3H, t, J=7 Hz). MS (DCl/NH$_3$) m/e 461 (M+H)$^+$.

Anal calcd for $C_{29}H_{29}NO_7 \cdot 0.5$ HOAc: C, 71.00; H, 6.99; N, 5.71. Found: C, 70.95; H, 7.00; N, 5.46.

EXAMPLE 52 trans,trans-2-(4-Methoxyphenyl)-4-(2,3-dihydrobenzofuran-5-yl)-1-(N-methyl-N-propyl) aminocarbonylmethyl)-pyrrolidine-3-carboxylic Acid

EXAMPLE 52A

2,3-Dihydrobenzofuran-5-carboxaldehyde

To a stirred solution of α,α-dichloromethyl methyl ether (2.15 g, 19 mmol, 1.35 eq) in methylene chloride (30 mL) at –40° C. was added successively stannic chloride (1.65 g, 17 mmol, 1.2 eq) and 15 minutes later, a solution of 2,3-dihydrobenzofuran (1.68 g, 14 mmol) in CH$_2$Cl$_2$ (5 mL) maintaining the temperature at or below –35° C. The mixture was warmed to 0° C., stirred 1 hour, then poured into ice-water, and stirred a further 30 minutes. The mixture was diluted with ether, and the phases separated. The organic phase was concentrated in vacuo, and the residue purified by vacuum distillation to yield the title compound (1.25 g, 60%) as a colorless liquid. b.p. 119°–121° C. at 0.3 mm Hg.

EXAMPLE 52B trans,trans-2-(4-Methoxyphenyl)-4-(2,3-dihydrobenzofuran-5-yl)-1-(N-methyl-N-propyl)aminocarbonylmethyl)-pyrrolidine-3-carboxylic Acid The title compound was prepared by the procedures described in Examples 1 and 49 substituting the compound resulting from Example 52A for piperonal in Example 49A. Rotational isomers are seen in the NMR. $^1$H NMR (300 MHz, CDCl$_3$) δ 7.33 (1H, d, J=8 Hz), 7.28 (1H, m), 7.19 (1H, m), 6.87 (1H, d, J=8 Hz), 6.73 (1H, d, J=8 Hz), 4.56 (1H, t, J=8 Hz), 3.83 (1H, d, J=10 Hz), 3.80 (3H, s), 3.63 (1H, m), 3.4–3.0 (9H, m), 2.87, 2.84 (3H, s), 1.51 (2H, septet, J=7 Hz), 0.88, 0.78 (3H, t, J=7 Hz). MS (DCl/NH$_3$) m/e 453 (M+H)$^+$.

Anal calc for $C_{26}H_{32}N_2O_5 \cdot 0.25 H_2O$: C, 68.33; H, 7.17; N, 6.13. Found: C, 68.60; H, 6.88; N, 5.80.

EXAMPLE 53 trans,trans-2,4-Bis(4-methoxyphenyl)-1-(N-methyl-N-propyl)aminocarbonylmethyl)-pyrrolidine-3-carboxylic Acid The title compound was prepared by the procedures described in Examples 1 and 49 substituting 4-methoxybenzaldehyde for piperonal in Example 49A. Rotational isomers are seen in the NMR. $^1$H NMR (300 MHz, CDCl$_3$) δ 7.37 (2H, d, J=7.5 Hz), 7.32 (2H, d, J=7.5 Hz), 6.86 (4H, m), 3.83 (1H, m), 3.81 (3H, s), 3.79 (3H, s), 3.64 (1H, m), 3.48–2.97 (6H, m), 2.87, 2.83 (3H, s), 2.85 (1H, m), 1.45 (2H, m), 0.84, 0.74 (3H, t, J=7.5 Hz). MS (DCl/NH$_3$) m/e 441 (M+H)$^+$.

Anal calc for $C_{25}H_{32}N_2O_5 \cdot 0.5 H_2O$: C, 66.80; H, 7.40; N, 6.23. Found: C, 67.15; H, 7.31; N, 6.00.

EXAMPLE 54 trans,trans-2-(4-Methoxyphenyl)-4-(3,4-dimethoxyphenyl)-1-(N-methyl-N-propyl)aminocarbonylmethyl)-pyrrolidine-3-carboxylic Acid The title compound was prepared by the procedures described in Examples 1 and 49 substituting 3,4-dimethoxybenzaldehyde for piperonal in Example 49A. Rotational isomers are seen in the NMR. $^1$H NMR (300 MHz, CDCl$_3$) δ 7.33 (2H, d, J=7.5 Hz), 7.07 (1H, d, J=2.0 Hz), 6.98 (1H, m), 6.85 (1H, d, 7.5 Hz), 6.82 (2H, d, 7.5 Hz), 3.91 (3H, s), 3.86 (3H, s), 3.83 (1H, m), 3.79 (3H, s), 3.64 (1H, m), 3.50–2.95 (6H, m), 2.87 (1H, m), 2.85, 2.83 (3H, s), 1.45 (2H, m), 0.84, 0.74 (3H, t, J=7.5 Hz). MS (DCl/NH$_3$) m/e 471 (M+H)$^+$.

Anal calc for $C_{26}H_{34}N_2O_6 \cdot 0.5 H_2O$: C, 65.12; H, 7.36; N, 5.84. Found: C, 65.22; H, 7.27; N, 5.59.

EXAMPLE 55 trans,trans-2-(4-Methoxyphenyl)-4-(3-methoxyphenyl)-1-(N-methyl-N-propyl)aminocarbonylmethyl)-pyrrolidine-3-carboxylic Acid The title compound was prepared by the procedures described in Examples 1 and 49 substituting 3-methoxybenzaldehyde for piperonal in Example 49A. Rotational isomers are seen in the NMR. $^1$H NMR (300 MHz, CDCl$_3$) δ 7.33 (2H, d, J=7.5 Hz), 7.24 (1H, t, J=7.5 Hz), 7.05 (2H, m), 6.85 (2H, dd, J7.5&2 Hz), 6.76 (1H, m), 3.83 (1H, m), 3.81 (3H, s), 3.79 (3H, s), 3.64 (1H, m), 3.48–2.97 (6H, m), 2.87, 2.83 (3H, s), 2.85 (1H, m), 1.45 (2H, m), 0.84, 0.74 (3H, t, J=7.5 Hz). MS (DCl/NH$_3$) m/e 441 (M+H)$^+$.

Anal calc for $C_{25}H_{32}N_2O_5 \cdot 0.5 H_2O$: C, 66.80; H, 7.40; N, 6.23. Found: C, 66.76; H, 7.36; N, 6.05.

EXAMPLE 56 trans,trans-2-(4-Methoxyphenyl)-4-(2-naphthyl)-1-(N-methyl-N-propyl)aminocarbonylmethyl)-pyrrolidine-3-carboxylic Acid The title compound was prepared by the procedures described in Examples 1 and 49 substituting naphthylene-2-carboxaldehyde for piperonal in Example 49A. Rotational isomers are seen in the NMR. $^1$H NMR (300 MHz, CDCl$_3$) δ 7.82 (4H, m), 7.69 (1H, m), 7.47 (2H, m), 7.37 (2H, dd, J=7.5&2 Hz), 6.85 (2H, dd, J=7.5&2 Hz), 3.90 (1H, d, J=8 Hz), 3.78 (3H, s), 3.57 (1H, m), 3.52–2.97 (6H, m), 2.93, 2.85 (3H, s), 2.90 (1H, m), 1.52 (2H, m), 0.86, 0.76 (3H, t, J=7.5 Hz). MS (DCl/NH$_3$) m/e 461 (M+H)$^+$.

Anal calc for C$_{28}$H$_{32}$N$_2$O$_4$·0.5H$_2$O: C, 71.62; H, 7.08; N, 5.97. Found: C, 71.58; H, 7.11; N, 6.01.

EXAMPLE 57 trans,trans-2-(4-Methoxyphenyl)-4-(1,3-benzo-dioxol-5-yl)-1-(2-(ethylsulfinyl)ethyl)-pyrrolidine-3-carboxylic Acid To the compound resulting from Example 1C (100 mg, 0.27 mmol) and 2-chloroethyl ethyl sulfide (67.5 mg, 0.5 mmol, 2 equivalents) dissolved in 6 mL of acetonitrile was added 10 mg of KI and 0.5 mL of diisopropylethylamine. The mixture was refluxed for 4 hours and then concentrated in vacuo. The residue obtained was purified by flash chromatography on silica gel eluting with 4:1 hexane-ethyl acetate to afford 93 mg (75%) of the ethylthioethyl compound.

To the sulfide (90 mg, 0.2 mmol) dissolved in 5 mL of CH$_2$Cl$_2$ in an ice bath was added 68 mg of 3-chloroperoxybenzoic acid. The mixture was stirred for 40 minutes in the ice bath and for 3 hours at room temperature. A 10% solution of sodium hydroxide (2 mL) was added, and the mixture was extracted with EtOAc (2×50 mL). The combined organic extracts were washed with water and brine, dried over sodium sulfate and concentrated in vacuo. The residue obtained was chromatographed on silica gel eluting with EtOAc and 10% MeOH in CH$_2$Cl$_2$ to afford the sulfoxide (62 mg, 65%).

The ethyl ester was hydrolyzed by the procedure described in Example 1D to afford the title compound as a diastereomeric mixture. m.p. 61°–63° C. MS (DCl/NH$_3$) m/e 446 (M+H)$^+$. $^1$H NMR (CDCl$_3$, 300 MHz) δ 1.25, 1.32 (t, J=9 Hz, 3H), 2.45–2.75 (m, 4H), 2.84–2.96 (m, 3H), 3.02–3.08 (m, 1H), 3.32, 336 (d, J=3 Hz, 1H), 3.47–3.58 (m, 2H), 3.65, 3.68 (d, J=7.5 Hz, 1H), 3.76, 3.80 (s, 3H), 5.94 (s, 2H), 6.72 (d, J=7.5 Hz, 1H), 3.84–3.89 (m, 3H), 7.02 (d, J=6 Hz, 1H), 7.30, 7.34 (d, J=7.5 Hz, 2H).

EXAMPLE 58 trans,trans-2-(4-Methoxyphenyl)-4-(1,3-benzo-dioxol-5-yl)-1-(2-(isopropylsulfonylamino)ethyl)-pyrrolidine-3-carboxylic Acid To 2-bromoethylamine hydrobromide (1 mmol) suspended in anhydrous CH$_3$CN was added 1 equivalent of Et$_3$N. The mixture was stirred for 30 minutes and then 1 equivalent of isopropyl sulfonyl chloride and 1 equivalent of Et$_3$N were added. The resulting mixture was stirred for 2 hours at room temperature and then added to a solution of the compound resulting from Example 1C (185 mg, 0.5 mmol) in 3 mL of CH$_3$CN. The mixture was warmed at 50°–60° C. for 2 hours, cooled to room temperature, treated with water and extracted with EtOAc. The combined organic extracts were washed with water and brine, dried and concentrated in vacuo. The residue obtained was chromatographed on silica gel eluting with 3:2 hexane-EtOAc to give 195 mg (75%) of the ethyl ester. The ethyl ester (160 mg, 0.31 mmol) was hydrolyzed by the procedure described in Example 1D to afford the title compound (133 mg, 88%). m.p. 94°–96° C. $^1$H NMR (CD$_3$OD, 300 MHz) δ 1.26 (d, J=6 Hz, 6H), 1.97 (s, 1H), 2.38 (m, 1H), 2.77 (m, 1H), 2.88 (t, J=9 Hz, 1H), 3.04 (m, 1H), 3.14 (t, J=7.5 Hz, 2H), 3.35 (m, 2H), 3.46 (m, 1H), 3.58 (m, 1H), 3.78 (s, 3H), 5.92 (s, 2H), 6.74 (d, J=9 Hz, 1H), 6.86 (dd, J=9 Hz,3 Hz, 1H), 6.92 (d, J=9 Hz, 2H), 7.00 (d, J=3 Hz, 1H), 7.36 (d, J=9 Hz, 2H). MS (DCl/NH$_3$) m/e (M+H)$^+$.

EXAMPLE 59 trans,trans-2-(4-Methoxyphenyl)-4-(1,3-benzo-dioxol-5-yl)-1-(2-(isobutoxy)ethyl)-pyrrolidine-3-carboxylic Acid The title compound was prepared by the procedures described in Example 1D from the compound resulting from Example 1C and 2-(isobutoxy)ethyl bromide. m.p. 68°–70° C. $^1$H NMR (CDCl$_3$, 300 MHz) δ 0.88 (d, J=6 Hz, 6H), 1.82 (quintet, J=6 Hz, 1H), 2.22 (m, 2H), 2.72–2.79 (m, 1H), 2.86 –2.95 (m, 2H), 3.13 (d, J=6 Hz, 2H), 3.45–3.56 (m, 4H), 3.68 (d, J=9 Hz, 1H), 3.79 (s, 3H), 5.94 (s, 2H), 6.72 (d, J=7.5 Hz, 1H), 6.85 (dd, J=9 Hz, 7.5 Hz, 3H), 7.08 (s, 1H), 7.34 (d, J=9 Hz, 2H). MS (DCl/NH$_3$) m/e 442 (M+H)$^+$.

EXAMPLE 60 trans,trans-2-(4-Methoxyphenyl)-4-(1,3-benzo-dioxol-5-yl)-1-(butylsulfonyl)-pyrrolidine-3-carboxylic Acid To 100 mg (0.271 mmol) of the compound resulting from Example 1C dissolved in 10 mL of THF was added 1-butanesulfonyl chloride (46.7 mg, 1.1 equivalents) and diisopropylethylamine (53 mg, 1.5 equivalents). The resulting mixture was stirred for 2.5 hours at room temperature and then the solvent evaporated. The crude product was purified by flash chromatography on silica gel eluting with 3:2 hexane-EtOAc to afford 120 mg (90%) of the ethyl ester.

The ester (120 mg, 0.244 mmol) was dissolved in 1 mL of EtOH, and a solution of 100 mg of NaOH in 1 mL of water was added. The mixture was stirred for 3 hours at room temperature and then concentrated under reduced pressure. Water (5 mL) was added and the solution was washed with ether to remove any unhydrolyzed trans-cis isomer. The aqueous solution was acidified to pH~6 with acetic acid and then extracted with EtOAc (2×50 mL). The combined organic extracts were washed with brine, dried over sodium sulfate and concentrated under reduced pressure to afford the pure title compound (60 mg, 53%) as a white solid. m.p. 67°–69° C. $^1$H NMR (CDCl$_3$, 300 MHz) δ 0.82 (t, J=7.5 Hz, 3H), 1.20–1.33 (m, 2H), 1.58–1.68 (m, 2H), 2.48–2.69 (m, 2H), 3.28 (dd, J=9 Hz, 1H), 3.49 (t, J=12 Hz, 1H), 3.65 (dd, J=12 Hz, 1H), 3.82 (s, 3H), 4.32 (dd, J=12 Hz, 1H), 5.17 (d, J=9 Hz, 2H), 5.95 (s, 2H), 6.70–6.78 (m, 3H), 6.92 (d, J=9 Hz, 2H), 7.35 (d, J=9 Hz, 2H). MS (DCl/NH$_3$) m/e 462 (M+H)$^+$.

EXAMPLE 61 trans,trans-2-(4-Methoxyphenyl)-4-(1,3-benzo-dioxol-5-yl)-1-(2-(N-methyl-N-isopropylcarbonylamino)ethyl)-pyrrolidine-3-carboxylic Acid

EXAMPLE 61A trans,trans-2-(4-Methoxyphenyl)-4-(1,3-benzo-dioxol-5-yl)-1-(2-bromoethyl)-pyrrolidine-3-carboxylic Acid Ethyl Ester To the mixture of cis,trans and trans,trans pyrrolidines resulting from Example 1C (400 mg) dissolved in 9 mL of 1,2-dibromoethane was added 0.7 mL of diisopropylethylamine and 30 mg of sodium iodide. The resultant mixture was heated at 100° C. for 1 hour, and then the solvents were removed in vacuo. The residue was taken up in EtOAc and washed sequentially with water and brine, dried and concentrated under reduced pressure. The crude product was purified by flash chromatography on silica gel eluting with 4:1 hexane-EtOAc to give 470 mg of the title product.

EXAMPLE 61B trans,trans-2-(4-Methoxyphenyl)-4-(1,3-benzo-dioxol-5-yl)-1-(2-(methylamino)ethyl)-pyrrolidine-3-carboxylic Acid Ethyl Ester To the compound resulting from Example 61A (450 mg) dissolved in 10 mL of EtOH was added 0.5 mL of 40% aqueous methylamine and 50 mg of sodium iodide. The mixture was heated at 80° C. for 1 hour, and then the solvents were removed in vacuo. The residue was taken up in EtOAc and washed sequentially with water and brine, dried and concentrated in vacuo. The resultant product was carried on without further purification.

EXAMPLE 61C trans,trans-2-(4-Methoxyphenyl)-4-(1,3-benzo-dioxol-5-yl)-1-(2-(N-methyl-N-isobutyrylamino)ethyl)-pyrrolidine-3-carboxylic Acid To the compound resulting from Example 61B (~150 mg) dissolved in 5 mL of 1,2-dichloroethane was added 0.3 mL of diisopropylethylamine. The solution was cooled to −40° C., isobutyryl chloride (0.17 mL) was added, the bath was removed, and the solution was allowed to warm to ambient temperature and stirred for 15 hours. The solvent was removed in vacuo; the residue was taken up in EtOAc and washed sequentially with 1:1 sodium bicarbonate solution/water and brine, dried and concentrated in vacuo. The product was purified by flash chromatography on silica gel eluting with a gradient 1:1 EtOAc-hexanes going to EtOAc and finally using 10% MeOH-EtOAc.

The ester was dissolved in 1.5 mL of EtOH; 0.75 mL of a 17% aqueous NaOH solution was added, and the resultant mixture was stirred at ambient temperature for 3 hours. The solvents were removed in vacuo; the residue was taken up in water and washed with ether. The aqueous phase was acidified with 1N $H_3PO_4$ to pH 3 and extracted twice with ether. The combined organic extracts were washed with brine and dried over $Na_2SO_4$. The solvents were removed in vacuo to provide 82 mg of the title compound as a white foam. Rotamers were seen in the NMR. $^1$H NMR (CDCl$_3$, 300 MHz) of the major rotamer δ 1.06 (d, 3H, J=10 Hz), 1.12 (d, 3H, J=10 Hz), 2.15 (m, 1H), 2.5–3.0 (m, 3H), 2.91 (s, 3H), 3.32 (m, 2H), 3.50 (m, 2H), 3.65 (m, 2H), 3.77 (s, 3H), 5.92 (s, 2H), 6.73 (d, 1H, J=8 Hz), 6.75–6.9 (m, 4H), 6.96 (d, 1H, J=2 Hz), 7.29 (m, 1H). MS (DCl/NH$_3$) m/z 469 (M+H)$^+$.

Analysis calcd for $C_{26}H_{32}N_2O_6$. 0.3 TFA: C, 63.55; H, 6.48; N, 5.57. Found: C, 63.44; H, 6.71; N, 5.24.

EXAMPLE 62 trans,trans-2-(4-Methoxyphenyl)-4-(1,3-benzo-dioxol-5-yl)-1-(2-(N-methyl-N-propionylamino)ethyl)-pyrrolidine-3-carboxylic Acid The title compound was prepared by the procedures described in Example 61 substituting propionyl chloride for isobutyryl chloride in Example 61C. $^1$H NMR (CDCl$_3$, 300 MHz) of the major rotamer δ 1.13 (t, 3H, J=8 Hz), 2.19 (m, 1H), 2.30 (m, 2H), 2.65–3.0 (m, 3H), 2.85 (s, 3H), 3.25–3.4 (m, 2H), 3.5–3.7 (m, 3H), 3.79 (s, 3H), 5.92 (s, 2H), 6.74 (d, 1H, J=8 Hz), 6.75–6.9 (m, 4H), 7.00 (bd s, 1H), 7.29 (bd s, 1H). MS (DCl/NH$_3$) m/z 455 (M+H)$^+$.

Analysis calcd for $C_{25}H_{30}N_2O_6$.1.0 $H_2O$: C, 63.55; H, 6.83; N, 5.93. Found: C, 63.55; H, 6.52; N, 5.73.

EXAMPLE 63 trans,trans-2-(4-Methoxyphenyl)-4-(1,3-benzo-dioxol-5-yl)-1-(N-methyl-N-benzylaminocarbonylmethyl)-pyrrolidine-3-carboxylic Acid Using the procedures described in Example 1 the title compound was prepared. $^1$H NMR (CDCl$_3$, 300 MHz) of the major rotamer δ 2.79 (s, 3H), 2.8–3.2 (m, 2H), 3.48 (m, 2H), 3.61 (m, 2H), 3.77 (s, 3H), 3.78 (m, 1H), 4.3–4.5 (m, 2H), 5.95 (d, 2H, J=2 Hz), 6.7–6.9 (m, 4H), 7.00 (m, 1H), 7.15–7.35 (m, 7H), MS (FAB/NBA) m/z 503 (M+H)$^+$.

Anal calcd for $C_{29}H_{30}N_2O_6$.0.5 $H_2O$: C, 68.36; H, 5.74; N, 5.50. Found: C, 68.41; H, 5.74; N, 5.36.

EXAMPLE 64 trans,trans-2-(4-Methoxyphenyl)-4-(1,3-benzo-dioxol-5-yl)-1-(N-ethyl-N-butylaminocarbonylmethyl)-pyrrolidine-3-carboxylic Acid Using the procedures described in Example 1 the title compound was prepared. $^1$H NMR (CDCl$_3$, 300 MHz) of the major rotamer δ 0.88 (t, 3H, J=7 Hz), 1.06 (t, 3H, J=7 Hz), 1.27 (m, 2H), 1.45 (m, 2H), 2.8–3.6 (m, 11H), 3.79 (s,3H), 3.80 (m, 1H), 5.92 (bd s, 2H), 6.75 (d, 1H, J=8 Hz), 6.85 (d, 1H, J=8 Hz), 6.92 (d, 2H, J=8 Hz), 7.03 (s, 1H), 7.33 (d, 1H, J=8 Hz). MS (DCl/NH$_3$) m/z 483 (M+H)$^+$.

Anal calcd for $C_{27}H_{34}N_2O_6$.0.5 HOAc: C, 65.61; H,7.08; N, 5.46. Found: C,65.51;H, 6.70; N, 5.66.

EXAMPLE 65 trans,trans-2-(4-Methoxyphenyl)-4-(1,3-benzo-dioxol-5-yl)-1-(N-methyl-N-(2,2-dimethylpropyl)aminocarbonylmethyl)-pyrrolidine-3-carboxylic Acid Using the procedures described in Example 1 the title compound was prepared. $^1$H NMR (CDCl$_3$, 300 MHz) of the major rotamer δ 0.90 (s, 9H), 2.8–3.1 (m, 4H), 2.94 (s, 3H), 3.3–3.5 (m, 3H), 3.61 (m, 1H), 3.80 (s, 3H), 3.82 (m, 1H), 5.94 (bd s, 2H), 6.74 (d, 1H, J=8 Hz), 6.86 (d, 2H, J=8 Hz), 6.87 (m, 1H), 7.03 (d, 1H, J=2 Hz), 7.33 (d, 2H, J=8 Hz). MS (DCl/NH$_3$) m/z 483 (M+H)$^+$.

EXAMPLE 66 trans,trans-2-(4-Methoxyphenyl)-4-(1,3-benzo-dioxol-5-yl)-1-(2-(N-methyl-N-butylsulfonylamino)ethyl)-pyrrolidine-3-carboxylic Acid To the compound resulting from Example 61B (60 mg, 0.13 mmol) dissolved in 5 mL of CH$_3$CN was added 0.2 mL of Et$_3$N and 22 mg (0.143 mmol, 1.1 equivalents) of 1-butanesulfonyl chloride. The mixture was stirred for 1 hour at room temperature and then concentrated in vacuo. The crude product was purified by column chromatography on silica gel eluting with 1:1 EtOAc-hexane to yield 64 mg (90%) of the ester. Ester hydrolysis by the procedure described in Example 1D afforded the title compound. m.p. 64°–66° C. $^1$H NMR (CDCl$_3$, 300 MHz) δ 0.92 (t, J=7.5 Hz, 3H), 1.39 (hexad, J=7.5 Hz, 2H), 1.68–1.76 (m, 2H), 2.16–2.25 (m, 1H), 2.72 (s, 3H), 2.75–2.92 (m, 5H), 3.12–3.20 (m, 1H), 3.25–3.34 (m, 1H), 3.46–3.55 (m, 2H), 3.65 (d, J=9 Hz, 1H), 3.78 (s, 3H), 5.53 (s, 2H), 6.72 (d, J=7.5 Hz, 1H), 6.82 (dd, J=7.5 Hz,3 Hz, 1H), 6.86 (d, J=9 Hz, 2H), 7.02 (d, J=3 Hz, 1H), 7.34 (d, J=9 Hz, 2H). MS (DCl/NH$_3$) m/e 519 (M+H)$^+$.

EXAMPLE 67 trans,trans-2-(4-Methoxyphenyl)-4-(1,3-benzo-dioxol-5-yl)-1-(2-(N-methyl-N-propylsulfonylamino)ethyl)-pyrrolidine-3-carboxylic Acid The title compound was prepared by the procedures described in Example 66 substituting 1-propanesulfonyl chloride for 1-butanesulfonyl chloride. m.p. 69°–70° C. $^1$H NMR (CDCl$_3$, 300 MHz) δ 1.02 (t, J=7.5 Hz, 3H), 1.78 (hexad, J=7.5 Hz, 2H), 2.18–2.26 (m, 1H), 2.72 (s, 3H), 2.75–2.95 (m, 6H), 3.13–3.22 (m, 1H), 3.25–3.35 (m, 1H), 3.47–3.58 (m, 2H), 3.66 (d, J=9 Hz, 1H), 3.80 (s, 3H), 5.96 (s, 2H), 6.74 (d, J=7.5 Hz, 1H), 6.84 (d,d, J=7.5 Hz, 3 Hz, 1H), 6.87 (d, J=9 Hz, 2H), 7.04 (d, J=3 Hz, 1H), 7.43 (d, J=9 Hz, 2H). MS (DCl/NH$_3$) m/e 505 (M+H)$^+$.

EXAMPLE 68 trans,trans-2-(4-Methoxyphenyl)-4-(1,3-benzo-dioxol-5-yl)-1-(2-(propylsulfonyl)ethyl)-pyrrolidine-3-carboxylic Acid To 1-propanethiol (3.5 g, 46.05 mmol) dissolved in 10 mL of anhydrous THF was added 632 mg (26.32 mmol) of NaH in portions under a nitrogen atmosphere. The mixture was heated at 60°–70° C. for 1 hours. To this mixture was added the compound resulting from Example 61A (180 mg, 0.38 mmol) in 2 mL THF. Heating was continued at 60°–70° C. for an additional 2 hours, and then the volatiles were removed under reduced pressure. The crude propylthioethyl adduct was purified by flash chromatography on silica gel eluting with 3:2 hexane-EtOAc to give 170 mg (95%).

To a solution of 170 mg (0.36 mmol) of the sulfide and 93 mg (0.8 mmol) of N-methylmorpholine N-oxide (NMO)in a mixture of 20 mL of acetone and 5 mL of H$_2$O was added a solution of osmium tetroxide (10 mg) in 0.3 mL of t-butanol. The resulting mixture was stirred overnight at room temperature and then concentrated under reduced pressure. The residue was partitioned between EtOAc and H$_2$O. The organic phase was washed with brine, dried over Na$_2$SO$_4$ and concentrated in vacuo. Flash chromatography afforded 177 mg (98%) of the ethyl ester which was hydrolyzed by the procedures described in Example 1D to afford the title compound. m.p. 73°–75° C. $^1$H NMR (CDCl$_3$, 300 MHz) δ 1.04 (t, J=7.5 Hz, 3H), 1.78 (hexad, J=7.5 Hz, 2H), 2.59–2.66 (m, 1H), 2.84–3.08 (m, 7H), 3.43 (dd, J=9 Hz, 3 Hz, 1H), 3.53–3.60 (m, 1H), 3.68 (d, J=9 Hz, 1H), 3.82 (s, 3H), 5.96 (s, 2H), 6.75 (d, J=7.5 Hz, 1H), 6.82 (dd, J=7.5 Hz, 3 Hz, 1H), 6.88 (d, J=9 Hz, 2H), 6.99 (d, J=3 Hz, 1H), 7.32 (d, J=9 Hz, 2H). MS (DCl/NH$_3$) m/e 476 (M+H)$^+$.

EXAMPLE 69 trans,trans-2-(4-Methoxyphenyl)-4-(1,3-benzo-dioxol-5-yl)-1-N-(trans-5-methylhex-2-enyl)-pyrrolidine-3-carboxylic Acid

EXAMPLE 69A trans-5-Methylhex-2-enoic Acid Ethyl Ester

Oil dispersion sodium hydride (0.85 g) was washed with hexanes and suspended in THF (20 mL), and the mixture was cooled in an ice bath to 0° C. Diisopropyl(ethoxycarbonylmethyl) phosphonate (5.0 mL) was added slowly and the mixture stirred for 20 minutes at 0° C. Isovaleraldehyde (2.0 mL) in THF (5 mL) was added dropwise over five minutes. The ice bath was removed and the mixture stirred for 18 hours at ambient temperature. Saturated ammonium chloride solution (50 mL) was added and the mixture extracted with diethyl ether (3×50 mL). The ether extracts were combined, dried with Na$_2$SO$_4$, and evaporated to give a colorless oil which was purified by flash chromatography on silica gel eluting with hexanes. The title compound was isolated as a colorless oil (2.1 g).

EXAMPLE 69B trans-5-Methylhex-2-en-1-ol

The compound resulting from Example 69A (2.0 g) was dissolved in toluene and cooled to 0° C. in an ice bath. Diisobutylaluminum hydride (1.5N in toluene, 20 mL) was added dropwise and the solution stirred at 0° C. for two hours. Citric acid solution (25 mL) was added very slowly to the cooled solution. The resulting mixture was stirred for 18 hours at ambient temperature. Diethyl ether (50 mL) was added, the solids removed by filtration and washed with additional ether (2×25 mL). The filtrate was extracted with ether (2×25 mL). The ether extractions and washings were combined, dried, and evaported to give a colorless oil which was purified by flash chromatography on silica gel eluting with 25% EtOAc-hexanes. The title compound was isolated as a colorless oil (1.25 g).

EXAMPLE 69C trans-1-Bromo-5-methylhex-2-ene

The compound resulting from Example 69B (1.0 g) was dissolved in diethyl ether and cooled to 0° C. in an ice bath. Phosphorus tribromide (2.5 g, 0.87 mL) was added dropwise and the solution stirred at 0° C. for two hours. The solution was poured onto ice, the layers separated, and the aqueous layer extracted with additional ether (3×25 mL). The ether layers were combined, dried, and evaporated to give a colorless oil which was used without further purification (0.95 g).

EXAMPLE 69D trans,trans-2-(4-Methoxyphenyl)-4-(1,3-benzo-dioxol-5-yl)-1-N-(trans-5-methylhex-2-enyl)-pyrrolidine-3-carboxylic Acid The title compound was synthesized using the methods detailed in Example 1D but substituting the compound resulting from Example 69C for N-propyl bromoacetamide. $^1$H NMR (CDCl$_3$, 300 MHz) δ 0.84 (d, 6H, J=8 Hz), 1.57 (heptet, 1H, J=8 Hz), 1.87 (t, 2H, J=6 Hz), 2.60 (dd, 1H, J=8 Hz,14 Hz), 2.86 (t, 1H, J=10 Hz), 2.96 (dd, 1H, J=8 Hz, 10 Hz), 3.20 (dd, 1H, J=5 Hz, 14 Hz), 3.29 (dd, 1H, J=3 Hz,10 Hz), 3.50 (m, 1H), 3.70 (d, 1H, J=10 Hz), 3.78 (s, 3H), 5.47 (m, 2H), 5.93 (s, 2H), 6.71 (d, 1H, J=8 Hz), 6.83 (d, 3H, J=9 Hz), 7.05 (s, 1H), 7.32 (d, 2H, J=9 Hz). MS (DCl/NH$_3$) m/e 438 (M+H)$^+$.

Anal calcd for C$_{26}$H$_{31}$NO$_5$: C, 71.37; H, 7.14; N, 3.20. Found: C, 71.16; H, 7.24; N, 3.17.

EXAMPLE 70 trans,trans-2-(4-Methoxyphenyl)-4-(1,3-benzo-dioxol-5-yl)-1-N-(trans-3,5-dimethylhex-2-enyl)-pyrrolidine-3-carboxylic Acid The title compound was prepared by the procedures described in Example 69 but substituting 4-methyl-2-pentanone for isovaleraldehyde in Example 69A, which gave ~7:1 mixture of trans/cis olefins. The crude product was purified by preparative HPLC (Vydac µC18) eluting with a 10–70% gradient of $CH_3CN$ in 0.1% TFA. The desired fractions were lyophilized to give the product (and its diastereomer) as a white solid. $^1H$ NMR of the major (trans) isomer: ($CDCl_3$, 300 MHz) δ 0.83 (d, 6H, J=8 Hz), 1.56 (s,3H), 1.74 (m, 1H), 1.92 (d, 2H, J=6 Hz), 3.3–3.5 (m, 3H), 3.6–3.8 (m,4H), 3.78 (s, 3H), 3.9–4.0 (m, 1H), 5.22 (m, 1H), 5.90 (d, 2H, J=12 Hz), 6.63 (m, 1H), 6.78 (m, 3H), 6.95 (s, 1H), 7.45 (d, 3H, J=8 Hz). MS ($DCI/NH_3$) m/e 438 $(M+H)^+$.

Anal calcd for $C_{27}H_{33}NO_5 \cdot 1.0$ TFA: C, 61.59; H, 6.06; N, 2.48. Found: C, 61.36; H, 6.10; N, 2.34.

EXAMPLE 71 trans,trans-2-(4-Methoxyphenyl)-4-(1,3-benzo-dioxol-5-yl)-1-(4-heptylcarbonylmethyl)-pyrrolidine-3-carboxylic Acid

EXAMPLE 71A

1-Chloro-3-propyl-2-hexanone

To 2-propylpentanoic acid (156.6 µl, 1.00 mmol) dissolved in anhydrous dichloromethane (2 mL) was added DMF (3 µL, 4 mole %), and the solution was cooled to 0° C. under a nitrogen atmosphere. To the solution was added oxalyl chloride (94.3 µL, 1.08 mmol) dropwise over a few minutes. The reaction was stirred 18 hours while warming to ambient temperature. The mixture was cooled to 0° C. and excess ~0.3M ethereal diazomethane solution was added. The reaction mixture was stirred 18 hours while warming to ambient temperature. The reaction mixture was washed with 1M aqueous sodium carbonate solution (30 mL), dried over anhydrous sodium sulfate, filtered and concentrated under reduced pressure. The residue was dissolved in ether (2 mL) and cooled to 0° C. under a nitrogen atmosphere. Hydrogen chloride as a 4N solution in dioxane (275 µL, 1.10 mmol) was added dropwise over a few minutes. The reaction was stirred 18 hours while warming to ambient temperature. The reaction mixture was concentrated under reduced pressure and the residual oil was used in the next step without further purification.

EXAMPLE 71B trans,trans-Ethyl-2-(4-methoxyphenyl)-4-(1,3-benzo-dioxol-5-yl)-1-(4-heptylcarbonylmethyl)-pyrrolidine-3-carboxylate To the compound resulting from Example 71A (1.00 mmol, maximum theoretical yield) was added a solution of the trans,trans ethyl carboxylate from Example 1C (295 mg, 0.80 mmol as a 50% solution in toluene), diisopropylethylamine (700 µL, 4.00 mmol) and acetonitrile (4 mL). To the resulting solution was added sodium iodide (12 mg, 10 mole %), and the reaction mixture was stirred 18 hours under a nitrogen atmosphere at ambient temperature. Additional sodium iodide (24 mg, 20 mole %) and acetonitrile (4 mL) were added, and the reaction mixture was heated at 45°–50° C. with stirring for 18 hours. The reaction mixture was concentrated under reduced pressure, and the residue was chromatographed on silica gel eluting with 1:9 ethyl acetate-hexane to give 237 mg (46%) of the title compound as a yellow oil.

EXAMPLE 71C trans,trans-2-(4-Methoxyphenyl)-4-(1,3-benzo-dioxol-5-yl)-1-(4-heptylcarbonylmethyl)-pyrrolidine-3-carboxylic Acid To the compound resulting from Example 71B (231 mg, 0.4532 mmol) dissolved in ethanol (10 mL) was added a solution of lithium hydroxide (38 mg, 0.9065 mmol) in water (2.5 mL). The solution was stirred for 18 hours under a nitrogen atmosphere, additional lithium hydroxide (19 mg, 0.4532 mmol) in water (0.5 mL) was added, and stirring was continued 24 hours. The reaction mixture was concentrated under reduced pressure to remove the ethanol, and the aqueous residue was diluted with water (45 mL) and washed with ether (50 mL). The aqueous layer was neutralized with 1N hydrochloric acid to cloudiness and then 10% aqueous citric acid was added to adjust the pH to ~5. This solution was then extracted with 10% ethanol in chloroform (4×25 mL). The combined organic extracts were dried over anhydrous sodium sulfate, filtered and concentrated under reduced pressure. The residue was purified by preparative TLC on silica gel eluted with 1:1 ethyl acetate-hexane to give 86 mg (39%) of the title compound as an off white powder. $^1H$ NMR ($CDCl_3$, 300 MHz) δ 0.73–0.97 (m, 6H), 1.03–1.33 (m, 6H), 1.36–1.58 (m, 2H), 2.46 (m, 1H), 2.80–2.98 (m, 3H), 3.38–3.64 (m, 3H), 3.75–3.90 (m, 1H), 3.79 (s, 3H), 5.94 (s, 2H), 6.75 (d, 1H), 6.86 (d, 2H), 6.92 (d, 1H), 7.12 (s, 1H), 7.32 (d, 2H). MS (FAB) m/e 482 $(M+H)^+$.

Anal calcd for $C_{28}H_{35}NO_6$: C, 69.83; H, 7.32; N, 2.91. Found: C, 69.57; H, 7.41; N, 2.73.

EXAMPLE 72 trans,trans-2-(4-Methoxyphenyl)-4-(1,3-benzo-dioxol-5-yl)-1-(valerylmethyl)-pyrrolidine-3-carboxylic Acid

EXAMPLE 72A

1-Chloro-2-hexanone

Using the procedure described in Example 71A and substituting pentanoic acid for 2-propylpentanoic acid afforded the title compound as an oil which was used in the next step without further purification.

EXAMPLE 72B trans,trans-Ethyl 2-(4-methoxyphenyl)-4-(1,3-benzo-dioxole-5-yl)-1-(valerylmethyl)-pyrrolidine-3-carboxylate Substituting the compound resulting from Example 72A for 1-chloro-3-propyl-2-hexanone and using the procedure described in Example 71B, except deleting the first addition of sodium iodide, stirring 18 hours at ambient temperature and purifying by silica gel chromatography eluting with 3:17 ethyl acetate-hexane, the title compound 305 mg (65%) was obtained as a yellow oil.

EXAMPLE 72C trans,trans-2-(4-Methoxyphenyl)-4-(1,3-benzodioxol-5-yl)1-(valerylmethyl)-pyrrolidine-3-carboxylic Acid By substituting the compound resulting from Example 72B for trans,trans-Ethyl 2-(4-methoxyphenyl)-4-(1,3-benzodioxol-5-yl)-1-(4-heptylcarbonylmethyl)-pyrrolidine-3-carboxylate and using the procedure described in Example 71 C, except only one solution of lithium hydroxide (81.5 mg, 1.942 mmol) in water (3.5 mL) was added followed by stirring for 18 hours, the title compound 130 mg (46%) was obtained as an off white powder. $^1$H NMR (CDCl$_3$, 300 MHz) δ 0.87 (t, 3H), 1.26 (m, 2H), 1.49 (m, 2H), 2.37 (m, 2H), 2.79–2.98 (m, 3H), 3.31–3.49 (m, 2H), 3.56 (m, 1H), 3.77, 3.79 (d,s, 4H), 5.94 (s, 2H), 6.75 (d, 1H), 6.81–6.93 (m, 3H), 7.09 (d, 1H), 7.33 (d, 2H). MS (FAB) m/e 440 (M+H)$^+$.

Anal. calcd for $C_{25}H_{29}NO_6$: C, 68.32; H, 6.65; N, 3.19. Found: C, 67.95; H, 6.64; N, 3.05.

EXAMPLE 73 trans,trans-2-(4-Methoxyphenyl)-4-(1,3-benzodioxol-5-yl)-1-(N-(3,4-dimethoxybenzyl)-N-methylaminocarbonylmethyl)pyrrolidine-3-carboxylic Acid

EXAMPLE 73A trans,trans- and cis,trans-2-(4-Methoxyphenyl)-4-(1,3-benzodioxol-5-yl)-1-((3,4-dimethoxybenzyl)aminocarbonylmethyl)pyrrolidine-3-carboxylic Acid Ethyl Ester Using the procedure of Example 1D, paragraph 1, substituting 3,4-dimethoxybenzyl bromoacetamide for dipropyl bromoacetamide, the desired product mixture was obtained as a white foam in 81% yield.

EXAMPLE 73B trans,trans- and cis,trans-2-(4-Methoxyphenyl)-4-(1,3-benzodioxol-5-yl)-1-(N-(3,4-dimethoxybenzyl)-N-methylaminocarbonylmethyl)pyrrolidine-3-carboxylic Acid Ethyl Ester The resultant product from Example 73A (220 mg, 0.404 mmol) was dissolved in 2 mL dry THF and added dropwise to a stirred, cooled (0° C.) suspension of sodium hydride (23 mg of a 60% by weight mineral oil suspension, 16.5 mg, 0.69 mmol)in 0.2 mL THF, under an argon atmosphere. The resulting mixture was stirred at 0° C. for 1 hour, then methyl iodide (28 μL, 64 mg, 0.45 mmol) was added. The reaction mixture was stirred at 0° C. for 45 minutes. TLC (Et$_2$O)indicated incomplete reaction. An additional portion of methyl iodide (28 μL, 64 mg, 0.45 mmol) and dry 1,3-dimethyl-3,4,5,6-tetrahydro-2(1H)pyrimidinone (50 μL, 0.41 mmol) were added. The reaction mixture was stirred at ambient temperature for 2 days. The reaction was poured into 25 mL of 0.5M aqueous citric acid and extracted with 2×25 mL EtOAc. The combined organic extracts were washed sequentially with 30 mL water and 30 mL brine, then dried (Na$_2$SO$_4$), filtered and concentrated under reduced pressure to produce 270 mg of crude material. Flash chromatography on silica gel eluting with Et$_2$O gave the title compounds as an inseparable mixture in 43% yield. $^1$H NMR (CDCl$_3$, 300 MHz) δ 2.79 (s) and 2.81 (s), for the N—CH$_3$ signals. MS m/z 591 (M+H)$^+$.

EXAMPLE 73C trans,trans-2-(4-Methoxyphenyl)-4-(1,3-benzodioxol-5-yl)-1-(N-(3,4-dimethoxybenzyl)-N-methylaminocarbonylmethyl)pyrrolidine-3-carboxylic Acid To the resultant compound from Example 73B (98 mg, 0.17 mmol) dissolved in 1 mL EtOH and cooled to 0° C. was added a solution of lithium hydroxide monohydroxide (17 mg, 0.41 mmol)in 0.5 mL H$_2$O. The resulting solution was stirred under a nitrogen atmosphere for 16 hours. The solution was concentrated in vacuo, and the residue was partitioned between 15 mL H$_2$O and 15 mL Et$_2$O. The aqueous phase was extracted with 5 mL Et$_2$O, then the aqueous phase was acidified with 10% aqueous citric acid. The acidic aqueous phase was saturated with NaCl and extracted with 3×15 mL EtOAc. The EtOAc extracts were combined, dried (Na$_2$SO$_4$), then filtered and concentrated in vacuo to give 40 mg (42%) of the title compound as a white foam. $^1$H NMR (CD$_3$OD, 300 MHz, two rotameric forms) δ 2.85 (s, 3H), 2.94–3.25 (br m, 3H), 3.35–3.70 (br m) and 3.64 (s, 4 H total), 3.70–3.97 (br m), 3.74 (s), 3.76 (s), 3.78 (s), 3.79 (s), 3.81 (s), and 4.03 (br d, J=14 Hz, 8H total), 4.43 (AB, 1H), 5.91 (s) and 5.93 (s, 2H total), 6.50–6.60 (m, 1H), 6.67–7.02 (br m, 6H), 7.29 (br d) and 7.35 (br d, 2H total). HRMS calcd for $C_{31}H_{35}N_2O_8$ (M+H)$^+$: 563.2393. Found: 563.2385.

EXAMPLE 74 trans,trans-2-(4-Methoxyphenyl)-4-(1,3-benzodioxol-5-yl)-1-(N-(3,4-dimethoxybenzyl) aminocarbonylmethyl)pyrrolidine-3-carboxylic Acid The procedure of Example 73C was used, with the substitution of the resultant compound from Example 73A for the resultant compound from Example 73B, to provide the title compound. $^1$H NMR (CD$_3$OD, 300 MHz) δ 2.85 (d, J=16 Hz, 1H), 2.92 (br t, J=9 Hz, 1H), 2.98 (br t, J=10 Hz, 1H), 3.32–3.39 (br m, 2H), 3.54–3.65 (br m, 1H), 3.67 (s, 3H), 3.78 (s, 3H), 3.80 (s, 3H), 3.85 (d, J=10 Hz, 1H), 4.21 (d, J=15 Hz, 1H), 4.41 (d, J=15 Hz, 1H), 5.91 (s, 2H), 6.67 (d, J=8 Hz, 1H), 6.75–6.95 (m, 7H), 7.33–7.40 (m, 2H). HRMS calcd for $C_{30}H_{32}N_2O_8$ (M+H)$^+$: 549.2237. Found: 549.2224.

EXAMPLE 75

(2R,3R,4R),2-(4-Methoxyphenyl)-4-(1,3-benzodioxol-5-yl)-1-((1R )-1-(N,N -dipropylaminocarbonyl)-1-butyl)pyrrolidine-3-carboxylic Acid

EXAMPLE 75A trans,trans, 2-(4-Methoxyphenyl)-4-(1,3-benzodioxol-5-yl)-1-((1R)-1-(benzyloxycarbonyl)butyl)pyrrolidine-3-carboxylic Acid Ethyl Ester The procedure of Fung, et. al., J. Med. Chem., 35(10): 1722–34 (1992) was adapted. The resultant compound from Example 6A (103 mg, 0.279 mmol) was dissolved in 0.7 mL of nitromethane and 0.7 mL of H$_2$O, and ammonium carbonate (34 mg, 0.35 mmol) and (2S)-benzyl 2-bromopentanoate (78 mg, 0.30 mmol) were added. The reaction was refluxed for 24 hours. The reaction was partitioned between 15 mL of 1M aqueous Na$_2$CO$_3$ and 25 mL of CH$_2$Cl$_2$. The aqueous phase was extracted with 2×10 mL CH₂Cl₂, and the combined organic phases were washed with 15 mL brine, dried (Na₂SO₄), then filtered and concentrated under reduced pressure to a brown oil (169 mg). The crude product was purified by silica gel chromatography eluting with 3:1 CH₂Cl₂-hexane to produce 106 mg (68%) of the title compound as a waxy solid. ¹H NMR indicated the presence of two diastereomeric products.

EXAMPLE 75B trans,trans-2-(4-Methoxyphenyl)-4-(1,3-benzodioxol-5-yl)-1-((1R)-1-(N,N-dipropylaminocarbonyl)-1-butyl)pyrrolidine-3-carboxylic Acid Ethyl Ester The resultant compound from Example 75A (101 mg, 0.180 mmol) and 30 mg of 10% palladium on charcoal were stirred in 2 mL EtOAc under 1 atmosphere of H₂ for 4 hours. The reaction mixture was filtered through a plug of Celite, using 15 mL MeOH to wash the catalyst. The combined filtrate and wash were concentrated in vacuo to give 81.4 mg (96%) of the crude acid as a white solid.

The above crude acid was combined with HOBt hydrate (41 mg, 0.27 mmol), dipropylamine (26 mg, 0.26 mmol), and 4-methylmorpholine (37 mg, 0.37 mmol) in 2 mL dry DMF. The solution was cooled to −15° C., then 1-ethyl-3-(3-dimethylaminopropyl)carbodiimide hydrochloride (44 mg, 0.23 mmol) was added. The mixture was stirred at −15° C. and allowed to warm slowly to room temperature overnight. The solvent was removed by distillation under reduced pressure, and the residue was partitioned between 20 mL EtOAc and 10 mL of 1M aqueous Na₂CO₃. The organic phase was washed with 10 mL of brine, dried (Na₂SO₄), then filtered and concentrated in vacuo. The crude product was purified by flash chromatography on silica gel, eluting with 1:2 Et₂O hexane. Further purification of overlap fractions by preparative TLC eluting with 1:2 Et₂O-hexane yielded 32 mg (34%) of a less polar product, and 44 mg (46%) of a more polar product.

EXAMPLE 75C (2R,3R,4R)-2-(4-Methoxyphenyl)-4-(1,3-benzodioxol-5-yl)-1-((1R)-1-(N,N-dipropylaminocarbonyl)-1-butyl)pyrrolidine-3-carboxylic Acid The procedure of Example 73C was followed, with the substitution of the less polar isomer from Example 75B for the resultant product from Example 73B, to provide the title compound in 94% yield. $[\alpha]_D=-52°$ (c=0.235, CH₃OH). ¹H NMR (CD₃OD, 300 MHz) δ 0.55 (t, J=7 Hz, 3H), 0.87 (t, J=7 Hz) and 0.87–0.94 (m, 6H total), 1.03–1.25 (br m, 2H), 1.25–1.68 (br m, 4H), 1.90–2.07 (br m, 1H), 2.75–2.94 (br m, 2H), 2.94–3.02 (br m, 2H), 3.20–3.40 (m, overlapping with CD₂HOD signal), 3.40–3.60 (br m, 2H), 3.79 (s, 3H), 4.04 (br d, J=9 Hz, 1H), 5.92 (dd, J=3,5 Hz, 2H), 6.72 (d, J=8 Hz, 1H), 6.79 (dd, J=1.5, 8 Hz, 1H), 6.92–6.98 (br m, 3H), 7.29–7.39 (m, 2H). MS m/z 525 (M+H)⁺.

EXAMPLE 76

(2S,3S,4S)-2-(4-Methoxyphenyl)-4-(1,3-benzodioxol-5-yl)-1-((1R)-1-(N,N -dipropylaminocarbonyl)-1-butyl)pyrrolidine-3-carboxylic Acid The procedure of Example 73C was followed, with the substitution of the more polar isomer from Example 75B for the resultant product from Example 73B, to provide the title compound in 88% yield. $[\alpha]_D=+58°$ (c=0.37, CH₃OH). ¹H NMR (CD₃OD, 300 MHz) δ 0.57 (br t, J=7 Hz, 3H), 0.88–0.98 (m, 6H), 1.08–1.35 (br m, 2H), 1.35–1.68 (br m, 4H), 1.75–1.90 (br m, 1H), 2.75–2.86 (br m, 2H), 3.10–3.30 (br m, 2H), 3.51–3.65 (br m, 2H), 3.69 (s, 3H), 4.03–4.16 (br m, 2H), 5.91 (s, 2H), 6.71–6.83 (m, 2H), 6.86–6.97 (m, 3H), 7.32 (br d, J=9 Hz, 2H). MS m/z 525 (M+H)⁺.

EXAMPLE 77

(2S,3S,4S)-2-(4-Methoxyphenyl)-4-(1,3-benzodioxol-5-yl)-1-((1S)-1-(N,N-dipropylaminocarbonyl)-1-butyl)pyrrolidine-3-carboxylic Acid

EXAMPLE 77A trans,trans-2-(4-Methoxyphenyl)-4-(1,3-benzodioxol-5-yl)-1-((1S)-1-(N,N-dipropylaminocarbonyl)-1-butyl)pyrrolidine-3-carboxylic Acid Ethyl Ester (2R)-N,N-dipropyl 2-hydroxypentanamide (106 mg, 0.528 mmol, made by standard procedure) was dissolved in 2 mL THF under an argon atmosphere, diisopropylethylamine (75 mg, 0.58 mmol) was added, then the solution was cooled to −20° C. Trifluoromethanesulfonic anhydride (95 µL, 159 mg, 0.565 mmol) was added to the cooled solution over 1 minute, and the reaction mixture was stirred at-20° C. for 1 hour, and at room temperature for an additional 1 hour. The resulting slurry was recooled to 0° C., and a solution of the resultant compound from Example 6A (195 mg, 0.528 mmol) and diisopropylethylamine (101 µL, 75 mg, 0.58 mmol) in 3 mL of CH₂Cl₂ was added. The reaction was stirred at 0° C. for 3 hours and for an additional 2 days at room temperature. TLC (Et₂O-hexane 1:2) indicated starting materials remained, so the mixture was warmed to reflux for 4 hours. The reaction was cooled, then partitioned between 30 mL EtOAc and 15 mL of 1M aqueous Na₂CO₃. The aqueous phase was extracted with 15 mL EtOAc, then the combined organic phases were washed with 20 mL brine, dried (Na₂SO₄), filtered and concentrated in vacuo to a yellowish oil. Purification by flash chromatography on silica gel eluting with 1:2 Et₂O-hexane gave 19.9 mg (7%) of a less polar product and 20.1 mg (7%) of a more polar product. ¹H NMR spectra and MS were the same as those of Example 76B.

EXAMPLE 77B (2S,3S,4S)-2-(4-Methoxyphenyl)-4-(1,3-benzodioxol-5-yl)-1-((1S)-1-(N,N-dipropylaminocarbonyl)-1-butyl)pyrrolidine-3-carboxylic Acid The procedure of Example 73C was followed, with the substitution of the less polar isomer from Example 77A for the resultant product from Example 73B, to provide the title compound in 100% yield. ¹H NMR (CD₃OD, 300 MHz) and MS identical to those of Example 75C.

EXAMPLE 78

(2R,3R,4R)-2-(4-Methoxyphenyl)-4-(1,3-benzodioxol-5-yl)-1-((1S )-1-(N,N-dipropylaminocarbonyl)-1-butyl)pyrrolidine-3-carboxylic Acid The procedure of Example 73C was followed, with the substitution of the more polar isomer from Example 77A for the resultant product from Example 73B, to provide the title compound in 88% yield. $^1$H NMR (CD$_3$OD, 300 MHz) and MS identical to those of Example 76.

EXAMPLE 79 trans,trans-2-(4-Methoxyphenyl)-4-(1,3-benzodioxol-5-yl)-1-(N,N-di(n-butyl)aminocarbonylmethyl)-3-(5-tetrazolyl)pyrrolidine Carbonyldiimidazole (510 mg, 3.148 mmol) was added to 1.020 g (2.00 mmol) of the compound resulting from Example 43 in 2.7 mL THF, and the mixture was heated for 40 minutes at 50° C. The reaction mixture was cooled in an ice bath, and 25% solution of ammonia in methanol was added. After 30 minutes, the solid which had formed was filtered, washed with ethanol and finally with ether to yield 850 mg (83%) of the 3-carboxamide compound. m.p. 194°–196° C.

Phosphorus oxychloride (1.06 g) was added to this amide in 7 mL of pyridine, and the mixture was stirred 1 hour at room temperature. Dichloromethane was added, and the solution was washed with potassium bicarbonate solution, dried over sodium sulfate, and concentrated. The residue was chromatographed on silica gel eluting with 2:1 hexane-ethyl acetate to give 790 mg (96%) of the 3-carbonitrile compound.

To this nitrile in 5 mL toluene was added 385 mg of trimethyl tin chloride and 126 mg sodium azide. The mixture was heated 20 hours at 125° C. (bath temp). After cooling, methanol (5 mL) was added, and the solution was concentrated in vacuo. To the resulting residue was added 6 mL of methanol and 6 mL of water containing 0.2 g phosphoric acid. After stirring 1 hour at room temperature, water was added and the mixture extracted with dichloromethane. The combined organic extracts were dried and concentrated, and the resulting residue was crystallized from ether to give a solid. The solid was dissolved in sodium hydroxide solution, filtered from insoluble material and acidified with acetic acid to get 532 mg (62%) of the title compound. m.p. 165°–167° C. $^1$H NMR (CDCl$_3$, 300 MHz) δ 0.85 (t, J=7 Hz, 3H), 0.87 (t, J=7 Hz, 3H), 1.10–1.50 (m, 8H), 3.0–3.6 (m, 8H), 3.70 (s, 3H), 3.7–3.8 (m, 1H), 3.90 (t, J=9 Hz, 1H), 4.37 (d, J=9 Hz, 1H), 5.86 (s, 2H), 6.62 (d, J=8 Hz, 1H), 6.65–6.73 (m, 3H), 6.95 (d, J=2 Hz, 1H), 7.11 (d, J=9 Hz, 2H).

EXAMPLE 80 trans,trans-2-(4-Fluorophenyl)-4-(1,3-benzodioxol-5-yl)-1-(N,N-di(n-butyl)aminocarbonylmethyl)pyrrolidine-3-carboxylic Acid The title compound was prepared as an amorphous solid from methyl (4-flourobenzoyl) acetate and 5-(2-nitrovinyl)-1,3-benzodioxole using the procedures described in Examples 1 and 43. $^1$H NMR (CDCl$_3$, 300 MHz) δ 0.81 (t, J=7 Hz, 3H), 0.90 (t, J=7 Hz, 3H), 1.0–1.55 (m, 8H), 2.81 (d, J=13 Hz, 1H), 2.90–3.10 (m, 4H), 3.15–3.30 (m, 1H), 3.32–3.45 (m, 3H), 3.55–3.65 (m, 1H), 3.86 (d, J=10 Hz, 1H), 5.94 (dd, J=2 Hz, 4 Hz, 2H), 6.72 (d, J=8 Hz, 1H), 6.86 (d, J=8 Hz, 1H), 6.95–7.07 (m, 3H), 7.32–7.45 (m, 2H).

EXAMPLE 81 trans,trans-2-(4-Methoxyphenyl)-4-(1,3-benzodioxol-5-yl)-1-(N,N-di(n-butyl)aminomethylcarbonyl)pyrrolidine-3-carboxylic Acid N,N-Dibutyl glycine (150 mg, 0.813 mmol), prepared by the method of Bowman, R. E., J. Chem. Soc. 1346 (1950), in 0.7 mL of THF was treated with mg (0.852 mmol) carbonyldiimidazole and heated for 30 minutes at 50° C. After cooling to room temperature, 250 mg (0.678 mmol) of ethyl trans,trans-2-(4-methoxyphenyl)-4-(1,3-benzodioxol-5-yl)-pyrrolidine-3-carboxylate, the compound resulting from Example 6A, was added, and the mixture was heated at 45° C. for 30 minutes. The product was chromatographed on silica gel, eluting with 1:1 hexane-ethyl acetate to give 306 mg of the intermediate ethyl ester.

The ester was hydrolyzed with sodium hydroxide in water and ethanol to give 265 mg of the title compound as a white powder. $^1$H NMR (CDCl$_3$, 300 MHz) δ rotational isomers –0.75 and 0.85 (2 t, J=7 Hz, 3H), 1.05–1.5 (m, 8H), 2.65–3.20 (m, 6H) 3.43–3.70 (m, 3H), 3.72 (s, 3H), 3.87 (d, J=15 Hz, 1H), 4.49 (dd, J=12 Hz, 6 Hz) and 5.23 (dd, J=12 Hz, 8 Hz) 2H), 5.90 (dd, J=2 Hz, 4 Hz, 2H), 6.63–6.78 (m, 3H), 6.86 and 7.04 (d, J=9 Hz, 2H), 7.22 (d, J=9 Hz, 2H).

EXAMPLE 82 trans,trans-2-(4-Methoxyphenyl)-4-(1,3-benzodioxol-5-yl)-1-(N-n-butyl)-N-(n-propyl) aminocarbonylmethyl)pyrrolidine-3-carboxylic Acid The title compound was prepared using the procedures described in Example 1. m.p. 160°–162° C. $^1$H NMR (CDCl$_3$, 300 MHz) rotational isomers δ 0.69, 0.80, 0.84, 0.87 (four triplets, J=7 Hz, 6H), 1.00–1.52 (m, 6H), 2.63 and 2.66 (two doublets, J=13 Hz, 1H), 2.90–3.10 (m, 4H), 3.23–3.61 (m, 5H), 3.71 and 3.75 (two doublets, J=10 Hz, 1H), 3.78 (s, 3H), 5.92–5.96 (m, 2H), 6.72 (d, J=8 Hz, 1H), 6.83–6.89 (m, 3H), 7.03 (d, J=2 Hz, 1H), 7.81 (d, J=9 Hz, 2H).

EXAMPLE 83 trans,trans-2-(4-Methoxyphenyl)-4-(1,3-benzodioxol-5-yl)-1-[2-(N,N-di(n-propyl)aminocarbonyl)ethyl]pyrrolidine-3-carboxylic Acid The compound resulting from Example 6A (250 mg, 0.677 mmol), 205 mg (1.36 mmol) diallyl acrylamide (Polysciences, Inc.), and 10 mg acetic acid were heated at 85° C. in 0.75 mL of methoxyethanol for one hour. Toluene was added, and the solution was washed with bicarbonate solution, dried; and concentrated. Chromatography on silica gel eluting with 3:1 hexane-ethyl acetate gave 283 mg (80%) of the diallyl compound.

The diallyl compound was hydrogenated using 10% Pd/C catalyst (27 mg) in ethyl acetate (25 mL) under a hydrogen atmosphere. The catalyst was removed by filtration, and the filtrate was concentrated to afford the dipropyl amide ethyl ester in 100% yield.

The ester was hydrolyzed to the title compound by the method of Example 1D in 83% yield. $^1$H NMR (CDCl$_3$, 300 MHz) δ 0.82 and 0.83 (two triplets, J=7 Hz, 6H), 1.39–1.54 (m, 4H), 2.35–2.60 (m, 3H), 2.80–3.07 (m, 5H), 3.14–3.21 (m, 2H), 3.31–3.38 (m, 1H), 3.51–3.61 (m, 1H), 3.73 (d, J=12H, 1H), 3.75 (s, 3H), 5.94 (s, 2H), 6,71 (d, J=9 Hz, 1H), 6.79–6.85 (m, 3H), 7.04 (d, J=2 Hz, 1H)<7.32 (d, J=9 Hz, 2H).

EXAMPLE 84 trans,trans-2-(4-Methoxyphenyl)-4-(1,3-benzodioxol-5-yl)-1-(N,N-di(n-butyl)aminocarbonyl)pyrrolidine-3-carboxylic Acid The title compound was prepared by the procedures described in Example 8 using dibutyl carbamoyl chloride, prepared by the method of Hoshino et al., Syn. Comm., 17:1887–1892 (1987), as a starting material. $^1$H NMR (CDCl$_3$, 300 MHz) δ 0.86 (t, J=7 Hz, 6H), 1.14–1.28 (m, 4H), 1.35–1.48 (m, 4H), 2.81–2.94 (m, 2H), 3.11 (t, J=12 Hz, 1H), 3.30–3.41 (m, 2H), 3.59–3.68 (m, 2H), 3.76 (s, 3H), 3.78–3.85 (m, 1H), 5.81 (d, J=9 Hz, 1H), 5.94 (s, 2H), 6.73–6.86 (m, 5H), 7.24 (d, J=9 Hz, 2H).

EXAMPLE 85 trans,trans-2-(4-Methoxyphenyl)-4-(1,3-benzodioxol-5-yl)-1-(N,N-di(n-butyl)aminocarbonylmethyl)pyrrolidine-3-carboxylic Acid Sodium Salt Sodium hydroxide (48.2 mg of 98.3% pure, 1.184 mmol) in 2 mL of MeOH was added to the compound resulting from Example 43 (610 mg, 1.196 mmol.) in 5 mL MeOH. The solution was concentrated to dryness, and the resulting powder was stirred with heptane. The heptane was removed in vacuo to give a powder which was dried in the vacuum oven for 2 hours at 60° C. to yield 627.5 mg of the title compound.

EXAMPLE 86 trans,trans-2-(4-Methoxyphenyl)-4-(1,3-1-benzodioxol-5-yl)-1-[2-(N,N-di(n-butyl) aminocarbonyl)ethyl]pyrrolidine-3-carboxylic Acid A solution of the bromoethyl compound resulting from Example 61A (150 mg), dibutylamine (150 mg) and sodium iodide (18 mg) in 0.75 mL ethanol was heated at 80° C. for 1 hour. After cooling, toluene was added, and the solution was washed with potassium bicarbonate solution, dried over Na$_2$SO$_4$ and concentrated. More toluene was added, and the solution was again concentrated to get rid of excess dibutylamine. The residue was dissolved in warm heptane and filtered from a small amount of insoluble material. The heptane was removed in vacuo to give 143 mg (87%) of the intermediate ethyl ester.

The ester was hydrolyzed by the method of Example 1D to give the title compound as a white powder. $^1$H NMR (CD$_3$OD, 300 MHz) δ 0.89 (t, J=7 Hz, 6H), 1.16–1.30 (m, 4H), 1.44–1.56 (m, 4H), 2.48–2.57 (m, 1H), 2.80–3.08 3.14–3.25 (m, 1H), 3.31–3.38 (m, 1H), 3.59–3.60 (m, 1H), 3.74 (s, 3H), 3.75 (d, J=10 Hz, 1H), 5.89 (s, 2H), 6.71 (d, J=9 Hz, 1H), 6.81 (dd, J=9 Hz, 2 Hz, 1H), 6.90 (d, J=10 Hz, 2H), 6.96 (d, J=2 Hz, 1H), 7.37 (d, J=10 Hz, 2H).

EXAMPLE 87 trans,trans-2-(4-Methoxyphenyl)-4-(1,3-benzodioxol-5-yl)-1-{2-[N-(N,N-di(n-butyl) aminocarbonyl)-N-methylamino]ethyl}pyrrolidine-3-carboxylic Acid Dibutyl carbamoyl chloride (135 mg) was added to the compound resulting from Example 61B (250 mg) and 150 mg triethylamine in 1 mL dichloromethane. After stirring 1 hour at room temperature, toluene was added, and the solution was washed with potassium bicarbonate solution, dried over Na$_2$SO$_4$ and concentrated. The residue was chromatographed on silica gel, eluting with a mixture of 38% EtOAc and 62% hexane to give 194 mg of the ethyl ester intermediate.

The ester was hydrolyzed by the method of Example 1D to afford 141 mg of the title compound. 1H NMR (CD$_3$OD, 300 MHz) δ 0.92 (t, J=7 Hz, 6H), 1.21–1.32 (m, 4H), 1.42–1.53 (m, 4H), 2.62 (s, 3H), 2.65–2.76 (m, 1H), 3.00–3.20 (m, 8H), 3.44–3.55 (m, 1H), 3.62–3.78 (m, 2H), 3.80 (s, 3H), 4.07 (d, J=12 Hz, 1H), 5.93 (s, 2H), 6.75 (d, J=9 Hz, 1H), 6.87 (dd, J=9 Hz, 2 Hz, 1H), 6.94 (d, J=10 Hz, 2H), 7.04 (d, J=2 Hz, 1H), 7.40 (d, J=10 Hz, 2H).

EXAMPLE 88 trans,trans-2-(4-Methoxyphenyl)-4-(1,3-benzodioxol-5-yl)-1-(N,N-di(n-butyl) aminocarbonyl)methyl)pyrrolidine-3-(N-methanesulfonyl)carboxamide Carbonyldiimidazole (75 mg, 0.463 mmol) was added to 150 mg (0.294 mmol) of the compound resulting from Example 43 in 0.4 mL of tetrahydrofuran, and the solution was stirred at 60° C. for 2 hours. After cooling, 50 mg (0.526 mmol) of methanesulfonamide and 68 mg (0.447 mmol) of DBU in 0.3 mL of THF were added. The mixture was stirred at 45° C. for 2 hours. The solvents were removed in vacuo, and the residue was dissolved in water. A few drops of acetic acid were added, and the solution was lyophilized to give 121 mg (70%) of the title compound. m.p. 170°–173° C. $^1$H NMR (CDCl$_3$, 300 MHz) δ 0.82 (t, J=7 Hz, 3H), 0.88 (t, J=7 Hz, 3H), 1.05–1.51 (m, 8H), 2.75–2.86 (m, 2H), 2.83–3.25 (m, 4H), 3.17 (s, 3H), 3.32–3.50 (m, 3H), 3.70–3.78 (m, 1H), 3.80 (s, 3H), 3.87 (d, J=10 Hz, 1H), 5.96 (dd, J=2 Hz, 4 Hz, 2H), 6.74 (d, J=9 Hz, 1H), 6.84 (dd, J=9 Hz, 2 Hz, 1H), 6.90 (d, J=10 Hz, 2H), 7.01 (d, J=2 Hz, 1H), 7.34 (d, J=10 Hz, 2H).

EXAMPLE 89 trans,trans-2-(4-Methoxyphenyl)-4-(1,3-benzodioxol-5-yl)-1-(N,N-di(N-butyl) aminocarbonyl)methyl)pyrrolidine-3-(N-benzenesulfonyl)carboxamide The compound resulting from Example 43 was converted to the title compound by the method of Example 88 substituting benzenesulfonamide for methanesulfonamide. m.p. 169°–171° C. for a sample recrystallized from acetonitrile. $^1$H NMR (CDCl$_3$, 300 MHz) δ 0.81(t, J=7 Hz, 3H), 0.89 (t, J=7 Hz, 3H), 1.02–1.50 (m, 8H), 2.65–2.80 (m, 2H), 2.90–3.25 (m, 4H), 3.80–3.95 (m, 3H), 3.50–3.60 (m, 1H), 3.65 (d, J=10 Hz, 1H), 3.81 (s, 3H), 5.94 (s, 2H), 6.70 (s, 2H), 6.81–6.90 (m, 3H), 7.17 (d, J=10 Hz, 2H), 7.55 (t, J=7 Hz, 2H), 7.66 (t, J=7 Hz, 1H), 8.95 (d, J=7 Hz, 2H).

EXAMPLE 90 trans,trans-2-(4-Methoxyphenyl)-4-(1,3-benzodioxol-5-yl)-1-[N,N-di(n-butyl) aminosulfonylmethyl)-pyrrolidine-3-carboxylic Acid Chloromethyl sulfenyl chloride, prepared by the method of Brintzinger et. al., Chem. Ber. 85:455–457 (1952), is reacted with dibutylamine by the method of E. Vilsmaier described in Liebigs Ann. Chem. 1055–1063 (1980) to give N,N-dibutyl chloromethyl sulfenyl chloride. Alternatively dimethyl(methylthio)sulfonium tetraflouroborate is reacted with dibutylamine to give N,N-dibutyl methylsulfenyl chloride which is chlorinated with N-chlorosuccinimide to give chloromethyl sulfenyl chloride by the method of E. Vilsmaier, described in the above reference.

The N,N-dibutyl chloromethyl sulfenyl chloride is reacted with the compound resulting from Example 6A to give etfiyl trans, trans-2-(4-Methoxyphenyl)-4-(1,3-benzodioxol-5-yl)-1-[N,N-di(n-butyl) aminosulfenylmethyl]-pyrrolidine-3- carboxylate. This is oxidized with osmium tetroxide and N-methyl morpholine N-oxide by the method of S. Kaldor and M. Hammond, Tet. Lett. 32:5043–5045 (1991) to give the title compound after hydrolysis of the ethyl ester.

EXAMPLE 91 trans,trans-2-(4-Methoxyohenyl)-4-(1,3-benzo-dioxol-5-yl)-1-[(N,N-dibutylamino) carbonyl-1-(RS)-ethyl]pyrrolidine-3-carboxylic Acid

EXAMPLE 91A (±)-Dibutyl 2-bromopropanamide

2-Bromopropanoic acid (510 mg, 3.33 mmol) and 4-methylmorpholine (0.74 mL, 6.73 mmol) were dissolved in 10 mL of $CH_2Cl_2$, the solution was cooled to 0° C. under a $N_2$ atmosphere, and then treated dropwise with isobutyl chloroformate (0.45 mL, 3.5 mmol). After 10 minutes at 0° C., dibutylamine (0.57 mL, 3.4 mmol) was added. The reaction was stirred at 0° C. for 1 hour and for an additional 16 hours at room temperature. The mixture was partitioned with 25 mL of 1.0 M aqueous $Na_2CO_3$ solution, then the organic phase was washed sequentially with 25 mL of 1M aqueous $NaHSO_4$ and 25 mL brine, dried ($Na_2SO_4$), filtered, and concentrated under reduced pressure to afford 698 mg (2.64 mmol, 79 %) of the crude bromoamide as a colorless oil. $^1$H NMR ($CDCl_3$, 300 MHz) δ 0.93 (t, J=7 Hz) and 0.97 (t, J=7.5 Hz, 6H total), 1.26–1.60 (m, 7H), 1.60–1.78 (m, 1H), 1.82 (d, J=6 Hz, 3H), 3.04–3.27 (m, 2H), 3.42–3.64 (m, 2H), 4.54 (q, J=7H, 1H). MS ($DCI/NH_3$) m/e 264 and 266 $(M+H)^+$.

EXAMPLE 91B trans,trans-and cis,trans-2-(4-Methoxyphenyl)-4-(1,3-benzodioxol-5-yl)-1-((N,N-dibutylamino) carbonyl-1-(RS)-ethyl)pyrrolidine-3-carboxylic Acid Ethyl Ester A solution of the resultant mixture of trans,trans and cis,trans compounds from Example 1C (232 mg, 0.628 mmol) and the resultant compound from Example 91A (183 mg, 0.693 mmol) in 2 mL of $CH_3CN$ was treated with diisopropylethylamine (0.22 mL, 1.3 mmol). The solution was stirred at 60°–80° C. under a $N_2$ atmosphere for 16 hours. The reaction was concentrated under reduced pressure, then the residue was partitioned between 30 mL $Et_2O$ and 10 mL of 1M aqueous $Na_2CO_3$ solution. The organic phase was washed with 20 mL water and 20 mL brine, dried over $Na_2SO_4$, filtered and concentrated under reduced pressure to afford the crude amino amide as a brown oil (339 mg, 98% crude). The product was obtained by flash chromatography on silica gel eluting with 20% EtOAc-hexane to provide 224 mg (70%) of the title compounds as a mixture of 4 diastereomers. $^1$H NMR ($CDCl_3$, 300 MHz) δ 0.66–1.55 (several m, 19H), 2.63–3.00 (m, 3H), 3.05–3.39 (m, 2H), 3.40–3.76 (m, 4H), 3.78–3.80 (4s, 3H), 3.84–4.25 (m, 2.6H), 4.38 (d, J=10.5 Hz, 0.2H) and 4.58 (d, J=10.5 Hz, 0.2H), 5.90–5.97 (m, 2H), 6.68–6.96 (m, 5H), 7.38–7.43 (m, 2H). MS ($DCI/NH_3$) m/e 553 $(M+H)^+$.

EXAMPLE 91C trans,trans-2-(4-Methoxyphenyl)-4-(1,3-benzo-dioxoi-5-yl)-1-((N,N-dibutylamino) carbonyl-1-(RS)-ethyl)pyrrolidine-3-carboxylic Acid The procedure of Example 73C was used, substituting the resultant compound from Example 91B for the resultant compound from Example 73B to give the title compound in 61% yield. $^1$H NMR ($CD_3OD$, 300 MHz) δ 0.70–1.05 (several m, 8H), 1.14 (d, J=6 Hz, 2H), 1.17–1.55 (m, 6H), 2.79–3.03 (m, 3.5H), 3.20–3.65 (br m, 4.6H plus $CD_2HOD$), 3.70–3.78 (m, 0.4H), 3.79 (s, 3H), 3.98 (d, J=8 Hz, 0.6H), 4.06 (t, J=7.5 Hz, 0.4H), 4.25 (d, J=8 Hz, 0.4H), 5.92 (s) and 5.94 (s, 2H total 6H), 6.73 (d, J=2.5 Hz) and 6.75 (d, J=3 Hz, 1H total), 6.78–6.85 (m, 1H), 6.91–7.00 (m, 3H), 7.30–7.38 (m, 2H). MS ($DCI/NH_3$) m/e 525 $(M+H)^+$.

Anal calcd for $C_{30}H_{40}N_2O_6 \cdot 0.5H_2O$: C, 67.52; H, 7.74; N, 5.25. Found: C, 67.63: H, 7.65; N, 5.21.

EXAMPLE 92 trans,trans-2-(Pentyl)-4-(1,3-benzodioxol-5-yl)-1-[(N,N-dibutylamino) carbonylmethyl]pyrrolidine-3-carboxylic Acid

EXAMPLE 92A

Methyl 2-(4-hexenoyl)-4-nitro-3-(1,3-benzodioxole-5-yl)butyrate

A solution of methyl 3-oxo-6-octenoate (502 mg, 2.95 mmol) in 10 mL of isopropanol was added to a solution of 5-(2-nitrovinyl)-1,3-benzodioxole (712 mg, 3.69 mmol) in 10 mL THF, then DBU (22 μL, 0.15 mmol) was added. The resulting reddish solution was stirred at room temperature for 20 minutes. TLC (ethyl acetate-hexane, 1:3) indicated complete consumption of ketoester. The solution was concentrated in vacuo and flash chromatographed on silica gel eluting with 18% ethyl acetate in hexane to produce 879 mg (2.42 mmol, 82%) of the title compound as a mixture of diastereomers in a 1:1 ratio. $^1$H NMR ($CDCl_3$, 300 MHz) δ 1.55–1.66 (m, 3H), 2.02–2.17 (br m, 1H), 2.20–2.37 (m, 1.5H), 2.49–2.76 (m, 1.5H), 3.57 (s, 1.5H), 3.74 (s, 1.5H), 3.97 (d, J=7.5H, 0.5H) and 4.05 (d, J=8 Hz, 0.5H), 4.10–4.20 (m, 1H), 4.68–4.82 (m, 2H), 5.06–5.52 (m, 2H), 5.95 (2s, 2H), 6.65 (m, 1H), 6.68 (br s, 1H), 6.75 (d, 7.5 Hz, 1H). MS ($DCI/NH_3$) m/e 381 $(M+NH_4)^+$.

Anal calcd for $C_{18}H_{21}N_7O_7$: C, 59.50; H, 5.82; N, 3.85. Found: C, 59.32; H, 5.71; N, 3.72.

EXAMPLE 92D

Methyl trans,trans.2-(pentyl)-4-(1,3-benzodioxol-5-yl)pyrrolidine-3-carboxylate

The procedures of Example 1B and Example 1C were followed, with the substitution of the resultant compound from Example 92A for the resultant compound from Example 1A, and the substitution of the this resultant compound for the resultant compound from Example 1B, to provide the title compound in crude form as a yellow oil. This crude compound was epimerized under the following conditions. A solution of the crude compound (660 mg, 2.07 mmol) in 3 mL methanol was treated with a solution of sodium methoxide (made by the addition of sodium metal (14 mg, 0.61 mmol) to 1 mL of methanol). The resultant solution was heated at reflux for 18 hours. The reaction was concentrated under reduced pressure, and the residue was partitioned between 25 mL saturated NaHCO$_3$ diluted with 10 mL water and 30 mL of CH$_2$Cl$_2$. The aqueous phase was extracted (2×30 mL CH$_2$Cl$_2$), then the combined organic phases were washed with 20 mL brine, dried over Na$_2$SO$_4$, filtered and the filtrate concentrated under reduced pressure to afford the crude product. Purification by flash chromatography on silica gel eluting with 3.5% methanol in CH$_2$Cl$_2$ gave 336 mg (57%) the title compound as a yellow oil. $^1$H NMR (CDCl$_3$, 300 MHz) δ 0.90 (br t, 3H), 1.25–1.70 (br m, 8H), 1.83–2.02 (br s, 2H), 2.58 (dd, J=8,9 Hz, 1H), 2.99 (dd, J=8,14 Hz, 1H), 3.34–3.45 (m, 2H), 3.53 (q, J=9 Hz, 1H), 3.66 (s, 3H), 5.94 (s, 2H), 6.65–6.75 (m, 3H). MS (DCI/NH$_3$) m/e 320 (M+H)$^+$.

Anal calcd for C$_{18}$H$_{25}$NO$_4$: C, 67.69; H, 7.89; N, 4.39. Found: C, 7.39; H, 7.84; N, 4.37.

EXAMPLE 92C trans,trans-2-(Pentyl)-4-(1,3-benzodioxol-5-yl)-1-[(N,N-dibutylamino) carbonylmethyl]pyrrolidine-3-carboxylic Acid The procedures of Example 1B-1D were used, with the substitution of the resultant compound from Example 92A for the resultant compound from Example 1B, to provide the title compound as a white foam. $^1$H NMR (CDCl$_3$, 300 MHz) δ 0.87 (brt) and 0.89 (brt, 6H total), 0.97 (t, J=7.5 Hz, 3H), 1.21–1.42 (br m, 10), 1.43–1.78 (br m, 6H), 2.76 (t, J=7 Hz, 1H), 3.02–3.30 (br m, 6H), 340–3.60 (m, 3H), 3.73 (d, J=14 Hz, 1H), 5.98 (AB, 2H), 6.70 (d, J=7 Hz, 1H), 6.77 (dd, J=1.5,7 Hz, 1H), 6.89 (d, J=1.5 Hz, 1H). MS (DCI/NH$_3$) m/e 475 (M+H)$^+$.

Anal calcd for C$_{27}$H$_{42}$N$_2$O$_5$.0.5H$_2$O: C, 67.05; H, 8.96; N, 5.79. Found: C, 67.30; H, 8.77; N, 5.68.

EXAMPLE 93 trans,trans-2-(Pentyl)-4-(1,3-benzodioxol-5-yl)-1-[2-(N-propyl-N-propylsulfonylamino) ethyl]pyrrolidine-3-carboxylic Acid

EXAMPLE 93A

Methyl trans,trans-2-(pentyl)-4-(1,3-benzodioxol-5-yl)-1-(2-bromoethyl) pyrrolidine-3-carboxylate The procedure of Example 61A was used, with the substitution of the resultant compound from Example 92B for the resultant compound from Example 1C, to provide the title compound as a yellow oil. $^1$H NMR (CDCl$_3$, 300 MHz) δ 0.89 (br t, J=7 Hz, 3H), 1.24–1.40 (br m, 6H), 1.60–1.80 (br m, 2H), 2.61–2.75 (m, 2H), 2.76–2.91 (m, 2H), 3.10–3.22 (m, 2H), 3.36–3.47 (m, 2H), 3.68 (s, 3H), 5.92 (s, 2H), 6.69–6.77 (m, 2H), 6.90–6.94 (m, 1H). MS (DCI/NH$_3$) m/e 426,428 (M+H)$^+$.

EXAMPLE 93B

Methyl trans,trans-2-(Pentyl)-4-(1,3-benzodioxol-5-yl)-1-[2-(N-propyl-N-propylsulfonylamino) ethyl] pyrrolidine-3-carboxylate A solution of the resultant compound from Example 93A (102 mg, 0.24 mmol) and tetrabutylammonium iodide (6 mg, 16 μmol) in 1 mL EtOH was treated with propylamine (60 μL, 0.73 mmol). The solution was warmed to 80° C. for 4 hours. The reaction was concentrated under reduced pressure, then the residue was dissolved in 35 mL ethyl acetate and extracted with 2×15 mL of 1M aqueous Na$_2$CO$_3$. The organic phase was washed with 15 mL brine, then dried over Na$_2$SO$_4$, filtered and concentrated under reduced pressure to provide the crude secondary amine as a yellow oil (94.2 mg). The crude amine was dissolved in 1 mL of CH$_2$Cl$_2$, diisopropylethylamine (65 μL, 0.373 mmol) was added, followed by propylsulfonyl chloride (29 μL, 0.26 mmol). The solution was stirred at room temperature for 4 hours. The reaction was quenched with 10% aqueous citric acid (to pH 4), and the mixture was extracted with 2×3 mL CH$_2$Cl$_2$. The combined organic extracts were washed with 2 mL brine, then dried over Na$_2$SO$_4$, filtered, concentrated in vacuo. Purification by flash chromatography eluting with 20% ethyl acetate in hexane provided 65.0 mg (53%) of the title compound as a waxy solid. R$_f$=0.17 (20%EtOAc-hexane). MS (DCI/NH$_3$) m/e 511 (M+H)$^+$.

EXAMPLE 93C trans,trans-2-(Pentyl)-4-(1,3-benzodioxol-5-yl)-1-[2-(N-propyl-N-propylsulfonylamino) ethyl]pyrrolidine-3-carboxylic Acid The procedure of Example 71C was followed, with the substitution of the resultant compound from Example 93B for the resultant compound from Example 71B, to provide the title compound as a white foam (47 mg, 80%), R$_f$=0.14 (5%MeOH-CH$_2$Cl$_2$). $^1$H NMR (CDCl$_3$, 300 MHz) δ 0.88 (br t) and 0.92 (t, J=7 Hz, 6H total), 1.22–1.52 (br m, 6H), 1.63 (sextet, J=8Hz, 2H), 1.75–2.10 (br m, 4H), 2.89–2.98 (m, 2H), 3.05 (br t, J=9 Hz, 1H), 3310–3.30 (m, 3H), 3.30–1.80 (br m, 7H), 5.94 (s, 2H), 6.71 (t, J=8 Hz, 1H), 6.77 (dd, J=1.5,8 Hz, 1H), 6.89 (d, J=1.5 Hz, 1H). MS (DCI/NH$_3$) m/e 497 (M+H)$^+$.

EXAMPLE 94 trans,trans-2-(Propyl)-4-(1,3-benzodioxol-5-yl)-1-[(N,N-dibutylamino) carbonylmethyl]pyrrolidine-3-carboxylic Acid

EXAMPLE 94A

Ethyl 2-(4-butanoyl)-4-nitro-3-(1,3-benzodioxole-5-yl)butyrate

The procedure of Example 92A was followed, with the substitution of ethyl butyryl acetate for methyl 3-oxo-6-octenoate, to provide the title compound as a mixture of trans and cis isomers (47 mg, 80%), R$_f$=0.28 (25%EtOAc-hexane). $^1$H NMR (CDCl$_3$, 300 MHz) δ 0.74 (t, J=7.5 Hz) and 0.91 (t, J=7.5 Hz, 3H total), 1.08 (t, J=7 Hz) and 1.28 (t, J=7 Hz, 3H total), 1.45 (sextet, J=7 Hz, 1.5H), 1.63 (sextet, J=7 Hz, approx. 1.5H), 2.17 (t, J=7 Hz) and 2.24 (t, J=7 Hz, 0.5H total)2.40–2.54 (m, 1H), 2.60 (t, J=7.5 Hz) and 2.67 (t, J=7.5 Hz, 0.5H total), 3.93–4.09 (m, 2H), 4.10–4.20 (br m, 1H), 4.23 (q, J=7 Hz, 1H), 4.67–4.85 9m, 2H), 5.94 (s, 2H), 6.62–6.75 (m, 3H). MS (DCI/NH$_3$) m/e 369 (M+NH$_4$)$^+$.

Anal calcd for C$_{17}$H$_{21}$NO$_7$: C, 58.11; H, 6.02; N, 3.99. Found: C, 58.21; H, 5.98; N, 3.81.

EXAMPLE 94B

Ethyl trans,trans-2-(propyl)-4-(1,3-benzodioxol-5-yl)pyrrolidine-3-carboxylate

The procedure of Example 92B was followed, with the substitution of the resultant compound from Example 94A for the resultant compound from Example 92A, to afford the title compound. MS (DCI/NH$_3$) m/e 306 (M+H)$^+$.

EXAMPLE 94C trans,trans-2-(Propyl)-4-(1,3-benzodioxol-5-yl)-1-((N,N-dibutylamino) carbonyl)methylpyrrolidine-3-carboxylic Acid The procedure of Example 92C was followed, with the substitution of the resultant product from Example 94B for the resultant product from Example 92B, to give the title compound. $^1$H NMR (CDCl$_3$, 300 MHz) δ 0.89 (t, J=7.5 Hz), 0.92 (t, J=7.5 Hz), and 0.97 (t, J=7.5H, 9H total), 1.22–1.80 (br m, 12H), 2.83 (t, J=7.5 Hz, 1H), 3.40–3.55 (br m, 2H), 3.55–3.68 (m, 1H), 3.78 (d, J=15 Hz, 1H) 5.92 (q, J=1 Hz, 2H), 6.70 (d, J=8 Hz, 1H), 6.79 (dd, J=1 Hz,8 Hz, 1H), 6.90 (d, J=1 Hz, H). MS (DCI/NH$_3$) m/e 447 (M+H)$^+$.

Anal calcd for C$_{25}$H$_{38}$N$_2$O$_5$·0.5 H$_2$O: C, 65.91; H, 8.63; N, 6.15. Found: C, 65.91; H, 8.68; N, 5.94.

EXAMPLE 95

(2R,3R,4S)-(+)-2-(4-Methoxyphenyl)-4-(1,3-benzodioxol-5-yl )-1-(tert-butyloxycarbonyl-aminocarbonylmethyl)-pyrrolidine-3-carboxylic Acid

EXAMPLE 95A trans,trans-2-(4-Methoxyphenyl)-4-(1,3-benzodioxol-5-yl)-1-(tert-butyloxycarbonyl-aminocarbonylmethyl)-pyrrolidine-3-carboxylic Acid The resulting mixture of 64% trans,trans- and cis,trans-pyrrolidines resulting from Example 1C (3.01 g, 8.15 mmol) was dissolved in 50 mL of methylene chloride. To this was added dropwise a solution of di-tert-butyl dicarbonate (1.96 g, 8.97 mmol) in 20 mL methylene chloride under a nitrogen atmosphere, and the resulting solution was stirred 30 minutes at which point TLC (ethyl acetate:hexane, 1:1 ) indicated that all of the starting material was consumed. The reaction mixture was concentrated and dried under high vacuum to give 3.94 g of the ethyl ester as a yellow-brown oil. $^1$H NMR (CDCL$_3$, 300 MHz) δ 0.99, 1.07 (br t, br t, J=7 Hz, 3H), 1.11–1.62 (several br m, 9H), 3.05 (br m, 1H), 3.44–3.95 (m, 3H), 3.81 (s, 3H), 4.04 (q, J=7 Hz, 1H), 4.14–4.28 (br m, 1H), 4.89–5.24 (br m, 1H), 5.94 (d, J=3 Hz, 2H), 6.69–6.90 (m, 5H), 7.06–7.20 (m, 2H). MS (DCI/NH$_3$) m/e 470 (M+H)$^+$.

To the ethyl ester dissolved in 170 mL of ethanol was added a solution of lithium hydroxide (1.06 g, 25.17 mmol) in 60 mL of water. The reaction mixture was vigorously stirred for 18 hours under a nitrogen atmosphere. The reaction mixture was concentrated to remove ethanol, diluted with 250 mL of water and extracted three times with 250 mL of ether. The organic phase acidified to slight cloudiness (pH ~7) with 1 N hydrochloric acid, then to pH 4 with 10% citric acid and extracted with 5% ethanol in methylene chloride (3×100 mL). The combined organic layers dried (Na$_2$SO$_4$), filtered, concentrated and dried on high vacuum to give the title compound as a white foam (2.19 g, 60%). $^1$H NMR (CDCl$_3$, 300 MHz) δ 1.16 (v br s, 9H), 3.11 (br m, 1H), 3.50–3.64 (m, 2H), 3.81 (s, 3H), 4.24 (br m, 1H), 4.96 (br m, 1H), 5.94 (s, 2H), 6.71–6.79 (m, 3H), 6.84–6.91 (m, 2H), 7.19 (d, J=9 Hz, 2H). MS (DCI/NH$_3$) m/e 442 (M+H)$^+$.

EXAMPLE 95B (2R,3R,4S )-(+)-2-(4-Methoxyphenyl)-4-(1,3-benzodioxol-5-yl) -1-(tert-butyloxycarbonylaminocarbonylmethyl)-pyrrolidine-3-carboxylic Acid The compound resulting from Example 95A (2.15 g, 4.86 mmol) and (+)-cinchonine (1.43 g, 4.86 mmol) were added to 100 mL of methylene chloride; this suspension was swirled with warming as necessary to get all solids to dissolve. The solution was then concentrated and dried on high vacuum to a white foam. This material was crystallized from a mixture of refluxing chloroform (64 mL) and hexane (360 mL). The resulting crystals were isolated by filtration and recrystallized under the same conditions seven additional times. Each time the resulting crystals and filtrate were monitored by $^1$H NMR and chiral HPLC. The amount of (2S,3S,4R)-(–)- enantiomer decreased first in the crystals and then in the filtrate with the predetermined endpoint achieved when the (2S,3S,4R)-(–)- enantiomer could no longer be detected in the filtrate. The pure (2R,3R,4S)-(+)-enantiomer thus obtained was partitioned between 100 mL of 10% citric acid and 100 mL of ether. The aqueous layer was further extracted twice with 100 mL of ether. The combined ether layers were washed with brine, dried (Na$_2$SO$_4$), filtered, concentrated and dried on high vacuum to a white powder (550 mg, 55 % of theoretical 50 % maximum, >99.5 ee). $^1$H NMR (CDCl$_3$, 300 MHz) δ 1.05–1.50 (br m, 9H), 3.12 (br m, 1H), 3.50–3.65 (m, 2H), 3.81 (s, 3H), 4.24 (m, 1H), 4.96 (br m, 1H), 5.95 (s, 2H), 6.70–6.79 (m, 3H), 6.86 (d, J=9 Hz, 2H), 7.19 (d, J=9 Hz, 2H). MS (DCI/NH$_3$) m/e 442 (M+H)$^+$.

EXAMPLE 95C (2R,3R,4S)-(+)-Ethyl 2-(4-methoxyphenyl)-4-(1,3-benzodioxol-5-yl) -pyrrolidine-3-carboxylate The compound resulting from Example 95B (251 mg, 0.568 mmol) was dissolved in 20 mL of a saturated solution of anhydrous HCl(g) in anhydrous ethanol. The resulting solution was heated at 50° C. with stirring for 18 hours at which point all of the precipitated solid had dissolved. The reaction mixture was concentrated to a solid which was partitioned between 0.8M aqueous sodium carbonate (50 mL) and methylene chloride (50 mL). The aqueous layer was further extracted with methylene chloride (2×50 mL). The combined organic layers were dried (Na$_2$SO$_4$), filtered, concentrated and dried under high vacuum to give the title compound as an almost colorless oil (158 mg, 69%). $^1$H NMR (CDCl$_3$, 300 MHz) δ 1.11 (t, J=7 Hz, 3H), 2.18 (v br s, 1H), 2.93 (t, J=9 Hz, 1H), 3.19,3.22 (dd, J=7 Hz, 1H), 3.50–3.69 (m, 2H), 3.80 (s, 3H), 4.07 (q, J=7 Hz, 2H), 4.49 (d, J=9 Hz, 1H), 5.94 (s, 2H), 6.73 (d, J=2 Hz, 2H), 6.81–6.92 (m, 3H), 7.34–7.41 (m, 2H). MS (DCI/NH$_3$) m/e 370 (M+H)$^+$.

EXAMPLE 95D (2R,3R,4S)-(+)-2-(4-Methoxyphenyl)-4-(1,3-benzodioxol-5-yl) -1-(tert-butyloxycarbonyl-aminocarbonylmethyl)-pyrrolidine-3-carboxylic Acid To the resulting compound from Example 95C (131 mg, 0.355 mmol) was added, diisopropylethylamine (137 mg, 185 μL, 1.06 mmol), acetonitrile (2 mL), N,N-di-(n-butyl) bromoacetamide (133 mg, 0.531 mmol), and the mixture was heated at 50° C. for 1.5 hours. The reaction mixture was concentrated to a solid, dried under high vacuum, and purified by chromatography on silica gel eluting with 1:3 ethyl acetate-hexane to give pure ester as a colorless oil. $^1$H NMR (CDCl$_3$, 300MHz) δ 0.81 (t, J=7 Hz, 3H), 0.88 (t, J=7 Hz, 3H), 1.10 (t, J=7 Hz, 3H), 1.00–1.52 (m, 8H), 2.78 (d, J=14 Hz, 1H), 2.89–3.10 (m, 4H), 3.23–3.61 (m, 5H), 3.71 (d, J=9 Hz, 1H), 3.80 (s, 3H), 4.04 (q, J=7 Hz, 2H), 5.94 (dd, J=1.5 Hz, 2H), 6.74 (d, J=9 Hz, 1H), 6.83–6.90 (m, 3H), 7.03 (d, J=2 Hz, 1H), 7.30 (d, J=9 Hz, 2H). MS (DCI/NH$_3$) m/e 539 (M+H)$^+$.

To the ethyl ester dissolved in 7 mL of ethanol was added a solution of lithium hydroxide (45 mg, 1.06 mmol) in water (2.5 mL). The mixture was stirred for 1 hour at ambient temperature and then warmed slowly to 40° C. over 2.5 hours at which point all of the starting material had been consumed. The reaction mixture was concentrated to remove the ethanol, diluted with 60 mL water and extracted with ether (3×40 mL). The aqueous solution was treated with 1 N aqueous hydrochloric acid until cloudy, and the pH was then adjusted to ~4–5 with 10% aqueous citric acid. This mixture was extracted with 1:19 ethanol-methylene chloride (3×50 mL). The combined extracts were dried (Na$_2$SO$_4$), filtered, concentrated and dried under high vacuum to give the title compound as a white foam (150 mg, 83%). $^1$H NMR (CDCl$_3$, 300 MHz) δ 0.80 (t, J=7 Hz, 3H), 0.88 (t, J=7 Hz, 3H), 1.08 (m, 2H), 1.28 (m, 3H), 1.44 (m, 3H), 2.70–3.77 (svr br m, 12H), 3.79 (s, 3H), 5.95 (m, 2H), 6.75 (d, J=8 Hz, 1H), 6.87 (br d, J=8 Hz, 3H), 7.05 (br s, 1H), 7.33 (v br s, 2H). MS (DCI/NH$_3$) m/e 511 (M+H)$^+$. [α]$^{22}$= +74.42°.

Anal calcd for C$_{29}$H$_{38}$N$_2$O$_6$·0.5 H$_2$O: C, 67.03; H, 7.56; N, 5.39. Found: C, 67.03; H, 7.59; N, 5.33.

EXAMPLE 95E

Alternate Preparation of (2R,3R,4S)-(+)-2-(4-Methoxyphenyl)-4-(1,3-benzodioxol-5-yl) -1-(tert-butyloxycarbonylaminocarbonylmethyl)-pyrrolidine-3-carboxylic Acid The product of Example 95A (2.858 g) was suspended in 10 mL of EtQAc. 0.7833 g of R (+) alpha methyl benzylamine in 3 mL ethyl acetate was added. On swirling all of the solids were dissolved. The ethyl acetate was removed in vacuum. Ether (13 ml) was added to the residue. When all of the residue had dissolved, 5 mg of seed crystals were added and these crystals were crushed with a metal spatula while cooling in ice. The product crystallized very slowly. After 1 hour the solid was filtered and washed with ether giving 1.4213 g, m.p. 163°–167°. The filtrate was concentrated, cooled and scratched with a spatula to give a second crop 0.1313 g, m.p. 164°–168°. The filtrate was concentrated again and put in the refrigerator and let stand overnight giving 1.6906 g, m.p. 102°–110°. (HPLC of this showed 20% of the desired enantiomer and 80% of the unwanted enantiomer.)

The first two batches of crystallized material were combined and suspended in 20 mL dichloromethane (Note: the unwanted isomer is more soluble in dichloromethane) and stirred for 2 minutes. The mixture was concentrated, but not to dryness, and ether (10 mL) was added. After stirring for a few minutes the crystals were filtered. Yield: 1.401 g, m.p. 164°–172°.

Treatment of the crystalline product with 10% citric acid and ether according the method described in Example 95B provided the title compound.

EXAMPLE 96 trans,trans-2-(4-Methoxyphenyl)-4-(1,3-benzodioxol-5- yl)-1-[2-(N-propyl-N-butyrylamino) ethyl] pyrrolidine-3-carboxylic Acid The title compound was prepared by the methods described in Example 61, but substituting propylamine for methylamine in Example 61B and butyryl chloride for isobutyryl chloride in Example 61C. The product was purified by preparative HPLC (Vydac μC18) eluting with a 10–70% gradient of CH$_3$CN in 0.1% TFA. The desired fractions were lyophilized to give the product as a white solid. $^1$H NMR (CDCl$_3$, 300 MHz) δ 0.80 (m, 3H), 0.90 (t, 3H, J=8 Hz), 1.42 (m, 2H), 1.58 (heptet, 2H, J=8Hz), 2.20 (t, 3H, J=8Hz), 2.94 (br m, 2H), 3.10 (br, m, 2H), 3.48 (br m, 4H), 3.76 (br m, 2H), 3.78 (s, 3H), 4.30 (br s, 1H), 5.95 (s, 2H), 6.75 (d, 1H, J=8 Hz), 6.84 (m, 1H), 6.85 (d, 2H, J=8 Hz), 7.04 (d, 1H, J=1 Hz), 7.40 (d, 2H, J=8 Hz). MS (DCI/NH$_3$) m/e 497 (M+H)$^+$.

Anal calcd for C$_{28}$H$_{36}$N$_2$O$_6$ 1.0 TFA: C, 58.82; H, 6.42; N, 4.57. Found: C, 58.77; H, 6.30; N, 4.42.

EXAMPLE 97 trans,trans-2-(4-Methoxyphenyl)-4-(1,3-benzodioxol-5-yl)-1-[2-(N-propyl-N-(ethylaminocarbonyl) amino)ethyl]pyrrolidine-3-carboxylic Acid The title compound was prepared by the methods described in Example 61, but substituting propylamine for methylamine in Example 61B and ethyl isocyanate for isobutyryl chloride in Example 61C. The crude product was purified by trituration with 1:1 diethyl ether-hexane. The resulting solid was dissolved in CH$_3$CN and water and lyophilized to give the product as a white solid. $^1$H NMR (CDCl$_3$, 300 MHz) mixture of rotamers δ 0.80 (t, J=8 Hz) and 1.05 (t, J=8 Hz) and 1.20 (m) and 1.42 (m) total of 8H for the four peaks, 2.35 (br s, 1H), 2.70 (m, 1H), 3.0 (m, 3H), 3.2 (m, 3H), 3.25 (dq, 1H, J=1,8 Hz), 3.42 (m, 1H), 3.6 (m, 1H), 3.75 (m, 1H), 3.78 (s, 3H), 4.8 (br s, 1H), 5.95 (s, 2H), 6.74 (d, 1H, J=8Hz), 6.85 (m, 3H), 7.00 (s, 1H), 7.30 (d, 2H, J=8 Hz). MS (DCI/NH$_3$) m/e 498 (M+H)$^+$.

Anal calcd for C$_{27}$H$_{35}$N$_3$O$_6$. 0.75 H$_2$O: C, 63.45; H, 7.20; N, 8.22. Found: C, 63.38; H, 7.29; N, 8.44.

EXAMPLE 98 trans,trans-2-(4-Methoxyphenyl)-4-(1,3-benzodioxol-5-yl)-1-[2-(N-butyl-N-butyrylamino) ethyl] pyrrolidine-3-carboxylic Acid The title compound was prepared by the methods described in Example 61, but substituting butylamine for methylamine in Example 61 B and butyryl chloride for isobutyryl chloride in Example 61C. The crude product was purified by trituration with 1:1 diethyl ether-hexane. The resulting solid was dissolved in CH$_3$CN and water and lyophilized to give the product as a white solid. $^1$H NMR (CDCl$_3$, 300 MHz) δ 0.80 (m, 3H), 0.90 (t, 3H, J=8 Hz), 1.45 (m, 4H), 1.6 (m, 2H), 2.20 (t, 3H, J=8 Hz), 2.94 (br m, 2H), 3.10 (br m, 2H), 3.5 (br m, 4H), 3.80 (br m, 2H), 3.82 (s, 3H), 4.30 (br s, 1H), 5.95 (s, 2H), 6.75 (d, 1H, J=8Hz), 6.84 (m, 1H), 6.85 (d, 2H, J=8 Hz), 7.04 (d, 1H, J=1 Hz), 7.40 (d, 2H, J=8 Hz). MS (DCI/NH$_3$) m/e 511 (M+H)$^+$. HRMS calcd for C$_{29}$H$_{38}$N$_2$O$_6$:511.2808. Found: 511.2809

EXAMPLE 99 trans,trans-2-(4-Methoxyphenyl)-4-(1,3-benzodioxol-5-yl)-1-[2-(N-propyl-N-ethoxycarbonylamino) ethyl]pyrrolidine-3-carboxylic Acid The title compound was prepared by the methods described in Example 61, but substituting propylamine for methylamine in Example 61B and ethyl chloroformate for isobutyryl chloride in Example 61C. The crude product was purified by trituration with 1:1 diethyl ether-hexane. The resulting solid was dissolved in CH$_3$CN and water and lyophilized to give the product as a white solid. $^1$H NMR (CDCl$_3$, 300 MHz) δ 0.80 (t, 3H, J=8 Hz), 1.05 (m, 2H), 1.22 (m, 3H), 1.45 (m, 3H), 2.08 (br s, 1H), 2.75 (m, 1H), 2.88 (br q, 2H, J=8 Hz), 3.08 (br m, 2H), 3.27 (br m, 2H), 3.44 (m, 1H), 3.54 (dt, 1H, J=1,8 Hz), 3.63 (d, 1H, J=8Hz), 3.78 (s, 3H), 4.02 (br d, 2H), 5.93 (s, 2H), 6.72 (d, 1H, J=8 Hz), 6.91 (dd, 1H, J=1,8 Hz), 6.85 (d, 2H, J=8 Hz), 7.00 (s, 1H), 7.30 (d, 2H, J=8 Hz). MS (DCI/NH$_3$) m/e 499 (M+H)$^+$.

Anal calcd for C$_{27}$H$_{34}$N$_2$O$_7$ . 0.5 H$_2$O: C, 63.89; H, 6.95; N. 5.52. Found: C, 64.03: H, 6.71: N, 5.30.

EXAMPLE 100 trans,trans-2-(4-Methoxyphenyl)-4-(1,3-benzodioxol-5-yl)-1-[2-(N-methyl-N-( 2-ethylbutyryl)amino)ethyl]pyrrolidine-3-carboxylic Acid To the compound resulting from Example 61B (190 mg) dissolved in THF (2 mL) was added HOBt (60 mg), EDCl (85 mg), N-methytmorpholine (50 μL), , and DMF (2 mL). 2-Ethylbutyric acid was added and the solution stirred overnight at ambient temperature. Water (10 mL) was added, and the mixture was extracted with EtOAc (2×25 mL). The combined organic extracts were washed with saturated sodium bicarbonate solution, 1 N H$_3$PO$_4$, and brine, dried with Na$_2$SO$_4$, and evaporated to give an oil which was purified by flash chromatography on silica gel eluting with 1:3 EtOAc-hexane. The resulting ethyl ester was saponified by the procedure described in Example 61C. The crude product was dissolved in CH$_3$CN and water and lyophilized to give the product as a white solid. $^1$H NMR (CDCl$_3$, 300 MHz) (mixture of rotamers) δ 0.66, 0.74, 0.80, 0.88 (all triplets, total of 6H, J=8 Hz), 1.05 (m, 2H), 1.25–1.75 (m, 5H), 2.16 (m, 1H), 2.32 (m, 1H), 2.45 (m, 1H), 2.70 (m, 1H), 2.86, 2.94 (s, total 3H), 2.95 (m, 1H), 3.35 (m, 1H), 3.52 (m, 2H), 3.65 (m, 1H), 3.80 (s, 3H), 5.94, 5.96 (s, total 2H), 6.73 (m, 1H), 6.84 (m, 3H), 6.97 (m, 1H), 7.30 (m, 2H). MS (DCI/NH$_3$) m/e 497 (M+H)$^+$.

Anal calcd for C$_{28}$H$_{36}$N$_2$O$_6$ . 0.25 H$_2$O: C, 67.11; H, 7.34; N, 5.59. Found: C, 67.13; H, 7.24; N, 5.56.

EXAMPLE 101 trans,trans,2-(4-Methoxyphenyl)-4-(1,3-benzodioxol-5-yl)-1-[2-(N-methyl-N-(2-propylvaleryl) amino)ethyl]pyrrolidine-3-carbexylic Acid The title compound was prepared by the procedure described in Example 100, but substituting 2-propylpentanoic acid for 2-ethylbutyric acid. The crude product was purified by preparative HPLC (Vydac μC18) eluting with a 10–70% gradient of CH$_3$CN in 0.1% TFA. The desired fractions were lyophilized to give the product as a white solid. $^1$H NMR (CDCl$_3$, 300 MHz) δ 0.79 (t, 3H, J=8 Hz), 0.82 (t, 3H, J=8 Hz), 1.10 (m, 4H), 1.2–1.5 (m, 4H), 2.55 (m, 1H). 2.96 (s, 3H), 3.15 (br m, 1H), 3.32 (br m, 1H), 3.56 (m, 2H), 3.68 (m, 1H) 3.68 (s, 3H), 3.70 (m, 1H), 3.80 (m, 2H), 4.65 (br d, 1H), 5.92 (s, 2H), 6.75 (d, 1H, J=8 Hz), 6.84 (m, 1H), 6.85 (d, 2H, J=8 Hz), 7.05 (s, 1H), 7.42 (d, 2H, J=8 Hz). MS (DCI/NH$_3$) m/e 525 (M+H)$^+$.

Anal calcd for C$_{30}$H$_{40}$N$_2$O$_6$. 1.25 TFA: C, 58.51; H, 6.23; N, 4.20. Found: C, 58.52; H, 6.28; N, 4.33.

EXAMPLE 102 trans,trans-2-(4-Methoxyphenyl)-4-(1,3-benzodioxol-5-yl)-1-[2-(N-propyl-N-(tert.-butyloxycarbonylmethyl)amino)ethyl]pyrrolidine-3-carboxylic Acid The title compound was prepared by the methods described in Example 61, but substituting propylamine for methylamine in Example 61B and t-butyl bromoacetate for isobutyryl chloride in Example 61C. The crude product was purified by trituration with 1:1 diethyl ether-hexane. The resulting solid was dissolved in CH$_3$CN and water and lyophilized to give the product as a white solid. $^1$H NMR (CDCl$_3$, 300 MHz) δ 0.82 (t, 3H, J=8 Hz), 1.18 (m, 2H), 1.19 (s, 9H), 2.12 (m, 1H), 2.46 (m, 2H), 2.70 (m, 3H), 2.85 (m, 2H), 3.20 (s, 2H), 3.40 (dd, 1H, J=2,8 Hz), 3.50 (dr, 1H, J=2,8 Hz), 3.62 (d, 1H, J=8 Hz), 3.78 (s, 3H), 5.95 (s, 2H), 6.72 (d, 1H, J=8 Hz), 6.84 (m, 1H), 6.85 (d, 2H, J=8 Hz), 7.05 (s, 1H), 7.16 (d, 2H, J=8 Hz). MS (DCI/NH$_3$) m/e 541 (M+H)$^+$.

Anal calcd for C$_{30}$H$_{40}$N$_2$O$_7$. 1.0 H$_2$O: C. 64.50; H, 7.58; N, 5.01. Found: C, 64.75; H, 7.35; N, 4.86.

EXAMPLE 103 trans,trans-2-(4-Methoxyphenyl)-4-(1,3-benzodioxol-5-yl)-1-[2-(N-propyl-N-(n-propylaminocarbonylmethyl)amino)ethyl]pyrrolidine-3-carboxylic Acid The title compound was prepared by the methods described in Example 61, but substituting propylamine for methylamine in Example 61B and N-propyl bromoacetamide for isobutyryl chloride in Example 61C. The crude product was purified by preparative HPLC (Vydac μC18) eluting with a 10–70% gradient of CH$_3$CN in 0.1% TFA. The desired fractions were lyophilized to give the product as a white solid. $^1$H NMR (CDCl$_3$, 300 MHz) δ 0.78 (t, 3H, J=8 Hz), 0.88 (t, 3H, J=8 Hz), 1.45 (m, 2H), 1.48 (m, 3H, J=8 Hz), 2.55–2.7 (m, 2H), 2.90 (m, 1H), 3.04 (m, 1H), 3.15 (m, 3H), 3.28 (t, 1H, J=8 Hz), 3.45 (t, 1H, J=8 Hz), 3.60 (m, 2H), 3.70 (d, 2H, J=8 Hz), 3.75 (m, 1H), 3.80 (s, 3H), 4.25 (d, 1H, J=8 Hz), 5.95 (s, 2H), 6.75(d, 1H, J=8 Hz), 6.86 (dt, 1H, J=1,8 Hz), 6.88 (d, 2H, J=8 Hz), 7.04 (d, 1H, J=1 Hz), 7.40 (d, 2H, J=8 Hz). MS (DCI/NH$_3$) m/e 526 (M+H)$^+$.

Anal calcd for C$_{29}$H$_{39}$N$_3$O$_6$. 1.85 TFA: C, 53.32; H, 5.59; N, 5.70. Found: C, 53.45; H, 5.62; N, 5.63.

EXAMPLE 104 trans,trans-2-(4-Methoxyphenyl)-4-(1,3-benzodioxol-5-yl)-1-[2-(N-propyl-N-(4-methoxyphenoxycarbonyl)amino)ethyl]pyrrolidine-3-carboxylic Acid The title compound was prepared by the methods described in Example 61, but substituting propylamine for methylamine in Example 61B and 4-methoxyphenylchloroformate for isobutyryl chloride in Example 61C. The crude product was purified by trituration with 1:1 diethyl ether-hexane. The resulting solid was dissolved in $CH_3CN$ and water and lyophilized to give the product as a white solid. $^1H$ NMR ($CD_3OD$, 300 MHz) mixture of rotamers δ 0.88 (m,3H), 1.57 (m, 2H), 2.45 (br s) and 2.60 (br s, total of 1H), 2.90–3.15 (m, 4H), 3.42–3.7 (m, 5H), 3.78 (s, 3H), 3.80 (s, 3H), 3.85 (m) and 4.0 (m, total of 1H), 5.95 (s) and 5.98 (s, total of 2H), 6.63(m, 1H), 6.72 (d, 1H, J=8 Hz), 6.81 (m, 2H), 6.93 (m, 5H), 7.40 (m, 2H). MS ($DCI/NH_3$) m/e 577 $(M+H)^+$.

Anal calcd for $C_{32}H_{36}N_2O_8$. 1.0 $H_2O$: C, 64.63; H, 6.44; N, 4.71. Found: C, 64.70; H, 6.38; N, 4.63.

EXAMPLE 105 trans,trans-2-(4-Methoxyphenyl)-4-(1,3-benzo-dioxol-5-yl)-1-[2-(N-propyl-N-(4-methoxybenzoyl)amino)ethyl]pyrrolidine-3-carboxylic Acid The title compound was prepared by the methods described in Example 61, but substituting propylamine for methylamine in Example 61B and anisoyl chloride for isobutyryl chloride in Example 61C. The crude product was purified by trituration with 1:1 diethyl ether-hexane. The resulting solid was dissolved in $CH_3CN$ and water and lyophilized to give the product as a white solid. $^1H$ NMR ($CDCl_3$, 300 MHz) mixture of rotamers δ 0.78 (m) and 0.98 (t, J=8 Hz) total of 3H, 1.47 (m) and 1.52 (q, J=8 Hz) total of 2H, 2.25 (br s, 1H), 2.78 (br s, 1H), 2.90 (br t. 2H), 3.12–3.68 (m, 7H), 3.80 (s, 3H), 3.82 (s, 3H), 5.94 (s, 2H), 6.75(d, 1H, J=8 Hz), 6.83 (m, 5H), 6.94 (m, 1H), 7.22 (m, 4H). MS (FAB) m/e 561 $(M+H)^+$.

Anal calcd for $C_{32}H_{36}N_2O_7$. 0.75 $H_2O$: C, 66.94; H, 6.58; N, 4.88. Found: C, 67.00; H, 6.38; N, 4.59.

EXAMPLE 106 trans,trans-2-(4-Methoxyphenyl)-4-(1,3-benzo-dioxol-5-yl)-1-[2-(N-propyl-N-benzoylamino) ethyl] pyrrolidine-3-carboxylic Acid The title compound was prepared by the methods described in Example 1, but substituting propylamine for methylamine in Example 61B and benzoyl chloride for isobutyryl chloride in Example 61C. The crude product was purified by trituration with 1:1 diethyl ether-hexane. The resulting solid was dissolved in $CH_3CN$ and water and lyophilized to give the product as a white solid. $^1H$ NMR ($CDCl_3$, 300 MHz) mixture of rotamers δ 0.65 and 0.9 (m, total of 3H), 1.4 and 1.55 (m, total of 2H), 2.05 and 2.15 (m, total of 1H), 2.6–3.6 (m, 8H), 5.92 (s, 2H), 6.70(d, 1H, J=8 Hz), 6.82 (m, 4H), 7.2–7.4 (m, 6H). MS ($DCI/NH_3$) m/e 531 $(M+H)^+$.

Anal calcd for $C_{31}H_{34}N_2O_6$ . 0.3 $H_2O$: C, 69.46; H, 6.51; N, 5.23. Found: C, 69.48; H, 6.19; N, 4.84.

EXAMPLE 107 trans,trans-2-(4-Methoxyphenyl)-4-(1,3-benzo-dioxol-5-yl)-1-[2-(N-propyl-N-benzyloxycarbonylamino)ethyl]pyrrolidine-3-carboxylic Acid The title compound was prepared by the methods described in Example 1, but substituting propylamine for methylamine in Example 61B and benzyl chloroformate for isobutyryl chloride in Example 61C. The crude product was purified by preparative HPLC (Vydac μC18) eluting with a 10–70% gradient of $CH_3CN$ in 0.1% TFA. The desired fractions were lyophilized to give the product as a white solid. $^1H$ NMR ($CDCl_3$, 300 MHz) δ 0.8 (m, 3H) 1.45 (m, 2H), 2.20 (br m, 1H), 2.75 (m, 1H), 2.93 (m, 1H), 3.15 (m, 2H), 3.32 (m, 3H), 3.52 (m, 2H), 3.66 (m, 1H), 3.78 (s, 3H), 5.00 (m, 2H), 5.94 (s, 2H), 6.72(d, 1H, J=8 Hz), 6.82 (m, 3H), 7.0 (br d, 1H, J=15 Hz), 7.2 (s, 4H), 7.30 (m, 3H). MS (FAB) m/e 561 $(M+H)^+$.

Anal calcd for $C_{32}H_{36}N_2O_7$. 1.0 TFA: C, 60.53; H, 5.53; N, 4.15. Found: C, 60.66; H, 5.34;N, 4.28.

EXAMPLE 108 trans,trans-2-(4-Methoxyphenyl)-4-(1,3-benzo-dioxol-5-yl)-1-[2-(N-propyl-N-(4-methoxybenzyloxycarbonyl)amino)ethyl]pyrrolidine-3-carboxylic Acid The title compound is prepared by the methods described in Example 61, substituting propylamine for methylamine in Example 61 B and 4-methoxybenzyl chloroformate for isobutyryl chloride in Example 61C.

EXAMPLE 109 trans,trans-2-(4-Methoxyphenyl)-4-(1,3-benzo-dioxol-5-yl)-1-[2-(N-butyl-N-ethoxycarbonylamino)ethyl]pyrrolicline-3-carboxylic Acid .

The title compound was prepared by the methods described in Example 61, but substituting butylamine for methylamine in Example 61B and ethyl chloroformate for isobutyryl chloride in Example 61C. The crude product was purified by preparative HPLC (Vydac μLC18) eluting with a 10–70% gradient of $CH_3CN$ in 0.1% TFA. The desired fractions were lyophilized to give the product as a white solid. $^1H$ NMR ($CDCl_3$, 300 MHz) δ 0.82 (t, 3H, J=8 Hz), 1.20 (m, 5H), 1.34 (m, 2H), 3.08 (m, 2H), 3.17 (m, 2H), 3.52 (m, 2H), 3.75 (m, 2H), 3.78 (s 3H), 4.06 (q, 2H, J=8 Hz), 4.35 (br s, 1H), 5.94 (s, 2H), 6.76 (d, 1H, J=8 Hz), 6.92 (d, 2H, J=8 Hz), 7.03 (br s, 1H), 7.17 (br s, 1H), 7.7 (br s, 2H). MS (FAB) m/e 513 $(M+H)^+$.

Anal calcd for $C_{28}H_{36}N_2O_7$. 0.5 TFA: C, 61.15; H, 6.46; N, 4.92. Found: C, 60.99; H, 6.80; N, 4.93.

EXAMPLE 110 trans,trans-2-(4-Methoxyphenyl)-4-(1,3-benzo-dioxol-5-yl)-1-[2-(N-butyl-N-propoxycarbonylamino)ethyl]pyrrolidine-3-carboxylic Acid The title compound was prepared by the methods described in Example 61, but substituting butylamine for methylamine in Example 61B and propyl chloroformate for isobutyryl chloride in Example 61C. The crude product was purified by trituration with 1:1 diethyl ether-hexane. The resulting solid was dissolved in $CH_3CN$ and water and lyophilized to give the product as a white solid. $^1H$ NMR ($CDCl_3$, 300 MHz) δ 0.80 (br s, 1 H), 0.85 (t, 3H, J=8 Hz), 0.92 (br s, 1H), 1.22 (m, 3H), 1.40 (m, 3H), 1.62 (br m, 1H), 2.15 (br s, 1H), 2.72 (m, 1H), 2.87 (m, 1H), 3.1–3.45 (m, 5H), 3.55 (m, 1H), 3.64 (d, 1H, J=8 Hz), 3.79 (s, 3H), 3.88 (br s, 1H), 3.97 (br s, 1H), 5.95 (s, 2H), 6.73(d, 1H, J=8 Hz), 6.85 (m, 3H, 7.0 (s, 1H), 7.30 (d, 2H, J=8 Hz). MS (FAB) m/e 527 $(M+H)^+$.

Anal calcd for $C_{29}H_{38}N_2O_7$. 0.15 $H_2O$: C, 65.80; H, 7.29; N, 5.29. Found: C, 65.79; H, 7.30; N, 5.21.

EXAMPLE 111 trans,trans-2-(4-Methoxyphenyl)-4-(1,3-benzodioxol-5-yl)-1-[2-(N-propyl-N-propoxycarbonylamino)ethyl]pyrrolidine-3-carboxylic Acid The title compound was prepared by the methods described in Example 61, but substituting propylamine for methylamine in Example 61B and propyl chloroformate for isobutyryl chloride in Example 61C. The crude product was purified by trituration with 1:1 diethyl ether-hexane. The resulting solid was dissolved in $CH_3CN$ and water and lyophilized to give the product as a white solid. $^1H$ NMR ($CDCl_3$, 300 MHz) δ 0.80 (t, 3H, J=8 Hz), 093 (m, 3H), 1.43 (m, 3H), 1.62 (m, 1H), 2.15 (br s, 1H), 2.68–3.45 (m, 8H), 3.54 (m, 1H), 3.66 (m, 1H), 3.78 (s, 3H), 3.94 (m, 2H), 5.94 (s, 2H), 6.72 (d, 1H, J=8 Hz), 6.82 (m, 1H), 6.84 (d, 2H, J=8 Hz), 7.00 (br s, 1H), 7.33 (m, 2H). MS ($DCI/NH_3$) m/e 513 $(M+H)^+$.

Anal calcd for $C_{28}H_{36}N_2O_7 \cdot 0.15 H_2O$: C, 65.26; H, 7.10; N, 5.44. Found: C, 5.22; H, 6.74; N, 5.06.

EXAMPLE 112 trans,trans-1-(N,N-Di(n-butyl)aminocarbonyl)methyl-2,4-di(1,3-benzodioxol-5-yl) pyrrolidine-3-carboxylic Acid Ethyl (3,4-methylenedioxybenzoyl)acetate, prepared by the method of Krapcho et al., Org. Syn. 47, 20 (1967) starting with 3,4-methylenedioxyacetophenone instead of 4-methoxyacetophenone, was reacted by the procedures described in Example 1 to give the title compound as a white solid. m.p. 58°–60° C. $^1H$ NMR ($CDCl_3$, 300 MHz) δ 0.87 (quintet, J=6 Hz, 6H), 1.12 (sextet, J=6 Hz, 2H), 1.24–1.51 (m, 6H), 2.80 (d, J=13 Hz, 1H), 2.94–3.12 (m, 4H), 3.28–3.50 (m, 4H), 3.58–3.62 (m, 1H), 3.78 (d, J=9 Hz, 1H), 5.95 (s, 4H), 6.73 (dd, J=8 Hz, 3 Hz, 2H), 6.84–6.89 (m, 2H), 6.92 (d, J=1 Hz, 1H), 7.01 (d, H=1 Hz, 1H). MS ($DCI/NH_3$) m/e 525 $(M+H)^+$.

EXAMPLE 113 trans,trans-1-(2-(N-(n-Butyl)-N-propylsulfonylamino)ethyl)-2-(4-methoxyphenyl) -4-(1,3-benzodioxol-5-yl)pyrrolidine-3-carboxylic Acid Using the procedures described in Example 66, the title compound was prepared as a white solid. m.p. 64°–65° C. $^1H$ NMR ($CDCl_3$, 300 MHz) δ 0.83 (t, J=7 Hz, 3H), 0.98 (t, J=7 Hz, 3H), 1.12–1.25 (m, 2H), 1.32–1.41 (m, 2H), 1.75 (sextet, J=7 Hz, 2H), 2.23–2.31 (m, 2H), 2.72–3.32 (m, 8H), 3.43 (dd, J=9 Hz, 3 Hz, 1H), 3.53–3.59 (m, 1H), 3.65 (d, J=9 Hz, 1H), 3.80 (s, 3H), 5.95 (s, 2H), 6.73 (d, J=8 Hz, 1H), 6.83 (dd, J=8 Hz, 1 Hz, 1H), 6.88 (d, J=9 Hz, 2H), 7.02 (d, J=1 Hz, 1H), 7.33 (d, J=9 Hz, 2H). MS ($DCI/NH_3$) m/e 547 $(M+H)^+$.

EXAMPLE 114 trans,trans-1-(N,N-Di(n-butyl)aminocarbonylmethyl)-2-(4-methoxyphenyl) -4-(1,3-benzodioxol-5-yl)pyrrolidine-3-carboxylic Acid Using the procedures described in Examples 28 and 43, the title compound was prepared as a white solid. m.p. 74°–76° C. $^1H$ NMR ($CDCl_3$, 300 MHz) δ 0.80 (t, J=6 Hz, 3H), 0.88 (t, J=8 Hz, 3H), 1.08 (sextet, J=8 Hz, 2H), 1.21–1.48 (m, 6H), 2.75 (d, J=12 Hz, 1H), 2.95–3.09 (m, 4H), 3.26–3.59 (m, 5H), 3.75 (d, J=9 Hz, 1H), 3.79 (s, 3H), 4.28 (s, 4H), 6.78 (d, J=9 Hz, 1H), 6.85 (d, J=9 Hz, 2H), 6.91 (d,d, J=3 Hz, 9 Hz, 1H), 6.98 (d, J=3 Hz, 1H), 7.32 (d, J=9 Hz, 2H). MS ($DCI/NH_3$) m/e 525 $(M+H)^+$.

EXAMPLE 115 trans,trans-1-(2-(N-Propyl-N-propylsulfonylamino) ethyl)-2-(4-methoxyphenyl) -4-(1,3-benzodioxol-5-yl)pyrrolidine-3-carboxylic Acid Using the procedures described in Example 66, the title compound was prepared as a white solid. m.p. 72°–73° C. $^1H$ NMR ($CDCl_3$, 300 MHz) δ 0.79 (t, J=8 Hz, 3H), 0.98 (t, J=8 Hz, 3H), 1.43 (sextet, J=8 Hz, 2H), 1.75 (sextet, J=8 Hz, 2H), 2.22–2.32 (m, 1H), 2.69–3.32 (m, 9H), 3.42 (dd, J=3 Hz, 12 Hz, 1H), 3.52–3.58 (m, 1H), 3.64 (d, J=12 Hz, 1H), 3.80 (s, 3H), 5.95 (s, 2H), 6.73 (d, J=11 Hz, 1H), 6.83 (dd, J=1 Hz, 11 Hz, 1H), 6.87 (d, J=11 Hz, 2H), 7.0 (d, J=2 Hz, 1H), 7.32 (d, J=11 Hz, 2H), MS ($DCI/NH_3$) m/e 553 $(M+H)^+$.

EXAMPLE 116 trans,trans-1-(2-(N-Butyl-N-butylsulfonylamio)ethyl)-2-(4-methoxyphenyl) -4-(1,3-benzodioxol-5-yl)pyrrolidine-3-carboxylic Acid Using the procedures described in Example 66, the title compound was prepared as a white solid. m.p. 62°–63° C. $^1H$ NMR ($CDCl_3$, 300 MHz) δ 0.82 (t, J=6 Hz, 3H), 0.91 )t, J=6 Hz, 3H), 1.20 (sextet, J=6 Hz, 2H), 1.33–1.42 (m, 4H), 1.68 (quintet, J=6 Hz, 3H), 2.23–2.32 (m, 1H), 2.70–3.28 (m, 9H), 3.41 (d, J=8 Hz, 1H), 3.52–3.58 (m, 1H), 3.65 (d, J=8 Hz, 1H), 3.79 (s, 3H), 5.95 (s, 2H), 6.72 (d, J=8 Hz, 1H), 6.82 (d, J=8 Hz, 1H), 6.87 (d, J=8 Hz, 2H), 7.01 (s, 1H), 7.32 (d, J=8 Hz, 2H). MS ($DCI/NH_3$) m/e 561 $(M+H)^+$.

EXAMPLE 117 trans,trans-1-(2-(N,N-Dibutylaminocarbonylmethyl)-2-(4-methoxymethoxyphenyl) -4-(1,3-benzodioxol-5-yl)pyrrolidine-3-carboxylic Acid 4-Hydroxyacetophenone was treated with chloromethyl methyl ether and triethylamine in THF at room temperature to give ethyl 4-methoxymethoxybenzoylacetate which was treated by the procedures described in Example 1 to afford the title compound as a white solid. m.p. 48°–49° C. $^1H$ NMR ($CDCl_3$, 300 MHz) δ 0.81 (t, J=7 Hz, 3H), 0.88 (t, J=7 Hz, 3H), 1.06 (sextet, J=7 Hz, 2H), 1.20–1.35 (m, 4H), 1.44 (quintet, J=7 Hz, 2H), 2.75 (d, J=12 Hz, 1H), 2.94–3.10 (m, 4H), 3.25–3.35 (m, 1H), 3.40 (d, J=12 Hz, 1H) 3.43–3.52 (m, 2H), 3.47 (s, 3H), 3.55–3.62 (m, 1H), 3.77 (d, J=9 Hz, 1H), 5.15 (s, 2H), 5.94 (m, 2H), 6.73 (d, J=8 Hz, 1H), 6.86 (dd, J=1 Hz, 8 Hz, 1H), 7.0 (d, J=8 Hz, 2H), 7.04 (d, J=1 Hz, 1H), 7.32 (d, J=8 Hz, 2H). MS ($DCI/NH_3$) m/e 541 $(M+H)^+$.

EXAMPLE 118 trans,trans-1-(2-(N,N-Dibutylaminocarbonylmetbyl)-2-(4-hydroxyphenyl)-4-(1,3-benzodioxol -5-yl)pyrrolidine-3-carboxylic Acid Hydrochloride Salt The compound resulting from Example 116 was treated with concentrated HCl in 1:1 THF-isopropanol to give the title compound as a white solid. m.p. 211°–21 2° C. $^1H$ NMR ($CD_3OD$, 300 MHz) δ 0.90 (t, J=8 Hz, 6H), 1.12–1.27 (m, 6H), 1.36–1.45 (m, 2H), 3.04 (bs, 1H), 3.14–3.35 (t, J=9

Hz, 1H), 3.90 (bs, 3H), 4.17 (d, J=15 Hz, 1H), 5.96 (s, 2H), 6.82–6.93 (m, 4H), 7.03 (d, J=1 Hz, 1H), 7.42 (bs, 2H). MS (DCI/NH$_3$) m/e 497 (M+H)$^+$.

EXAMPLE 119 trans,trans-1-(2-(N-Isobutyl-N-propylsulfonylamino) ethyl)-2-(4-methoxyphenyl) -4-(1,3-benzodioxol-5-yl)pyrrolidine-3-carboxylic Acid Using the procedures described in Example 66, the title compound was prepared as a white solid. m.p. 73°–74° C. $^1$H NMR (CDCl$_3$, 300 MHz) δ 0.80 (d, J=6 Hz, 6H), 0.98 (t, J=8 Hz, 3H), 1.62 (sextet, J=6 Hz, 1H), 1.74 (sextet, J=8 Hz, 2H), 2.23–2.34 (m, 1H), 2.68–2.98 (m, 7H), 3.08–3.18 (m, 1H), 3.26–3.42 (m, 2H), 3.52–3.58 (m, 1H), 3.65 (d, J=9 Hz, 1H), 3.80 (s, 3H), 5.90 (s, 2H), 6.74 (d, J=8 Hz, 1H), 6.82 (d, J=8 Hz, 1H), 6.86 (d, J=8 Hz, 2H), 6.98 (d, J=1 Hz, 1H), 7.33 (d, J=8 Hz, 2H). MS (DCI/NH$_3$) m/e 547 (M+H)$^+$.

EXAMPLE 120 trans,trans-1-(2-(N-Benzenesulfonyl-N-propylamino)ethyl)-2-(4-methoxyphenyl) -4-(1,3-benzodioxol-5-yl)pyrrolidine-3-carboxylic Acid Using the procedures described in Example 66, the title compound was prepared as a white solid. m.p. 89°–91° C. $^1$H NMR (CDCl$_3$, 300 MHz) δ 0.74 (t, J=6 Hz, 3H), 1.33 (sextet, J=6 Hz, 2H), 2.20–2.30 (m, 1H), 2.62–2.72 (m, 1H), 2.85–3.05 (m, 4H), 3.12–3.22 (m, 1H), 3.38 (dd, J=3Hz, 9Hz, 1H), 3.49–3.57 (m, 1H), 3.62 (d, J=9 Hz, 1H), 3.82 (s, 3H), 5.96 (s, 2H), 6.73 (d, J=8 Hz, 1H), 6.84 (dd, J=1 Hz, 8 Hz, 1H), 6.85 (d, J=9 Hz, 2H), 7.02 (d, J=1 Hz, 1H), 7.28 (d, J=9 Hz, 2H), 7.39–7.54 (m, 3H), 7.70 (d, J=7 Hz, 2H). MS (DCI/NH$_3$) m/e 567 (M+H)$^+$.

EXAMPLE 121 trans,trans-1-(2-(N-(4-Methoxybenzenesulfonyl)-N-propylamino)ethyl)-2-(4-methoxyphenyl) -4-(1,3-benzodioxol-5-yl)pyrrolidine-3-carboxylic Acid Using the procedures described in Example 66, the title compound was prepared as a white solid. m.p. 96°–97° C. $^1$H NMR (CDCl$_3$, 300 MHz) δ 0.73 (t, J=7 Hz, 3H), 1.34 (sextet, J=7 Hz, 2H), 2.20–2.30 (m, 1H), 2.62–2.71 (m, 1H), 2.82–3.03 (m, 4H), 3.08–3.18 (m, 2H), 3.38 (dd, J=3 Hz, 9 Hz, 1H), 3.48–3.56 (m, 1H), 3.62 (d, J=9 Hz, 1H), 3.81 (s, 3H), 3.86 (s, 3H), 5.95 (s, 2H), 6.73 (d, J=8 Hz, 1H), 6.81–6.89 (m, 5H), 7.01 (d, J=1 Hz, 1H), 7.28 (d, J=8 Hz, 2H), 7.62 (d, J=8 Hz, 2H). MS (DCI/NH$_3$) m/e 597 (M+H)$^+$.

EXAMPLE 122 trans,trans-1-(N,N-Di(n-butyl)aminocarbonylmethyl)-2-(2-methoxyethoxy-4-methoxyphenyl) -4-(1,3-benzodioxol-5-yl)pyrrolidine-3-carboxylic Acid 2-Hydroxy-5-methoxyacetophenone was treated with sodium hydride and bromoethyl methyl ether in THF at 70° C. to provide ethyl 2-methoxyethoxy-4-methoxybenzoylacetate which was treated by the procedures described in Example 1 to provide the title compound as a white solid. m.p. 63°–65° C. $^1$H NMR (CDCl$_3$, 3 MHz) δ 0.84 (t, J=7 Hz, 3H), 0.89 (t, J=7 Hz, 3H), 1.16 (sextet, J=7 Hz, 2H), 1.28 (sextet, J=7 Hz, 2H), 1.45–1.52 (m, 4H), 2.87–2.94 (m, 2H), 3.00–3.16 (m, 3H), 3.26–3.36 (m, 2H), 3.43 (s, 3H), 3.47–3.54 (m, 3H), 3.66–3.72 (m, 2H), 3.78 (s, 3H), 3.76–3.84 (m, 1H), 4.02–4.10 (m, 2H), 4.25 (d, J=9 Hz, 1H), 5.92 (s, 2H), 6.40 (d, J=2 Hz, 1H), 6.52 (dd, J=2 Hz, 9 Hz, 1H), 6.70 (d, J=8 Hz, 1H), 6.83 (dd, J=1 Hz, 8 Hz, 1H), 5.98 (d, J=2Hz, 1H), 7.53 (d, J=9 Hz, 1H). MS (DCI/NH$_3$) m/e 585 (M+H)$^+$.

EXAMPLE 123 trans,trans-1-(2-(N-Propyl-N-(2,4-dimethylbenzenesulfonyl)amino)ethyl)-2-(4-methoxyphenyl) -4-(1,3-benzodioxol-5-yl)pyrrolidine-3-carboxylic Acid Using the procedures described in Example 66, the title compound was prepared as a white solid. m.p. 88°–90° C. $^1$H NMR (CDCl$_3$, 300 MHz) δ 0.69 (t, J=7Hz, 3H), 1,32(sextet, J=7Hz, 2H),2.12–2.20(m, 1H),2.32(s, 3H), 2.47 (s, 3H), 2.62–2.69 (m, 1H), 2.78 (t, J=9Hz, 1H), 2.89 (dd, J=8 Hz, 1H), 3.02 (sextet, J=9Hz, 2H), 3.15–3.32 (m, 3H), 3.46–3.55 (m, 1H), 3.60 (d, J=9Hz, 1H), 3.82 (s, 3H), 5.96 (s, 2H), 6.72 (d, J=7 Hz, 1H), 6.80 (dd, J=1 Hz, 9Hz, 1H), 6.86 (d, J=9 Hz, 2H), 6.97 (d, J=1 Hz, 1H), 7.03 (bs, 2H), 7.29 (d, J=9 Hz, 1H). MS (DCI/NH$_3$) m/e 595 (M+H)$^+$.

EXAMPLE 124 trans,trans-1-(2-(N-Propyl-N-(3-chloropropylsulfonyl)amino )ethyl)-2-(4-methoxyphenyl)-4-(1,3-benzodioxol-5-yl) pyrrolidine-3-carboxylic Acid Using the procedures described in Example 66, the title compound was prepared as a white solid. m.p. 75°–76° C. $^1$H NMR (CDCl$_3$, 300 MHz) δ 0.80 (t, J=7 Hz, 3H), 1.45 (sextet, J=7Hz, 2H), 2.15–2.31 (m, 3H), 2.70–2.80 (m, 1H), 2.85–3.10 (m, 6H), 3.23–3.31 (m, 2H), 3.43 (bd, J=9 Hz, 1H), 3.55–3.66 (m, 4H), 3.81 (s, 3H), 5.94 (s, 2H), 6.73 (d, J=8 Hz, 1H), 6.82 (d, J=8 Hz, 1H), 6.86 (d, J=8 Hz, 2H), 7.00 (s, 1H), 7.33 (d, J=8 Hz, 2H). MS (DCI/NH$_3$) m/e 567 (M+H)$^+$.

EXAMPLE 125 trans,trans-1-(2-(N-Propyl-N-(2-methoxyethylsulfonyl)amino)ethyl)-2-(4-methoxyphenyl) -4-(1,3-benzodioxol-5-yl)pyrrolidine-3-carboxylic Acid Using the procedures described in Example 66, trans,trans-1-(2-(N-Propyl -N-(vinylsulfonyl)amino)ethyl)-2-(4-methoxyphenyl)-4-(1,3-benzodioxol-5-yl) pyrrolidine-3-carboxylic acid was prepared. Ester hydrolysis using aqueous sodium hydroxide in methanol afforded the title compound as a white solid. m.p. 62°–64° C. $^1$H NMR (CDCl3. 300 MHz) δ 0.78 (t, J=7 Hz, 3H), 1.42 (sextet, J=7 Hz, 2H), 2.23–2.32 (m, 1H), 2.72–2.79 (m, 1H), 2.86–3.05 (m, 4H), 3.10–3.27 (m, 4H), 3.32 (s, 3H), 3.43 (dd, J=3 Hz, 9 Hz, 1H), 3.53–3.58 (m, 4H), 3.65 (d, J=9 Hz, 1H), 3.69 (t, J=6 Hz, 2H), 3.80 (s, 3H), 5.94 (s, 2H), 6.73 (d, J=8 Hz, 1H), 6.82 (dd, J=1 Hz, 8 Hz, 1H), 6.87 (d, J=8 Hz, 2H), 7.02 (d, J=1 Hz, 1H), 7.33 (d, J=8 Hz, 2H). MS (DCI/NH$_3$) m/e 549 (M+H)$^+$.

EXAMPLE 126 trans,trans-1-(2-(N-Propyl-N-(2-ethoxyethylsulfonyl) amino)ethyl)-2-(4-methoxyphenyl) -4-(1,3-benzodioxol-5-yl)pyrrolidine-3-carboxylic Acid Using the procedures described in Example 66, the title compound was prepared as a white solid. m.p. 58°–60° C. $^1$H NMR (CDCl$_3$, 300 MHz) δ 0.78 (t, J=7 Hz, 3H), 1.18 (t, J=7 Hz, 3H), 1.43 (sextet, J=7 Hz, 2H), 2.24–2.33 (m, 1H), 2.70–2.80 (m, 1H), 2.87–3.05 (m, 4H), 3.13–3.20 (m, 2H), 3.22–3.32 (m, 2H), 3.42 (dd, J=2 Hz, 9 Hz, 1H), 3.46 (q, J=7 Hz, 2H), 3.52–3.58 (m, 1H), 3.65 (d J=9 Hz, 1H), 3.72 (t, J=6 Hz, 2H), 3.80 (s, 3H), 5.95 (s, 2H), 6.73 (d, J=7 Hz, 1H), 6.83 (dd, J=1 Hz, 7 Hz, 1H), 6.87 (d, J=8 Hz, 2H), 7.00 (d, J=1 Hz, 1H), 7.32 (d, J=8 Hz, 2H). MS (DCI/NH$_3$) m/e 563 (M+H)$^+$.

EXAMPLE 127 trans,trans-1-(2-(N-Propyl-N-(5-dimethylamino-1-naphthylsulfonyl) amino)ethyl)-2-(4-methoxyphenyl) ,4-(1,3-benzodioxol-5-yl)pyrrolidine -3-carboxylic Acid Using the procedures described in Example 66, the title compound was prepared as a yellow solid. m.p. 102°–104° C. $^1$H NMR (CDCl$_3$, 300 MHz) δ 0.62 (t, J=7 Hz, 3H), 1.28 (sextet, J=7 Hz, 2H), 2.12–2.20 (m, 1H), 2.78 (t, J=9 Hz, 1H), 2.88 (s, 6H), 2.72–2.89 (m, 1H), 3.05–3.12 (m, 2H), 3.26–3.45 (m, 3H), 3.45–3.52 (m, 1H), 3.58 (d, J=9 Hz, 1H), 6.97 (d, J=1 Hz, 1H), 7.13 (d, J=7 Hz, 1H), 7.26 (d, J=8 Hz, 1H), 7.42–7.50 (m, 2H), 8.08 (dd, J=1 Hz, 7 Hz, 1H), 8.20 (d, J=8 Hz, 1H), 8.48 (d, J=8 Hz, 1H). MS (DCI/NH$_3$) m/e 660 (M+H)$^+$.

EXAMPLE 128 trans,trans-1-(2-(N-Propyl-N-(ethylsulfonyl)amino-)ethyl)-2-(4-methoxyphenyl) -4-(1,3-benzodioxol-5-yl)pyrrolidine-3-carlooxylic Acid Using the procedures described in Example 66, the title compound was prepared as a white solid. m.p. 70°–72° C. $^1$H NMR (CDCl$_3$, 300 MHz) δ 0.79 (t, J=8 Hz, 3H), 1.28 (t, J=7 Hz, 3H), 1.43 (q, J8 Hz, 2H), 2.22–2.30 (m, 1H), 2.71–2.80 (m, 1H), 2.82–3.10 (m, 6H), 3.18–3.32 (m, 2H), 3.43 (dd, J=3 Hz, 9 Hz, 1H), 3.53–3.60 (m, 1H), 3.65 (d, J=9 Hz, 1H), 3.80 (s, 3H), 5.96 (s, 2H), 6.73 (d, J=7 Hz, 1H), 6.82 (dd, J=1 Hz, 7 Hz, 1H), 6.88 (d, J8 Hz, 2H), 7.00 (d, J=1 Hz, 1H), 7.32 (d, J=8 Hz, 2H). MS (DCI/NH$_3$) m/e 519 (M+H) $^+$.

EXAMPLE 129 trans,trans-1-(2-(N-Propyl-N-(4-methylbenzenesulfonyl)amino)ethyl)-2-(4-methoxyphenyl) -4-(1,3-benzodioxol-5-yl)pyrrolidine-8-carboxylic Acid Using the procedures described in Example 66, the title compound was prepared as a white solid. m.p. 78°–79° C. $^1$H NMR (CDCl$_3$, 300 MHz) δ 0.73 (t, J=7 Hz, 3H), 1,33 (sextet, J=7 Hz, 2H), 2.20–2.30 (m, 1H), 2.40 (s, 3H), 2.61–2.72 (m, 1H), 2.83–3.05 (m, 4H), 3.08–3.19 (m, 2H), 3.48 (dd, J=3 Hz, 9 Hz, 1H), 3.49–3.57 (m, 1H), 3.62 (d, J9 Hz, 1H), 3.81 (s, 3H), 5.95 (s, 2H), 6.73 (d, J=8 Hz, 1H), 6.82 (d, J=8 Hz, 1H), 6.87 (d, J=8 Hz, 2H), 7.00 (s, 1H), 7.21 (d, J=8 Hz, 2H), 7.29 (d, J=8 Hz, 2H), 7.57 (d, J=8 Hz, 2H). MS (DCI/NH$_3$) m/e 581 (M+H)$^+$.

EXAMPLE 130 trans,trans-1-(N,N-Di(n-butyl)aminocarbonylmethyl)-2-(3-pyridyl)-4-(1,3-benzodioxol-5-yl) pyrrolidine-3-carboxylic Acid Methyl nicotinoyl acetate was prepared by the method of Wenkerr, et al., J. Org. Chem. 48:5006 (1983) and treated by the procedures described in Example 1 to provide the title compound as a white solid. m.p. 167°–168° C. $^1$H NMR (CDCl$_3$, 300 MHz) δ 0.82 (t, J=7 Hz, 3H), 0.89 (t, J=7 Hz, 3H), 1.14 (sextet, J=7 Hz, 2H), 1.23–1.48 (m, 6H), 2.86–3.20 (m, 6H), 3.34–3.43 (m, 2H), 3.57 (dd, J=3 Hz, 9 Hz, 1H), 3.75–3.83 (m, 1H), 4.08 (d, J=9 Hz, 1H), 5.93 (s, 2H), 6.73 (d, J=8 Hz, 1H), 6.90 (dd, J=2 Hz, 8 Hz, 1H), 7.03 (d, J=2 Hz, 1H), 7.38 (dd, J=4 Hz, 8 Hz, 1H), 8.04 (d, J=8 Hz, 1H), 8.48 (dd, J=2 Hz, 4 Hz, 2H). MS (DCI/NH$_3$) m/e 482 (M+H)$^+$.

EXAMPLE 131 trans,trans-1-(2-(N-Propyl-N-(n-butylsulfonyl)amino)ethyl)-2-(4-methoxyphenyl) -4-(1,3-benzodioxol-5-yl)pyrrolidine-3-carboxylic Acid Using the procedures described in Example 66, the title compound was prepared as a white solid. m.p. 65°–66° C. $^1$H NMR (CDCl$_3$, 300 MHz) δ 0.78 (t, J=7 Hz, 3H), 0.92 (t, J=7 Hz, 3H), 1,31–1.46 (m, 4H), 1.68 (quintet, J=7 Hz, 2H), 2.21–2.32 (m, 1H), 2.70–3.08 (m, 7H), 3.12–3.23 (m, 2H), 3.42 (dd, J=2 Hz, 9 Hz, 1H), 3.52–3.58 (m, 1H), 3.64 (d, J=9 Hz, 1H), 3.80 (s, 3H), 5.96 (s, 2H), 6.72 (d, J=7 Hz, 1H), 6.83 (dd, J=1 Hz, 7 Hz, 1H), 6.86 (d, J=8 Hz, 2H), 7.00 (d, J=1 Hz, 1H), 7.32 (d, J=8 Hz, 2H). MS (DCI/NH$_3$) m/e 547 (M+H)$^+$.

EXAMPLE 132 trans,trans-1-(2-(N-Propyl-N-(4-chlorobenzenesulfonyl)amino)ethyl)-2-(4-methoxyphenyl) -4-(1,3-benzodioxol-5-yl)pyrrolidine-3-carboxylic Acid Using the procedures described in Example 66, the title compound was prepared as a white solid. m.p. 105°–106° C. $^1$H NMR (CDCl3.300 MHz) δ 0.72 (t, J=7 Hz, 3H), 1,34 (sextet, J=7 Hzm 2H), 2.56–2.62 (m, 1H), 2.78–2.86 (m, 1H), 2.96–3.03 (m, 3H), 3.13–3.26 (m, 3H), 3.51 (dd, J=5 Hz, 9 Hz, 1H), 3.62–3.68 (m, 1H), 3.80 (s, 3H), 3.94 (d, J=9 Hz, 1H), 5.92 (s, 2H), 6.75 (d, J=8 Hz, 1H), 6.84 (dd, J=2 Hz, 8 Hz, 1H), 6.94 (d, J=8 Hz, 2H), 6.98 (d, J=2 Hz, 1H), 7.36 (d, J=8 Hz, 1H), 7.49 (d, J=8 Hz, 1H), 7.68 (d, J=8 Hz, 1H). MS (DCI/NH$_3$) m/e 601 (M+H)$^+$.

EXAMPLE 133 trans,trans-1-(2-(N-Propyl-N-(benzylsulfonyl)amino)ethyl)-2-(4-methoxyphenyl) -4-(1,3-benzodioxol-5-yl)pyrrolidine-3-carboxylic Acid Using the procedures described in Example 66, the title compound was prepared as a white solid. m.p. 88°–89° C. $^1$H NMR (CDCl$_3$, 300 MHz) δ 0.72 (t, J=7 Hz, 3H), 1,32 (sextet, J=7 Hz, 2H), 2.06–2.16 (m, 1H), 2.56–2.67 (m, 1H), 2.75–3.10 (m, 6H), 3.30 (dd, J=2 Hz, 9 Hz, 1H), 5.95 (s, 2H), 6.73 (d, J=7 Hz, 1H), 6.80 (dd, J=1 Hz, 7 Hz, 1H), 6.86 (d, J=8 Hz, 2H), 6.97 (d, J=1 Hz, 1H), 7.27–7.35 (m, 7H). MS (DCI/NH$_3$) m/e 581 (M+H)$^+$.

EXAMPLE 134 trans,trans-1-(2-(N-Propyl-N-(4-fluorobenzenesulfonyl)amino)ethyl)-2-(4-methoxyphenyl) -4-(1,3-benzodioxol-5-yl)pyrrolidine-3-carboxylic Acid Using the procedures described in Example 66, the title compound was prepared as a white solid. m.p. 91°–93° C. $^1$H NMR (CDCl$_3$, 300 MHz) δ 0.73 (t, J=7 Hz, 3H), 1.44 (sextet, J=7 Hz, 2H), 2.18–2.27 (m, 1H), 2.56–2.67 (m, 1H), 2.78–2.87 (m, 2H), 2.97 (septet, J=8 Hz, 2H), 3.11–3.16 (m, 2H), 3.33 (dd, J=2 Hz, 9 Hz, 1H), 3.43–3.50 (m, 1H), 3.57 (d, J=9 Hz, 1H), 3.78 (s, 3H), 7.08 (t, J=8 Hz, 2H), 7.24 (d, J=8 Hz, 2H), 7.69 (dd, J=5 Hz, 8 Hz, 2H). MS (DCI/NH$_3$) m/e 585 (M+H)$^+$.

EXAMPLE 135 trans,trans-1-(N-Methyl-N-propylaminocarbonylmethyl)-2-(4-methoxyphenyl)-4-(4-benzofuranyl) pyrrolidine-3-carboxylic Acid

EXAMPLE 135A

Benzofuran-4-carboxaldehyde

To a suspension of 60% sodium hydride in mineral oil (4.00 g, 100 mmol, 1.25 eq) in DMF (60 mL) at 0° C. was added a solution of 3-bromophenol (13.8 g, 80 mmol) in DMF (5 mL). After 10 minutes, bromoacetaldehyde diethyl acetal (14.9 mL, 96.6 mmol, 1.24 eq) was added, and the resultant mixture then heated at 120° C. for 2.5 hours. The mixture was cooled to room temperature and was poured into water, and extracted once with ether. The organic solution was dried over MgSO$_4$, filtered, evaporated and vacuum distilled to yield a colorless liquid (17.1 g, 74%). b.p. 160°–163° C. at 0.4 mm Hg.

To warm polyphosphoric acid (15.3 g) was added a solution of the above compound (17.1 g, 59.3 mmol) in benzene (50 mL). The resultant mixture was heated under reflux with vigorous stirring for 4 hours, after which time the benzene layer was carefully decanted off, and the lower layer washed once with hexanes. The combined organic solutions were concentrated in vacuo, and then vacuum distilled to yield a colorless liquid (8.13 g, 70%). b.p. 62°–72° C. at 0.6 mm Hg.

To a solution of the above compounds (8.11 g, 41.5 mmol) in ether (80 mL) at −78° C. was added 1.7M t-butyllithium (48.8 mL, 83 mmol, 2 eq) such that the temperature did not exceed −70° C. After stirring for 15 minutes, a solution of DMF (6.5 mL, 83 mmol, 2 eq) in ether (20 mL) was added, and the mixture allowed to warm to room temperaure over 2 hours. The mixture was poured into water and the phases separated. The organic solution was dried over MgSO$_4$ and concentrated in vacuo. The residue was purified by flash chromatography on silica gel eluting with 10% ether in hexanes to yield benzofuran-6-carboxaldehyde (1.22 g) and benzofuran-4ocarboxaldehyde (1.86 g), both as colorless oils.

Example 135B trans,trans-1-(N-Methyl-N-propylaminocarbonylmethyl),2-(4-methoxyphenyl)-4-(4-benzofuranyl) pyrrolidine-3-carboxylic Acid The title compound was prepared using the procedures described in Examples 1 and 49 substituting the compound resulting from Example 135A in Example 49A for piperonal. $^1$H NMR (300 MHz, CDCl$_3$) (minor rotamer) δ 7.59 (1H, t, J=3 Hz), 7.4–7.2 (6H, m), 6.8 (2H, d, J=8 Hz), 4.03 (1H, m), 3.94 (1H, dd, J=8 Hz, 3 Hz), 3.77 (3H, s), 3.61 (1H, dd, J=8 Hz, 7 3 Hz), 3.42 (1H, dd, J=11 Hz, 5 Hz), 3.40–2.90 (5H, m), 2.82 (2.81) (3H, s), 1.50 (2H, septet, J=7 Hz), 0.82 (0.75) (3H, t, J=7 Hz). MS (DCi/NH$_3$) m/e 451 (M+H)$^+$.

Anal.calc. for C$_{26}$H$_{30}$N$_2$O$_5$ . AcOH: C, 65.87; H, 6.71; N, 5.49. Found: C, 66.04; H, 6.42; N, 5.60. s

EXAMPLE 136 trans,trans-1-(N-Methyl-N-propylaminocarbonylmethyl)-2-(4-methoxyphenyl)-4-(6-benzofuranyl) pyrrolidine-3-carboxylic Acid The title compound was prepared using the procedures described in Examples 1 and 49 substituting benzofuran-6-carboxaldehyde, prepared as described in Example 135A, in Example 49A for piperonal. $^1$H NMR (300 MHz, CDCl$_3$) (minor rotamer) δ 7.65 (1H, bd), 7.60 (1H, d, J=2 Hz), 7.55 (1H, d, J=8 Hz), 7.35 (3H, m), 6.85 (2H, dd, J=8 Hz, 3 Hz), 6.75 (1H, dd, J=3 Hz, 2 Hz), 3.83 (2H, m), 3.79 (3H, s), 3.60–3.0 (7H, m), 2.91 (2.83)(s, 3H), 1.51 (2H, septet, J=7 Hz), 0.83 (0.78) (3H, t, J=7 Hz). MS (DCI/NH$_3$) m/e 451 (M+H)$^+$.

Anal.calc. for C$_{26}$H$_{30}$N$_2$O$_5$. 0.5 H$_2$O: C, 67.96; H, 6.80; N, 6.10. Found: C, 67.90; H, 6.71;N, 6.07.

EXAMPLE 137 trans,trans-1-(N-Methyl-N-propylaminocarbonylmethyl)-2-(4-methoxyphenyl)-4-(6-benzo-2,3-dihydrofuranyl) pyrrolidine-3-carboxylic Acid The title compound was prepared by catalytic hydrogenation (4 atmospheres of H$_2$ in AcOH, followed by preparative hplc) of the compound resulting from Example 136 $^1$H NMR (300 MHz, CDCl$_3$) (minor rotamer) δ 7.49 (7.47) (2H, d, J=8 Hz), 7.19 (1H, d, J=8 Hz), 7.00 (1H, m), 7.82 (3H, m), 5.40 (1H, dd, J=11 Hz, 7 Hz), 4.58 (2H, t, J=8 Hz), 4.18 (1H, m), 4.10 (1H, m), 3.88 (1H, m), 3.79 (3H, s), 3.60 (1H, m), 3.35 (1H, m), 3.19 (2H, t, J=8 Hz), 3.00 (4H, m), 2.91 (2.78) (s, 3H), 1.53 (1.40) (2H, septet, J=7 Hz), 0.88 (0.78) (3H, t, J=7 Hz). MS (DCI/NH$_3$) m/e 453 (M+H)$^+$.

Anal.calc. for C$_{26}$H$_{32}$N$_2$O$_5$. 1.25 TFA: C, 57.53; H, 5.63; N, 4.71. Found: C, 57.68; H, 5.68; N, 4.70.

EXAMPLE 138 trans,trans-1-(N,N-Dibutylaminocarbonylmethyl)-2-(4-metho xyphenyl)-4-(4-benzofuranyl) pyrrolidine-3-carboxylic Acid The title compound was prepared by the procedures described in Examples 1 and 49 substituting benzofuran-4-carboxaldehyde in Example 49A for piperonal and substituting N,N-dibutyl bromoacetamide for N-methyl-N-propyl bromoacetamide. $^1$H NMR (300 MHz, CDCl$_3$) δ 7.62 (1H, d, J=3 Hz), 7.39 (1H, dt, J=8 Hz, 2 Hz), 7.34 (3H, m), 7.26 (1H, d, J=2 Hz), 7.23 (1H, d, J=8 Hz), 6.84 (2H, d, J=8 Hz), 4.02 (1H, ddd, J=8, 6 Hz,4 Hz), 3.89 (1H, d, J=9 Hz) 3.79 (3H, s), 3.67 (1H, dd, J=10 Hz, 3 Hz), 3.44 (2H, m), 3.35–3.15 (3H, m) 3.00 (2H, m), 2.84 (1H, d, J=14 Hz), 1.43 (3H, m), 1.23 (3H, m), 1.08 (2H, m), 0.87 (3H, t, J=7 Hz), 0.82 (3H, t, J=7 Hz). MS (DCI/NH$_3$) m/e 507 (M+H)$^+$.

Anal.calc. for C$_{30}$H$_{38}$N$_2$O$_5$: C, 71.12; H, 7.56; N, 5.53. Found: C, 70.86; H, 7.45: N, 5.24.

EXAMPLE 139 trans,trans-1-(N,N-Dibutylaminocarbonytmethyl)-2-(4-metho xyphenyl)-4-(4-benzofuranyl) pyrrolidine-3-carboxylic Acid The title compound was prepared by the procedures described in Examples 1 and 49 substituting benzofuran-5-carboxaldehyde, prepared by the procedures described in Example 135A substituted 4-bromophenol for 3-bromophenol, in Example 49A for piperonal and substituting N,N-dibutyl bromoacetamide for N-methyl-N-propyl bromoacetamide. $^1$H NMR (300 MHz, CDCl$_3$) δ 7.64 (1H, bd), 7.59 (1H, d, J=2 Hz), 7.43 (2H, m), 7.33 (2H, d, J=8 Hz), 6.85 (2H, d, J=8 Hz), 6.73 (1H, dd, J=3 Hz, 1 Hz), 3.82 (1H, d, J=11 Hz), 3.89 (1H, d, J=9 Hz) 3.79 (3H, s), 3.53 (1H, dd, J=10 Hz, 3 Hz), 3.44 (2H, m), 3.30 (1H, m), 3.20–2.95 (5H, m), 2.82 (1H, d, J=14 Hz), 1.43 (3H, m), 1.23 (3H, m), 1.08 (2H, m), 0.87 (3H, t, J=7 Hz), 0.82 (3H, t, J=7 Hz). MS (DCI/NH$_3$) m/e 507 (M+H)$^+$.

Anal.calc. for C$_{30}$H$_{38}$N$_2$O$_5$: C, 71.12; H, 7.56; N, 5.53. Found: C, 70.73; H, 7.45; N, 5.29.

EXAMPLE 140 trans,trans-1-(N,N-Dibutylaminocarbonylmethyl)-2-(4-methoxyphenyl)-4-(6-benzofuranyl) pyrrolidine-3-carboxylic Acid The title compound was prepared by the procedures described in Examples 1 and 49 substituting benzofuran-6-carboxaldehyde in Example 49A for piperonal and substituting N,N-dibutyl bromoacetamide for N-methyl-N-propyl bromoacetamide. $^1$H NMR (300 MHz, CDCl$_3$) δ 7.63 (1H, bd), 7.59 (1H, d, J=2 Hz), 7.53 (1H, d, J8 Hz), 7.36 (3H, m), 6.85 (2H, d, J=8 Hz), 6.73 (1H, dd, J=3 Hz, 1 Hz), 3.82 (1H, d, J=11 Hz), 3.89 (1H, d, J=9 Hz) 3.79 (3H, s), 3.53 (1H, dd, J=10 Hz, 3 Hz), 3.44 (2H, m), 3.30 (1H, m), 3.20–2.95 (5H, m), 2.80 (1H, d, J=14 Hz), 1.43 (3H, m), 1.23 (3H, m), 1.08 (2H, m), 0.87 (3H, t, J=7 Hz), 0.82 (3H, t, J=7 Hz). MS (DCI/NH$_3$) m/e 507 (M+H)$^+$.

Anal.calc. for C$_{30}$H$_{38}$N$_2$O$_5$. 0.75 H$_2$O: C, 69.28; H, 7.65; N, 5.39. Found: C, 69.11;H, 7.33; N. 5.32.

EXAMPLE 141 trans,trans-1-(N,N-Dibutylaminocarbonylmethyl)-2-(4-methoxyphenyl)-4-(6-benzo-2,3-dihydrofuranyl) pyrrolidine-3-carboxylic Acid The title compound was prepared by catalytic hydrogenation of the compound resulting from Example 140 (4 atmospheres of H$_2$ in AcOH, followed by preparative hplc). $^1$H NMR (300 MHz, CDCl$_3$) δ 7.40 (2H, d, J=8 Hz), 7.16 (1H, d, J=8 Hz), 6.97 (1H, dd, J=8 Hz, 2 Hz), 6.89 (3H, m), 5.90 (1H, bs) 4.57 (2H, t, J=9 Hz), 4.93 (2H, m), 3.80 (3H, s), 3.70–3.58 (2H, m), 3.40 (1H, m). 3.30–2.90 (8H, m), 1.40 (2H, m), 1.29 (3H, m), 1.08 (2H, m), 0.92 (3H, t, J=7 Hz), 0.82 (3H, t, J=7 Hz). MS (DCI/NH$_3$) m/e 509 (M+H)$^+$ Anal.calc. for C$_{30}$H$_{40}$N$_2$O$_5$. 0.85 TFA: C, 62.88; H, 6.80; N, 4.63. Found: C, 63.04; H, 6.66; N, 4.60.

EXAMPLE 142 trans,trans-1-(N-Methyl-N-propylaminocarbonylmethyl)-2-methoxyphenyl)-4-(5-indanyl) pyrrolidine-3-carboxylic Acid

EXAMPLE 142A

Indane-5-carboxaldehyde

Indane-5-carboxaldehyde was prepared by formylation of indane under the conditions described for 2,3-dihydrobenzofuran in Example 52A. The resultant mixture of 4- and 5-carboxaldehydes was purified as follows: to a 6:1 mixture of indane-4-carboxaldehyde and indane-5-carboxaldehyde (3.46 g, 23 mmol) was added aniline (2.20 g, 23 mmol, 1 eq). The resultant solution slowly solidfied to a mixture of imines which was recrystailized from hot acetonitrile to yield the 5-aldimine as a white solid. The aldimine (2.65 g) was suspended in water (6 mL), and treated with 4 N hydrochloric dioxane (10 mL). The mixture was boiled for 1 hour, cooled to room temperature, and poured into ether. The organic solution was dried over MgSO$_4$, fiitered, and concentated/n vacuo. Vacuum distillation of the residue afforded indane-5-carboxaldehyde (1.54 g, 88%) as a colorless liquid. b.p. 88°–90° C. at 0.9 mm Hg.

EXAMPLE 142B trans,trans-1-(N-Methyl-N-propylaminocarbonylmethyl)-2-(4-methoxyphenyl)-4-(5-indanyl) pyrrolidine-3-carboxylic Acid The title compound was prepared by the procedures described in Examples 1 and 49 substituting indane-5-carboxaldehyde for piperonal in Example 49A. $^1$H NMR (300 MHz, CDCl$_3$) (minor rotamer) δ 7.25–7.1 (5H, m), 6.78 (2H, d, J=8 Hz), 3.89 (1H, d, J=8 Hz), 3.75 (3H, s), 3.50–2.90 (6H, m), 2.88 (6H, t, J=6 Hz), 2.82 (2.80) (3H, s), 2.04 (2H, t, J=8 Hz), 1.48 (2H, septet, J=7 Hz), 0.83 (0.73) (3H, t, J=7 Hz). MS (DCI/NH$_3$) m/e 451 (M+H)$^+$, 473 (M+Na)$^+$.

Anal.calc. for C$_{27}$H$_{34}$N$_2$O$_4$ . 2.5 H$_{20}$ .C, 65.44; H, 7.93; N, 5.65. Found: C, 65.36; H, 7.45; N, 5.53.

EXAMPLE 143 trans,trans-1-(N-Methyl-N-propylaminocarbonylmethyl)-2-(4-methoxyphenyl)-4-(6-indolyl) pyrrolidine-3-carboxylic Acid The title compound was prepared by the procedures described in Examples 1 and 49 substituting indole-6-carboxaldehyde, prepared by the method of Rapoport, J. Org. Chem. 51:5106 (1986 ), for piperonal in Example 49A. $^1$H NMR (300 MHz, CDCl$_3$) (minor rotamer) δ 8.43 (1H, brs), 7.57 (1H, d, J=8 Hz), 7.43 (1H, s), 7.31 (2H, dd, J=6 Hz, 3 Hz), 7.22 (1H, d, J=8 Hz), 7.1 (1H, t, J=3 Hz), 6.78 (2H,dd, J=6 Hz, 3 Hz), 6.45 (1H, m), 3.93 (1H, dd, J=6 Hz, 3 Hz), 3.80 (1H, m), 3.73 (3H, s), 3.60–2.90 (6H, m), 2.86 (2.82)(3H, s), 1.47 (2H, septet, J=7 Hz), 0.83 (0.73) (3H, t, J=7 Hz). MS (DCI/NH$_3$) m/e 450 (M+H)$^+$.

Anal.calc. for C$_{26}$H$_{31}$N$_3$O$_4$. 0.75 H$_2$O: C, 67.44; H, 7.07; N, 9.07. Found: C, 67.42; H, 7.09; N, 8.91.

EXAMPLE 144 trans,trans-1-(N-Methyl-N-propylaminocarbonylmethyl)-2-(4-methoxyphenyl)-4-(3,4-difluprophenyl) pyrrolidine-3-carboxylic Acid The title compound was prepared by the procedures described in Examples 1 and 49 substituting 3,4-difluorobenzaldehyde for piperonal in Example 49A. $^1$H NMR (300 MHz, CDCl$_3$) (minor rotamer) δ 7.60–7.3 (4H, m), 7.13 (1H, q, J=9 Hz), 6.90 (2H, d, J=8 Hz), 3.90 (1H, m), 3.79 (3H, s), 3.60–2.95 (6H, m), 2.92 (2.78) (3H, s), 1.55 (2H, septet, J=7 Hz), 0.88 (0.73) (3H, t, J=7 Hz). MS (DCI/NH$_3$) m/e 447 (M+H)$^+$.

Anal.calc. for C$_{24}$H$_{28}$F$_2$N$_2$O$_4$ . 1.80 H$_2$O: C, 60.19; H, 6.65; N, 5.85. Found: C, 60.13; H, 6.34; N, 5.84.

EXAMPLE 145 trans,trans-1-(N-Methyl-N-propylaminocarbonylmethyl),2-(4-methoxyphenyl)-4-(phenyl) pyrrolidine-3-carboxylic Acid The title compound was prepared by the procedures described in Examples 1 and 49 substituting benzaldehyde for piperonal in Example 49A. $^1$H NMR (300 MHz, CDCl$_3$) (minor rotamer) δ 7.53 (4H, d, J=6 Hz), 7.40–7.20 (3H, m), 6.88 (2H, d, J=8 Hz), 3.90 (1H, m), 3.79 (3H, s), 3.70–2.95 (8H, m), 2.90 (2.79) (3H, s), 1.50 (2H, sept, J=7 Hz), 0.87 (0.72) (3H, t, J=7 Hz). MS (DCI/NH$_3$) m/e 411 (M+H)$^+$.

Anal.calc. for C$_{24}$H$_{30}$N$_2$O$_4$ . 2.00 H$_2$O: C, 64.55; H, 7.67; N, 6.27. Found: C, 64.37; H, 7.43; N, 6.29.

EXAMPLE 146 trans,trans-1-(N-Methyl-N-propylaminocarbonylmethyl)-2-(4-methoxyphenyl)-4-(4-hydroxyphenyl) pyrrolidine-3-carboxylic Acid The title compound was prepared by the procedures described in Examples 1 and 49 substituting 4-hydroxybenzaldehyde for piperonal in Example 49A. $^1$H NMR (300 MHz, CDCl$_3$-CD$_3$OD) (minor rotamer) δ 7.35 (2H, d, J8 Hz), 7.28 (2H, dd, J=7 Hz, 3 Hz), 6.90 (2H, dd, J=7 Hz, 3 Hz), 6.89 (2H, d, J=8 Hz), 3.81 (3H, s), 3.65 (1H, d, J=8 Hz), 3.70–3.00 (8H, m), 2.92 (2.83) (3H, s), 1.50 (2H, septet, J=7 Hz), 0.87 (0.77) (3H, t, J=7 Hz). MS (DCI/NH$_3$) m/e 427 (M+H)$^+$.

Anal.calc. for C$_{24}$H$_{30}$N$_2$O$_5$. 1.00 H$_2$O: C, 64.85; H, 7.26; N, 6.30. Found: C, 64.82; H, 7.39; N, 6.46.

EXAMPLE 147 trans,trans-1-(N-Methyl-N-propylaminocarbonylmethyl)-2-(4-methoxyphenyl)-4-(2,4-dimethoxyphenyl) pyrrolidine-3-carboxylic Acid The title compound was prepared by the procedures described in Examples 1 and 49 substituting 2,4-dimethoxybenzatdehyde for piperonal in Example 49A. $^1$H NMR (300 MHz, CDCl$_3$-CD$_3$OD) (minor rotamer) 8 7.61 (1H, d, J=8 Hz), 7.30 (2H, d, J=8 Hz), 6.82 (2H, d, J=8 Hz), 6.55 (1H, d, J=8 Hz), 6.45 (1H, d, J=3 Hz), 3.90 (1H, m), 3.81 (3H, s), 3.79 (3H, s), 3.77 (3H, s), 3.70–2.90 (8H, m), 2.85 (3H, s), 1.50 (2H, sept, J=7 Hz), 0.87 (0.77) (3H, t, J=7 Hz). MS (DCI/NH$_3$) m/e 471 (M+H)$^+$.

Anal.calc. for C$_{26}$H$_{34}$N$_2$O$_6$ . 0.75 H$_2$O: C, 64.51; H, 7.39; N, 5.79. Found: C, 64.65; H, 7.07; N, 5.75.

EXAMPLE 148 trans,trans-1-(N,N-Dibutylaminocarbonylmethyl)-2-(4-methoxyphenyl)-4-(5-benzo-2,3-dihydrofuranyl) pyrrolidine-3-carboxylic Acid The title compound was prepared by the procedures described in Examples 1 and 49 substituting 2,3-dihydrobenzofuran-5-carboxaldehyde for piperonal in Example 49A. $^1$H NMR (300 MHz, CDCl$_3$) δ 7.31 (2H, d, J=8 Hz), 7.27 (1H, d, J=2 Hz), 7.18 (1H, dd, J=7 Hz, 3 Hz), 6.86 (2H, d, J=8 Hz), 6.72 (1H, d, J=8 Hz), 4.56 (2H, t, J=7 Hz), 3.78 (3H, s), 3.62 (1H, m), 3.50–3.25 (4H, m), 3.17 (2H, t, J=7 Hz), 3.15–2.90 (5H, m), 2.79 (1H, d, J=14 Hz), 1.43 (3H, m), 1.26 (3H, m), 1.08 (2H, m), 0.87 (3H, m), 0.81 (3H, t, J=7 Hz). MS (DCI/NH$_3$) m/e 509 (M+H)$^+$.

Anal.calc. for C$_{30}$H$_{40}$N$_2$O$_5$. 0.25 H$_2$O: C, 70.22; H, 7.95; N, 5.46. Found: C, 70.21; H, 7.92; N, 5.36.

EXAMPLE 149 trans,trans-1-(N,N-Dibutylaminocarbonylmethyl)-2-(4-methoxyphenyl)-4-(4-methexyphenyl) pyrrolidine-3-carboxylic Acid The title compound was prepared by the procedures described in Examples 1 and 49 substituting 4-methoxybenzaldehyde for piperonal in Example 49A. $^1$H NMR (300 MHz, CDCl$_3$) δ 7.38 (2H, d, J=8 Hz), 7.30 (2H, d, J=8 Hz), 6.87 (4H, dd, J=7 Hz, 3 Hz), 3.78 (3H, s), 3.76 (3H, s), 3.63 (1H, m), 3.50–3.20 (4H, m), 3.15–2.90 (5H, m), 2.78 (1H, d, J=14 Hz), 1.43 (3H, m), (3H, m), 1.09 (2H, m), 0.87 (3H, t, J=7 Hz), 0.81 (3H, t, J=7 Hz). MS (DCI/NH$_3$) m/e 497 (M+H)$^+$.

Anal.calc. for C$_{29}$H$_{40}$N$_2$O$_5$: C, 70.13; H, 8.12; N, 5.64. Found: C, 69.78; H, 8.10; N, 5.54.

EXAMPLE 150 trans,trans-1-(N,N-Dibutylaminocarbonylmethyl)-2-(4-methoxyphenyl)-4-(3,4-difluprophenyl) pyrrolidine-3-carboxylic Acid The title compound was prepared by the procedures described in Examples 1 and 49 substituting 3,4-difluorobenzaldehyde for piperonal in Example 49A. $^1$H NMR (300 MHz, CDCl$_3$) δ 7.35 (1H, m), 7.30 (2H, d, J=8 Hz), 7.20–7.00 (2H, m), 6.87 (2H, d, J=8 Hz), 3.78 (3H, s), 3.79 (1H, m), 3.62 (1H, m), 3.50–3.30 (3H, m), 3.23 (1H, m), 3.15–2.90 (4H, m), 2.78 (1H, d, J=14 Hz), 1.43 (2H, m), 1.27 (4H, m), 1.08 (2H, m), 0.85 (3H, t, J=7 Hz), 0.80 (3H, t, J=7 Hz). MS (DCI/NH$_3$) m/e 503 (M+H)$^+$.

Anal.calc. for C$_{28}$H$_{36}$F$_2$N$_2$O$_4$. 1H$_2$O: C, 64.60; H, 7.36; N, 5.38. Found: C, 64.59; H, 7.20; N, 5.35.

EXAMPLE 151 trans,trans-1-(N,N-Dibutylaminocarbonylmethyl)-2-(4-methoxyphenyl)-4-(2,4-dimethoxyphenyl) pyrrolidine-3-carboxylic Acid The title compound was prepared by the procedures described in Examples 1 and 49 substituting 2,4-dimethoxybenzaldehyde for piperonal in Example 49A. $^1$H NMR (300 MHz, CDCl3) δ 7.37 (2H, d, J=8 Hz), 7.20 (1H, d, J=8 Hz), 6.92 (2H, d, J=8 Hz), 6.60 (1H, d, J=3 Hz), 6.49 (1H, dd, J=6 Hz, 2 Hz), 5.35 (1H, d, J=8 Hz), 4.20 (3H, m), 4.10 (3H, s), 3.83 (3H, s), 3.81 (3H, s), 3.75 (3H, m), 3.17 (2H, hep, J=7 Hz), 3.05 (2H, t, J=7 Hz), 1,30 (4H, m), 1.07 (4H, m), 0.87 (3H, t, J=7 Hz), 0.80 (3H, t, J=7 Hz). MS (DCI/NH$_3$) m/e 527 (M+H)$^+$.

Anal.calc. for C$_{30}$H$_{42}$N$_2$O$_6$. 1.30 TFA: C, 58.02: H, 6.47; N, 4.15. Found: C, 7.92; H, 6.43; N, 4.07.

EXAMPLE 152 trans,trans-1-(N,N-Dibutylaminocarbonylmethyl)-2-phenyl-4-(1,3-benzodioxol-5-yl) pyrrolidine-3-carboxylic Acid The title compound was prepared by the procedures described in Examples 1 and 49 substituting ethyl benzoylacetate in Example 49B. $^1$H NMR (300 MHz, CDCl$_3$) δ 7.50–7.25 (5H, m), 7.04 (1H, d, J=3 Hz), 6.87 (1H, dd, J=7

Hz, 3 Hz), 6.74 (1H, d, J=8 Hz), 5.94 (1H, d, J=4 Hz), 5.92 (1H, d, J=4 Hz), 3.85 (1H, d, J=8 Hz), 3.64 (1H, m), 3.42 (3H, m), 3.27 (2H, m), 3.20–2.90 (5H, m), 2.81 (1H, d, J=14 Hz), 1.43 (2H, m), 1.27 (4H, m), 1.05 (2H, m), 0.85 (3H, t, J=7 Hz), 0.80 (3H, t, J=7 Hz). MS (DCI/NH$_3$) m/e 481 (M+H)$^+$.

Anal.calc. for $C_{28}H_{36}N_2O_5$: C, 69.98; H, 7.55; N, 5.83. Found: C, 69.69; H, 7.63; N, 5.71.

EXAMPLE 153 trans,trans-1-(N,N-Dibutylaminocarbonylmethyl)-2-phenyl-4-(5-benzo-2,3-dihydrofuranyl) pyrrolidine-3-carboxylic Acid The title compound was prepared by the procedures described in Examples 1 and 49 substituting ethyl benzoylacetate in Example 49B and 2,3-dihydrobenzofuran-5-carboxaldehyde for piperonal in Example 49A. $^1$H NMR (300 MHz, CDCl$_3$) δ 7.53 (2H, m), 7.40 (4H, m), 7.13 (1H, dd, J=7 Hz, 3 Hz), 6.72 (1H, d, J8 Hz), 5.40 (1H, d, J=10 Hz), 4.56 (2H, t, J=8 Hz), 4.18 (1H, d, J=14 Hz), 4.07 (2H, m), 3.79 (2H, m), 3.48 (1H, d, J=14 Hz), 3.35 (1H, m), 3.28 (3H, m), 2.95 (2H, m), 1.47 (2H, m), 1.28 (4H, m), 1.10 (2H, m), 0.93 (3H, t, J=7 Hz), 0.78 (3H, t, J=7 Hz). MS (DCI/NH$_3$) m/e 479 (M+H)$^+$.

Anal.calc. for $C_{29}H_{38}N_2O_4$ . 1.10 TFA: C, 62.04; H, 6.52; N, 4.64. Found: C, 61.89; H, 6.44; N, 4.57.

EXAMPLE 154 trans,trans-1-(N,N-Dibutylaminocarbonylmethyl)-2-(4-t-butylphenyl)-4-(5-benzo-2,3-dihydrofuranyl) pyrrolidine-3-carboxylic Acid The title compound was prepared by the procedures described in Examples 1 and 49 substituting t-butyl benzoylacetate, prepared by the method of Krapcho et al., Org. Syn. 47:20 (1967) starting from 4-t-butylacetophenone, in Example 49B and 2,3-dihydrobenzofuran-5-carboxaldehyde for piperonal in Example 49A. $^1$H NMR (300 MHz, CDCl$_3$) δ 7.60–7.30 (6H, m), 6.90 (1H, m), 4.50 (2H, m), 3.95 (1H, m), 3.85–2.95 (11H, m), 2.90 (1H, d, J=14 Hz), 1.58 (2H, m), 1.50 (7H, m), 1.41 (6H, s), 1.10 (2H, m), 1.00 (3H, t, J=7 Hz), 0.90 (3H, t, J=7 Hz). MS (DCI/NH$_3$) m/e 535 (M+H)$^+$.

Anal.calc. for $C_{33}H_{46}N_2O_4$ . 0.25 H$_2$O: C, 73.50; H, 8.69; N, 5.19. Found: C, 73.57; H, 8.58; N, 5.14.

EXAMPLE 155 trans,trans-2-(N,N-Dibutylaminocarbonylmethyl)-2-(4-methoxyphenyl)-4-(4-fluorophenyl) pyrrolidine-3-carboxylic Acid The title compound was prepared by the procedures described in Examples 1 and 49 substituting 4-fluorobenzaldehyde for piperonal in Example 49A. $^1$H NMR (300 MHz, CDCl$_3$) δ 7.50 (1H, m), 7.42 (1H, dd, J=7 Hz, 3 Hz), 7.36(2H, d,J=8 Hz),7.01 (3H, t,J=8 Hz),6.87 (1H, d,J=8 Hz),3.83(1H, m), 3.8 (3H, s), 3.67 (1H, m), 3.47 (3H, m), 3.30–2.90 (5H, m), 2.82 (1H, d, J=14 Hz), 1.43 (2H, m), 1.28 (4H, m), 1.08 (2H, m), 0.90 (3H, t, J=7 Hz), 0.82 (3H, t J=7 Hz). MS (DCI/NH$_3$) m/e 485 (M+H)$^+$.

Anal.calc. for $C_{28}H_{37}FN_2O_4$: C, 69.40; H, 7.70; N, 5.78. Found: C, 69.03; H, 8.00; N, 5.74.

EXAMPLE 156 trans,trans-1-(N,N-Dibutylaminocarbonylmethyl)-2-(3-furyl)-4-(1,3-benzodioxol-5-yl) pyrrolidine-3-carboxylic Acid The title compound was prepared by the procedures described in Examples 1 and 49 substituting p-oxo-3-furanpropionate in Example 49B. $^1$H NMR (300 MHz, CDCl$_3$) δ 7.41 (2H, m), 6.97 (1H, d, J=3 Hz), 6.85 (1H, dd, J=7 Hz, 3 Hz), 6.72 (1H, d, J=8 Hz), 6.42 (1H, s), 5.94 (1H, d, J4 Hz), 5.92 (1H, d, J=4 Hz), 3.90 (1H, m), 3.70–3.25 (5H, m), 3.20–2.90 (4H, m), 2.85 (1H, d, J=14 Hz), 1.43 (2H, m), 1.40–1.05 (6H, m), 0.90 (6H, m). MS (DCI/NH$_3$) m/e 471 (M+H)$^+$.

Anal.calc. for $C_{26}H_{34}N_2O_6$: C, 66.36; H, 7.28; N, 5.95. Found: C, 66.09; H, 7.24; N, 5.87.

EXAMPLE 157 trans,trans-1-(N,N-Dibutylaminocarbonylmethyl)-2-(isopropyl)-4-(1,3-benzodioxol-5-yl) pyrrolidine-3-carboxylic Acid The title compound was prepared by the procedures described in Examples 1 and 49 substituting ethyl isobutyrylacetate in Example 49B. 1H NMR (300 MHz, CDCl$_3$) δ 6.85 (1H, d, J=2 Hz), 6.76 (1H, dd, J=6 Hz, 2 Hz), 6.71 (1H, d, J=8 Hz), 5.92 (2H, s), 3.75 (1H, d, J=14 Hz), 3.66 (1H, q, J=7 Hz), 3.42 (3H, m), 3.25 (3H, m), 3.11 (2H,m), 2.83 (1H, t, J=7 Hz), 1.88 (1H, m), 1.55 (4H, m), 1.32 (4H, m), 0.92 (12H, m). MS (DC! /NH$_3$) m/e 447 (M+H)$^+$.

Anal.calc. for $C_{25}H_{38}N_2O_5$. 0.50 H$_2$O: C, 65.91; H, 8.63; N, 6.15. Found: C, 66.07; H, 8.10; N, 6.03.

EXAMPLE 158 trans,trans-1-(N,N-Dibutylaminocarbonylmethyl)-2-(4-t-butylphenyl)-4-(1,3-benzodioxol-5-yl) pyrrolidine-3-carboxylic Acid The title compound was prepared by the procedures described in Examples 1 and 49 substituting ethyl 4-t-butylbenzoylacetate, prepared by the method of Krapcho et al., Org. Syn. 47:20 (1967) starting with 4-t-butylacetophenone), in Example 49B. $^1$H NMR (300 MHz, CDCl$_3$) δ 7.32 (4H, d, J3 Hz), 7.04 (1H, d, J=2 Hz), 6.87 (1H, dd, J=8 Hz, 3 Hz), 6.74 (1H, d, J=9 Hz), 5.94 (1H, d, J=4 Hz), 5.92 (1H, d, J=4H.z), 3.77 (1H, d, J=14 Hz), 3.65–3.25 (5H, m), 3.15–2.85 (4H, m), 2.73 (1H, d, J=14 Hz), 1.45 (2H, m), 1.29 (13H, s), 1.00 (2H, m), 0.86 (3H, t, J=7 Hz), 0.76 (3H, t, J=7 Hz). MS (DCI/NH$_3$) m/e 537 (M+H)$^+$.

Anal.calc. for $C_{32}H_{44}N_2O_5$: C, 71.61;H, 8.26; N, 5.22. Found: C, 71.43; H, 8.09; N, 5.11.

EXAMPLE 159 trans,trans-1-(N,N-Dibutylaminocarbonylmethyl)-2-(4-t-butylphenyl)-4-(5-benzo-2,3-dihydrofuranyl) -pyrrolidine-3-carboxylic Acid The title compound was prepared by the procedures described in Examples 1 and 49 substituting ethyl isobutyrylacetate in Example 49B and 2,3-dihydrobenzofuran-5ocarboxaldehyde for piperonal in Example 49A. $^1$H NMR (300 MHz, CDCl$_3$) δ 7.30 (1H, s), 7.13 (1H, dd, J=7 Hz, 2 Hz), 6.82 (1H, d, J=8 Hz), 4.68 (2H, t, J=8 Hz), 4.48 (1H, s), 3.19 (3H, m), 3.80 (3H, m), 3.48 (2H, m), 3.3 (SH, m), 2.41 (1H, m), 1.65 (4H, m), 1.44 (4H, m), 1.21 (3H, d, J=5 Hz), 1.17 (3H, d, J=5 Hz), 1.05 (6H, m). MS (DCI/NH$_3$) m/e 445 (M+H)$^+$.

Anal.calc. for C$_{26}$H$_{40}$N$_2$O$_4$ . 1.2 TFA: C, 58.67; H, 7.14; N, 4.8.2 Found: C, 58.54; H, 7.25; N, 4.74.

EXAMPLE 160 trans,trans-1-(N,N-Dibutylaminocarbonylmethyl)-2-(anti-4-methoxycycohexyl)-4-(1,3-benzodioxol-5-yl) pyrrolidine-3-carboxylic Acid

EXAMPLE 160A syn and anti Ethyl 4-methoxycyclohexanoylacetate

Syn, anti-4-Methoxycyclohexane carboxylic acid (5.00 g, 31.6 mmol) and carbonyldiimidazole (6.15 g, 37.9 mmol, 1.2 eq) were stirred in anhydrous tetrahydrofuran (50 mL) for 6 hours at room temperature. At the same time, magnesium chloride (3.01 g, 31.6 mmol) and ethyl malonate potassium salt (7.52 g, 44.2 mmol, 1.4 equivalents) were stirred in anhydrous tetrahydrofuran (75 mL) for 6 hours at 50° C. The mixture was cooled to room temperature, and the imidazole-acid mixture added to it. The reaction stirred overnight at room temerature. The solvents were removed under reduced pressure, and the residue was taken up in chloroform/water. The organic phase washed with 5% potassium bisulfate, water, and brine, dried with magnesium sulfate, filtered, and concentrated under reduced pressure. The residue was purified by flash chromatography on 175 g silica gel, eluting with 20% ethyl acetate in hexanes. Pure fractions of the syn and anti methoxycyclohexyl β-keto esters were obtained. The solvents were removed under reduced pressure to yield the trans-4-methoxycyclohexyl β-keto ester (914 mg) as a colorless oil and the cis 4-methoxycyclohexyl β keto ester (1.07 g) as a colorless oil.

EXAMPLE 160B trans,trans-1-(N,N-Dibutylaminocarbonylmethyl)-2-(anti-4-methoxycyclohexyl)-4-(1,3-benzodioxol-5-yl) pyrrolidine-3-carbexylic Acid The title compound was prepared by the procedures described in Examples 1 and 49 substituting the anti-compound resulting from Example 160A in Example 49B. $^1$H NMR (300 MHz, CDCl$_3$) δ 6.84 (1H, d, J=2 Hz), 6.76 (1H, dd, J=7 Hz, 2 Hz), 6.61 (1H, d, J=8 Hz), 5.92 (2H, s), 3.69 (2H, m), 3.50–3.27 (5H, m), 3.26 (3H, s), 3.25–3.00 (3H, m), 2.88 (1H, m), 1.95 (2H, m), 1.62 (7H, m), 1.33 (9H, m), 0.97 (3H, t, J=7 Hz), 0.92 (3H, t, J=7 Hz). MS (DCI/NH$_3$) m/e 517 (M+H)$^+$.

Anal.calc. for C$_{29}$H$_{44}$N$_2$O$_6$ . 0.50 H$_2$O: C, 66.26; H, 8.63; N, 5.33. Found: C, 66.27.; H, 8.50; N, 5.13.

EXAMPLE 161 trans,trans-1-(N,N-Dibutylaminocarbonylmethyl)-2-(syn-4-methoxycyclohexyl)-4-(1,3-benzodioxol-5-yl) pyrrolidine-3-carboxylic Acid The title compound was prepared by the procedures described in Examples 1 and 49 substituting the syn-compound resulting from Example A in Example 49B. $^1$H NMR (300 MHz, CDCl$_3$) δ 6.84 (1H, d, J=2 Hz), 6.77 (1H, dd, J=6 Hz, 2 Hz), 6.61 (1H, d, J=8 Hz), 5.92 (2H, s), 3.65 (2H, m), 3.42 (2H, m), 3.32 (3H, s), 3.30–3.00 (6H, m), 2.82 (1H, m), 2.10 (2H, m), 1.83 (2H, m), 1.52 (6H, m), 1.33 (4H, m), 1.20–1.00 (4H, m), 0.96 (3H, t, J=7 Hz), 0.91 (3H, t, J=7 Hz). MS (DCI/NH$_3$) m/e 51 7 (M+H)$^+$.

Anal.calc. for C$_{29}$H$_{44}$N$_2$O$_6$. 0.30 H$_2$O: C, 66.72; H, 8.61;N, 5.37. Found: C, 66.76; H, 8.65; N, 5.28.

EXAMPLE 162 trans,trans-1-(N,N-Dibutylaminocarbonylmethyl)-2,4-di(5-benzo-2,3-dihydrofuranyl) pyrrolidine-3-carboxylic Acid

EXAMPLE 162A

5-Acetyl-2,3-dihydrobenzofuran

To a 0° C. solution of acetyl chloride (1.64 mL, 23.0 mmol, 1.3 equivalents) in methylene chloride (30 mL) was added stannic chloride (2.49 mL. 21.3 mmol, 1.2 equivalents), maintaining the temperature below 5° C. The solution was stirred 15 minutes at 0° C., and then a solution of 2,3-dihydrofuran (2.00 mL, 17.7 mmol) in methylene chloride (5 mL) was added dropwise while maintaining the temperature below 8° C. The dark red solution was stirred 1 hour at 2° C. and then poured into 50 mL of ice water. The reaction was stirred an additional 30 minutes, and the layers were separated. The organic layer was washed with water and aqueous sodium bicarbonate, dried over magnesium sulfate, filtered, and concentrated under reduced pressure. The residue was purified by flash chromatography on 150 g silica gel, eluting with 18% ethyl acetate in hexanes. The solvents were removed under reduced pressure to yield the title compound (2.68 g, 93%) as a yellow solid.

EXAMPLE 162B trans,trans-1-(N,N-Dibutylaminocarbonylmethyl)-2,4-di(5-benzo-2,3-dihydrofuranyl) -2-pyrrolidine-3-carboxylic Acid The title compound was prepared by the procedures described in Examples 1 and 49 substituting the compound resulting from Example 162A in Example 49B and 2,3-dihydrobenzofuran-5-carboxaldehyde for piperonal in Example 49A. $^1$H NMR (300 MHz, CDCl$_3$) δ 7.43 (1H, s), 7.38 (1H, s), 7.06 (2H, m), 6.75 (1H, d, J=6 Hz), 6.70 (1H, d, J=6 Hz), 5.40 (1H, d, J=9 Hz), 4.58 (4H, q, J=7 Hz), 4.16 (1H, d, J=14 Hz), 4.09 (2H, m), 3.82 (2H, m), 3.57 (1H, d, J=14 Hz), 3.38 (1H, m), 3.30–3.05 (6H, m), 2.95 (2H, q, J=6 Hz), 1.50 (2H, m), 1,30 (4H, m), 1.15 (2H, m), 0.94 (3H, t, J=7 Hz), 0.83 (3H, t, J=7 Hz). MS (DCI/NH$_3$) m/e 521 (M+H)$^+$.

Anal.calc. for C$_{31}$H$_{40}$N$_2$O$_5$. 1.25 TFA: C, 60.67; H, 6.27; N, 4.22. Found: C, 60.49; H, 6.18; N, 4.13.

EXAMPLE 163 trans,trans-1-(N,N-Dibutylaminocarbonylmethyl)-2-(3-furyl)-4-(5-benzo-2,3-dihydrofuranyl) pyrrolidine-3-carboxylic Acid The title compound was prepared by the procedures described in Examples 1 and 49 substituting ethyl p-oxo-3-furanpropionate in Example 49B and 2,3-dihydrobenzofuran-5-carboxaldehyde for piperonal in Example 49A. $^1$H NMR (300 MHz, CDCl$_3$) δ 7.42 (1H, m), 7.38 (1H, m), 7.13 (1H, s), 7.16 (1H, dd, J=7 Hz, 3 Hz), 6.70 (1H, d, J=8 Hz), 6.41 (1H, m), 4.57 (2H, t, J=7 Hz), 3.95 (1H, d, J=8 Hz), 3.63 (1H, m), 3.55 (1H, d, J=14), 3.50–3.25 (4H, m), 3.18 (2H, t, J=6 Hz), 3.15–2.95 (3H, m), 2.87 (1H, d, J=14 Hz), 1.45 (4H, m), 1.35–1.10 (4H, m), 0.85 (6H, m). MS (DCI/NH$_3$) m/e 469 (M+H)$^+$.

Anal.calc. for $C_{27}H36N_2O_5$. 0.25 H$_2$O: C, 68.55; H, 7.78; N, 5.92. Found: C, 68.62; H, 7.68; N, 5.82.

EXAMPLE 164 trans,trans-1-(N,N-Dibutylaminocarbonylmethyl)-2-(4-metho xyphenyl)-4-(3-fluorophenyl) pyrrolidine-3-carboxylic Acid The title compound was prepared by the procedures described in Examples 1 and 49 substituting 3-fluorobenzenecarboxaldehyde for piperonal in Example 49A. $^1$H NMR (300 MHz, CDCl$_3$) δ 7.30 (2H, d, J=8 Hz), 7.22 (2H, m), 6.91 (1H, m), 6.86 (2H, d, J=8 Hz), 3.79 (1H, m), 3.78 (3H, s), 3.68 (1H, m), 3.55–3.37 (3H, m), 3.29 (1H, m), 3.15–2.90 (5H, m), 2.78 (1H, d, J=14 Hz), 1.43 (2H, m), 1.25 (4H, m), 1.07 (2H, m), 0.87 (3H, t, J=7 Hz), 0.80 (3H, t, J=7 Hz). MS (DCI/NH$_3$) m/e 485 (M+H)$^+$ Anal.calc. for $C_{28}H_{37}FN_2O_4$ . 0.25 H$_2$O: C, 68.76; H, 7.73; N, 5.73. Found: C, 68.87; H, 7.69; N, 5.67.

EXAMPLE 165 trans,trans-1-(N,N-Dibutylaminocarbonylmethyl)-2-(4-methoxyphenyl)-4-(3-pyridyl) pyrrolidine-3-carboxylic Acid The title compound was prepared by the procedures described in Examples 1 and 49 substituting 3-pyridinecarboxaldehyde for piperonal in Example 49A. The nitro styrene was prepared by the method of Bourguignon et al., Can. J. Chem. 63:2354 (1985). $^1$H NMR (300 MHz, CDCl$_3$) δ 8.82 (1H, bs), 8.73 (1H, bd, J=9 Hz), 8.62 (1H, bd, J=7 Hz), 7.78 (1H, bdd, J=9 Hz, 3 Hz), 7.38 (2H, d, J=10 Hz), 6.90 (2H, d, J=10 Hz), 4.39 (1H, d, J=12 Hz), 3.95 (1H, m), 3.80 (3H, s), 3.79 (1H, m), 3.68 (1H, d, J=18 Hz), 3.50–3.30 (3H, m), 3.25–2.90 (6H, m), 1.47 (2H, m), 1,31 (4H, m), 1.20 (2H, m), 0.92 (3H, t, J=7 Hz), 0.83 (3H, t, J=7 Hz). MS (DCI/NH$_3$) m/e 468 (M+H)+.

Anal.calc. for $C_{27}H_{37}N_3O_4$. 1.65 TFA: C, 55.50; H, 5.94; N, 6.41. Found: C, 55.53; H, 5.90; N, 6.27.

EXAMPLE 166 trans,trans-1-(N,N-Dibutylaminocarbonylmethyl)-2-(2-fluorophenyl)-4-(1,3-benzodioxol-5-yl) pyrrolidine-3-carboxylic Acid The title compound was prepared by the procedures described in Examples 1 and 49 substituting ethyl 2-fluorobenzoylacetate in Example 49B. $^1$H NMR (300 MHz, CDCl$_3$) δ 7.52 (1H, dr, J=7 Hz, 3 Hz), 7.25 (1H, m), 7.13 (1H, dt, J=7 Hz, 3 Hz), 7.02 (2H, m), 6.88 (1H, dd, J=7 Hz, 3 Hz), 6.73 (1H, d, J=8 Hz), 5.93 (1H, d, J=4 Hz), 5.92 (1H, d, J=4 Hz), 4.25 (1H, d, J=9 Hz), 3.68 (1H, m, 3.42 (3H, m), 3.39 (1H, m), 3.20–2.95 (4H, m), 2.91 (1H, d, J=14 Hz), 1.45 (3H, m), 1.26 (3H, m), 1.08 (2H, m), 0.87 (3H, t, J=7 Hz), 0.81 (3H, t, J=7 Hz). MS (DCI/NH$_3$) m/e 499 (M+H)$^+$.

Anal.calc. for $C_{28}H_{35}FN_2O_5$. 0.25 H$_2$O: C, 66.85; H. 7.11; N, 5.57. Found: C, 66.51; H, 6.67; N, 5.18.

EXAMPLE 167 trans,trans-1-(N,N-Dibutylaminocarbonylmethyl)-2-(3-fluorophenyl)-4-(1,3-benzodioxol) pyrrolidine-3-carboxylic Acid The title compound was prepared by the procedures described in Examples 1 and 49 substituting ethyl 3-fluorobenzoylacetate in Example 49B. $^1$H NMR (300 MHz, CDCl$_3$) δ 7.38 (1H, m), 7.18 (1H, d, J=7 Hz), 7.15 (1H, m), 7.00 (1H, d, J=2 Hz), 6.95 (1H, m), 6.86 (1H, dd, J=7 Hz, 2 Hz), 6.75 (1H, d J=8 Hz), 5.93 (1H, d, J=4 Hz), 5.92 (1H, d, J=4 Hz), 3.94 (1H, d, J=14 Hz), 3.63 (1H, m), 3.42 (3H, m), 3.35–2.95 (5H, m), 2.87 (1H, d, J=14 Hz), 1.44 (3H, m), 1.27 (3H, m), 1.10 (2H, m), 0.88 (3H, t, J=7 Hz), 0.81 (3H, t, J=7 Hz). MS (DCI/NH$_3$) m/e 499 (M+H)$^+$.

Anal.calc. for $C_{28}H_{35}FN_2O_5$: C, 67.45; H, 7.08; N, 5.62. Found: C, 67.32; H, 7.05; N, 5.40.

EXAMPLE 168 trans,trans-1-(4-N,N-Dibutylaminophenyl)-2-(4-methoxyphenyl)-4-(1,3-benzodioxol-5-yl) pyrrolidine-3-carboxylic Acid 4-Nitro-1-fluorobenzene, ethyl trans,trans-2-(4-methoxyphenyl)-4-(1,3-benzodioxol-5-yl) -pyrrolidine-3-carboxylate (the compound resulting from Example 6A), and diisopropylethylamine are heated in dioxane to give ethyl trans, trans-2-(4-methoxyphenyl)-4-(1,3-benzodioxol-5-yl)-1-(4-nitrophenyl)-pyrrolidine-3-carboxylate. The nitro compound is hydrogenated to give the corresponding aminophenyl compound. The aminophenyl compound is reacted with butyraldehyde and sodium cyanoborohydride according to the method of Botch, J. Am Chem. Soc. 93:2897 (1971) to give the corresponding N,N-dibutylaminophenyl compound. Hydrolysis with sodium hydroxide using the method of Example 1D affords the title compound.

EXAMPLE 169 trans,trans-1-(2-N,N-Dibutylaminopyrimidin-4-yl)-2-(4-methoxyphenyl)-4-(1,3-benzodioxob5-yl) pyrrolidine-3-carboxylic Acid 2-(Dibutylamino)-4-chloropyrimidine is prepared from 2,4-dichloropyrimidine according to the method of Gershon, J. Heterocyclic Chem. 24:205 (1987) and reacted with ethyl trans,trans-2-(4-methoxyphenyl)-4-(1,3-benzodioxol-5-yl)-pyrrolidine-3-carboxylate (the compound resulting from Example 6A) and diisoproplyethylamine in dioxane with heating to give the intermediate ethyl ester, which is hydrolyzed with sodium hydroxide using the method of Example 1D to the title compound.

EXAMPLES 170–266

Using the procedures described in Examples 1,4, 5, 7, 8 and 9 and Scheme X, the following compounds can be prepared.

Ex. No. Name 170   trans,trans-2-(4-Methoxyphenyl)-4-(1,3-benzodioxol-5-yl)-1-(isopropylaminocarbonylmethyl)  -pyrrolidine-3-carboxylic Acid;

171   trans,trans-2-(4-Methoxyphenyl)-4-(1,3-benzodioxol-5-yl)-1-(ethylaminocarbonylmethyl)-pyrrolidine-3-carboxylic Acid;

172  trans,trans-2-(4-Methoxyphenyl)-4-(1,3-benzodioxol-5-yl)-1-(1-methylpropylaminocarbonylmethyl)-pyrrolidine-3-carboxylic Acid;

173  trans,trans-2-(4-Methoxyphenyl)-4-(1,3-benzodioxol-5-yl)-1-(phenylaminocarbonylmethyl)-pyrrolidine-3-carboxylic Acid;

174  trans,trans-2-(4-Methoxyphenyl)-4-(1,3-benzodioxol-5-yl)-1-(piperidinylcarbonylmethyl)-pyrrotidine-3-carboxylic Acid;

175  trans,trans-2-(4-Methoxyphenyl)-4-(1,3-benzodioxol-5-yl)-1-(1-(propylaminocarbonyl)ethyl)-pyrrolidine-3-carboxylic Acid;

176  trans,trans-2-(4-Methoxyphenyl)-4-(1,3-benzodioxol-5-yl)-1-(α-(propylaminocarbonyl)benzyl)-pyrrolidine-3-carboxylic Acid;

177  trans,trans-2-(4-Methoxyphenyl)-4-(1,3-benzodioxol-5-yl)-1-(bis-(propylaminocarbonyl)methyl)-pyrrolidine-3-carboxylic Acid;

178  trans,trans-2-(4-Methoxyphenyl)-4-(1,3-benzodioxol-5-yl)-1-(2-(propylaminocarbonyl)ethyl)-pyrrolidine-3-carboxylic Acid;

179  trans,trans-2-(4-Methoxyphenyl)-4-(1,3-benzodioxol-5-yl)-1-(propylaminosulfonylmethyl)-pyrrolidine-3-carboxylic Acid;

180  trans,trans-2-(4-Methoxyphenyl)-4-(1,3-benzodioxol-5-yl)-1-(2-phenethyl)-pyrrolidine-3-carboxylic Acid;

181  trans,trans-2-(4-Methoxyphenyl)-4-(1,3-benzodioxol-5-yl)-1-(pentanoylmethyl)-pyrrolidine-3-carboxylic Acid;

182  trans,trans-2-(4-Methoxyphenyl)-4-(1,3-benzodioxol-5-yl)-1-(benzoylmethyl)-pyrrolidine-3-carboxylic Acid;

183  trans,trans-2-(4-Methoxyphenyl)-4-(1,3-benzodioxol-5-yl)-1-(hexyl)-pyrrolidine-3-carboxylic Acid;

184  trans,trans-2-(4-Methoxyphenyl)-4-(1,3-benzodioxol-5-yl)-1-(2-hexynyl)-pyrrolidine-3-carboxylic Acid;

185  trans,trans-2-(4-Methoxyphenyl)-4-(1,3-benzodioxol-5-yl)-1-(propoxymethylcarbonyl-pyrrolidine-3-carboxylic Acid;

186  trans,trans-2-(4-Methoxyphenyi)-4-(1,3-benzodioxol-5-yl)-1-(phenylacetyl)-pyrrolidine-3-carboxylic Acid;

187  trans,trans-2-(4-Methoxyphenyl)-4-(1,3-benzodioxol-5-yl)-1-(anilinylcarbonyl)-pyrrolidine-3-carboxylic Acid;

188  trans,trans-2-(4-Methoxyphenyl)-4-(1,3-benzodioxol-5-yl)-1-(2-acetylaminoethyl)-pyrrolidine-3-carboxylic Acid;

189  trans,trans-2-(4-Methoxyphenyl)-4-(1,3-benzodioxol-5-yl)-1-(2-phenoxyethyl)-pyrrolidine-3-carboxylic Acid;

190  trans,trans-2-(4-Methoxyphenyl)-4-(1,3-benzodioxol-5-yl)-1-(2-benzodioxanylmethyl)-pyrrolidine-3-carboxylic Acid;

191  trans,trans-2-(4-Methoxyphenyl)-4-(1,3-benzodioxol-5-yl)-1-(2-tetrahydrofuranylmethyl)-pyrrolidine-3-carboxylic Acid;

192  trans,trans-2-(4-Methoxyphenyl)-4-(1,3-benzodioxol-5-yl)-1-(2-(propylaminocarbonylamino)ethenyl)-pyrrolidine-3-carboxylic Acid;

193  trans,trans-2-(4-Methoxyphenyl)-4-(1,3-benzodioxol-5-yl)-1-(2-(propylaminocarbonylamino)ethyl)-pyrrolidine-3-carboxylic Acid;

194  trans,trans-2-(4-Methoxyphenyl)-4-(1,3-benzodioxol-5-yl)-1-(3-oxohex-1-enyl)-pyrrolidine-3-carboxylic Acid;

195  trans,trans-2-(2,4-Dimethoxyphenyl)-4-(1,3-benzodioxol-5-yl)-1-(propylaminocarbonylmethyl)-pyrrolidine-3-carboxylic Acid;

196  trans,trans-2-(2-Carboxylmethoxyphenyl)-4-(1,3-benzodioxol-5-yl)-1-(propylami nocarbonylmethyl)-pyrrolidine-3-carboxylic Acid;

197  trans,trans-2-(2-Aminocarbonyl-4-methoxyphenyl)-4-(1,3-benzodioxol-5-yl)-1-(propylami nocarbonylmethyl)-pyrrolidine-3-carboxylic acid;

198  trans,trans-2-(2-Methanesulfonamido-4-methoxyphenyl)-4-(1,3-benzodioxol-5-yl) -1-(propylaminocarbonylmethyl)-pyrrolidine-3-carboxylic Acid;

199  trans,trans-2-(2-Aminocarbonylmethoxy-4-methoxyphenyl)-4-(1,3-benzodioxol-5-yl)-1-(propylaminocarbonylmethyl) -pyrrolidine-3-carboxylic Acid;

200  trans,trans-2-(2-Methoxyethoxy-4-methoxyphenyl)-4-(1,3-benzodioxol-5-yl)-1-(propylaminocarbonylmethyl) -pyrrolidine-3-carboxylic Acid;

201  trans,trans-2-(2-Carboxymethoxy-4-methoxyphenyl)-4-(1,3-benzodioxolo-5-yl)-1-(propylaminocarbonylmethyl) -pyrrolidine-3-carboxylic Acid;

202  trans,trans-2-(4-Methoxy-2-tetrazolylmethoxyphenyl)-4-(1,3-benzodioxol-5-yl)-1-(propylaminocarbonylmethyl) -pyrrolidine-3-carboxylic Acid;

203  trans,trans-2-(2-Allyloxy-4-methoxyphenyl)-4-(1,3-benzodioxol-5-yl)-1-(propylaminocarbonylmethyl) -pyrrolidine-3-carboxylic Acid;

204  trans,trans 2,4-Bis(4-methoxyphenyl)-1-(propylaminocarbonylmethyl) -pyrrolidine-3-carboxylic Acid;

205  trans,trans 2,4-Bis(1,3-benzodioxol-5-yl)-1-(propylaminocarbonylmethyl) -pyrrolidine-3-carboxylic Acid;

206  trans,trans-2-(4-Methoxyphenyl)-4-(1,3-benzodioxol-5-yl)-1-(N-methyl-N-propylaminocarbonylmethyl) -pyrrolidine-3-carboxylic Acid;

207  trans,trans-2-(4-Methoxyphenyl)-4-(1,3-benzodioxole-5-yl)-1-(N-methyl-N-butylaminocarbonyl) -pyrrolidine-3-carboxylic Acid;

208  trans,trans-2-(4-Methoxyphenyl)-4-(1,3-benzodioxol-5-yl)-1-(N-methyl-N-(4-methoxyphenyl)aminocarbonyl) -3-pyrrolidine-3-carboxylic acid;

209  trans,trans-2-(4-Methoxyphenyl)-4-(1,3-benzodioxol-5-yl)-1-(N-methyl-N-phenylaminocarbonyl) -pyrrolidine-3-carboxylic Acid;

210  trans,trans-2-(4-Methoxyphenyl)-4-(1,3-benzodioxol-5-yl)-1-(N-methyl-N-allylaminocarbonylmethyl) -pyrrolidine-3-carboxylic Acid;

211  trans,trans-2-(4-Methoxyphenyl)-4-(1,3-benzodioxol-5-yl)-1-(N-methyl-N-(n-butyl)aminocarbonylmethyl) -pyrrolidine-3-carboxylic Acid;

212  trans,trans-2-(4-Methoxyphenyl)-4-(1,3-benzodioxol-5-yl)-1-(N-methyl-N-isobutylaminocarbonylmethyl) -pyrrolidine-3-carboxylic Acid;

213  trans,trans-2-(4-Methoxyphenyl)-4-(1,3-benzodioxol-5-yl)-1-(N-methyl-N-cyclopentylaminocarbonylmethyl) -pyrrolidine-3-carboxylic Acid;

214  trans,trans-2-(4-Methoxyphenyl)-4-(1,3-benzodioxol-5-yl)-1-(N-methyl-N-(2-methoxyethyl) aminocarbonyl)-pyrrolidine-3-carboxylic Acid;

215  trans,trans-2-(4-Methoxyphenyl)-4-(1,3-benzodioxol-5-yl)-1-(N-methyl-N-butoxyethylaminocarbonyl) -pyrrolidine-3-carboxylic Acid;

216 trans,trans-2-(1,3-Benzodioxol-5-yl)-4-(4-methoxyphenyl)-1-(N-methyl-N-propylaminocarbonylmethyl) -pyrrolidine-3-carboxylic Acid;

217 trans,trans-2-(4-Methoxyphenyl)-4-(1,4-benzodioxan-6-yl)-1-(N-methyl-N-propylaminocarbonylmethyl) -pyrrolidine-3-carboxylic Acid;

218 trans,trans-2-(4-Methoxyphenyl)-4-(1,3-benzodioxol-5-yl)-1-(N-methyl-N-isopropylaminocarbonylmethyl) -pyrrolidine-3-carboxylic Acid;

219 trans,trans-2-(4-Methoxyphenyl)-4-(1,3-benzodioxol-5-yl)-1-(N-methyl-N-ethylaminocarbonylmethyl) -pyrrolidine-3-carboxylic Acid;

220 trans,trans-2-(4-Methoxyphenyl)-4-(1,3-benzodioxol-5-yl)-1-(N-methyl-N-(1-methylpropyl) aminocarbonylmethyl)-pyrrolidine-3-carboxylic Acid;

221 trans,trans-2-(4-Methoxyphenyl)-4-(1,3-benzodioxol-5-yl)-1-(N-methyl-N-phenylaminocarbonylmethyl) -pyrrolidine-3-carboxylic Acid;

222 trans,trans-2-(4-Methoxyphenyl)-4-(1,3-benzodioxol-5-yl)-1-(1-(N-methyl-N-propylaminocarbonyl)ethyl) -pyrrolidine-3-carboxylic Acid;

223 trans,trans-2-(4-Methoxyphenyl)-4-(1,3-benzodioxol-5-yl)-1-(α-(N-methyl-N-propylaminocarbonyl) benzyl)-pyrrolidine-3-carboxylic Acid;

224 trans,trans-2-(4-Methoxyphenyl)-4-(1,3-benzodioxol-5-yl)-1-(N-ethyl-N-propylaminocarbonylmethyl) -pyrrolidine-3-carboxylic Acid;

225 trans,trans-2-(4-Methoxyphenyl)-4-(1,3-benzodioxole-5-yl)-1-(N-ethyl-N-butylaminocarbonyl) -pyrrolidine-3-carboxylic Acid;

226 trans,trans-2-(4-Methoxyphenyl)-4-(1,3-benzodioxol-5-yl)-1-(N-ethyl-N-(4-methoxyphenyl)aminocarbonyl) -3-pyrrolidine-3-carboxylic Acid;

227 trans,trans-2-(4-Methoxyphenyl)-4-(1,3-benzodioxol-5-yl)-1-(N-ethyl-N-phenylaminocarbonyl) -pyrrolidine-3-carboxylic Acid;

228 trans,trans-2-(4-Methoxyphenyl)-4-(1,3-benzodioxol-5-yl)-1-(N-ethyl-N-allylaminocarbonylmethyl) -pyrrolidine-3-carboxylic Acid;

229 trans,trans-2-(4-Methoxyphenyl)-4-(1,3-benzodioxol-5-yl)-1-(N-ethyl-N-isobutylaminocarbonylmethyl) -pyrrolidine-3-carboxylic Acid;

230 trans,trans-2-(4-Methoxyphenyl)-4-(1,3-benzodioxol-5-yl)-1-(N-ethyl-N-cyclopentylaminocarbonylmethyl) -pyrrolidine-3-carboxylic Acid;

231 trans,trans-2-(4-Methoxyphenyl)-4-(1,3-benzodioxol-5-yl)-1-(N-ethyl-N-methoxyethylaminocarbonyl) -pyrrolidine-3-carboxylic Acid;

232 trans,trans-2-(4-Methoxyphenyl)-4-(1,3-benzodioxol-5-yl)-1-(N-ethyl-N-butoxyethylaminocarbonyl) -pyrrolidine-3-carboxylic Acid;

233 trans,trans-2-(1,3-Benzodioxol-5-yl)-4-(4-methoxyphenyl)-1-(N-ethyl-N-propylaminocarbonylmethyl) -pyrrolidine-3-carboxylic Acid;

234 trans,trans-2-(4-Methoxyphenyl)-4-(1,4-benzodioxan-6-yl)-1-(N-ethyl-N-propylaminocarbonylmethyl) -pyrrolidine-3-carboxylic Acid;

235 trans,trans-2-(4-Methoxyphenyl)-4-(1,3-benzodioxol-5-yl)-1-(N-ethyl-N-isopropylaminocarbonylmethyl) -pyrrolidine-3-carboxylic Acid;

236 trans,trans-2-(4-Methoxyphenyl)-4-(1,3-benzodio x ol-5-yl)-1-(N,N-diethylaminocarbonylmethyl) -pyrrolidine-3-carboxylic Acid;

237 trans,trans-2-(4-Methoxyphenyl)-4-(1,3-benzodioxol-5-yl)-1-(N-ethyl-N-(1-methylpropyl)aminocarbonylmethyl) -pyrrolidine-3-carboxylic Acid;

238 trans,trans-2-(4-Methoxyphenyl)-4-(1,3-benzodioxol-5-yl)-1-(N-ethyl-N-phenylaminocarbonylmethyl) -pyrrolidine-3-carboxylic Acid;

239 trans,trans-2-(4-Methoxyphenyl)-4-(1,3-benzodioxol-5-yl)-1-(1-(N-ethyl-N-propylaminocarbonyl)ethyl) -pyrrolidine-3-carboxylic Acid;

240 trans,trans-2-(4-Methoxyphenyl)-4-(1,3-benzodioxol-5-yl)-1-(α-(N-ethyl-N-propylaminocarbonyl)benzyl) -pyrrolidine-3-carboxylic Acid;

241 trans,trans-2-(4-Methoxyphenyl)-4-(1,3-benzodioxol-5-yl)-1-(N-methyl-N-isobutylaminocarbonylmethyl) -pyrrolidine-3-carboxylic Acid;

242 trans,trans-2-(4-Methoxyphenyl)-4-(1,3-benzodioxol-5-yl)-1-(N-methyl-N-cyclohexylaminocarbonylmethyl) -pyrrolidine-3-carboxylic Acid;

243 trans,trans-2-(4-Methoxyphenyl)-4-(13-benzodioxol-5-yl)-1-(N,N-dipropylaminocarbonylmethyl) -pyrrolidine-3-carboxylic Acid;

244 trans,trans-2-(4-Methoxyphenyl)-4-(1,3-benzodioxol-5-yl)-1-(isobutyloxyethyl) -pyrrolidine-3-carboxylic Acid;

245 trans,trans-2-(4-Methoxyphenyl)-4-(13-benzodioxol-5-yl)-1-(butylsulfonyl) -pyrrolidine-3-carboxylic Acid;

246 trans,trans-2-(4-Methoxyphenyl)-4-(1,3-benzodioxol-5-yl)-1-(isopropylsulfonylaminoethyl) -pyrrolidine-3-carboxylic Acid;

247 trans,trans-2-(4-Methoxyphenyl)-4-(13-benzodioxol-5-yl)-1-(ethoxymethylcarbonylmethyl)-pyrrolidine -3-carboxylic Acid;

248 trans,trans-2-(4-Methoxyphenyl)-4-(13-benzodioxol-5-yl)-1-(2-ethylbutyrylmethyl) -pyrrolidine-3-carboxylic Acid;

249 trans,trans-2-(4-Methoxyphenyl)-4-(1,3-benzodioxol-5-yl)-1-(N-methyl-N-(3,4-dimethoxybenzyl) aminocarbonylmethyl)-pyrrolidine-3-carboxylic Acid;

250 trans,trans-2-(4-Methoxyphenyl)-4-(1,3-benzodioxol-5-yl)-1-[(1R)-1-(N-methyl-N-propylaminocarbonyl)butyl]-pyrrolidine-3-carboxylic Acid;

251 trans,trans-2-(4-Methoxyphenyl)-4-(1,3-benzodioxol-5-yl)-1-[(1S)-1-(N-methyl-N-propylaminocarbonyl)butyl]-pyrrolidine-3-carboxylic Acid;

b 252trans,trans-2-(4-Methoxyphenyl)-4-(1,3-benzodioxol-5-yl)-1-(3-isopropoxypropyl) -pyrrolidine-3-carboxylic Acid;

253 trans,trans-2-(4-Methoxyphenyl)-4-(1,3-benzodioxol-5-yl)-1-(5-methylhexyl) -pyrrolidine-3-carboxylic Acid;

254 trans,trans-2-(4-Methoxyphenyl)-4-(1,3-benzodioxol-5-yl)-1-(5-methyl-2-hexenyl) -pyrrolidine-3-carboxylic Acid; 255 trans,trans-2-(4-Methoxyphenyl)-4-(1,3-benzodioxol-5-yl)-1-(5-methyl-4-hexenyl) -pyrrolidine-3-carboxylic Acid;

256 trans,trans-2-(4-Methoxyphenyl)-4-(1,3-benzodioxol-5-yl)-1-(3,5-dimethyl-2-hexenyl) -pyrrolidine-3-carboxylic Acid;

257 trans,transo2-(4-Methoxyphenyl)-4-(1,3-benzodioxol-5-yl)-1-(2-(N-methyl-N-isobutyrylamino)ethyl) -pyrrolidine-3-carboxylic Acid;

258 trans,trans-2-(4-Methoxyphenyl)-4-(1,3-benzodioxol-5-yl)-1-(N-methyl-N-(2,2-dimethylpropyl) aminocarbonylmethyl)-pyrrolidine-3-carboxylic Acid;

259 trans,trans-2-(4-Methoxyphenyl)-4-(1,3-benzodioxol-5-yl)-1-(N-ethyl-N-butylaminocarbonylmethyl)-pyrrolidine-3-carboxylic Acid;

260 trans,trans-2-(4-Methoxyphenyl)-4-(1,3-benzodioxol-5-yl)-1-(N-methyl-N-benzylaminocarbonylmethyl)-pyrrolidine-3-carboxylic acid:

262 trans,trans-2-(4-Methoxyphenyl)-4-(5-indanyl)-1-(N-methyl-N-propylaminocarbonylmethyl)-pyrrolidine-3-carboxylic Acid;

262 trans,trans-2-(4-Methoxyphenyt)-4-(2,3-dihydrobenzofuran-5-yl)-1-(N-methyl-N-propylaminocarbonylmethyl)-pyrrolidine-3-carboxylic Acid;

263 trans,trans-2-(4-Metho xyphenyl)-4-(1-methylindol-5-yl)-1-(N-methyl-N-propylaminocarbonylmethyl)-pyrrolidine-3-carboxylic Acid;

264 trans,transo2-(4-Methoxyphenyl)-4-(2-naphthyl)-1-(N-methyl-N-propylaminocarbonylmethyl)-pyrrolidine-3-carboxylic Acid;

265 trans,trans-2-(4-Methoxyphenyl)-4-(1,2-dimethoxy-4-phenyl)-1-(N-methyl-N-propylaminocarbonylmethyl)-pyrrolidine-3-carboxylic Acid;

266 trans,trans-2-(4-Methoxyphenyl)-4-(1-methoxy-3-phenyl)-1-(N-methyl-N-propylaminocarbonylmethyl)-pyrrolidine-3-carboxylic Acid;

EXAMPLES 267–288

Following the procedures described in Example 1 and Scheme II, the following compounds can be prepared.

267 trans,trans-3-(4-Methoxyphenyl)-5-(13-benzodioxol-5-yl)-1-(propylaminocarbonylmethyl)-piperidine-4-carboxylic Acid;

268 trans,trans-3-(4-Methoxyphenyl)-5-(13-benzodioxol-5-yl)-1-(aminocarbonylmethyl)-piperidine-4-carboxylic Acid;

269 trans,trans-3-(4-Methoxyphenyl)-5-(13-benzodioxol-5-yl)-1-(4-fluorobenzyl)-piperidine-4-carboxylic Acid;

270 trans,trans-3-(4-Methoxyphenyl)-5-(13-benzodioxol-5-yl)-1-(2-ethoxyethyl)-piperidine-4-carboxylic Acid;

271 trans,trans-3-(4-Methoxyphenyl)-5-(1,3-benzodioxol-5-yl)-1-(2-propoxyethyl)-piperidine-4-carboxylic Acid;

272 trans,trans-3-(4-Methoxyphenyl)-5-(1;3-benzodioxol-5-yl)-1-[2-(2methoxyethoxy)ethyl]-piperidine-4-carboxylic Acid;

273 trans,trans-3-(4-Methoxyphenyl)-5-(13-benzodioxol-5-yl)-1-[2-(2pyridyl)ethyl]-piperidine-4-carboxylic Acid;

274 trans,trans-3-(4-Methoxyphenyl)-5-(1,3-benzodioxol-5-yl)-1-(morpholin-4-ylcarbonyl)-piperidine-4-carboxylic Acid;

275 trans,trans-3-(4-Methoxyphenyl)-5-(13-benzodioxole-5-yl)-1-(butylaminocarbonyl)-piperidine-4-carboxylic Acid; 276 trans,trans-3-(4-Methoxyphenyl)-5-(1,3-benzodioxol-5-yl)-1-(4-ethoxyphenylaminocarbonyl)-3-piperidine-4-carboxylic Acid;

277 trans,trans-3-(4-Methoxyphenyl)-5-(1,3-benzodioxol-5-yl)-1-acetylpiperidine-3-carboxylic Acid;

278 trans,trans-3-(4-Methoxyphenyl)-5-1,3-benzodioxol-5-yl)-1-(2-furoyl)-piperidine-3-carboxylic Acid;

279 trans,trans-3-(4-Methoxyphenyl)-5-1,3-benzodioxol-5-yl)-1-(phenylaminocarbonyl)-piperidine-4-carboxylic Acid;

280 trans,trans-3-(4-Methoxyphenyl)-5-1,3-benzodioxol-5-yl)-1-(allylaminocarbonylmethyl)-piperidine-4-carboxylic Acid;

281 trans,trans-3-(4-Methoxyphenyl)-5-1,3-benzodioxol-5-yl)-1-(n-butylaminocarbonylmethyl)-piperidine-4-carboxylic Acid;

282 trans,trans-3-(4-Methoxyphenyl)-5-1,3-benzodioxol-5-yl)-1-(N-n-butyl-N-methylaminocarbonylmethyl)-piperidine-4-carboxylic Acid;

283 trans,trans-3-(4-Methoxyphenyl)-5-1,3-benzodioxol-5-yl)-1-(pyrrolidin-1-ylcarbonylmethyl)-piperidine-4-carboxylic Acid;

284 trans,trans-3-(4-Methoxyphenyl)-5-1,3-benzodioxol-5-yl)-1-(isobutylaminocarbonylmethyl)-piperidine-4-carboxylic Acid;

285 trans,trans-3-(4-Methoxyphenyl)-5-1,3-benzodioxol-5-yl)-1-(cyclopentylaminocarbonylmethyl)-piperidine-4-carboxylic Acid;

286 trans,trans-3-(4-Methoxyphenyl)-5-1,3-benzodioxol-5-yl)-1-(morpholin-4-ylaminocarbonylmethyl)-piperidine-4-carboxylic Acid;

287 trans,trans-3-(4-Methoxyphenyl)-5-1,3-benzodioxol-5-yl)-1-(2-phenoxyethyl)-piperidine-4-carboxylic Acid;

288 trans,trans-3-(4-Methoxyphenyl)-5-1,3-benzodioxol-5-yl)-1-(methoxyethylaminocarbonyl)-piperidine-4-carboxylic acid.

EXAMPLE 289 trans,trans-2-(4-Methoxyphenyl)-4-(1,3-benzodioxol-5-yl)-1-(4-dibutylaminophenyl)-pyrrolidine-3-carboxylic acid 4-Nitro-fluorobenzene, ethyl trans,trans-2-(4-methoxyphenyl)-4-(1,3-benzodioxol-5-yl)-pyrrolidine-3-carboxylate (example 6A) and di-isopropyl ethylamine are heated in dioxane to give ethyl trans,trans-2-(4-methoxyphenyl)-4-(1,3-benzodioxol-5-yl)-1-(4-nitrophenyl)-pyrrolidine-3-carboxylate. The nitro compound is hydrogenated to the corresponding aminophenyl compound. This is reacted with butyraldehyde and sodium cyanoborohydride according to the method of Borch (J. Am Chem. Soc., 93, 2897, 1971) to give the corresponding N,N-dibutylaminophenyl compound, which is hydrolyzed with sodium hydroxide using the method of example 1D to give the title compound.

EXAMPLE 290 trans,trans-2-(4-Methoxyphenyl)-4-(1,3benzodioxol-5-yl)-1-(2-dibutylaminopyrimidine-4-yl)-pyrrolidine-3-carboxylic acid 2-(Dibutylamino) 4-chlpropyrimidine is prepared from 2-4-dichlpropyrimidine according to the method of Gershon (J. Heterocyclic Chem. 24, 205, 1987). This compound, ethyl trans,trans-2-(4-methoxyphenyl)-4-(1,3-benzodioxol-5-yl)-pyrrolidine-3-carboxylate (example 6A), and di-isopropyl ethylamine are heated in dioxane to give the intermediate ethyl ester, which is hydrolyzed with sodium hydroxide using the method of example 1D to give the title compound.

EXAMPLE 291 trans,trans-2-(4-Methoxyphenyl)-4-(1,3-benzodioxol-5-yl)-1-(N-butyl-N-phenylaminocarbonylmetbyl)-pyrrolidine-3-carboxylic acid The title compound was prepared according to the general procedure of Example 1.

MS (DCI/NH$_3$): 531 (M+H)$^+$.

Anal calcd for C$_{31}$H$_{34}$N$_2$O$_6$: C, 70.17; H, 6.46; N, 5.28. Found: C, 70.36; H, 6.52: N, 4.99. NMR (CD$_3$OD): δ 0.87 (t,3H,J=8); 1.2–1.35 (m,2H); 1.35–1.5 (m,2H); 2.78 (m, 2H); 3.10 (t,1H, J=9); 3.26 (d,1H,J=15); 3.44 (dd,1H,J=5, 10); 3.5–3.7 (m,3H); 3.77 (m,1H); 3.78 (s,3H); 5.93 (s,2H); 6.7–6.9 (m,4H); 7.0–7.2 (m,5H); 7.4 (m,3H).

EXAMPLE 292

Sodium trans,trans-2-(4-Methoxyphenyl)-4-(1,3-benzodioxol-5-yl)-1-(N,N-di(n-butyl)aminocarbonylmethyl)-pyrrolidine-3-carboxylate

EXAMPLE 292A

Ethyl 3-(4-methoxyphenyl)-3-oxopropionate

Simultaneous reactions were run in both a 65-L reactor and a 35-L reactor that share the same reflux system. A nitrogen atmosphere was maintained in both. 4.0 kg (100 moles) of 60% sodium hydride in mineral oil and 32 L toluene were charged into the ambient temperature reactors. The mixture was agitated for 5 minutes and allowed to settle. 20 L of the toluene solution was aspirated. 28 L of toluene was added, agitated for 5 minutes, allowed to settle and 28 L of the toluene solution was aspirated. 68 L of toluene and 8.4 L (69.7 moles) diethyl carbonate were added. The agitation was begun and the flow of Syltherm (Note 4) in reactor jackets was initiated. A solution of 5.0 kg (33.3 moles) 4-methoxyacetophenone in 12 L toluene was added over 20 minutes. When additions were complete, the jacket temperaturewas reduced to 10° C. and stirring continued for 16 hours. A solution of 6.7 L (117 moles) glacial acetic acid in 23 L deionized water was fed at the same rate that was previously used for the acetophenone solution. When addition was complete, agitation was stopped and the layers separated. The aqueous layer was washed once with 13 L toluene. The combined organic layers were washed twice with 6.7 L portions of 7% (w:w) aqueous sodium bicarbonate. The toluene solution was washed once with 6.7 L of 23% (w:w) aqueous sodium chloride. The organinc solution was dried over 10 kg sodium sulfate, filtered, and the solvent removed on the rotary evaporator to provide the desired product.

EXAMPLE 292B 3,4-Methylenedioxy-1-(2-nitroethenyl)-benzene

In a 45-L cryogenic reactor with a contoured, anchor stirrer was dissolved 5.537 kg (36.9 moles) piperonal in 9 L methanol and 2.252 kg (36.9 moles) nitromethane at 15°–20° C. The jacket temperature was set to –5° C. and the reaction solution cooled to a temperature of +3.5° C. A 21° C. solution of 3.10 kg (38.8 moles) 50% (w:w) aqueous sodium hydroxide diluted with 3.7 L water was pumped in. The reaction temperature was maintained between 10°–15° C. When addition was complete, the jacket temperature was reset to 1° C. and stirring continued for 30 minutes. A mixture of 7 kg ice in 19 L water was added to dissolve most of the solid. The reaction mixture was filtered through canvas and then a 27R10SV Honeycomb filter. The filtered solution was metered into a 21° C. mixture of 7.4 L concentrated hydrochloric acid in 11.1 L deionized water. The final reaction temperature was 26° C. The resulting product was centrifuged and washed until the wash pH rose to at least 6 (by pH indicating paper). The crude product was dissolved in 92 L dichloromethane and the layers separated. The aqueous layer was washed once with 8 L dichloromethane. The combined organics were dried over 1.32 kg magnesium sulfate and filtered through Whatman #1 paper. The volume was reduced to 20% and the solution cooled to 4° C. Filtration through Whatman #1 paper, followed by ambient temperature drying in vacuo with an air leak afforded 1.584 kg (22%) of a first crop Concentration of the MLS to 25% followed by similar cooling, filtration, and drying afforded 0.262 kg (4%) of a second crop. The yellow product darkened on standing in light and air.

EXAMPLE 192C

Ethyl 2-(4-methoxybenzoyl)-3-(3.4-methylenedioxy-phenyl)-4-nitro-butanoate

Into a 45-L stirred reactor at ambient temperature were charged 5.819 kg (30.1 moles) 3,4-methylenedioxy-1-(2-nitroethenyl)-benzene and 24 L ethyl acetate. A solution of 5.355 kg (24.1 moles) ethyl 3-(4-methoxyphenyl)-3-oxopropionate in 16 L ethyl acetate was added. 280 g (275 ml, 1.84 moles) of 1,8-diaza-bicyclo[5.4.0]undec-7-ene in four equal portions was added over a 2.5 hour period. The reaction mixture was filtered through dicalite and the resulting filtered solution was used in the next step without any further purification.

EXAMPLE 292D

Ethyl 2-(4-methoxyphenyl)-4-(3,4-methylenedioxybenyl)-4,5-dihydro-3H-pyrrol-3-carboxylate The product of Example 292C (1316 ml solution consisting of 300 g Ethyl 2-(4-methoxybenzoyl)-3-(3,4-methylenedioxyphenyl)-4 -nitrobutanoate in ethyl acetate) was added to a glass reactor containing RaNi #28 (300 g). The reaction mixture was shaken under a hydrogen environment of 4 atm at room temperature for 18 hoursand filtered through a nylon 0.20 micron 47 mm millipore.

The filtrate was concentrated to 1.4 kg of dark solution and purified by normal phase silica gel chromatography eluting with 85:15, hexanes: ethyl acetate. The pure fractions were combined and concentrated (as above) until crystals formed. The solution was cooled to 0° C. and filtered. The solid was washed with 2 L of 85:15, hexane: ethyl acetate (0° C). The solids were dried in vacuo at 50° C. to a constant weight of 193.4 g (21% yield, melting point 80°–81° C.) of the title compound. A further 200 g (23% yield) of product was obtained from the mother liquors.

EXAMPLE 292E

Ethyl 2-(4-methoxyphenyl)-4-(3,4-methylenediexyphenyl)-pyrrolidine-3-carboxylate Into a 12-L flask equipped with magnetic stirring, addition funnel, temperature probe, and nitrogen inlet was charged 0.460 kg ethyl 2-(4-methoxyphenyl)-4-(3,4-methylenedioxyphenyl)-4,5-dihydro-3H -pyrrole-3-carboxylate (1.25 mol). The reaction vessel was degassed with nitrogen. Absolute 3.7 L ethanol and 1.12 L of THF were added. 31 mg bromocresol green and 94.26g sodium cyanoborohydride (1.5 mol) were added. A solution containing 400 mL absolute ethanol and 200 mL of 12M HCl was then added. The reaction mixture was stirred for 30 minutes after addition was complete. After the starting material was consumed, 0.5 L of 7% aq. NaHCO$_3$ was added. The reaction mixture was concentrated and diluted with 5 L ethyl acetate.

The organic layer was washed twice with 2 L of 7% aq. NaHCO₃ and once with 2.5 L of 23% aq. NaCl, the dried over 190g MgSO₄, filtered, and concentrated to give 447 g of the title compound as a thick yellow oil.

EXAMPLE 292F

Ethyl 2-(4-methoxypheny)-4-(3,4-methylenedioxyphenyl)-1-(N,N-dibutylaminocarbonylmethyl) pyrrolidine-3-carboxylate Into a 22-L flask equipped with overhead stirring, nitrogen inlet, and condenser was charged ethyl 2-(4-methoxyphenyl)-4-(3,4-methylenedioxyphenyl) -pyrrolidine-3-carboxylate (2.223 kg,6.02 mol). The reaction vessel was degassed with nitrogen. 13.2 L ofacetonitrile, 3.66 L diisopropylethylamine (2.71 kg, 20.9 mol), and 1.567 kg dibutylamidomethyl bromide (6.26 mol) were added. The mixture was refluxed at 78° C. for 17 hrs. After the disappearance of starting material, the mixture was concentrated until crystals formed. The solid was filtered and washed with 4 L ethyl acetate (0° C.). Concentrating of the filtrate was continued as above until all votatiles were removed. The residue was diluted with 40 L ethyl acetate and washed with 20 L deionized water. The organic layer was washed with 8 L of 23% aq. NaCl and dried over 0.399 kg MgSO₄ and filtered. Concentration as above provided 3.112 kg (96 % yield) of the title compound as a dark oil.

EXAMPLE 292G ethyl trans,trans 2-(4-methoxyphenyl)-4-(3,4-dioxyphenyl)-pyrrolidine-3-carboxylate and preparation of trans,trans 2-(4-methexyphenyl)-4-(3,4-dioxyphenyl)-pyrrolidine-3-carboxylic Acid Into a 35-L reactor equipped with overhead stirring, nitrogen inlet, and condenser was charged 3.112 kg ethyl 2-(4-methoxyphenyl)-4-(3,4-methylenedioxyphenyl)-pyrrolidine 3-carboxylate (5.78 mol). 16.4 L of absolute ethanol was added and the reaction vessel was degassed with nitrogen. 0.115 kg of sodium ethoxide (1.69 mol) was added and the mixture was refluxed at 79° C. for 1 hr. The mixture was cooled to 15° C. and 5 L of 7.6M NaOH solution (38.1 mol) was added. The mixture was stirred at 15° C.for 18 hrs. The solvent was evaporated and the residue dissolved in 15.8 L of deionized water and extracted with 28 L of ether. The ether solution was washed with 9.5 L deionized water. The aqueous wash was extracted with 3 L ether. 0.340 L of 12M HCl was added to the aqueous layer. The aqueous layer was extracted with 24 L of ethyl acetate. The organic layer was washed with 9 L of 23% aq. NaCl, dried with 0.298 kg MgSO₄, filtered, and concentrated to give 2.132 kg of a dark oil. The oil was triturated with 18 L ether. The undesired solids were filtered and saved for later use. The mother liquors were concentrated to obtain 1.102 kg of light foam. The foam was dissolved in 5.5 L ethyl acetate with heating to 65° C. 14 L hexane was added slowly enough to keep the solution refluxing. The reaction mixture was cooled to 10° C. and filtered. The crystals were washed with 2 L ether (0° C.) and dried to constant weight in vacuo at 50° C. to give 0.846 kg (43% yield, melting point 119–120) of crude product, which was further purified by normal phase silica gel chromatography.

EXAMPLE 292H

Sodium trans,trans-2-(4-methoxyphenyl)-4-(3,4-methylenedioxyphenyl)-1-(N,N-dibutylaminocarbenylmethyl)pyrrolidine-3-carboxylate Into a 20-L flask was charged trans,trans 2-(4-methoxyphenyl)-4-(3,4-methyledioxyphenyl)-1-(N,N-dibutylamino-carbonyl methyl)pyrrolidine-3-carboxylic acid (0.927 kg, 1.819 mol). A solution of 0.0720 kg NaOH (1.80 mol) dissolved in 4.65 L methanol was added. The reaction mixture was concentrated to an oil. Pentane (4 L) was added and the solution concentrated again. Pentane (4 L) was added again and concentration of this solution gave a light tan foam. The foam was dried in vacuo at 50° C. to a constant weight of 0.937 kg (97% yield) of the title compound.

EXAMPLE 293

Using methods described in the above examples, the compounds disclosed in Table 1 can be prepared.

TABLE 1.

TABLE 1-continued
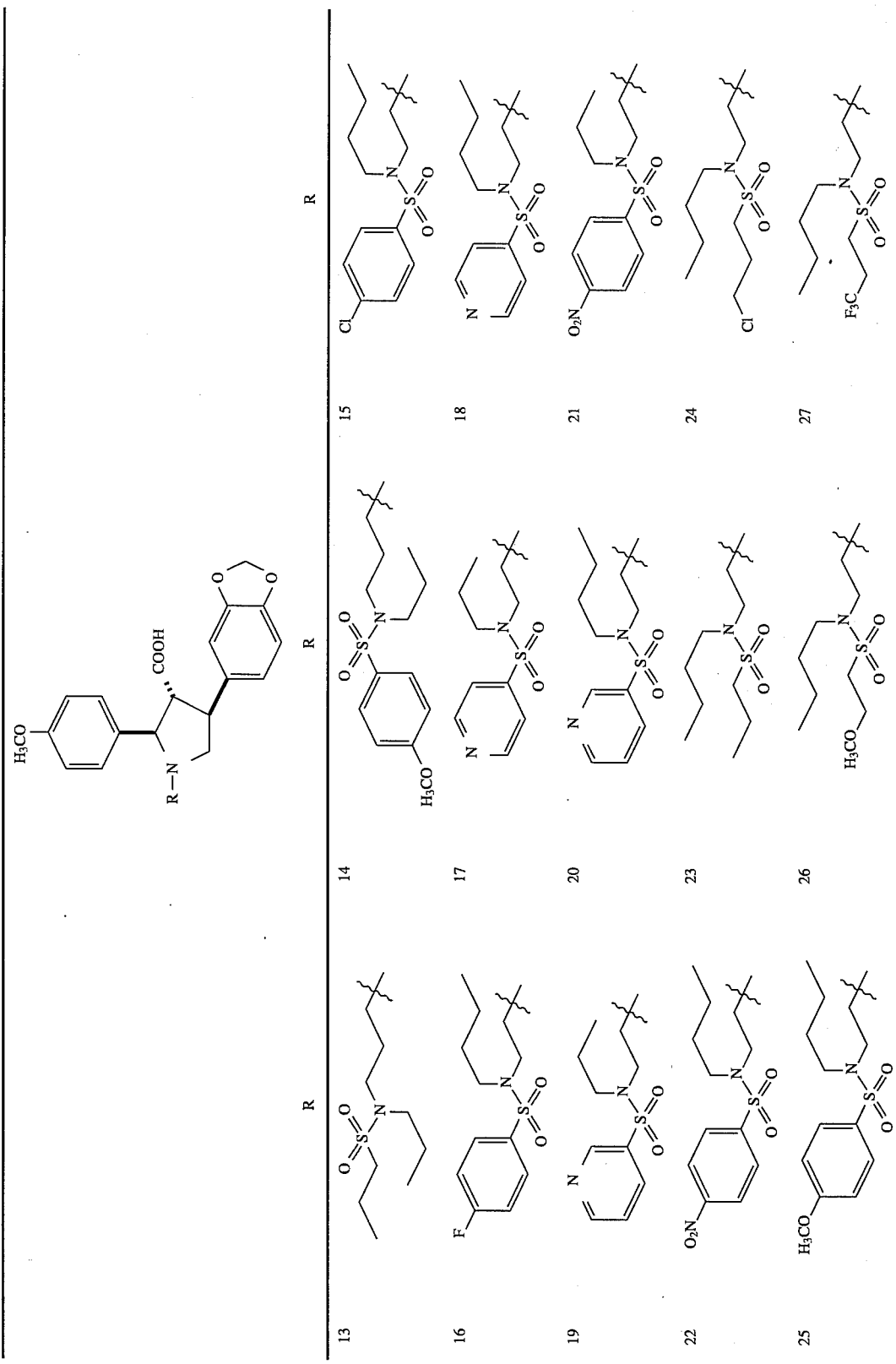

TABLE 1-continued (structure: pyrrolidine core with H3CO-phenyl, COOH, and benzodioxole substituents, N-R)

| # | R | # | R | # | R |
|---|---|---|---|---|---|
| 28 | sulfonyl with propyl and CH2CF3 | 29 | sulfonyl with butyl and CH2FH2 | 30 | sulfonyl with propyl and CH2FH2 |
| 31 | sulfonyl with butyl and CH2CF2H | 32 | sulfonyl with butyl and CH2FH2 | 33 | sulfonyl with butyl and CH2CF2H |
| 34 | sulfonyl with butyl and CH2CF2H | 35 | sulfonyl with butyl and CH2CF3 | 36 | sulfonyl with propyl and CH2CF3 |
| 37 | sulfonyl with butyl and butyl | 38 | sulfonyl with propyl and isobutyl | 39 | sulfonyl with propyl and CH2CF3 |
| 40 | sulfonyl with butyl and CH2CF3 | 41 | 4-F3CO-phenylsulfonyl with butyl | 42 | 4-F3CO-phenylsulfonyl with butyl |

TABLE 1-continued

TABLE 1-continued

TABLE 1-continued
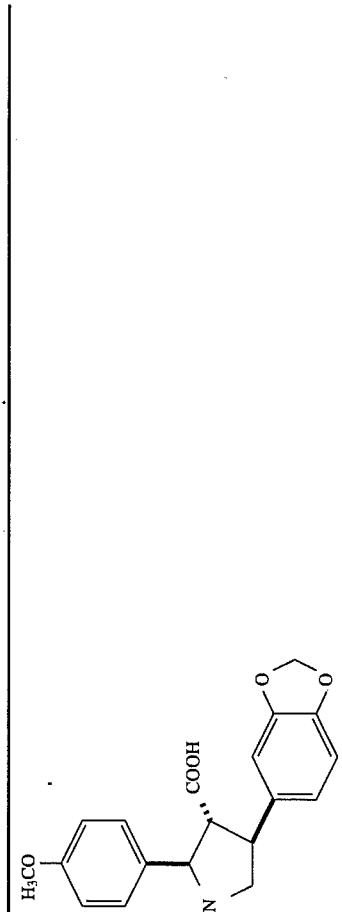
| | | |
|---|---|---|
| 67 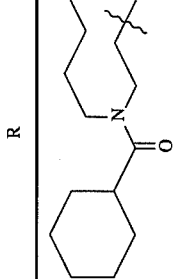 | 68 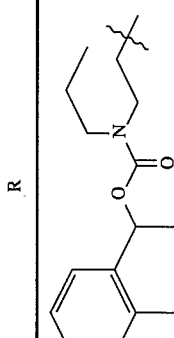 | 69 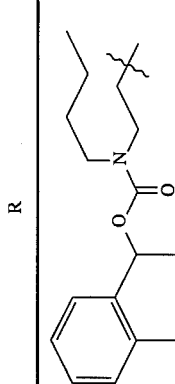 |
| 70 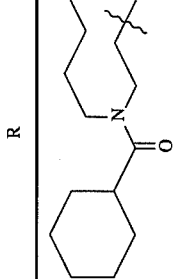 | 71 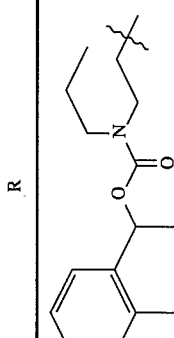 | 72 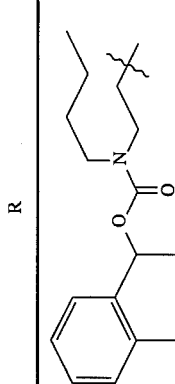 |
| 73 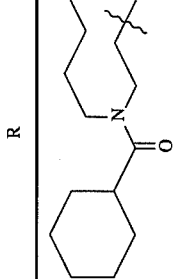 | 74 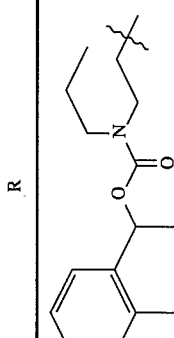 | 75 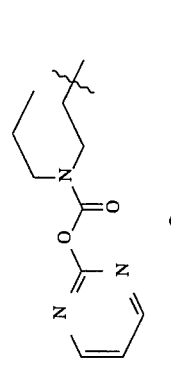 |
| 76 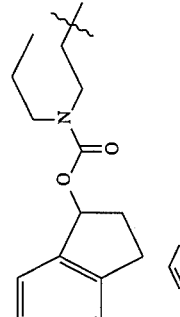 | 77 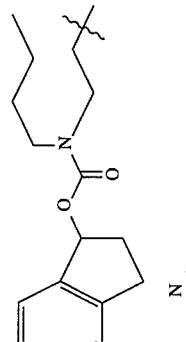 | 78 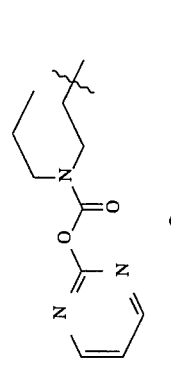 |

TABLE 1-continued

TABLE 1-continued
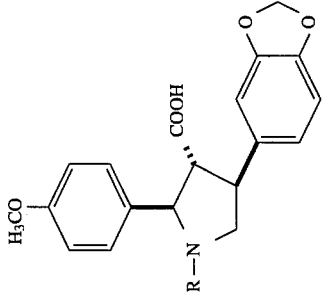

TABLE 1-continued
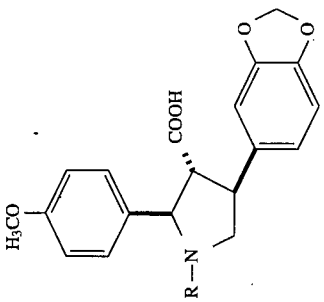

TABLE 1-continued

TABLE 1-continued

TABLE 1-continued
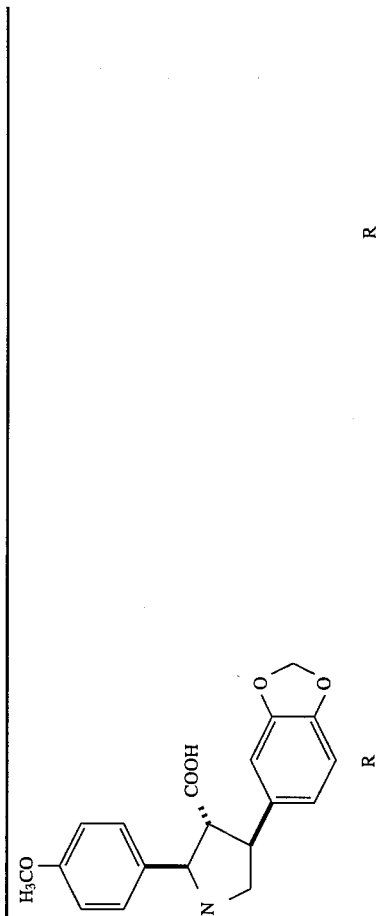
| | R | | R | | R |
|---|---|---|---|---|---|
| 136 |  | 137 | 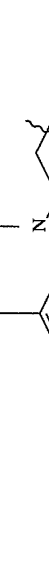 | 138 | 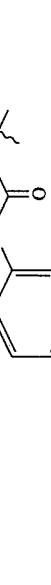 |
| 139 |  | 140 |  | 141 | 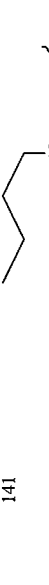 |
| 142 |  | 143 |  | 144 |  |
| 145 | | | | | |

EXAMPLE 294
Using methods described in the above examples, compounds comprising a parent structure selected from those disclosed in Table 2A and an R substituent selected from those disclosed in Table 2B can be prepared.
TABLE 2A
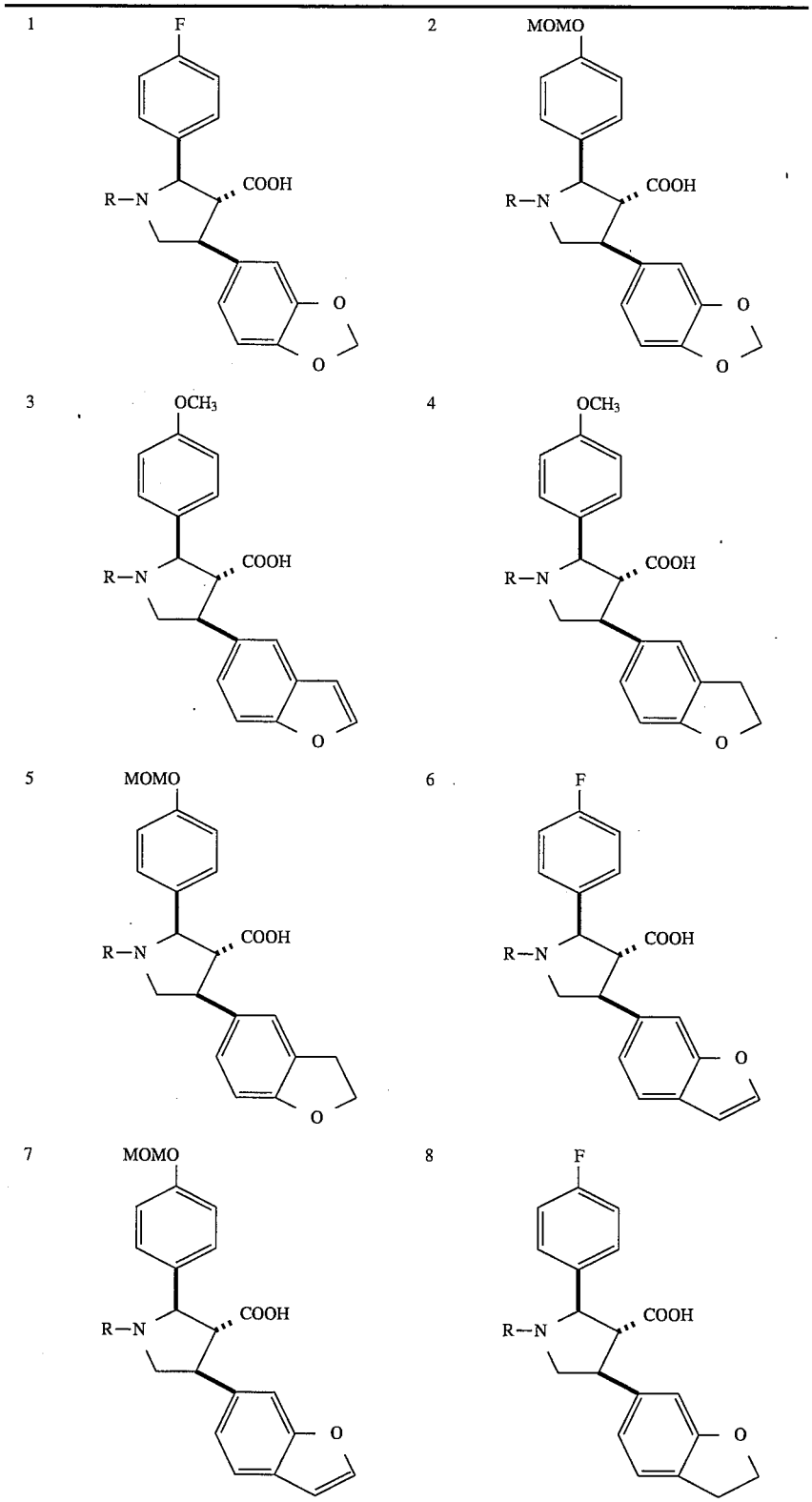

TABLE 2A-continued
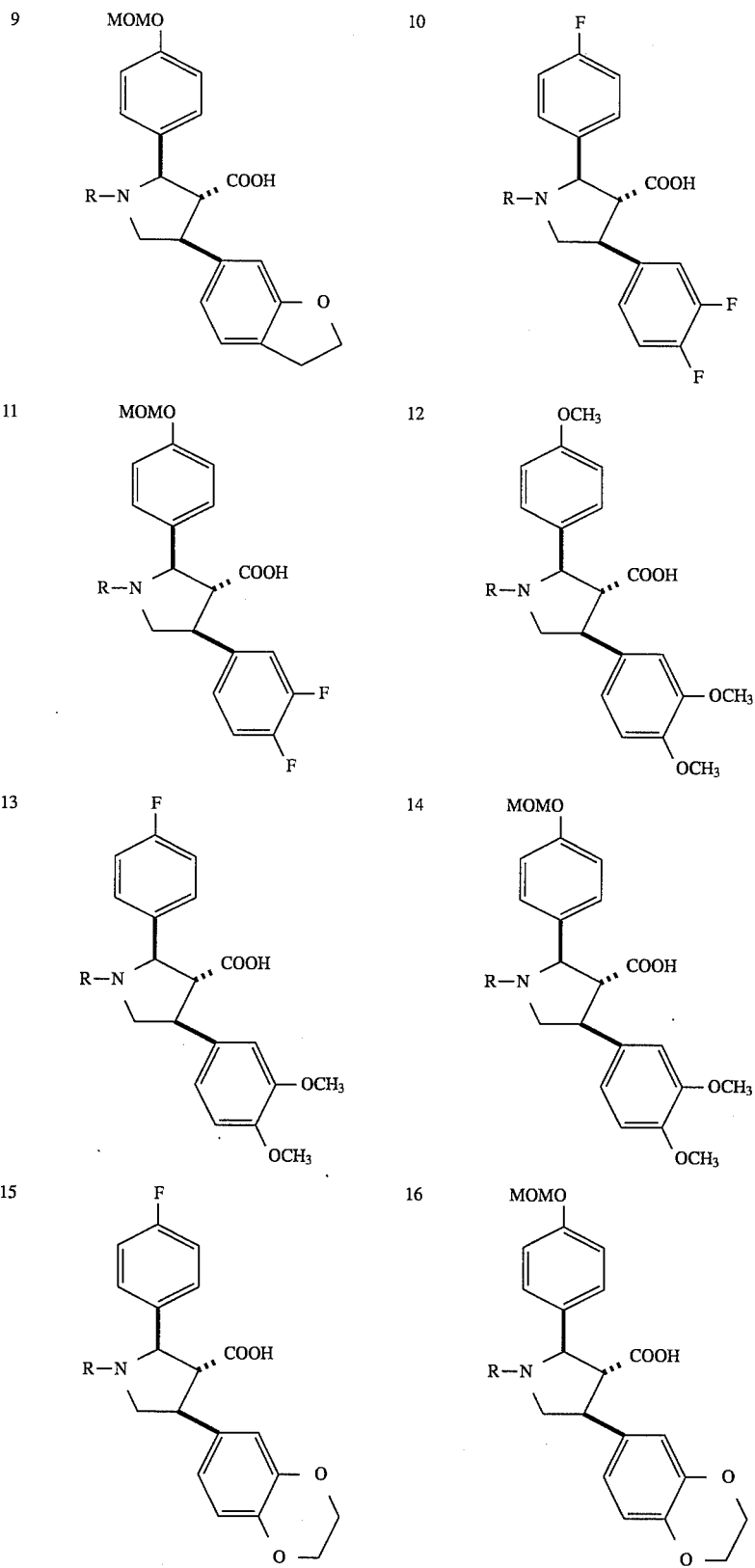

TABLE 2A-continued
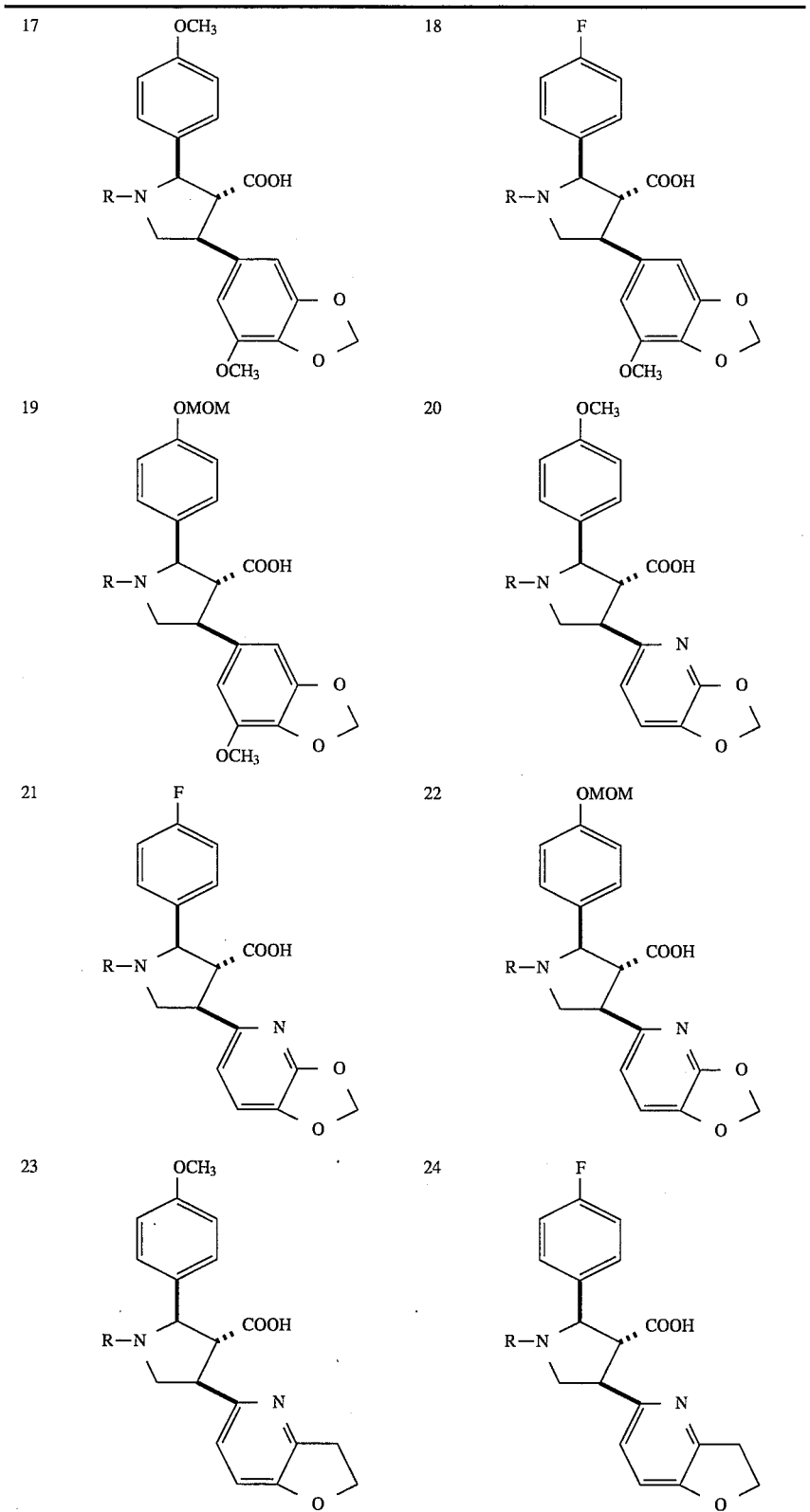

TABLE 2A-continued
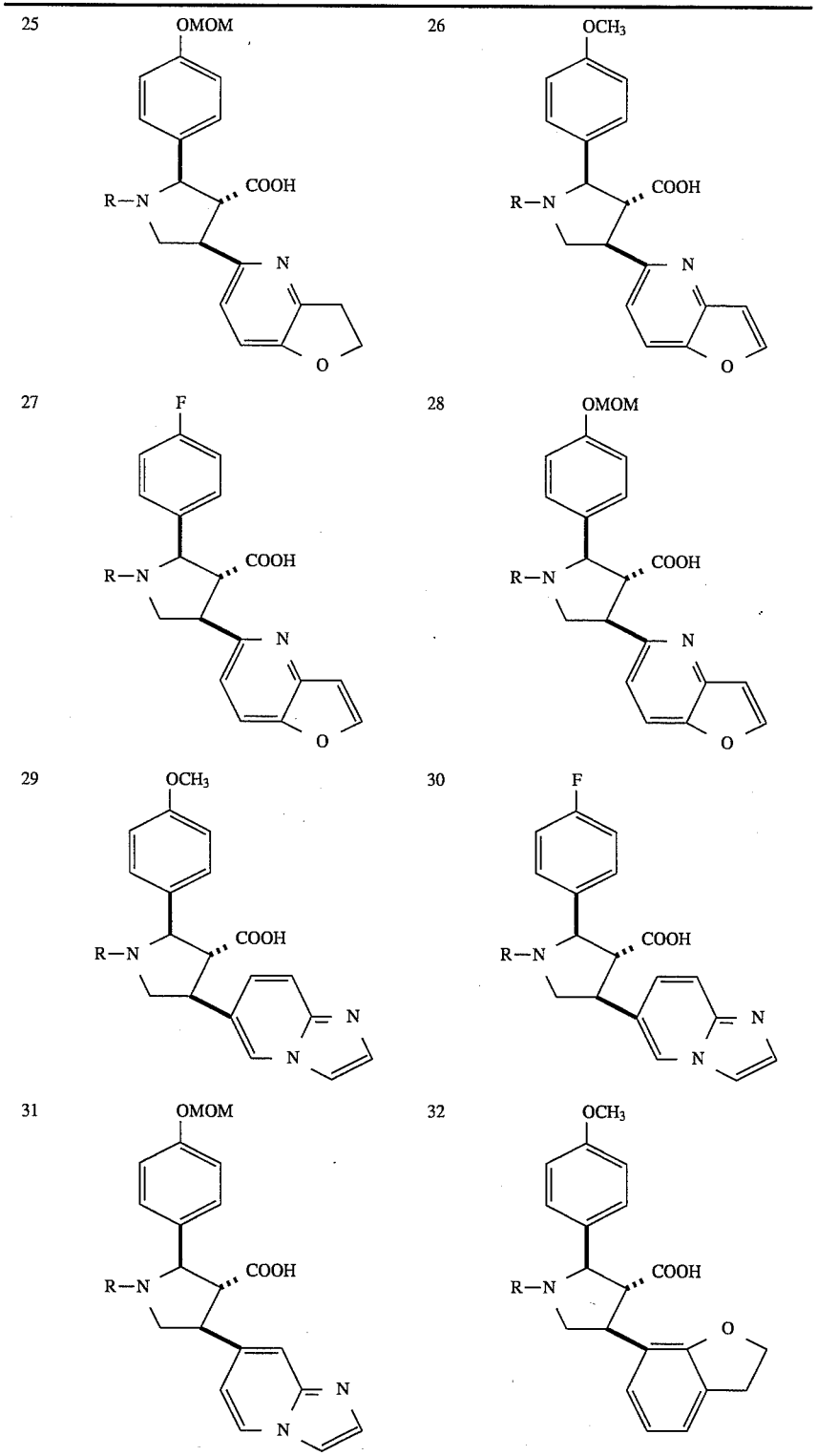

TABLE 2A-continued
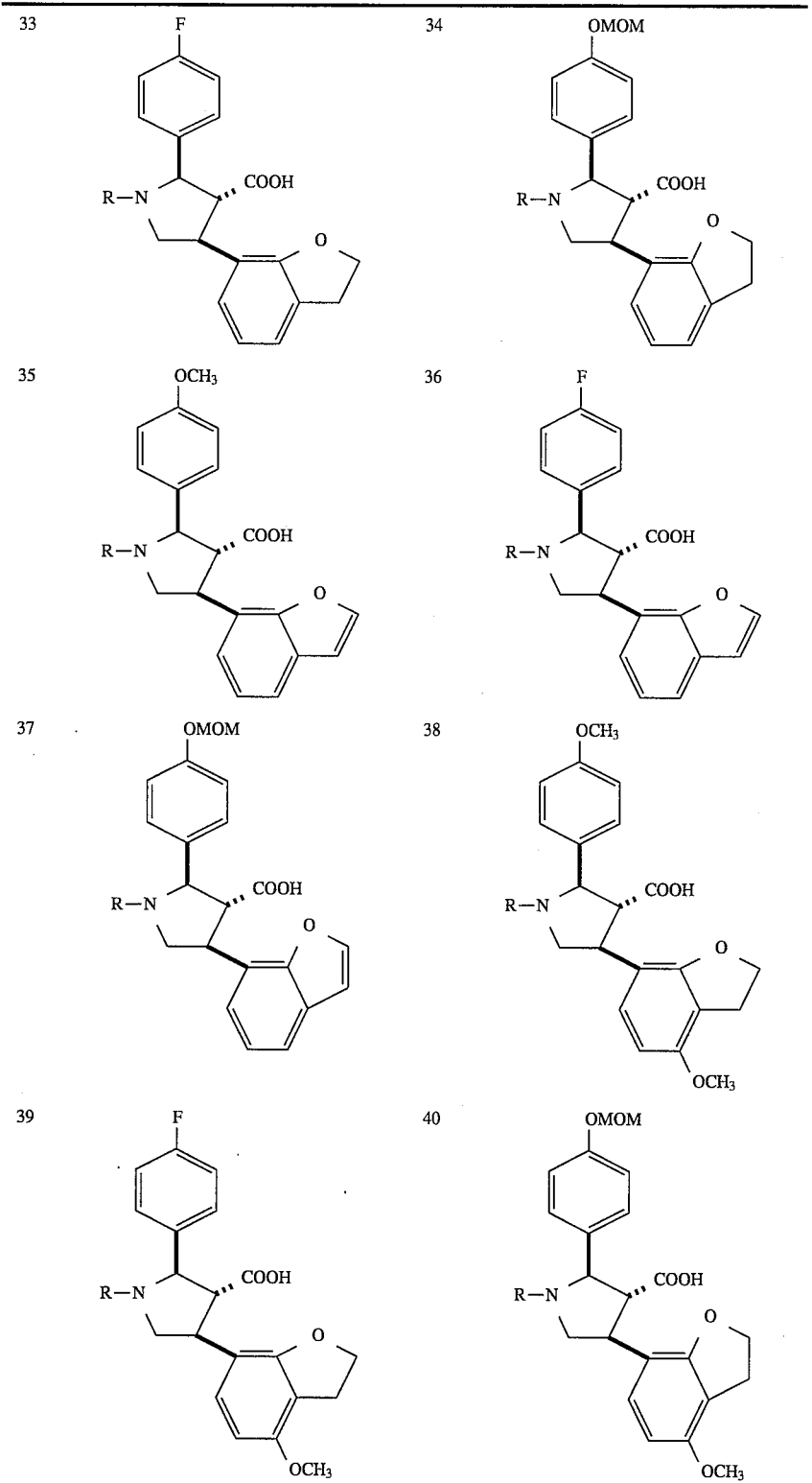

TABLE 2A-continued
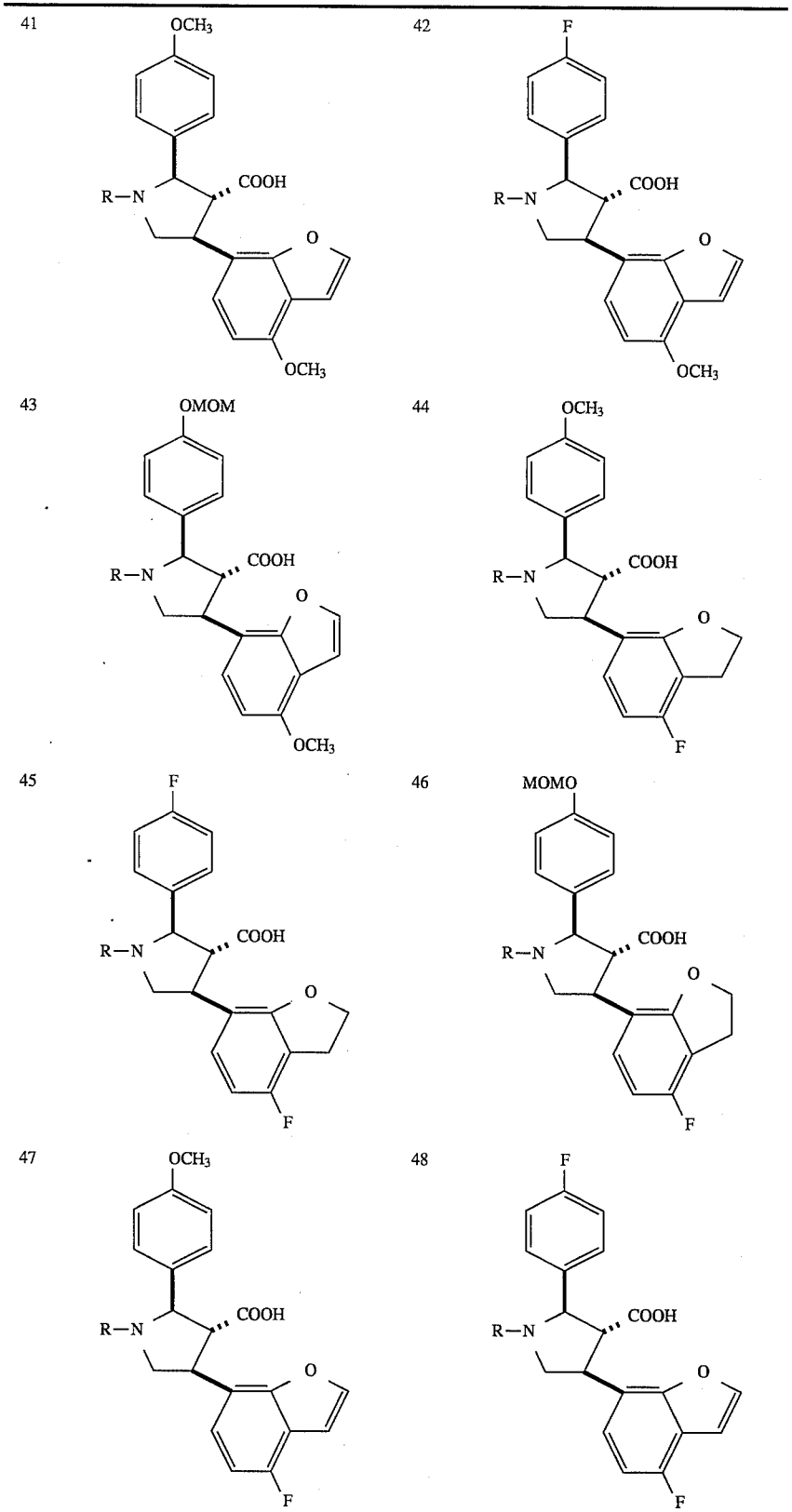

TABLE 2A-continued
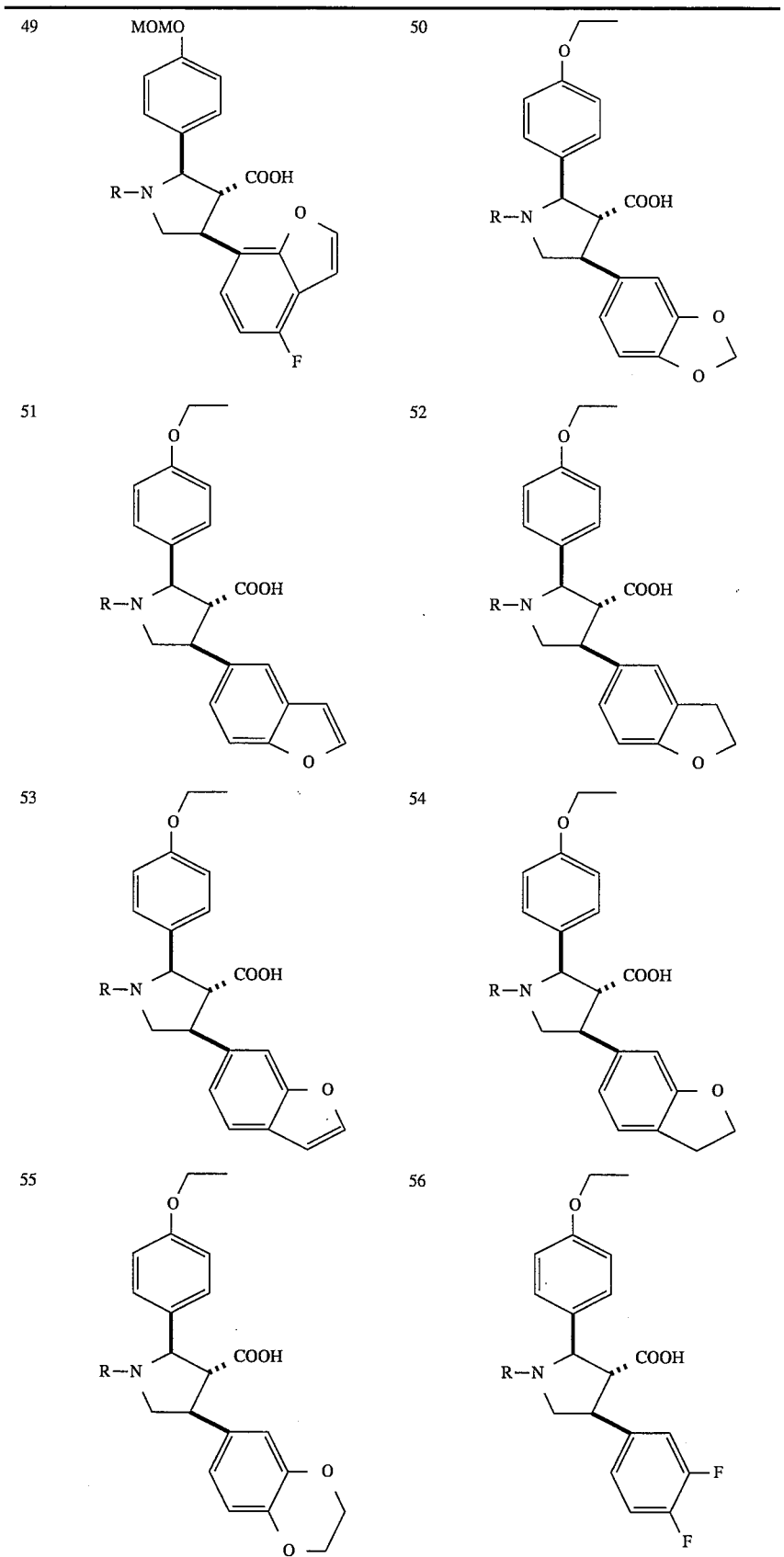

TABLE 2A-continued
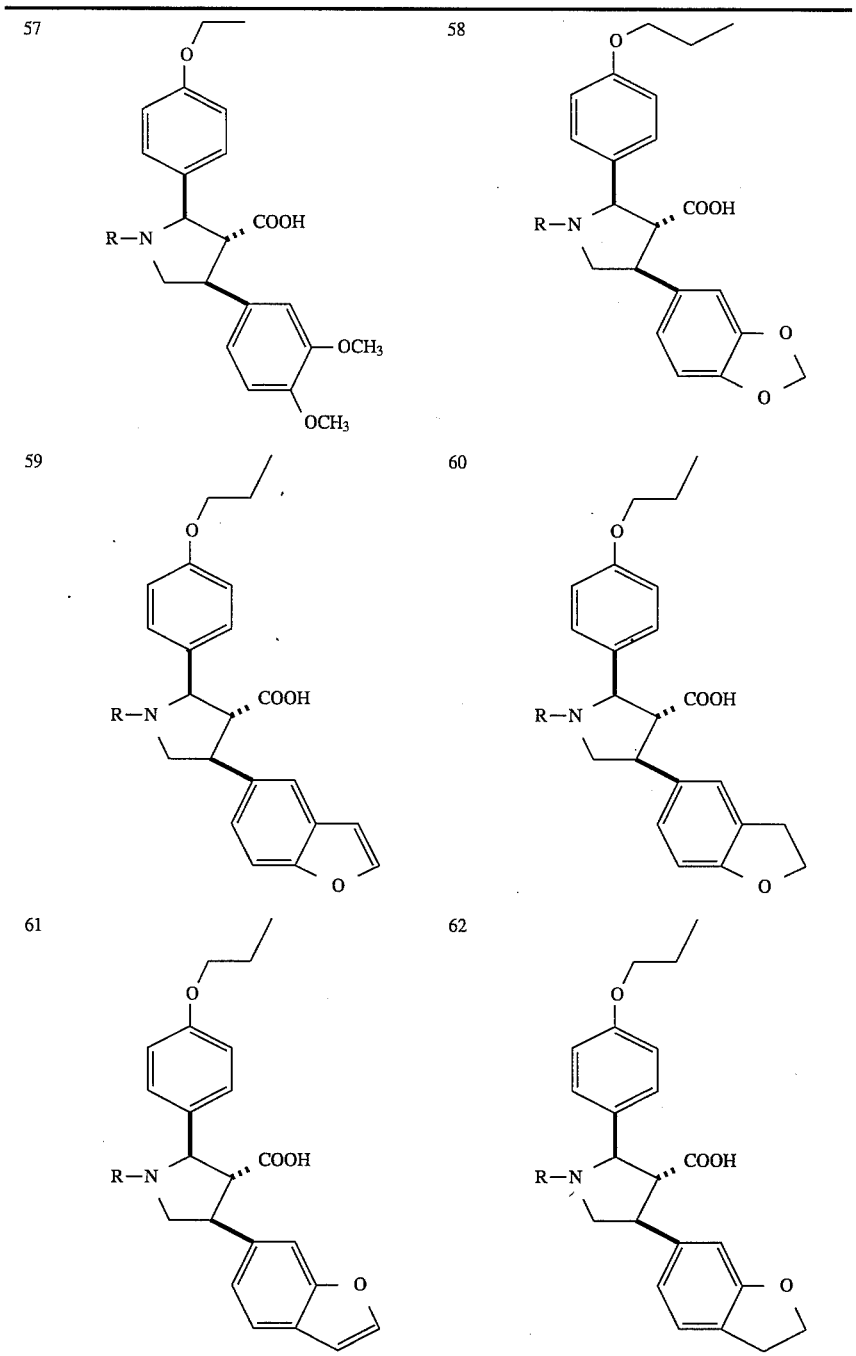

TABLE 2A-continued
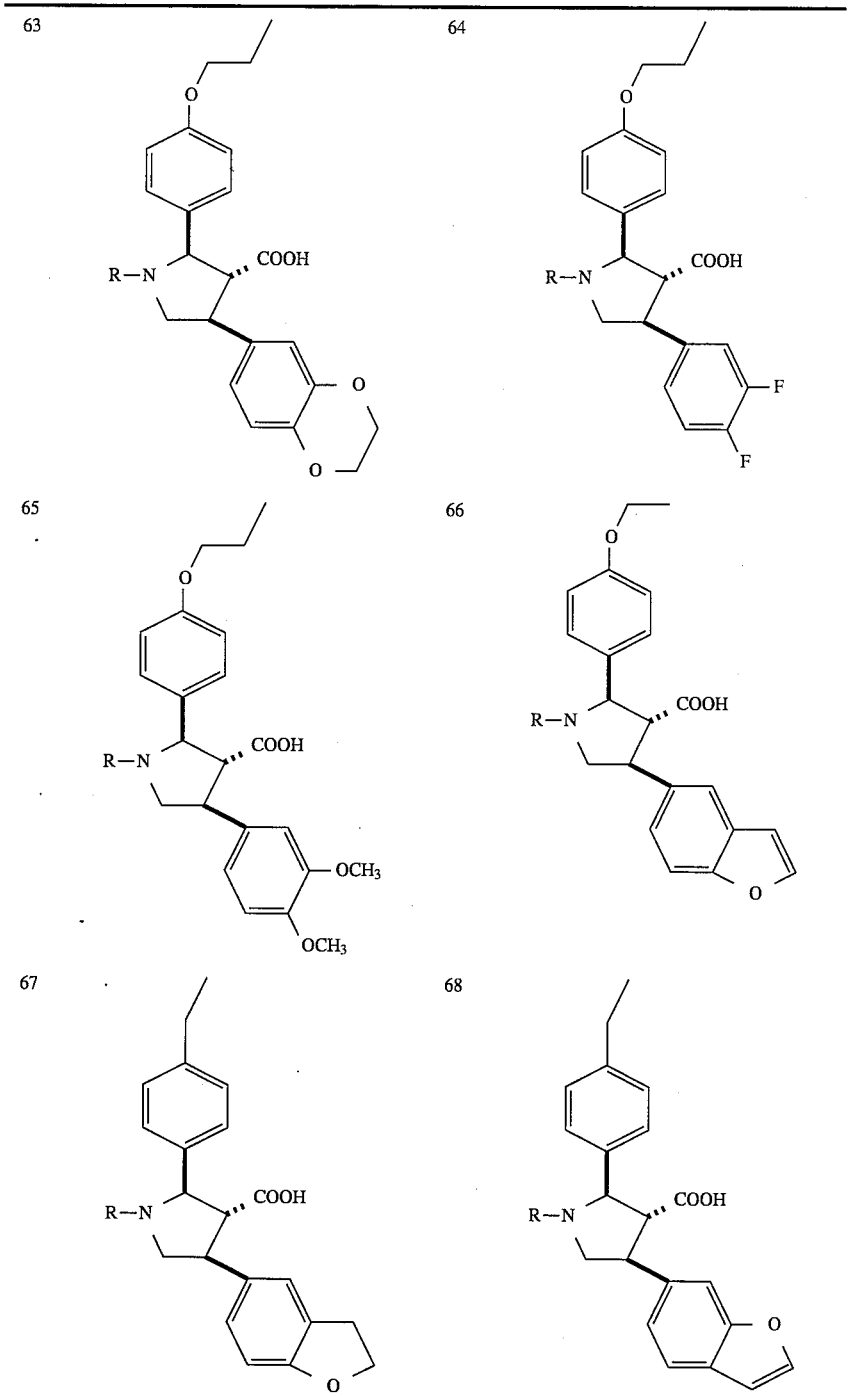

TABLE 2A-continued
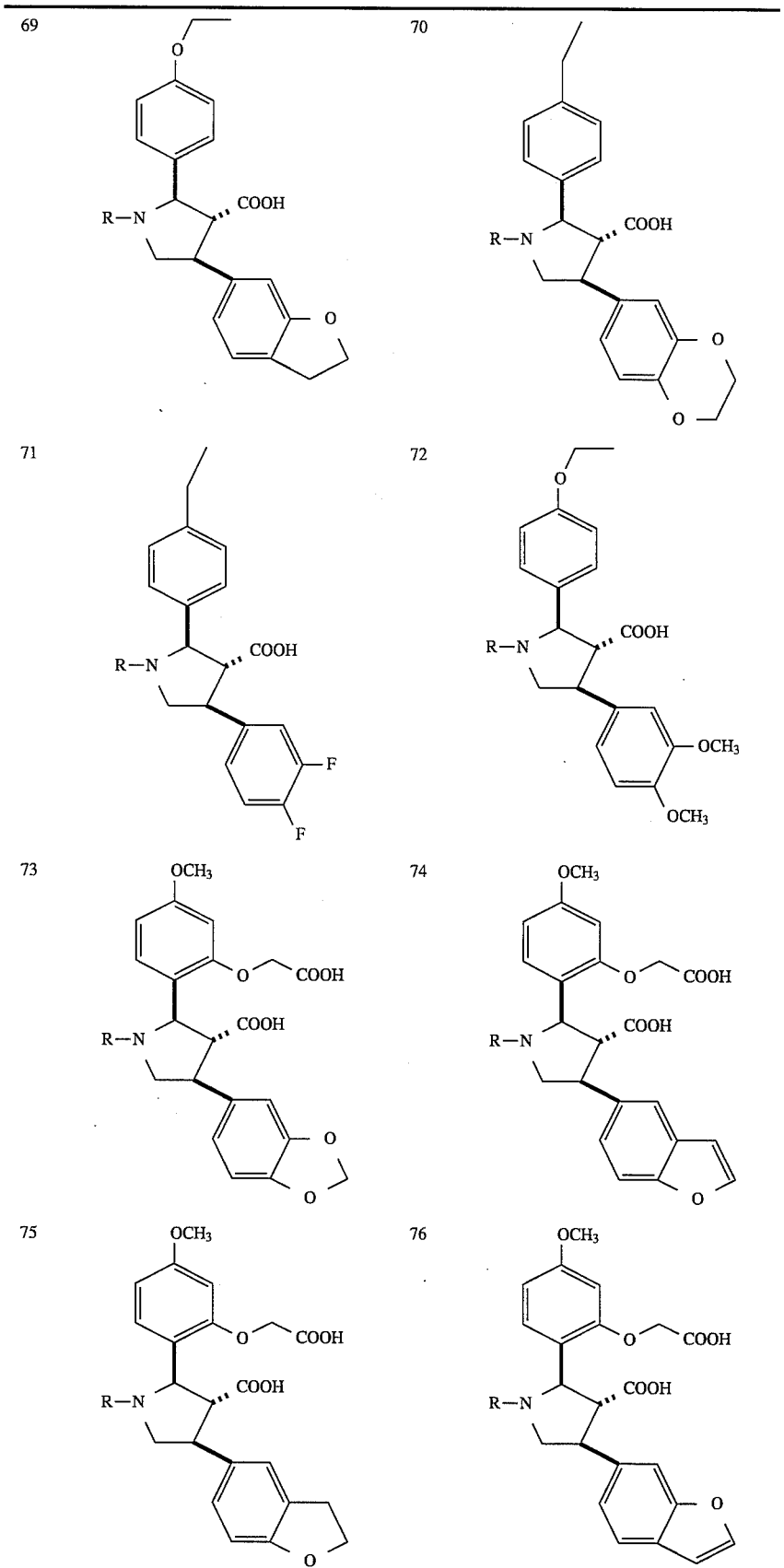

TABLE 2A-continued
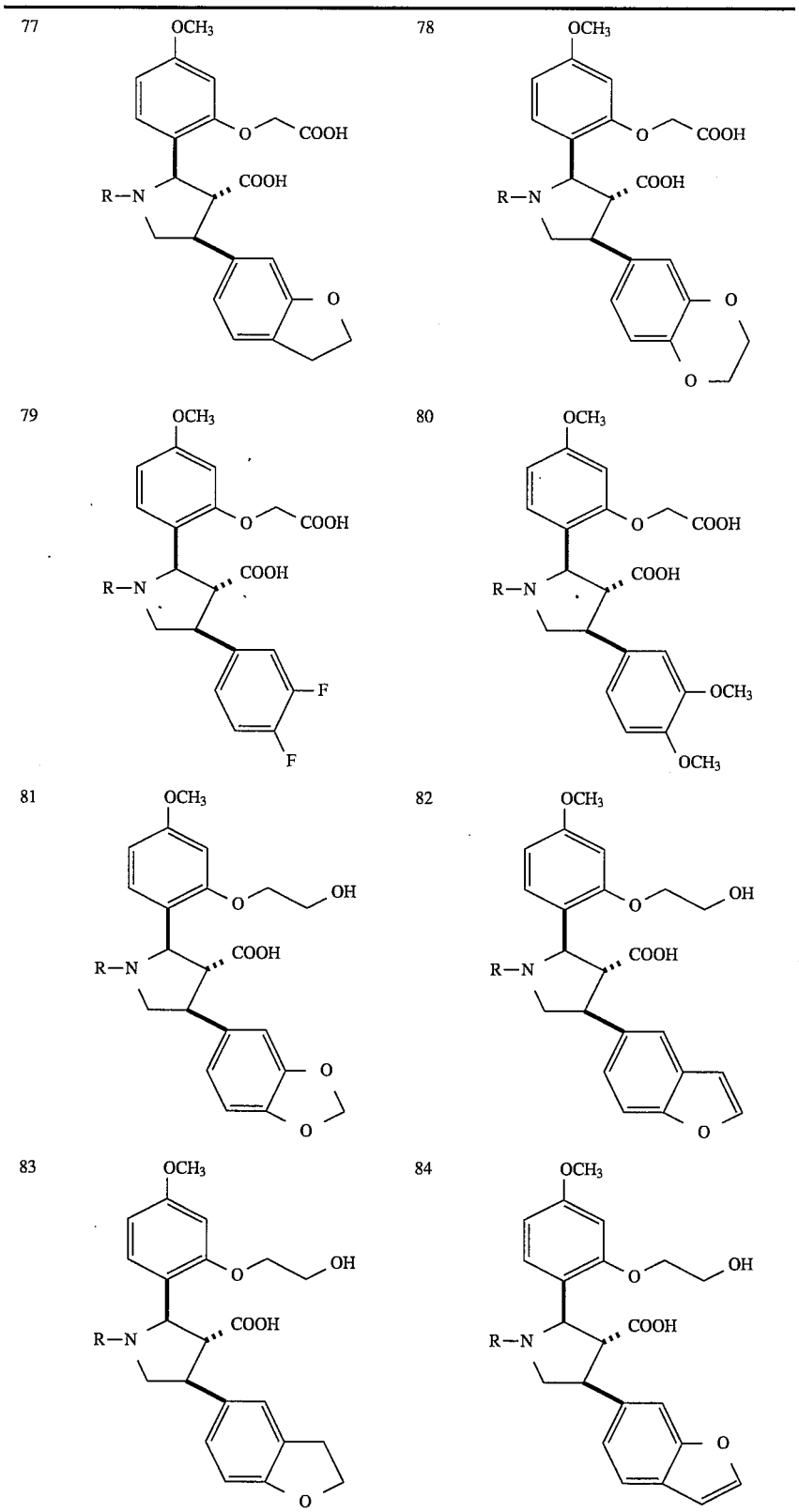

TABLE 2A-continued
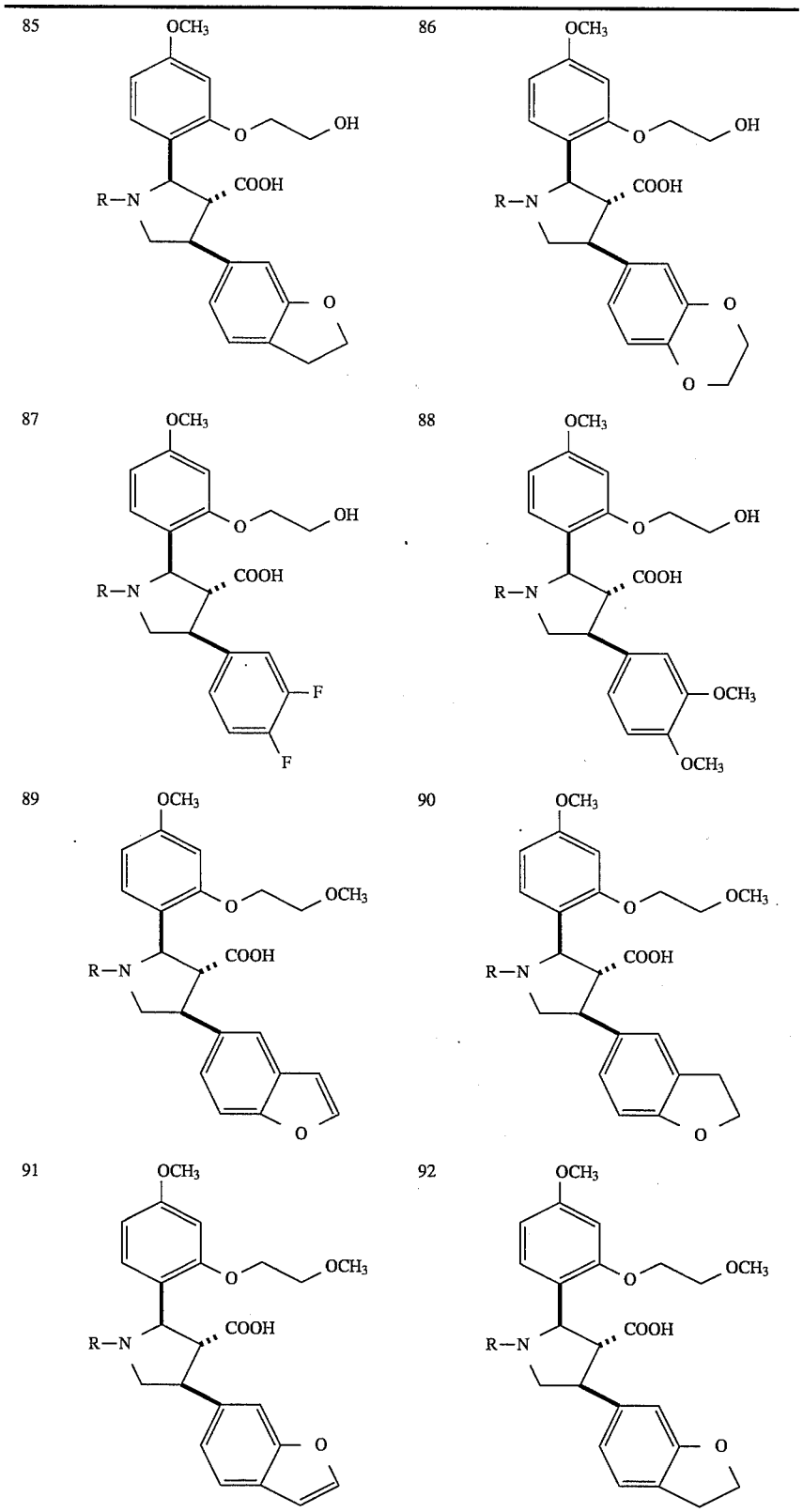

TABLE 2A-continued
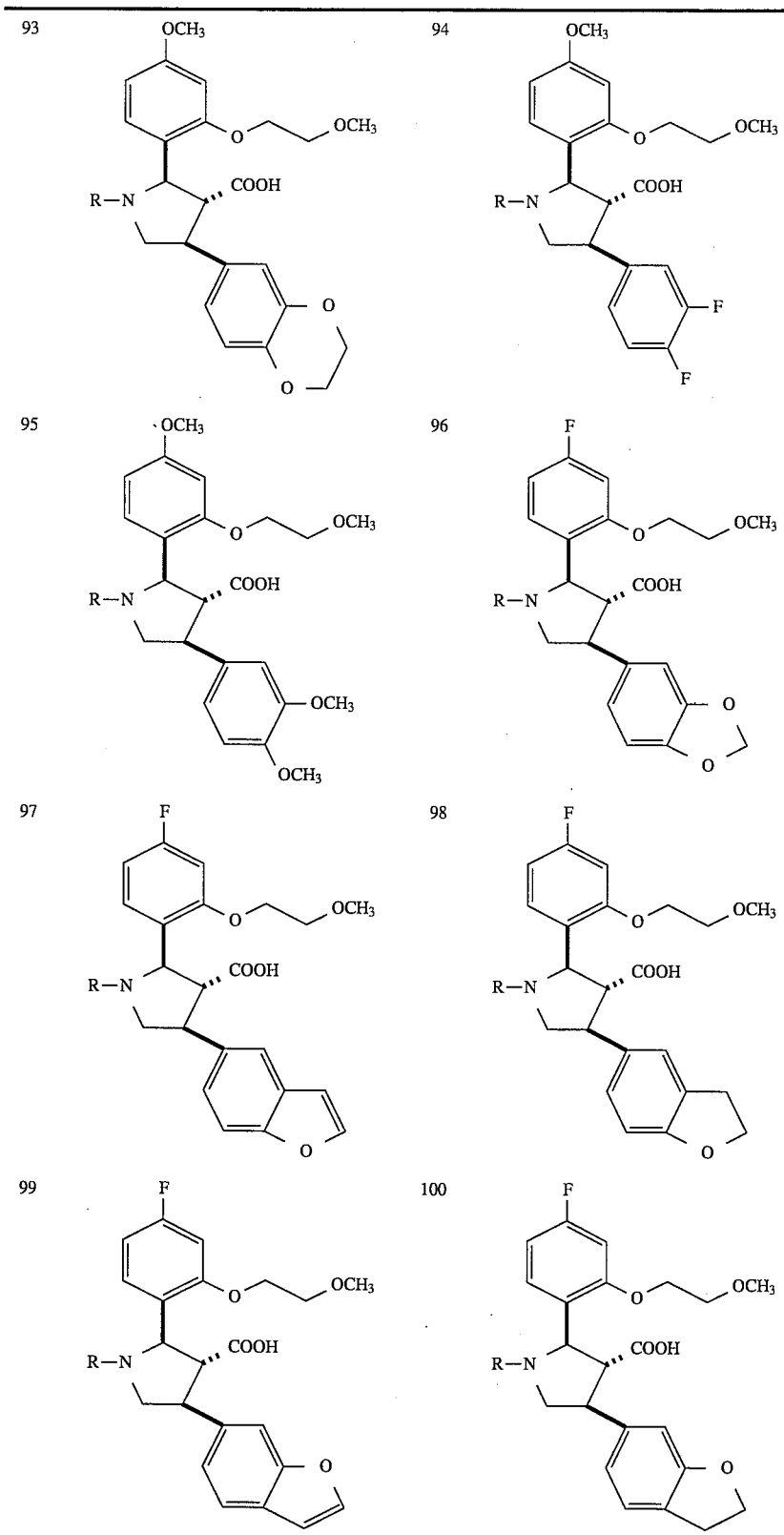

TABLE 2A-continued
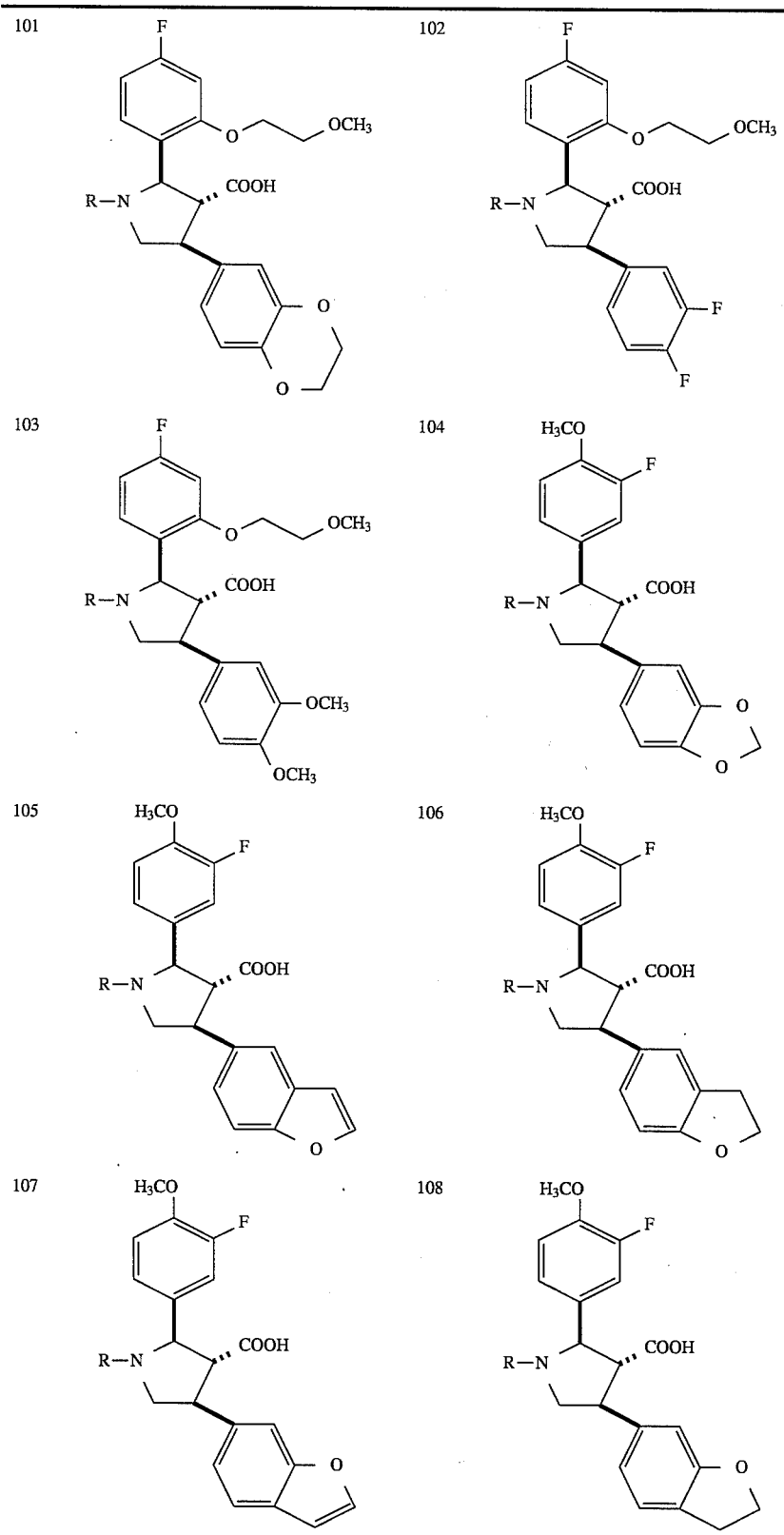

TABLE 2A-continued
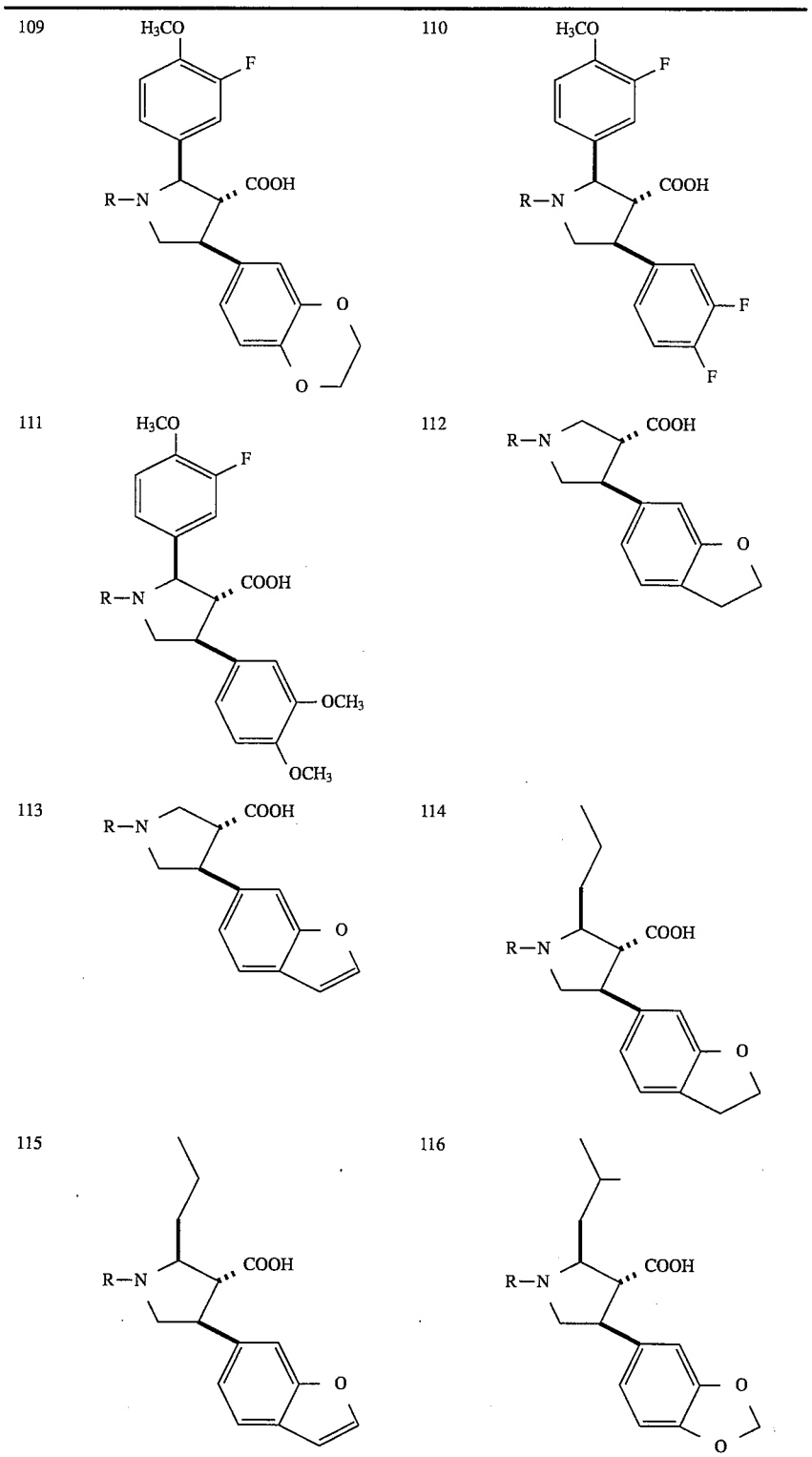

TABLE 2A-continued
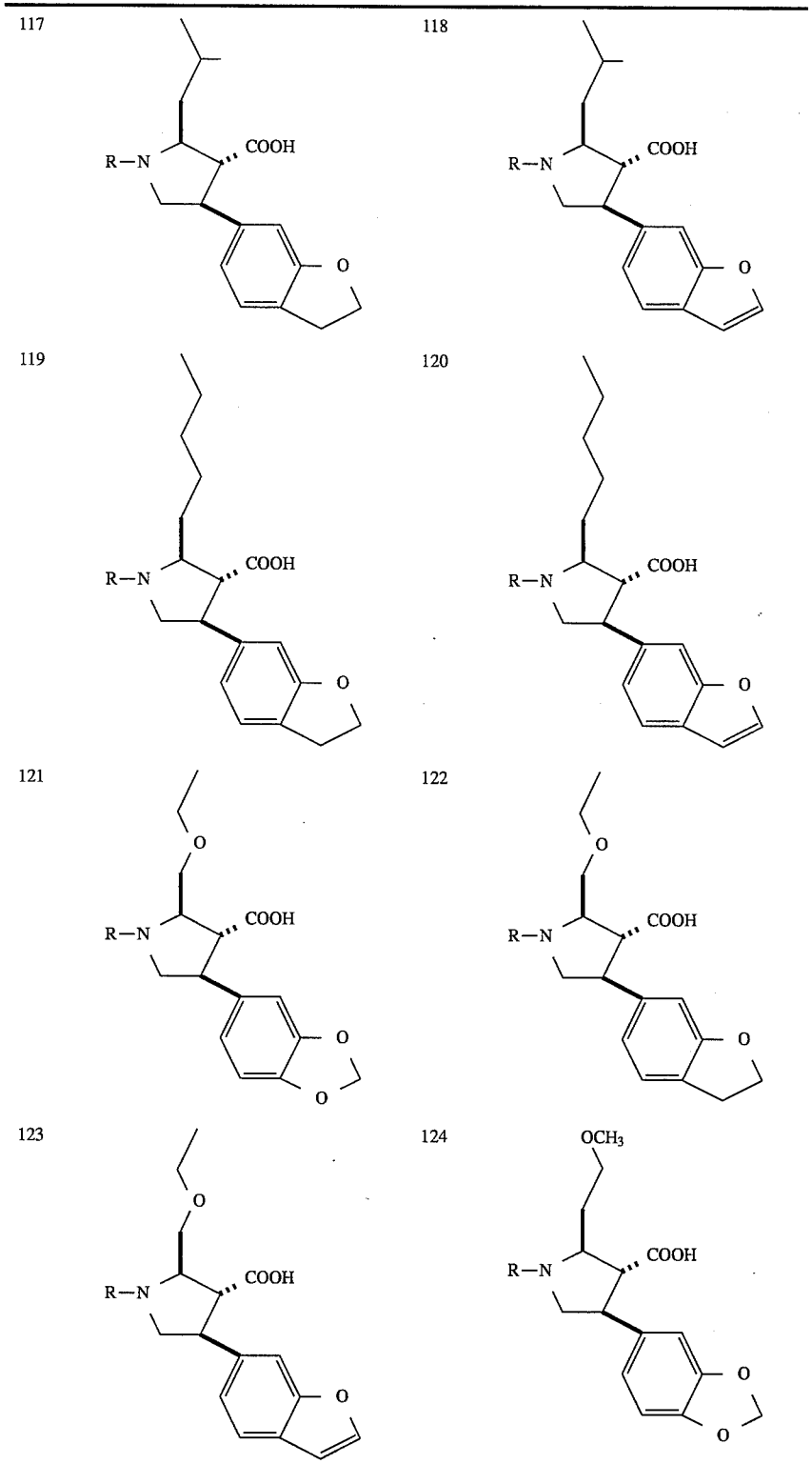

TABLE 2A-continued
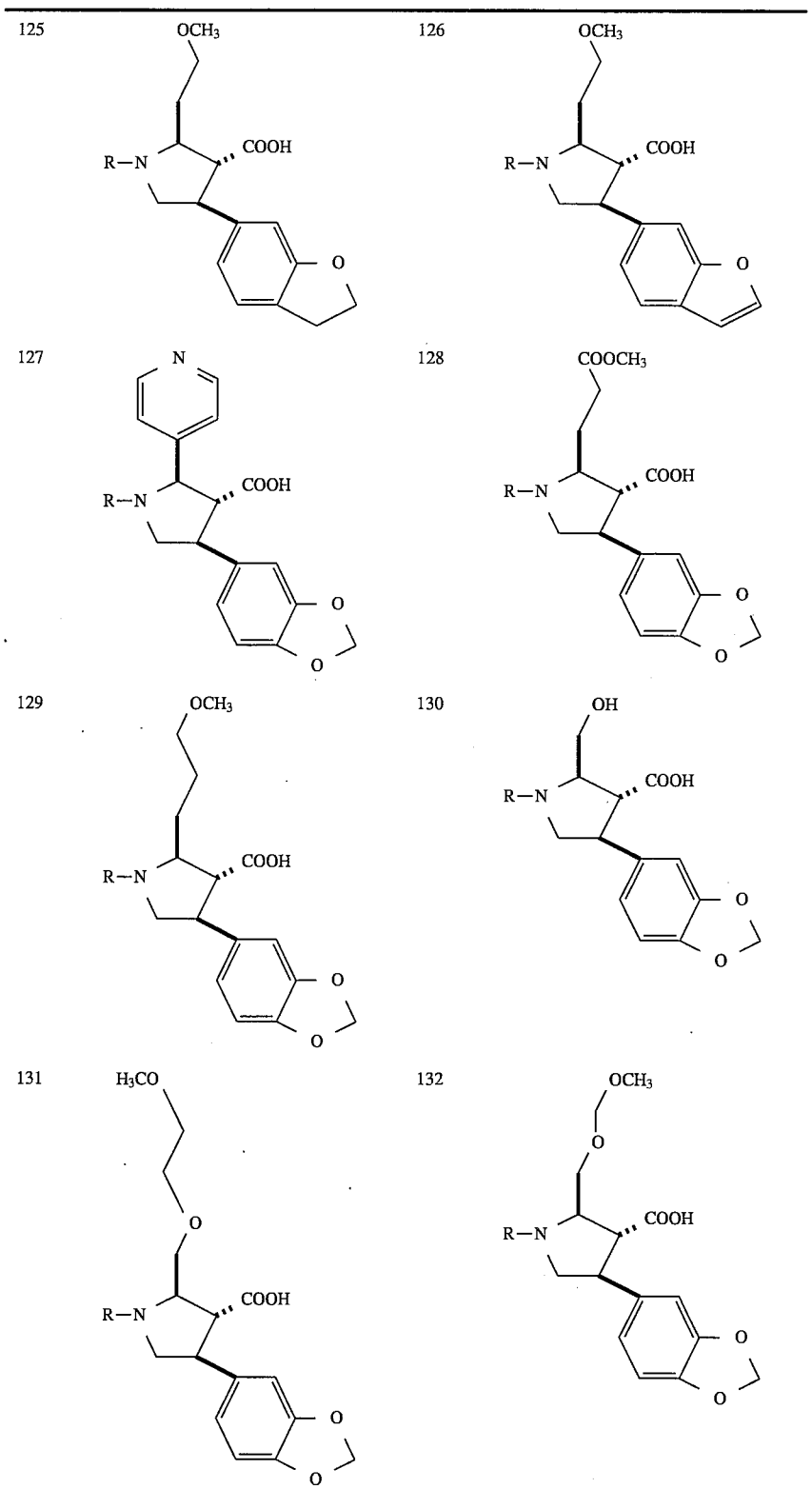

TABLE 2A-continued
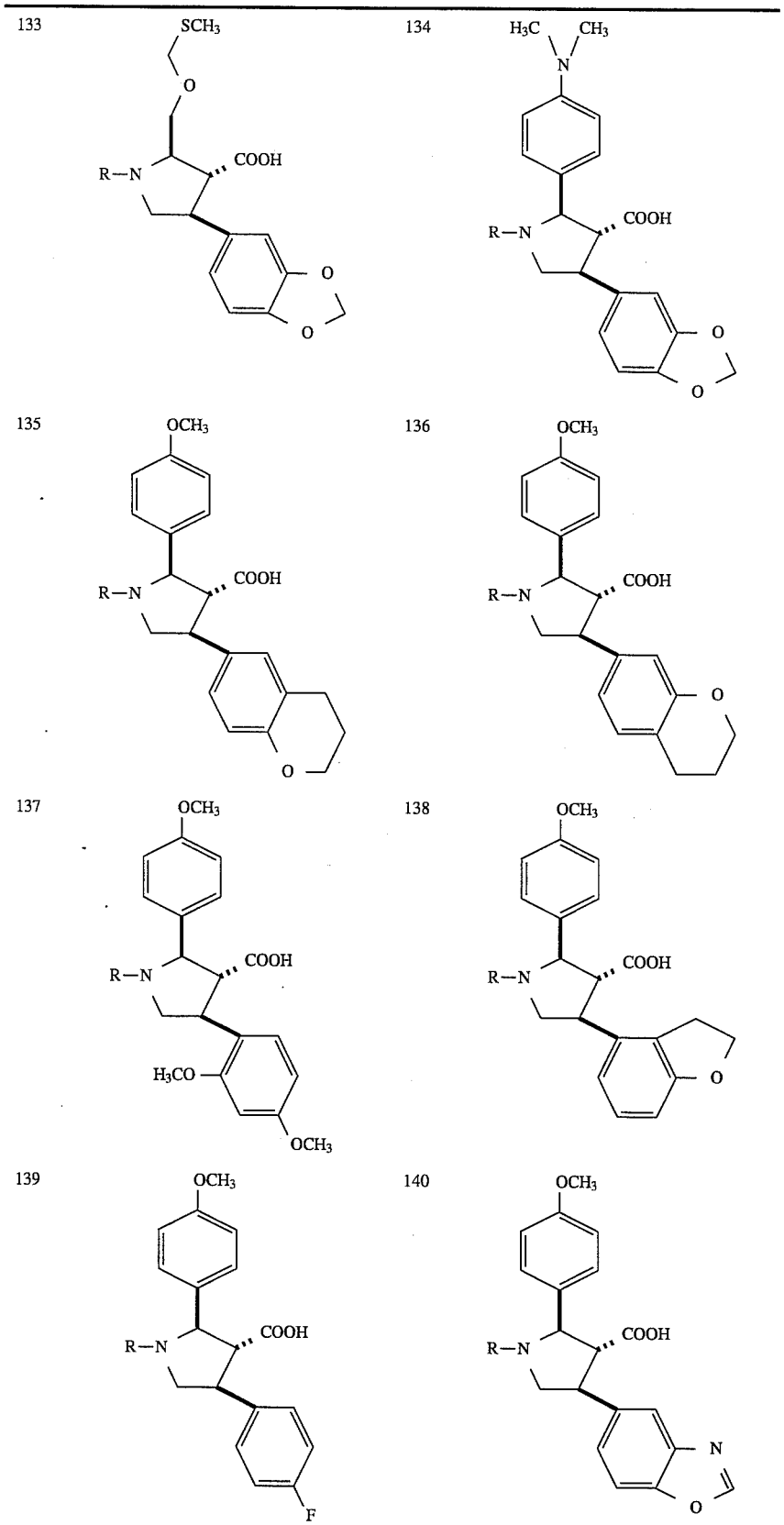

TABLE 2A-continued
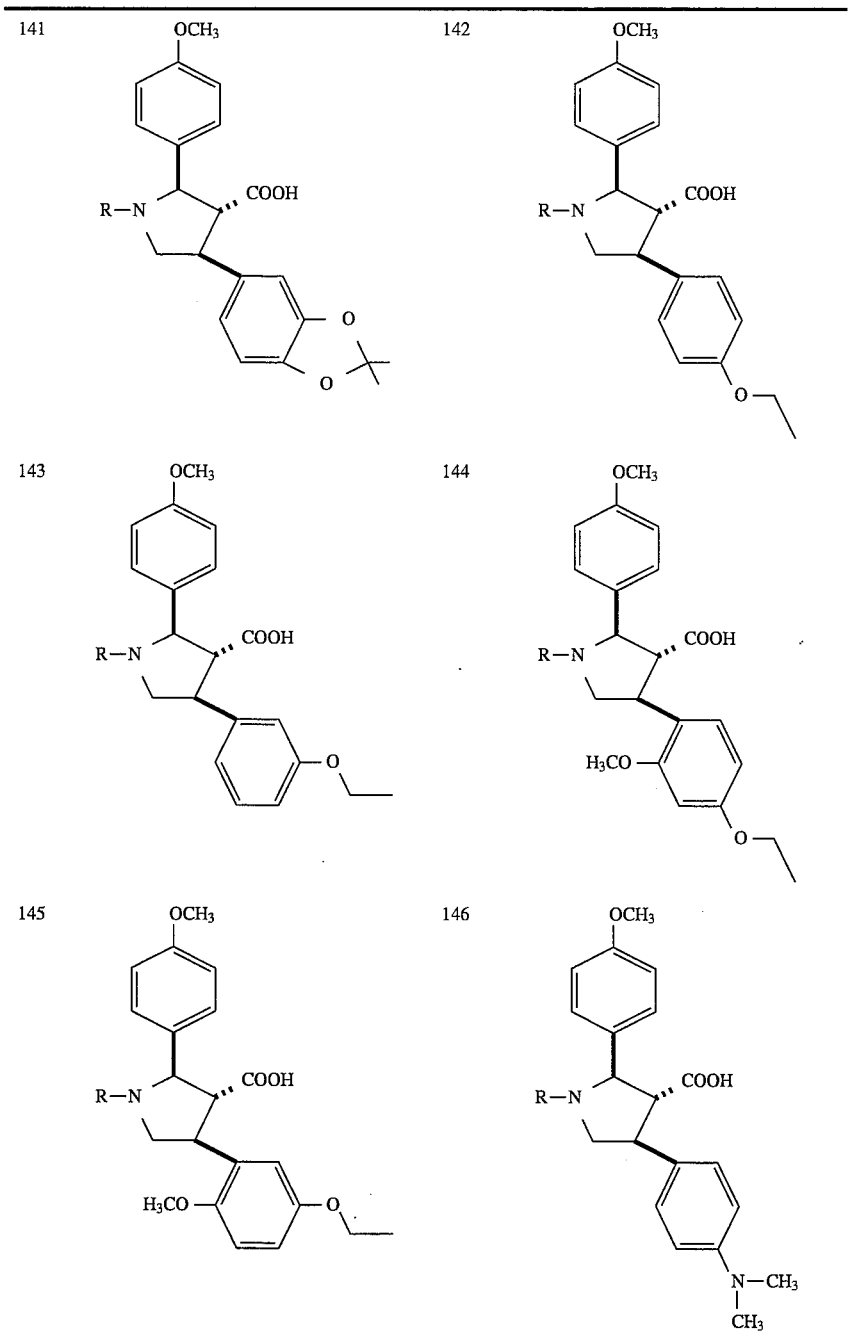

TABLE 2A-continued
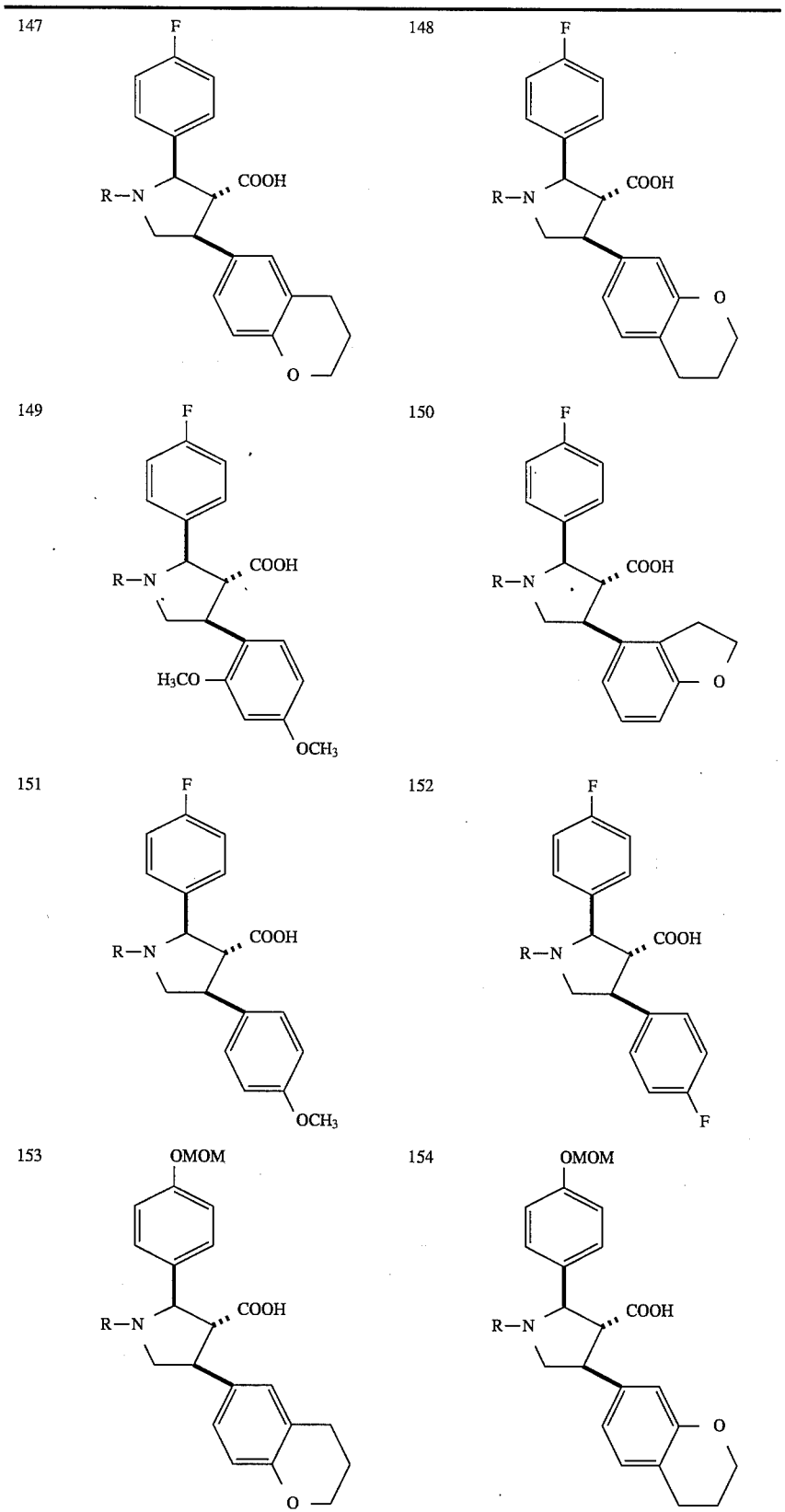

TABLE 2A-continued
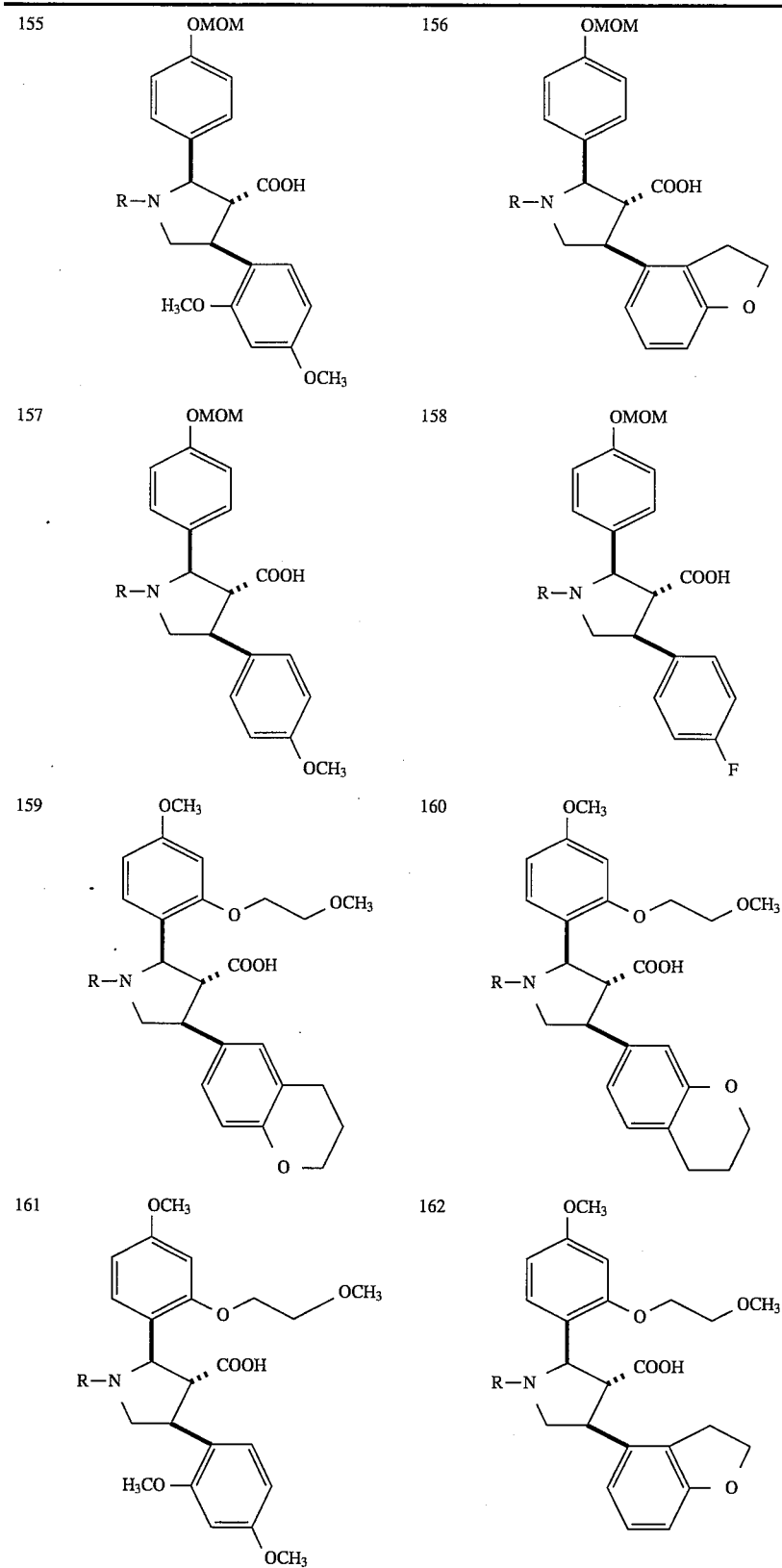

TABLE 2A-continued
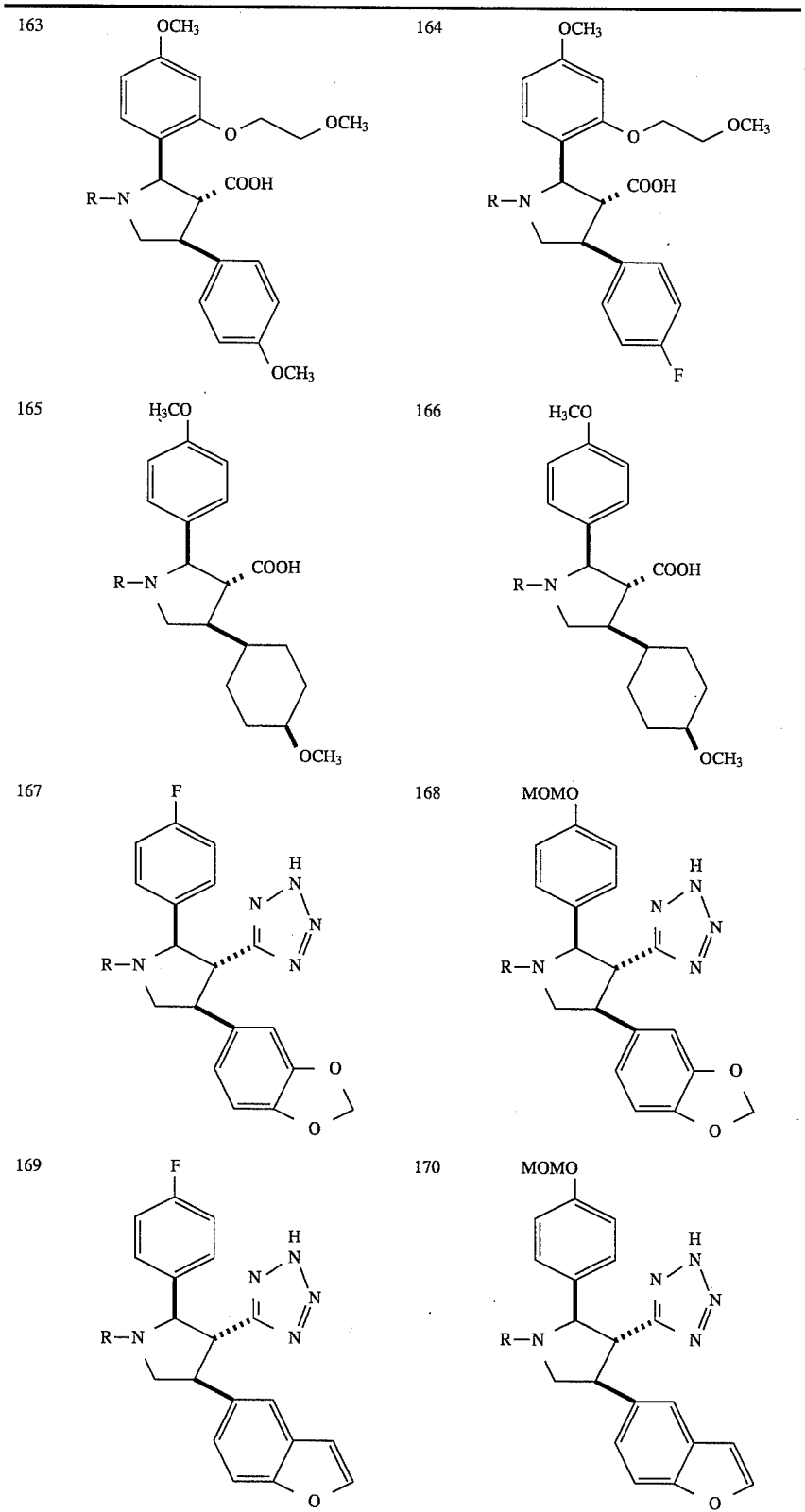

TABLE 2A-continued
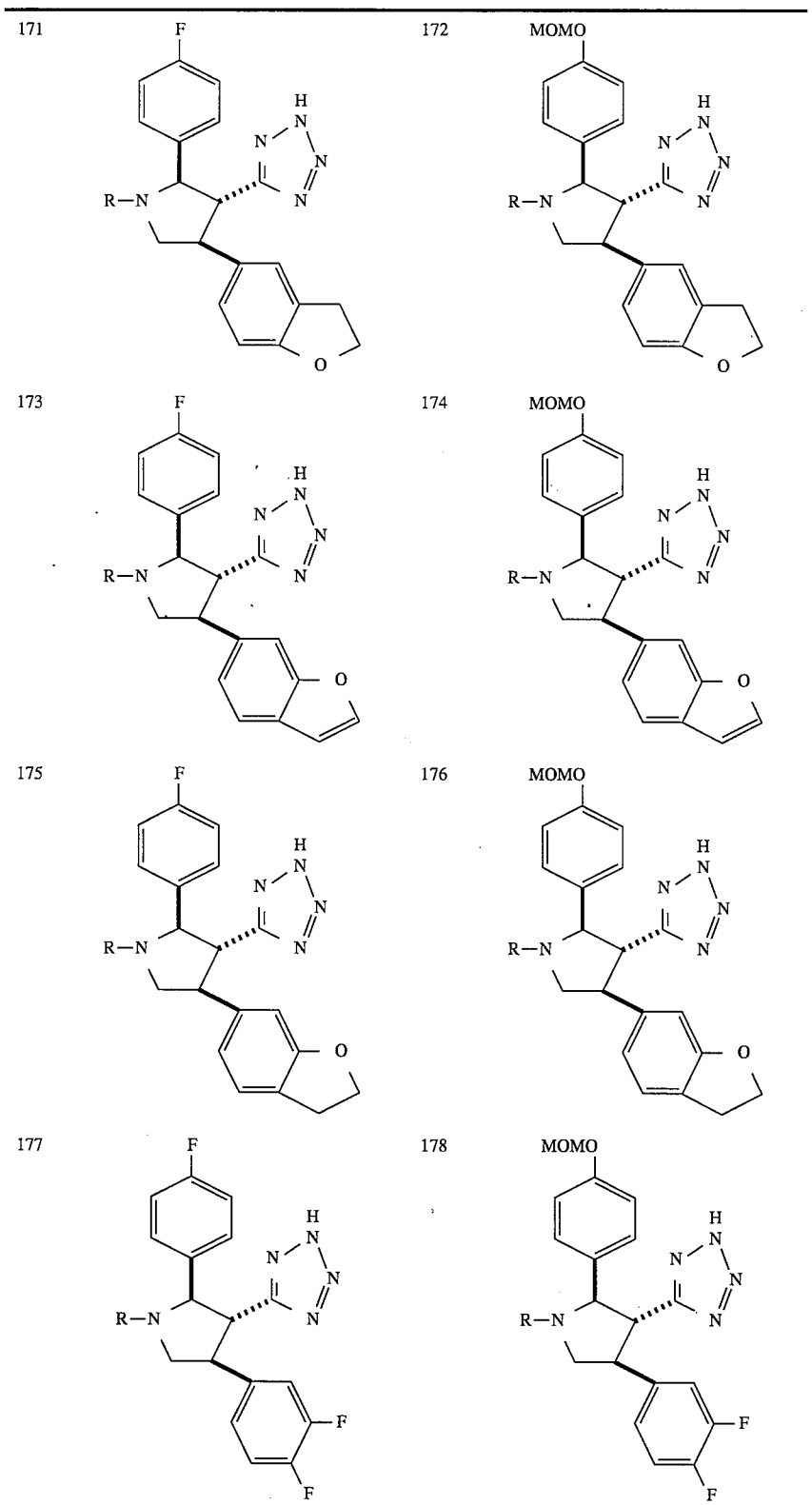

TABLE 2A-continued
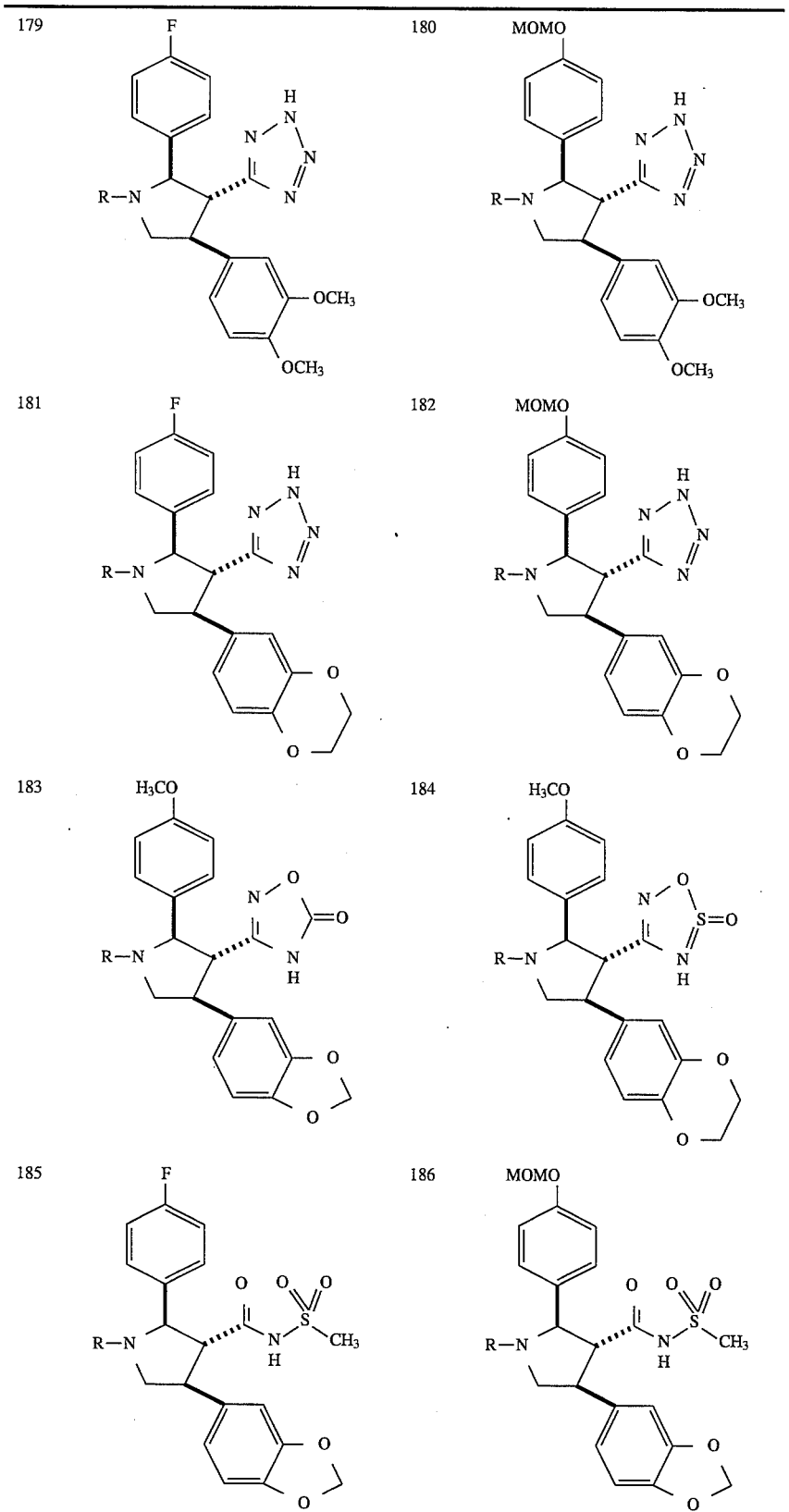

TABLE 2A-continued
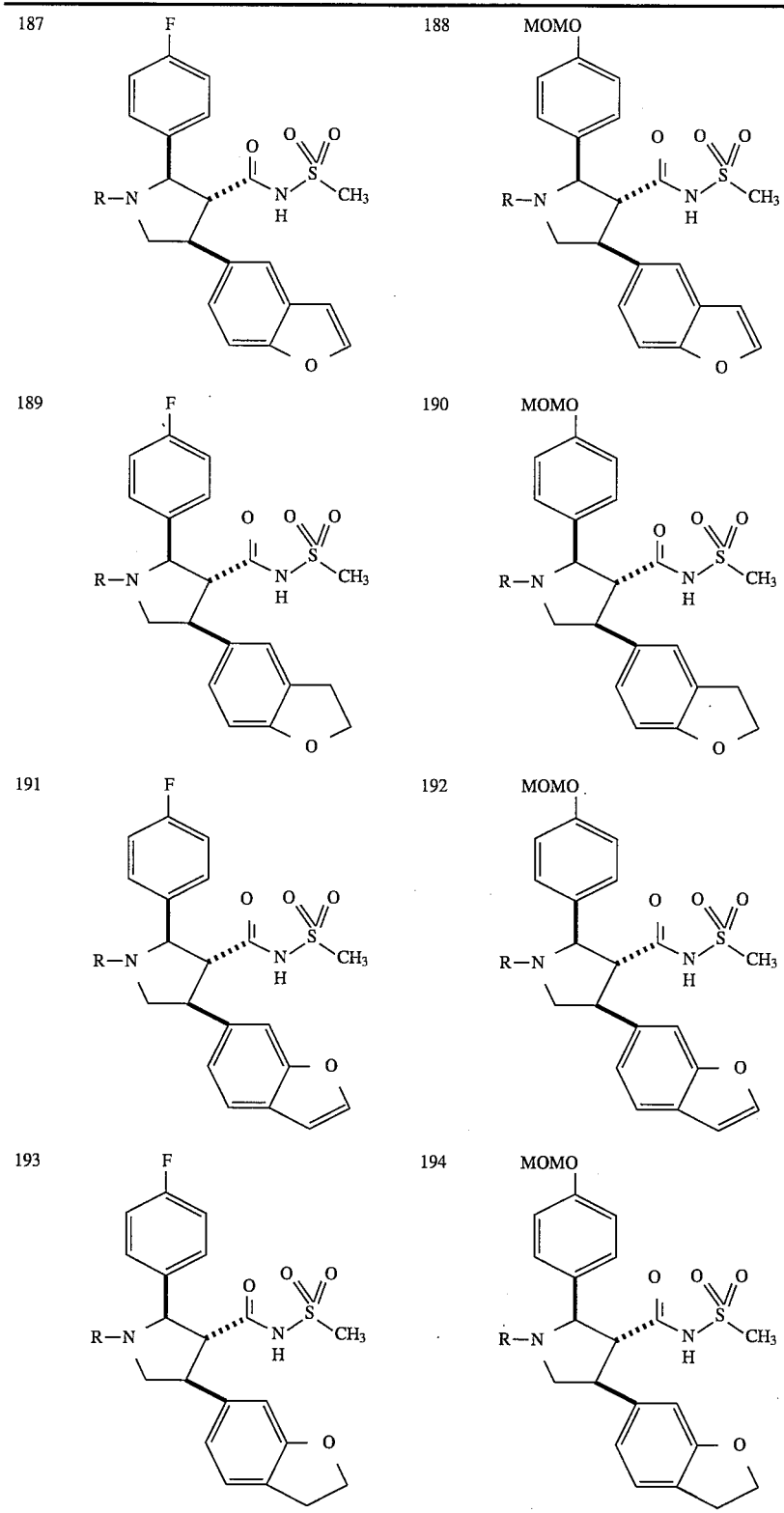

TABLE 2A-continued
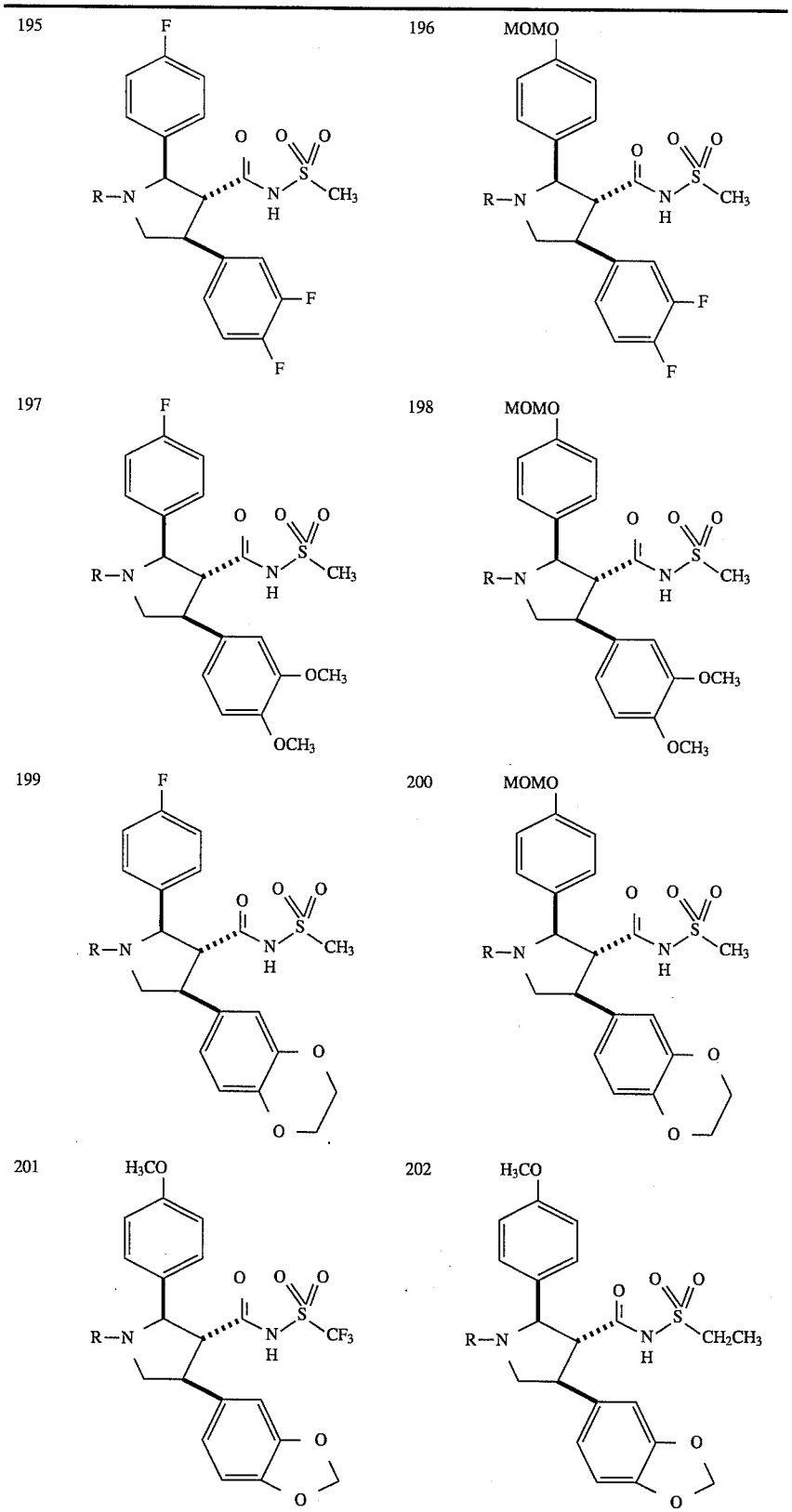

TABLE 2A-continued
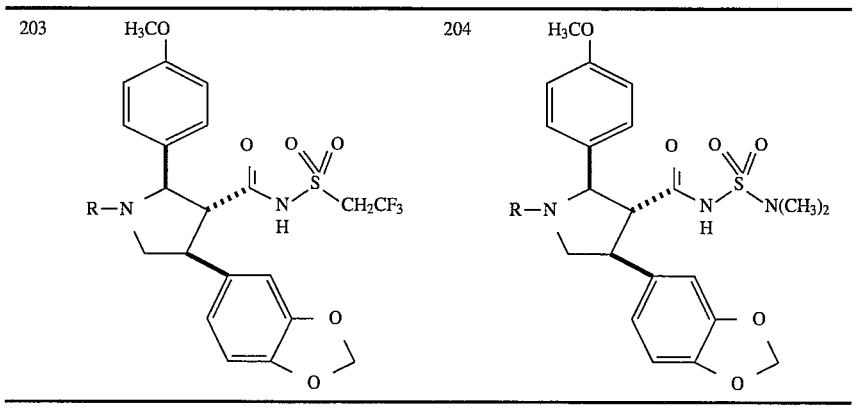

TABLE 2B
| R | | R | | R | |
|---|---|---|---|---|---|
| 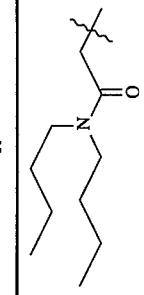 | 1 | 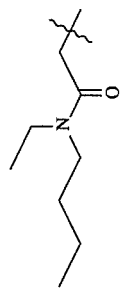 | 2 | 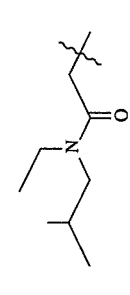 | 3 |
| 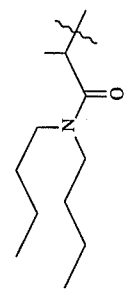 | 4 | 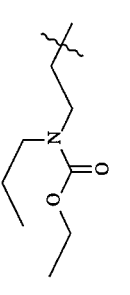 | 5 | 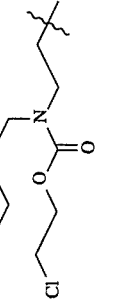 | 6 |
| 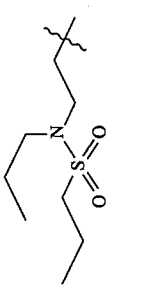 | 7 |  | 8 | 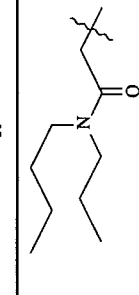 | 9 |
| 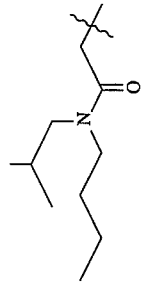 | 10 | 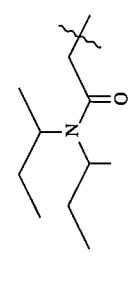 | 11 | 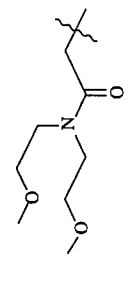 | 12 |
| 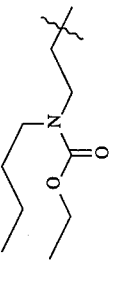 | 13 | 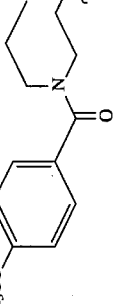 | 14 | 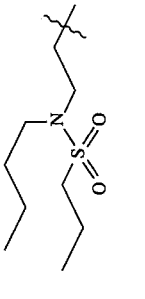 | 15 |
|  | 16 | 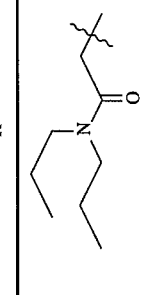 | 17 | 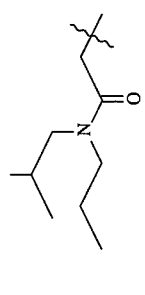 | 18 |
| 19 | | 20 | | 21 | |

TABLE 2B-continued

TABLE 2B-continued

TABLE 2B-continued

EXAMPLE 295
Using methods described in the above examples, compounds comprising a parent structure selected from those disclosed in Table 3A and an R substituent selected from those disclosed in Table 3B can be prepared.
TABLE 3A
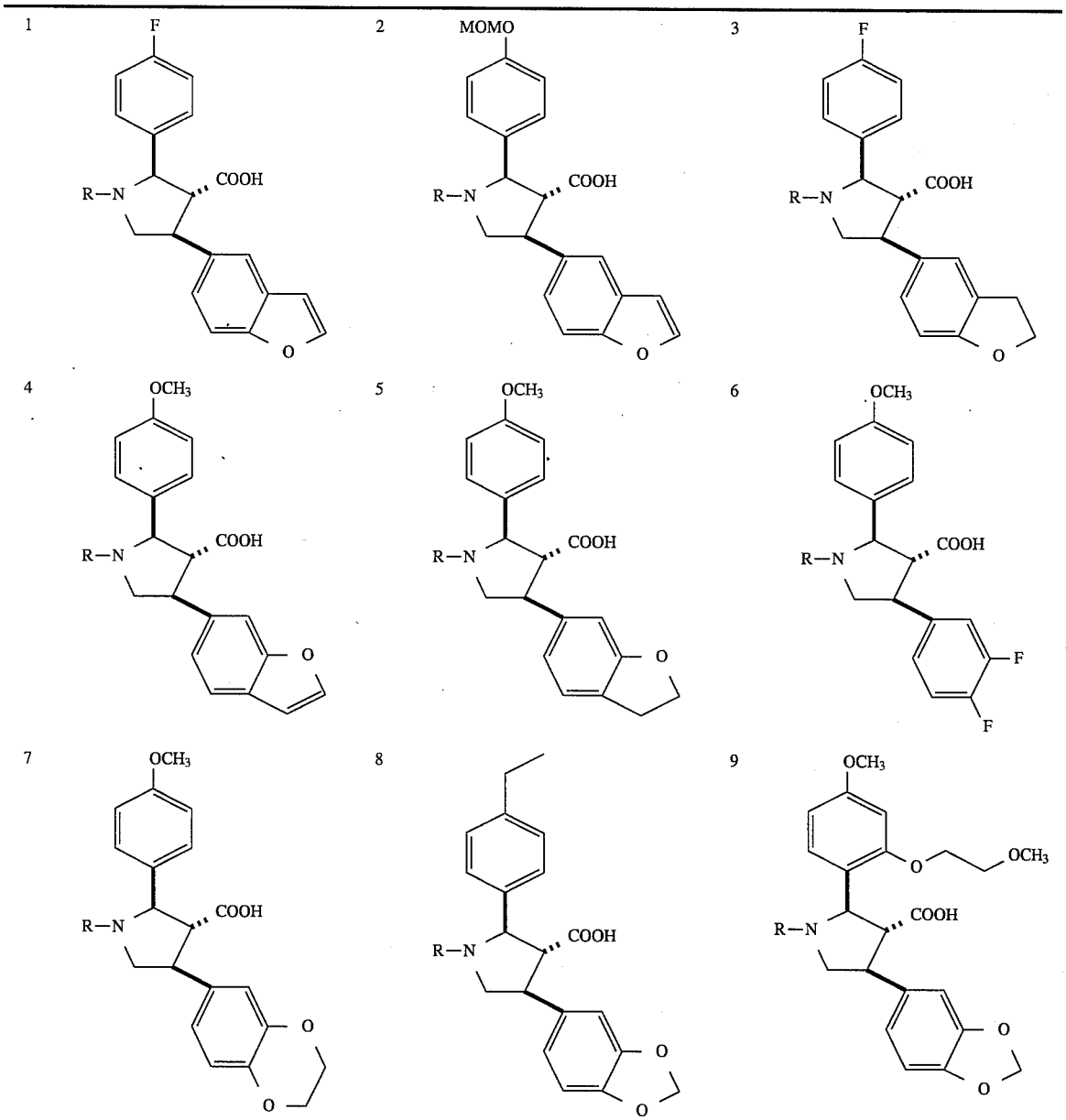

TABLE 3A-continued
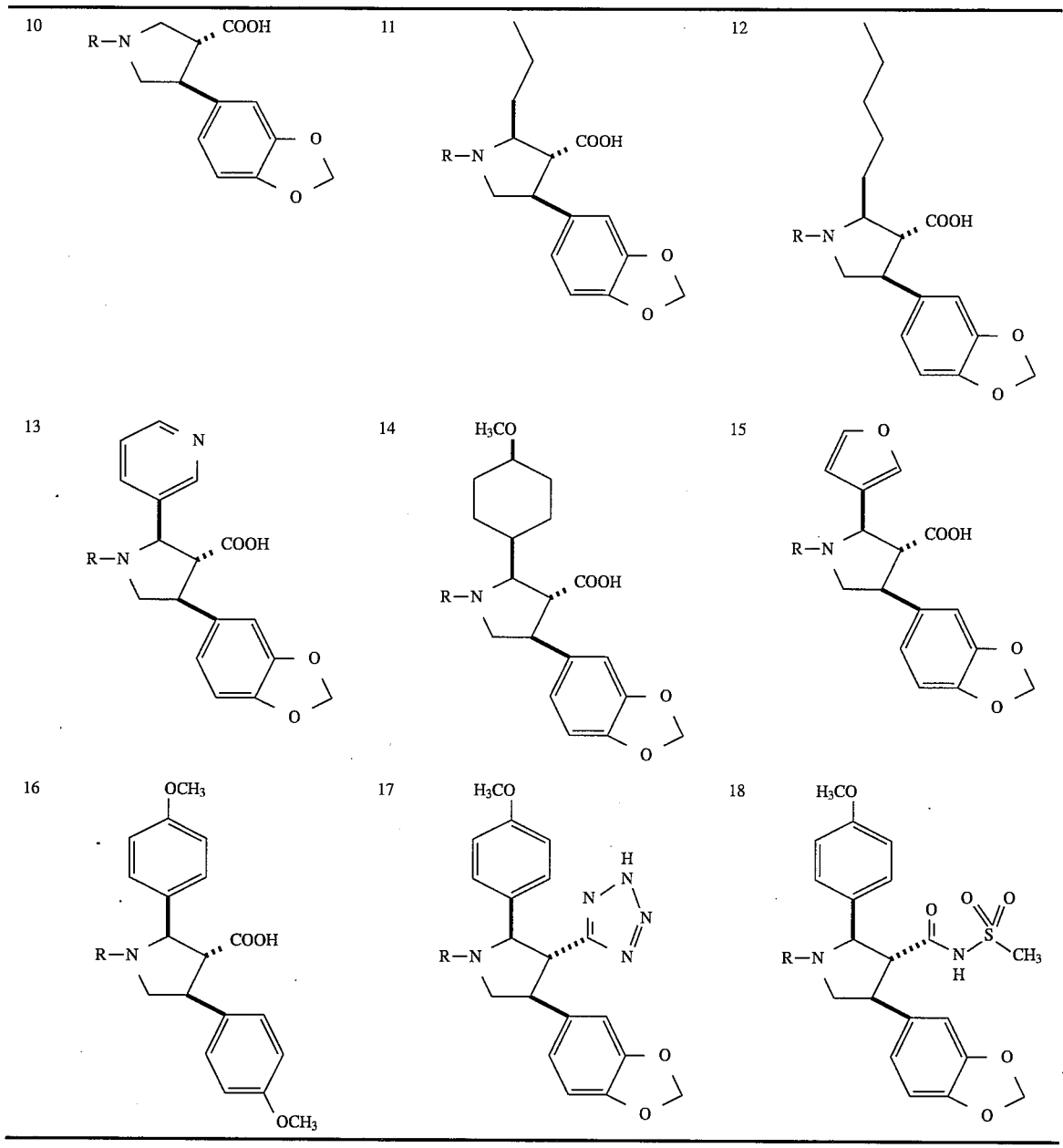

TABLE 3B

TABLE 3B-continued

TABLE 3B-continued

TABLE 3B-continued
| | R | | R | | R |
|---|---|---|---|---|---|
| 64 | 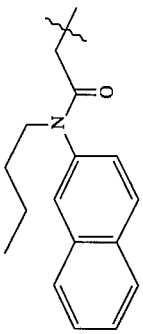 | 65 | 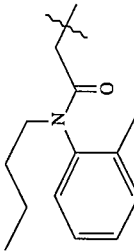 | 66 | 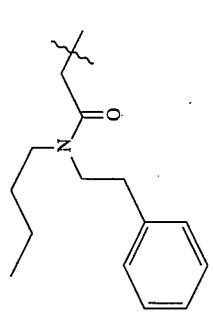 |
| 67 | 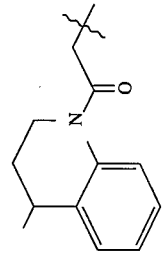 | 68 | 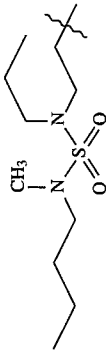 | 69 | 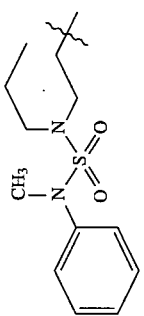 |
| 70 | 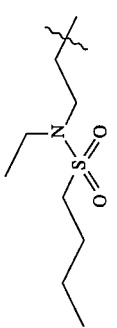 | 71 | 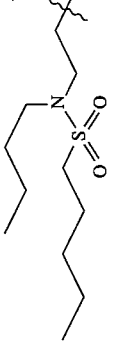 | 72 | 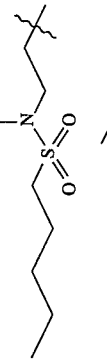 |
| 73 | 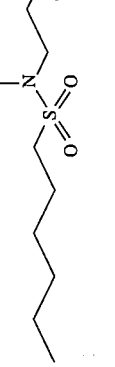 | 74 |  | 75 | 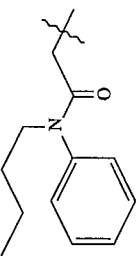 |
| 76 | 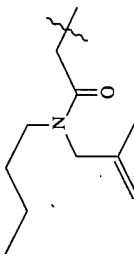 | 77 | 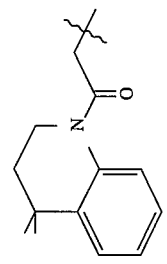 | 78 | 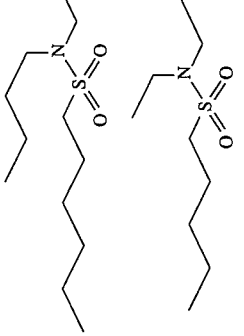 |
| 79 | 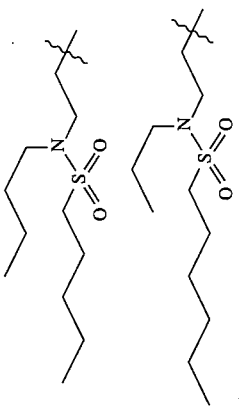 | | | | |

As an indication that the compounds described herein act through binding to endothelin receptors, the compounds have been evaluated for their ability to displace endothelin from its receptor.

BINDING ASSAY

ET$_A$ Receptor

Preparation of membranes from MMQ cells

MMQ [MacLeod/MacQueen/Login cell line (prolactin secreting rat pituitary cells)] cells from 150 mL culture flasks were collected by centrifugation (1000 xg for 10 min) and then homogenized in 25 mL of 10 mM Hepes (pH 7.4) containing 0.25M sucrose and protease inhibitors [3 mM EDTA, 0.1 mM PMSF, and 5 pg/mL Pepstatin A] by a micro ultrasonic cell disruptor (Kontes). The mixture was centrifuged at 1000 xg for 10 min. The supernatant was collected and centrifuged at 60,000 xg for 60 min. The precipitate was resuspended in 20 mM Tris, pH 7.4 containing the above protease inhibitors and centrifuged again. The final pellet was resuspended in 20 mM Tris, pH 7.4 containing protease inhibitors and stored at −80° C. until used. Protein content was determined by the Bio-Rad dye-binding protein assay.

[$^{125}$I]ET-1 binding to membranes

Binding assays were performed in 96-weLl microtiter plates pretreated with 0.1% BSA. Membranes prepared from cells were diluted ~100 fold in Buffer B (20 mM Tris, 100 mM NaCl, 10 mM MgCl$_2$, pH 7.4, with 0.2% BSA, 0.1 mM PMSF, 5 µg/mL Pepstatin A, 0.025% bacitracin, and 3 mM EDTA) to a final concentration of 0.2 mg/mL of protein. In competition studies, membranes (0.02 mg) were incubated with 0.1 nM of [1 251]ET-1 in Buffer B (final volume: 0.2 mL) in the presence of increasing concentrations of unlabeled ET-1 or a test compound for 4 hours at 25° C. After incubation, unbound ligands were separated from bound ligands by a vacuum filtration method using glass-fiber filter strips in PHD cell harvesters (Cambridge Technology, Inc., MA), followed by washing the filter strips with saline (1 mL) for three times. Nonspecific binding was determined in the presence of 1 µM ET-1. The data are shown in Table 4. The per cent inhibition at a concentration of 1 µM is shown. The data show that the compounds of the invention bind to the endothelin receptor.

TABLE 4

Binding Data

| Example | % Inhibition of ET$_A$ at 1 µM | Example | % Inhibition of ET$_A$ at 1 µM |
|---|---|---|---|
| 1D | 96.4 | 30 | 80.0 |
| 2 | 58.4 | 31B | 93.6 |
| 3 | 42.2 | 34 | 95.5 |
| 4 | 78.2 | 35 | 91.8 |
| 5 | 95.1 | 36 | 94.5 |
| 6B | 34.9 | 37 | 47.9 |
| 7 | 63.4 | 38 | 100.0 |
| 8 | 53.7 | 39 | 83.6 |
| 9 | 69.2 | 40 | 94.8 |
| 10 | 66.1 | 41 | 89.9 |
| 14 | 86.6 | 42 | 95.2 |
| 15 | 84.8 | 43 | 99.2 |
| 16 | 96.0 | 44 | 91.3 |
| 17 | 73.9 | 45 | 85.4 |
| 18 | 97.3 | 46 | 90.4 |
| 19 | 90.3 | 47 | 95.1 |
| 20 | 80.9 | 48 | 96.3 |
| 21 | 56.3 | 52 | 84.0 |
| 22 | 86.3 | 54 | 64.6 |

TABLE 4-continued

Binding Data

| Example | % Inhibition of ET$_A$ at 1 µM | Example | % Inhibition of ET$_A$ at 1 µM |
|---|---|---|---|
| 23 | 85.9 | 55 | 50.5 |
| 26 | 83.0 | 56 | 34.3 |
| 27 | 61.2 | 57 | 93.2 |
| 28 | 63.8 | 58 | 81.9 |
| 29 | 85.3 | 59 | 70.8 |
| 60 | 42.8 | 93C | 59.2 |
| 61C | 90.6 | 95D | 82.1 |
| 62 | 94.1 | 96 | 86.1 |
| 63 | 92.0 | 97 | 89.0 |
| 64 | 95.0 | 98 | 86.8 |
| 65 | 82.8 | 99 | 92.1 |
| 66 | 87.7 | 100 | 76.8 |
| 67 | 96.3 | 101 | 89.2 |
| 68 | 84.6 | 102 | 75.2 |
| 69D | 37.4 | 103 | 69.0 |
| 70 | 62.7 | 104 | 98.0 |
| 71 | 81.4 | 105 | 98.6 |
| 72C | 80.7 | 106 | 90.0 |
| 73C | 96.3 | 107 | 97.2 |
| 74 | 95.6 | 109 | 96.8 |
| 75C | 95.3 | 110 | 94.4 |
| 76 | 93.1 | 111 | 101.8 |
| 79 | 100.4 | 112 | 94.9 |
| 80 | 89.4 | 113 | 94.3 |
| 82 | 90.3 | 114 | 86.2 |
| 83 | 85.0 | 115 | 88.4 |
| 84 | 65.3 | 116 | 79.3 |
| 86 | 52.6 | 117 | 95.2 |
| 87 | 62.4 | 118 | 93.2 |
| 88 | 84.3 | 119 | 86.6 |
| 89 | 84.6 | 120 | 99.5 |
| 91C | 91.6 | 121 | 98.6 |
| 92C | 107.4 | 122 | 95.3 |
| 123 | 89.7 | 146 | 25.0 |
| 124 | 91.0 | 147 | 73.0 |
| 125 | 97.2 | 148 | 94.7 |
| 126 | 91.7 | 149 | 84.6 |
| 127 | 91.4 | 150 | 93.6 |
| 128 | 95.4 | 151 | 80.5 |
| 129 | 100.1 | 152 | 86.9 |
| 130 | 91.0 | 153 | 97.1 |
| 131 | 89.5 | 154 | 80.2 |
| 132 | 90.0 | 155 | 92.7 |
| 133 | 88.6 | 156 | 92.6 |
| 134 | 92.2 | 157 | 83.8 |
| 135B | 77.7 | 158 | 91.8 |
| 136 | 79.4 | 159 | 36.2 |
| 138 | 83.0 | 160B | 80.3 |
| 139 | 98.6 | 161 | 93.6 |
| 140 | 106.3 | 162B | 91.5 |
| 141 | 92.8 | 163 | 90.6 |
| 142B | 78.7 | 164 | 98.6 |
| 143 | 20.6 | 165 | 54.1 |
| 144 | 78.2 | 166 | 91.6 |
| 145 | 32.4 | 167 | 94.4 |
|  |  | 291 | 100.0 |

As further demonstration of the efficacy of the described compounds as functional antagonists of endothelin, the ability of the described compounds to inhibit ET-1-induced phosphatidylinositol hydrolysis was measured.

Determination of Phosphatidylinositol (PI) Hydrolysis

MMQ cells (0.4×106 cells/mL) were labeled with 10 µCi/mL of [$^3$H]myoinositol in RPMI for 16 hours. The cells were washed with PBS, then incubated with Buffer A containing protease inhibitors and 10 mM LiCl for 60 minutes. The cells were then incubated with test compounds for 5 minutes, and then challenged with 1 nM ET-1. ET-1 challenge was terminated by the addition of 1.5 mL of 1:2 (v/v) chloroform-methanol. Total inositol phosphates were extracted after adding chloroform and water to give final proportions of 1:1:0.9 (v/v/v) chloroform-methanol-water of as described by Berridge (Biochem. J. 206 587–595 (1982)). The upper aqueous phase (1 mL) was retained and a small portion (100 µL) was counted. The rest of the aqueous sample was analyzed by batch chromatography using artion-exchange resin AG1-X8 (BioRad). The $IC_{50}$ is the concentration of test compound required to inhibit the ET-induced increase in PI turnover by 50%. The results of the above study clearly indicate that the compounds act as functional ET antagonists.

TABLE 5

| Phosphatidylinositol Hydrolysis | |
|---|---|
| Example | $IC_{50}$ µM |
| 1D | 0.025 |
| 14 | 0.017 |
| 15 | 0.010 |
| 16 | 0.009 |
| 18 | 0.009 |
| 19 | 0.024 |
| 30 | 0.001 |
| 31B | 0.002 |
| 43 | 0.0001 |
| 46 | 0.002 |
| 47 | 0.0005 |
| 48 | 0.0004 |

The ability of the compounds of the invention to lower blood pressure can be demonstrated according to the methods described in Matsumura, et al., Eur. J. Pharmacol. 185 103 (1990) and Takata, et al., Clin. Exp. Pharmacol. Physiol. 10 131 (1983).

The ability of the compounds of the invention to treat congestive heart failure can be demonstrated according to the method described in Marguiles, et al., Circulation 82 2226 (1990).

The ability of the compounds of the invention to treat myocardial ischemia can be demonstrated according to the method described in Watanabe, et al., Nature 344 114 (1990).

The ability of the compounds of the invention to treat coronary angina can be demonstrated according to the method described in Heistad, et al., Circ. Res. 54 711 (1984).

The ability of the compounds of the invention to treat cerebral vasospasm can be demonstrated according to the methods described in Nakagomi, et al., J. Neurosurg. 66 915 (1987) or Matsumura, et al., Life Sci. 49 841–848 (1991).

The ability of the compounds of the invention to treat cerebral ischemia can be demonstrated according to the method described in Hara et al., European. J. Pharmacol. 197: 75–82, (1991).

The ability of the compounds of the invention to treat acute renal failure can be demonstrated according to the method described in Kon, et al., J. Clin. Invest. 83 1762 (1989).

The ability of the compounds of the invention to treat chronic renal failure can be demonstrated according to the method described in Benigni, et al., Kidney Int. 44 440–444 (1993).

The ability of the compounds of the invention to treat gastric ulceration can be demonstrated according to the method described in Wallace, et al., Am. J. Physiol. 256 G661 (1989).

The ability of the compounds of the invention to treat cyclosporin-induced nephrotoxicity can be demonstrated according to the method described in Kon, et al., Kidney Int. 37 1487 (1990).

The ability of the compounds of the invention to treat endotoxin-induced toxicity (shock) can be demonstrated according to the method described in Takahashi, et al., Clinical Sci. 79 619 (1990).

The ability of the compounds of the invention to treat asthma can be demonstrated according to the method described in Potvin and Varma, Can. J. Physiol. and Pharmacol. 67 1213 (1989).

The ability of the compounds of the invention to treat transplant-induced atherosclerosis can be demonstrated according to the method described in Foegh, et al., Atherosclerosis 78 229–236 (1989).

The ability of the compounds of the invention to treat atherosclerosis can be demonstrated according to the methods described in Bobik, et al., Am. J. Physiol. 258 C408 (1990) and Chobanian, et al., Hypertension 15 327 (1990).

The ability of the compounds of the invention to treat LPL-related lipoprotein disorders can be demonstrated according to the method described in Ishida, et al., Blochem. Pharmacol. 44 1431–1436 (1992).

The ability of the compounds of the invention to treat proliferative diseases can be demonstrated according to the methods described in Bunchman ET and CA Brookshire, Transplantation Proceed. 23 967–968 (1991); Yamagishi, et al., Blochem. Biophys. Res. Comm. 191 840–846 (1993); and Shichiri, et al., J. Clin. Invest. 87 1867–1871 (1991). Proliferative diseases include smooth muscle proliferation, systemic sclerosis, cirrhosis of the liver, adult respiratory distress syndrome, idiopathic cardiomyopathy, lupus erythematosus, diabetic retinopathy or other retinopathies, psoriasis, scleroderma, prostatic hyperplasia, cardiac hyperplasia, restenosis following arterial injury or other pathologic stenosis of blood vessels.

The ability of the compounds of the invention to treat acute or chronic pulmonary hypertension can be demonstrated according to the method described in Bonvallet et al., Am. J. Physiol. 266 H1327 (1994). Pulmonary hypertension can be associated with congestive heart failure, mitral valve stenosis, emphysema, lung fibrosis, chronic obstructive pulmonary disease (COPD), acute repiratory distress syndrome (ARDS), altitude sickness, chemical exposure, or may be idiopathic.

The ability of the compounds of the invention to treat plaletet aggregation, and thrombosis, can be demonstrated according to the method described in McMurdo et al. Eu. J. Pharmacol. 259 51 (1994).

The ability of the compounds of the invention to treat cancers can be demonstrated according to the method described in Shichiri, et al., J. Clin. Invest. 87 1867 (1991).

The ability of the compounds of the invention to treat IL-2 (and other cytokine) mediated cardiotoxicity and vascular permeability disorders can be demonstrated according to the method described in Klemm et al., Proc. Nat. Acad. Sci. 92 2691 (1995).

The ability of the compounds of the invention to treat nociception can be demonstrated according to the method described in Yamamoto et al., J. Pharmacol. Exp. Therap. 271 156 (1994).

The compounds of the present invention can be used in the form of salts derived from inorganic or organic acids. These salts include but are not limited to the following:

acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Basic addition salts can be prepared in situ during the final isolation and purification of the compounds of formula (I), or separately by reacting the carboxylic acid function with a suitable base such as the hydroxide, carbonate or bicarbonate of a pharmaceutically acceptable metal cation or with ammonia, or an organic primary, secondary or tertiary amine. Such pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

The compounds of the invention are useful for antagonizing endothelin in a human or other mammal. In addition, the compounds of the present invention are useful (in a human or other mammal) for the treatment of hypertension, acute or chronic pulmonary hypertension, Raynaud's disease, congestive heart failure, myocardial ischemia, repedusion injury, coronary angina, cerebral ischemia, cerebral vasospasm, chronic or acute renal failure, non-steroidal antiinflammatory drug induced gastric ulceration, cyclosporin induced nephrotoxicity, endotoxin-induced toxicity, asthma, fibrotic or proliferative diseases, including smooth muscle proliferation, systemic sclerosis, cirrhosis of the liver, adult respiratory distress syndrome, idiopathic cardiomyopathy, lupus erythematosus, diabetic retinopathy or other retinopathies, psoriasis, scleroderma, prostatic hyperplasia, cardiac hyperplasia, restenosis following arterial injury or other pathological stenosis of blood vessels, LPL-related lipoprotein disorders, transplantation-induced atherosclerosis or atherosclerosis in general, platelet aggregation, thrombosis, cancers, IL-2 and other cytokine mediated cardiotoxicity and permeability disorders, and nociception.

Total daily dose administered to a host in single or divided doses may be in amounts, for example, from 0.001 to 1000 mg/kg body weight daily and more usually 0.1 to 100 mg/kg for oral administration or 0.01 to 10 mg/kg for parenteral administration. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, sublingually, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be The title compound was prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lameilar hydrated liquid crystals that are dispersed in an aqueous medium. Any non-toxic, physiologically aceptable and metabolizable lipid capabale of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

While the compounds of the invention can be administered as the sole active pharmaceutical agent, they can also be used in combination with one or more cardiovascular agents independently selected from diuretics, adrenergic blocking agents, vasodilators, calcium channel blockers, renin inhibitors, angiotensin converting enzyme (ACE) inhibitors, angiotensin II antagonists, potassium channel activators and other cardiovascular agents.

Representative diuretics include hydrochlorothiazide, chlorothiazide, acetazolamide, amiloride, bumetanide, benzthiazide, ethacrynic acid, furosemide, indacrinone, metolazone, spironolactone, triamterene, chlorthalidone and the like or a pharmaceutically acceptable salt thereof.

Representative adrenergic blocking agents include phentolamine, phenoxybenzamine, prazosin, terazosin, tolazine, atenolol, metoprolol, nadolol, propranolol, timolol, carteolol and the like or a pharmaceutically acceptable salt thereof.

Representative vasodilators include hyclralazine, minoxidil, diazoxide, nitroprusside and the like or a pharmaceutically acceptable salt thereof.

Representative calcium channel blockers include amrinone, bencyclane, diltiazem, fendiline, flunarizine, nicardipine, nimodipine, perhexilene, verapamil, gallopamil, nifedipine and the like or a pharmaceutically acceptable salt thereof.

Representative renin inhibitors include enalkiren, zankiren, RO 42–5892, PD-134672 and the like or a pharmaceutically acceptable salt thereof.

Representative angiotensin II antagonists include DUP 753, A-81988 and the like.

Representative ACE inhibitors include captopril, enalapril, lisinopril and the like or a pharmaceutically acceptable salt thereof.

Representative potassium channel activators include pinacidil and the like or a pharmaceutically acceptable salt thereof.

Other representative cardiovascular agents include sympatholytic agents such as methyldopa, clonidine, guanabenz, reserpine and the like or a pharmaceutically acceptable salt thereof.

The compounds of the invention and the cardiovascular agent can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents.

When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds, processes, compositions and methods. Variations and changes which are obvious to one skilled in the art are intended to be within the scope and nature of the invention which are defined in the appended claims.

What is claimed is:

1. A compound of the formula:

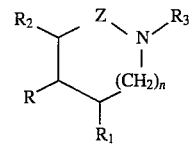

wherein

Z is $-C(R_{18})(R_{19})-$ or $-C(O)-$ wherein $R_{18}$ and $R_{19}$ are independently selected from hydrogen and loweralkyl;

n is 1;

R is $-(CH_2)_m-W$ wherein m is an integer from 0 to 6 and W is
(a) $-C(O)_2-G$ wherein G is hydrogen or a carboxy protecting group,
(b) $-PO3H_2$,
(c) $-P(O)(OH)E$ wherein E is hydrogen, loweralkyl or arylalkyl,
(d) $-ON$,
(e) $-C(O)NHR_{17}$ wherein $R_{17}$ is loweralkyl,
(f) alkylaminocarbonyl,
(g) dialkylaminocarbonyl,
(h) tetrazolyl,
(i) hydroxy,
(j) alkoxy,
(k) sulfonamido,
(l) $-C(O)NHS(O)_2R_{16}$ wherein $R_{16}$ is loweralkyl, haloalkyl, phenyl or dialkylamino,
(m) $-S(O)_2NHC(O)R_{16}$,

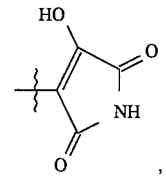 (n)

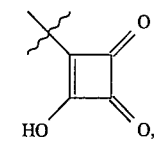 (o)

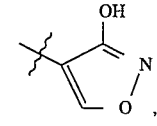 (p)

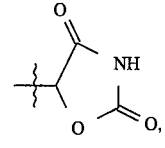 (q)

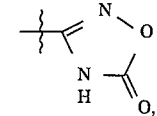 (r)

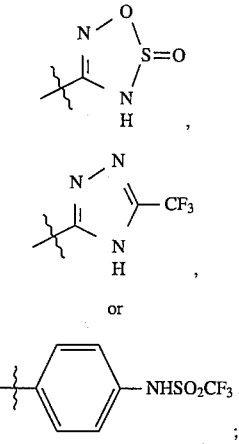

(s)

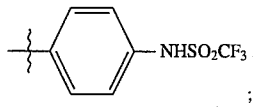

(t)

or (u)

$R_1$ and $R_2$ are independently selected from hydrogen, loweralkyl, alkoxyalkyl, alkoxycarbonylalkyl, hydroxyalkyl, alkoxyalkoxyalkyl, thioalkoxyalkoxyalkyl, cycloalkyl, aryl, arylalkoxyalkyl and heterocyclic, with the proviso that one of $R_1$ and $R_2$ is other than hydrogen; $R_3$ is (a) $R_4$—C(O)—$R_5$—, $R_6$—S(O)$_2$—$R_7$— or $R_{26}$—S(O)—$R_{27}$— wherein $R_5$ is (i) a covalent bond, (ii) alkylene, (iii) alkenylene, (iv) —N($R_{20}$)—$R_8$— or —$R_{8a}$—N($R_{20}$)—$R_8$— wherein $R_8$ and $R_{8a}$ are independently selected from alkylene and $R_{20}$ is hydrogen, loweralkyl, alkenyl, cylcoalkyl or cycloalkylalkyl or (v) —O—$R_9$— or —$R_{9a}$—O—$R_9$ wherein $R_9$ and $R_{9a}$ are independently selected from alkylene; $R_7$ is (i) a covalent bond, (ii) alkylene, (iii) alkenylene or (iv) —N($R_{21}$)—$R_{10}$— wherein $R_{10}$ is alkylene and $R_{21}$ is hydrogen or loweralkyl; $R_4$ and $R_6$ are independently selected from the group consisting of (i) ($R_{11}$)($R_{12}$)N— wherein $R_{11}$ and $R_{12}$ are independently selected from
(1) hydrogen,
(2) loweralkyl,
(3) alkoxyalkyl,
(4) alkenyl,
(5) alkynyl,
(6) cycloalkyl,
(7) cycloalkylalkyl,
(8) aryl,
(9) heterocyclic,
(10) arylalkyl, and
(11) (heterocyclic)alkyl,
(ii) loweralkyl,
(iii) alkenyl,
(iv) alkynyl,
(v) cycloalkyl,
(vi) cycloalkylalkyl,
(vii) aryl,
(viii) an/lalkyl,
(ix) heterocyclic,
(x) (heterocyclic)alkyl and
(xi) alkoxyalkyl;
$R_{26}$ is (i) loweralkyl, (ii) haloalkyl, (iii) alkenyl, (iv) alkynyl, (v) cycloalkyl, (vi) cycloalkylalkyl, (vii) and, (viii) arylalkyl, (ix) heterocyclic, (x) (heterocyclic)alkyl, (xi) alkoxyalkyl or (xii) alkoxy-substituted haloalkyl; and $R_{27}$ is alkylene or alkenylene;

(b) $R_{22}$O—C(O)—$R_{23}$— wherein $R_{22}$ is a carboxy protecting group or heterocyclic and $R_{23}$ is (i) a covalent bond, (ii) alkylene, (iii) alkenylene or (iv) —N($R_{24}$)—$R_{25}$— wherein $R_{25}$ is alkylene and $R_{24}$ is hydrogen or loweralkyl, (c) loweralkyl,
(d) alkenyl,
(e) alkynyl,
(f) cycloalkyl,
(g) cycloalkylalkyl,
(h) aryl,
(i) arylalkyl,
(j) aryloxyalkyl,
(k) heterocyclic,
(l) (heterocyclic)alkyl,
(m) alkoxyalkyl,
(n) alkoxyalkoxyalkyl, or
(o) $R_{13}$—C(O)—CH($R_{14}$)— wherein $R_{13}$ is amino, alkylamino or dialkylamino and $R_{14}$ is aryl or $R_{15}$—C(O)— wherein $R_{15}$ is amino, alkylamino or dialkylamino;
or a pharmaceutically acceptable salt thereof with the proviso that when Z is $CH_2$—$R_1$ is loweralkyl or aryl, $R_2$ is hydrogen and R is hydroxy or hydroxyalkyl, then $R_3$ is other than loweralkyl, alkenyl, alkynyl, cycloalkyl, cycloalkylalkyl, —C(O)O-loweralkyl,—C(O)O-alkenyl, or $R_4$—C(O)—$R_5$, wherein $R_5$ is a covalent bond or alkylene and $R_4$ is loweralkyl, cycloalkyl or cycloalkylalkyl.

2. The compound according to claim 1 wherein n is 1 and Z is —$CH_2$—.

3. The compound according to claim 1 wherein n is 1, Z is —$CH_2$—, and $R_3$ is $R_4$—C(O)—$R_5$—, $R_6$—$SO_2$—$R_7$— or $R_{26}$—S(O)—$R_{27}$— wherein $R_4$, $R_5$, $R_6$, $R_7$, $R_{26}$ and $R_{27}$ are as defined therein.

4. The compound according to claim 1 wherein n is 1, Z is —$CH_2$—, and $R_3$ is alkoxyalkyl or alkoxyalkoxyalkyl.

5. The compound according to claim 1 wherein n is 1, Z is —$CH_2$—, and $R_3$ is $R_4$—C(O)—$R_5$— wherein $R_4$ is ($R_{11}$)($R_{12}$)N— as defined therein and $R_5$ is alkylene or $R_3$ is $R_6$—S(O)$_2$—$R_7$— or $R_{26}$—S(O)—$R_{27}$— wherein $R_7$ is alkylene, $R_{27}$ is alkylene and $R_6$ and $R_{26}$ are as defined therein.

6. The compound according to claim 1 wherein n is 1, Z is —$CH_2$— and $R_3$ is $R_4$—C(O)—N($R_{20}$)—$R_8$— or $R_6$—S(O)$_2$—N($R_{21}$)—$R_{10}$— wherein $R_8$ and $R_{10}$ and $R_4$, $R_6$, $R_{20}$ and $R_{21}$ are as defined therein.

7. The compound according to claim 1 wherein n is 1, R is tetrazolyl or —C(O)$_2$—G wherein G is hydrogen or a carboxy protecting group or R is —C(O)—NHS(O)$_2R_{16}$ wherein $R_{16}$ is loweralkyl or and, Z is —$CH_2$—, $R_1$ and $R_2$ are independently selected from (i) loweralkyl, (ii) cylcoalkyl, (iii) substituted aryl wherein aryl is phenyl substituted with one or two substituents independently selected from loweralkyl, alkoxy, halo, alkoxyalkoxy and carboxyalkoxy and (iv) substituted or unsubstituted heterocyclic, and $R_3$ is $R_4$—C(O)—$R_5$— wherein $R_4$ is ($R_{11}$)($R_{12}$)N— wherein $R_{11}$ and $R_{12}$ are independently selected from loweralkyl, aryl and arylalkyl and $R_5$ is alkylene; or $R_3$ is $R_4$—C(O)—N($R_{20}$)—$R_8$— or $R_6$—S(O)$_2$—N($R_{21}$)—$R_{10}$— wherein $R_4$ is loweralkyl, aryl, alkoxy, alkylamino, aryloxy or arylalkoxy and $R_6$ is loweralkyl, haloalkyl, alkoxyalkyl, aryl or arylalkyl, $R_8$ and $R_{10}$ are alkylene and $R_{20}$ and $R_{21}$ are loweraikyl; or $R_3$ is $R_6$—S(O)$_2$—$R_7$— or $R_{26}$—S(O)—$R_{27}$— wherein $R_6$ is loweralkyl, $R_7$ is alkylene, $R_{26}$ is loweralkyl and $R_{27}$ is alkylene.

8. The compound according to claim 1 wherein n is 1, R is —C(O)2—G wherein G is hydrogen or a carboxy protecting group. Z is —$CH_2$—, $R_1$ is (i) loweralkyl, (ii) cycloalkyl, (iii) phenyl, (iv) pyridyl. (v) furanyl or (vi) substituted or unsubstituted 4-methoxyphenyl, 4-fluorophenyl, 3-fluorophenyl, 2-fluorophenyl, 4-methoxymethoxyphenyl, 4-hydroxyphenyl, 4-t-butylphenyl, 1,3-benzodioxolyl, 1,4-benzodioxanyl or dihydrobenzofuranyl wherein the substituent is selected from alkoxy, alkoxyalkoxy and carboxyalkoxy, $R_2$ is 1,3-benzodioxolyl, 1,4-benzodioxanyl, dihydrobenzofuranyl, 4-methoxyphenyl, dimethoxyphenyl, fluorophenyl or difluorophenyl and $R_3$ is $R_4$—C(O)—N($R_{20}$)—$R_8$— or $R_6$—S(O)$_2$—N($R_{21}$)—$R_{10}$— wherein $R_8$ and $R_{10}$ are alkylene, $R_{20}$ and $R_{21}$ are loweralkyl, $R_4$ is loweralkyl, an/l, alkoxy, alkylamino, aryloxy or arylalkoxy and $R_6$ is loweralkyl, haloalkyl, alkoxyalkyl, aryl or arylalkyl.

9. The compound according to claim 1 wherein n is 1, R is —C(O)$_2$—G wherein G is hydrogen or a carboxy protecting group, Z is —CH$_2$—, $R_1$ is (i) loweralkyl, (ii) cycloalkyl, (iii) phenyl, (iv) pyridyl, (v) furanyl or (vi) substituted or unsubstituted 4-methoxyphenyl, 4-fluorophenyl, 3-fluorophenyl, 2-fluorophenyl, 4-methoxymethoxyphenyl, 4-hydroxyphenyl, 4-t-butylphenyl, 1,3-benzodioxolyl, 1,4-benzodioxanyl or dihydrobenzofuranyl wherein the substituent is selected from alkoxy, alkoxyalkoxy and carboxyalkoxy, $R_2$ is 1,3-benzodioxolyl, 1,4-benzodioxanyl, dihydrobenzofuranyl, 4-methoxyphenyl, dimethoxyphenyl, fluorophenyl or difluorophenyl and $R_3$ is $R_4$—C(O)—$R_5$— wherein $R_5$ is alkylene and $R_4$ is ($R_{11}$)($R_{12}$)N— wherein $R_{11}$ and $R_{12}$ are independently selected from loweralkyl, aryl and arylalkyl.

10. The compound according to claim 1 of the formula:

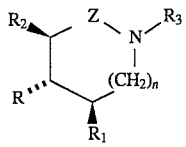

wherein Z is —C($R_{18}$)($R_{19}$)— or —C(O)— wherein $R_{18}$ and $R_{19}$ are independently selected from hydrogen and loweralkyl; n is 1; R is —(CH$_2$)$_m$—W wherein m is an integer from 0 to 6 and W is (a) —C(O)$_2$—G wherein G is hydrogen or a carboxy protecting group,
(b) —PO$_3$H$_2$,
(c) —P(O)(OH)E wherein E is hydrogen, loweralkyl or arylalkyl,
(d) —CN,
(e) —C(O)NHR$_{17}$ wherein $R_{17}$ is loweralkyl,
(f) alkylaminocarbonyl,
(g) dialkylaminocarbonyl,
(h) tetrazolyl,
(i) hydroxy,
(j) alkoxy,
(k) sulfonamido,
(l) —C(O)NHS(O)$_2$R$_{16}$ wherein $R_{16}$ is loweralkyl, haloalkyl, phenyl or dialkylamino,
(m) —S(O)$_2$NHC(O)R$_{16}$,

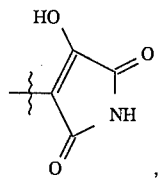

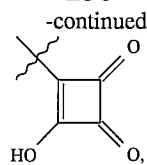

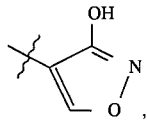

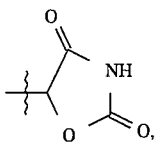

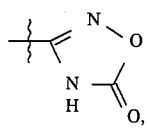

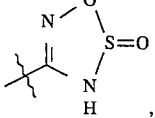

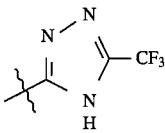

or

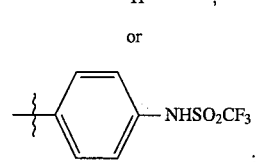

;

$R_1$ and $R_2$ are independently selected from hydrogen, loweralkyl, alkoxyalkyl, alkoxycarbonylalkyl, hydroxyalkyl, alkoxyalkoxyalkyl, thioalkoxyalkoxyalkyl, cycloalkyl, aryl, arylalkoxyalkyl and heterocyclic, with the proviso that one of $R_1$ and $R_2$ is other than hydrogen; $R_3$ is (a) $R_4$—C(O)—$R_5$—, $R_6$—S(O)$_2$—$R_7$— or $R_{26}$—S(O)—$R_{27}$ wherein $R_5$ is (i) a covalent bond, (ii) alkylene, (iii) alkenylene, (iv) —N($R_{20}$)—$R_8$— or —$R_{8a}$—N($R_{20}$)—$R_8$— wherein $R_8$ and $R_{8a}$ are independently selected from alkylene and $R_{20}$ is hydrogen, loweralkyl, alkenyl, cylcoalkyl or cycloalkylalkyl or (v) —O—$R_9$— or —$R_{9a}$—O—$R_9$ wherein $R_9$ and $R_{9a}$ are independently selected from alkylene; $R_7$ is (i) a covalent bond, (ii) alkylene, (iii) alkenylene or (iv) —N($R_{21}$)—$R_{10}$— wherein $R_{10}$ is alkylene and $R_{21}$ is hydrogen or loweralkyl; $R_4$ and $R_6$ are independently selected from the group consisting of (i) ($R_{11}$)($R_{12}$)N— wherein $R_{11}$ and $R_{12}$ are independently selected from
  (1) hydrogen,
  (2) loweralkyl,
  (3) alkoxyalkyl,
  (4) alkenyl,
  (5) alkynyl,
  (6) cycloalkyl,
  (7) cycloalkylalkyl,
  (8) aryl,
  (9) heterocyclic,

(10) arylalkyl, and
(11) (heterocyclic)alkyl,
(ii) loweralkyl,
(iii) alkenyl,
(iv) alkynyl,
(v) cycloalkyl,
(vi) cycloalkylalkyl,
(vii) aryl,
(viii) arylalkyl,
(ix) heterocyclic,
(x) (heterocyclic)alkyl and
(xi) alkoxyalkyl;

$R_{26}$ is (i) loweralkyl, (ii) haloalkyl, (iii) alkenyl, (iv) alkynyl, (v) cycloalkyl, (vi) cycloalkylalkyl, (vii) aryl, (viii) arylalkyl, (ix) heterocyclic, (x) (heterocyclic)alkyl, (xi) alkoxyalkyl or (xii) alkoxy-substituted haloalkyl; and $R_{27}$ is alkylene or alkenylene;

(b) $R_{22}$—O—C(O)—$R_{23}$— wherein $R_{22}$ is a carboxy protecting group or heterocyclic and $R_{23}$ is (i) a covalent bond, (ii) alkylene, (iii) alkenylene or (iv) —N($R_{24}$)—$R_{25}$— wherein $R_{25}$ is alkylene and $R_{24}$ is hydrogen or loweralkyl, (c) loweralkyl,
(d) alkenyl,
(e) alkynyl,
(f) cycloalkyl,
(g) cycloalkylalkyl,
(h) aryl,
(i) arylalkyl,
(j) aryloxyalkyl,
(k) heterocyclic,
(l) (heterocyclic)alkyl,
(m) alkoxyalkyl,
(n) alkoxyalkoxyalkyl, or
(o) $R_{13}$—C(O)—CH($R_{14}$)— wherein $R_{13}$ is amino, alkylamino or dialkylamino and $R_{14}$ is aryl or $R_{15}$—C(O)— wherein $R_{15}$ is amino, alkylamino or dialkylamino;

or a pharmaceutically acceptable salt thereof with the proviso that when Z is $CH_2$, $R_1$ is loweralkyl or aryl, $R_2$ is hydrogen and R is hydroxy or hydroxyalkyl, then $R_3$ is other than loweralkyl, alkenyl, alkynyl, cycloalkyl, cycloalkylalkyl, —C(O)O-loweralkyl, —C(O)O-alkenyl, or $R_4$—C(O)—$R_5$, wherein $R_5$ is covalent bond or alkylene and $R_4$ is loweralkyl, cycloalkyl or cycloalkylalkyl.

11. The compound according to claim 10 wherein n is 1 and Z is —$CH_2$—.

12. The compound according to claim 10 wherein n is 1, Z is —$CH_2$—, and $R_3$ is $R_4$—C(O)—$R_5$—, $R_6$—$SO_2$—$R_7$— or $R_{26}$—S(O)—$R_{27}$— wherein $R_4$, $R_5$, $R_6$, $R_7$, $R_{26}$ and $R_{27}$ are as defined therein.

13. The compound according to claim 10 wherein n is 1, Z is —$CH_2$—, and $R_3$ is alkoxyalkyl or alkoxyalkoxyalkyl.

14. The compound according to claim 10 wherein n is 1, Z is —$CH_2$—, and $R_3$ is $R_4$—C(O)—$R_5$— wherein $R_4$ is ($R_{11}$)($R_{12}$)N— as defined therein and $R_5$ is alkylene $R_3$ is $R_6$—S(O)$_2$—$R_7$— or $R_{26}$—S(O)—$R_{27}$— wherein $R_7$ is alkytene, $R_{27}$ is alkylene and $R_6$ and $R_{26}$ are as defined therein.

15. The compound according to claim 10 wherein n is 1, Z is —$CH_2$—, and $R_3$ is $R_4$—C(O)—N($R_{20}$)—$R_8$— or $R_6$—S(O)$_2$—N($R_{21}$)—$R_{10}$— wherein $R_8$ and $R_{10}$ and $R_4$, $R_6$, $R_{20}$ and $R_{21}$ are as defined therein.

16. The compound according to claim 10 wherein n is 1, R is tetrazolyl or —C(O)$_2$—G wherein G is hydrogen or a carboxy protecting group or R is —C(O)—NHS(O)$_2R_{16}$ wherein $R_{16}$ is loweralkyl or awl, Z is —$CH_2$—, $R_1$ and $R_2$ are independently selected from (i) loweralkyl, (ii) cylcoalkyl, (iii) substituted aryl wherein aryl is phenyl substituted with one or two substituents independently selected from loweralkyl, alkoxy, halo, alkoxyalkoxy and carboxyalkoxy and (iv) substituted or unsubstituted heterocyclic, and $R_3$ is $R_4$—C(O)—$R_5$— wherein $R_4$ is ($R_{11}$)($R_{12}$)N— wherein $R_{11}$ and $R_{12}$ are independently selected from loweralkyl, aryl and arylalkyl and $R_5$ is alkylene; or $R_3$ is $R_4$—C(O)—N($R_{20}$)—$R_5$— or $R_6$—S(O)$_2$—N($R_{21}$)—$R_{10}$— wherein $R_4$ is loweralkyl, aryl, alkoxy, alkylamino, aryloxy or arylalkoxy and $R_6$ is loweralkyl, haloalkyl, alkoxyalkyl, awl or arylalkyl, $R_8$ and $R_{10}$ are alkylene and $R_{20}$ and $R_{21}$ are loweralkyl; or $R_3$ is $R_6$—S(O)$_2$—$R_7$— or $R_{26}$—S(O)—$R_{27}$— wherein $R_6$ is loweralkyl, $R_7$ is alkylene, $R_{26}$ is loweralkyl and $R_{27}$ is alkylene.

17. The compound according to claim 10 wherein n is 1, R is —C(O)$_2$—G wherein G is hydrogen or a carboxy protecting group, Z is —$CH_2$—, $R_1$ is (i) loweralkyl, (ii) cycloalkyl, (iii) phenyl, (iv) pyddyl, (v) furanyl or (vi) substituted or unsubstituted 4-methoxyphenyl, 4-fluorophenyl, 3-fluorophenyl, 2-fluorophenyl, 4-methoxymethoxyphenyl, 4-hydroxyphenyl, 4-t-butylphenyl, 1,3-benzodioxolyl, 1,4-benzodioxanyl or dihydrobenzofuranyl wherein the substituent is selected from alkoxy, alkoxyalkoxy and carboxyalkoxy, $R_2$ is 1,3-benzodioxolyl, 1,4-benzodioxanyl, dihydrobenzofuranyl, 4-methoxyphenyl, dimethoxyphenyl, fluorophenyl or difluorophenyl and $R_3$ is $R_4$—C(O)—N($R_{20}$)—$R_8$— or $R_6$—S(O)$_2$—N($R_{21}$)—$R_{10}$— wherein $R_8$ and $R_{10}$ are alkylene, $R_{20}$ and $R_{21}$ are loweralkyl, $R_4$ is loweralkyl, aryl, alkoxy, alkylamino, aryloxy or arylalkoxy and $R_6$ is loweralkyl, haloalkyl, alkoxyalkyl, aryl or arylalkyl.

18. The compound according to claim 10 wherein n is 1, R is —C(O)$_2$—G wherein G is hydrogen or a carboxy protecting group, Z is —$CH_2$—, $R_1$ is (i) loweralkyl, (ii) cycloalkyl, (iii) phenyl, (iv) pyddyl, (v) furanyl or (vi) substituted or unsubstituted 4-methoxyphenyl, 4-fluorophenyl, 3-fluorophenyl, 2-fluorophenyl, 4-methoxymethoxyphenyl, 4-hydroxyphenyl, 4-t-butylphenyl, 1,3-benzodioxolyl, 1,4-benzodioxanyl or dihydrobenzofuranyl wherein the substituent is selected from alkoxy, alkoxyalkoxy and carboxyalkoxy, $R_2$ is 1,3-benzodioxolyl, 1,4-benzodioxanyl, dihydrobenzofuranyl, 4-methoxyphenyl, dimethoxyphenyl, fluorophenyl or difluorophenyl and $R_3$ is $R_4$—C(O)—$R_5$— wherein $R_5$ is alkylene and $R_4$ is ($R_{11}$)($R_{12}$)N— wherein $R_{11}$ and $R_{12}$ are independently selected from loweralkyl, aryl and arylalkyl.

19. A pharmaceutical composition for antagonizing endothelin comprising a therapeutically effective amount of the compound of claim 1 and a pharmaceutically acceptable carrier.

20. A pharmaceutical composition for antagonizing endothelin comprising a therapeutically effective amount of the compound of claim 10 and a pharmaceutically acceptable carrier.

21. A method for antagonizing endothelin comprising administering to a mammal in need of such treatment a therapeutically effective amount of a compound of claim 1.

22. A method for antagonizing endothelin comprising administering to a mammal in need of such treatment a therapeutically effective amount of a compound of claim 10.

* * * * *

UNITED STATES PATENT AND TRADEMARK OFFICE
CERTIFICATE OF CORRECTION

PATENT NO. : 5,622,971
DATED : April 22, 1997
INVENTOR(S) : Winn et al.

It is certified that error appears in the above-indentified patent and that said Letters Patent is hereby corrected as shown below:

Column 232, line 24, change "-PO3H$_2$" to --PO$_3$H$_2$--.

Column 232, line 27, change "-ON" to ---CN--.

Column 233, line 54, change "an/lalkyl" to --arylalkyl--.

Column 233, line 59, change "and" to --aryl--.

Column 233, line 63, change "R$_{22}$O" to --R$_{22}$-O--.

Column 234, line 41, change "R$_8$ and R$_{10}$" to --R$_8$ and R$_{10}$ are alkylene--.

Column 234, line 46, change "or and" to --or aryl--.

Column 234, line 63, change "-C(O)2-G" to ---C(O)$_2$-G--.

Column 235, line 9, change "an/l" to --aryl--.

Column 236, line 42, change "alkoxyaikoxyalkyl" to --alkoxyalkoxyalkyl--.

Column 236, line 46, change "R$_{27}$" to --R$_{27}$- --.

Column 237, line 59, change "alkylene" to --alkylene or--.

Column 237, line 61, change "alkytene" to --alkylene--.

Column 237, line 65, change "R$_8$ and R$_{10}$" to --R$_8$ and R$_{10}$ are alkylene--.

Column 238, line 4, change "awl" to --aryl--.

UNITED STATES PATENT AND TRADEMARK OFFICE
CERTIFICATE OF CORRECTION

PATENT NO. : 5,622,971
DATED : April 22, 1997
INVENTOR(S) : Winn et al.

It is certified that error appears in the above-indentified patent and that said Letters Patent is hereby corrected as shown below:

Column 238, line 13, change "$R_5$" to --$R_8$--.

Column 238, line 16, change "awl" to --aryl--.

Column 238, line 22, change "pyddyl" to --pyridyl--.

Column 238, line 39, change "pyddyl" to --pyridyl--.

Signed and Sealed this

Nineteenth Day of August, 1997

Attest:

BRUCE LEHMAN

Attesting Officer     Commissioner of Patents and Trademarks